United States Patent
Pak et al.

(10) Patent No.: US 12,178,121 B2
(45) Date of Patent: Dec. 24, 2024

(54) LUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventors: Hankyu Pak, Suwon-si (KR); Eunjae Jeong, Hwaseong-si (KR); Sanghyun Han, Hwaseong-si (KR); Dongjun Kim, Suwon-si (KR); Minji Kim, Hwaseong-si (KR); Sohee Jo, Cheonan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 609 days.

(21) Appl. No.: 17/445,815

(22) Filed: Aug. 24, 2021

(65) Prior Publication Data

US 2022/0123213 A1    Apr. 21, 2022

(30) Foreign Application Priority Data

Oct. 21, 2020  (KR) ...................... 10-2020-0136728

(51) Int. Cl.
| | |
|---|---|
| C07C 211/61 | (2006.01) |
| C07D 209/86 | (2006.01) |
| C07D 209/88 | (2006.01) |
| C07D 333/76 | (2006.01) |
| H10K 85/60 | (2023.01) |
| H10K 50/15 | (2023.01) |

(52) U.S. Cl.
CPC .......... *H10K 85/633* (2023.02); *C07C 211/61* (2013.01); *C07D 209/86* (2013.01); *C07D 209/88* (2013.01); *C07D 333/76* (2013.01); *H10K 85/626* (2023.02); *H10K 85/636* (2023.02); *H10K 85/6572* (2023.02); *C07C 2603/18* (2017.05); *C07C 2603/94* (2017.05); *H10K 50/15* (2023.02)

(58) Field of Classification Search
None
See application file for complete search history.

(56) References Cited

U.S. PATENT DOCUMENTS

| | | |
|---|---|---|
| 4,720,432 A | 1/1988 | VanSlyke et al. |
| 5,061,569 A | 10/1991 | VanSlyke et al. |
| 6,242,115 B1 | 6/2001 | Thomson et al. |
| 7,431,997 B2 | 10/2008 | Hwang et al. |
| 2019/0237668 A1 | 8/2019 | Miyake et al. |

FOREIGN PATENT DOCUMENTS

| | | | | |
|---|---|---|---|---|
| CN | 115504890 A | * | 12/2022 | ........... C07C 211/61 |
| JP | 11-144873 A | | 5/1999 | |
| JP | 2003-133075 A | | 5/2003 | |
| JP | 4103493 B2 | | 6/2008 | |
| JP | 4573923 B2 | | 11/2010 | |
| JP | 4589223 B2 | | 12/2010 | |
| KR | 10-1072214 B1 | | 10/2011 | |
| KR | 10-2015-0051830 A | | 5/2015 | |
| KR | 10-1695270 B1 | | 1/2017 | |
| KR | 10-1857518 B1 | | 5/2018 | |
| KR | 10-2078171 B1 | | 2/2020 | |
| KR | 20200113389 A | * | 10/2020 | ........... C07C 211/54 |
| KR | 20220077279 A | * | 6/2022 | ........... C07C 211/61 |

\* cited by examiner

*Primary Examiner* — Robert S Loewe
(74) *Attorney, Agent, or Firm* — Lewis Roca Rothgerber Christie LLP

(57) ABSTRACT

An organic electroluminescence device includes a first electrode, a hole transport region on the first electrode, an emission layer on the hole transport region, an electron transport region on the emission layer, and a second electrode on the electron transport region. The hole transport region may include an amine compound represented by Formula 1, thereby exhibiting high luminous efficiency:

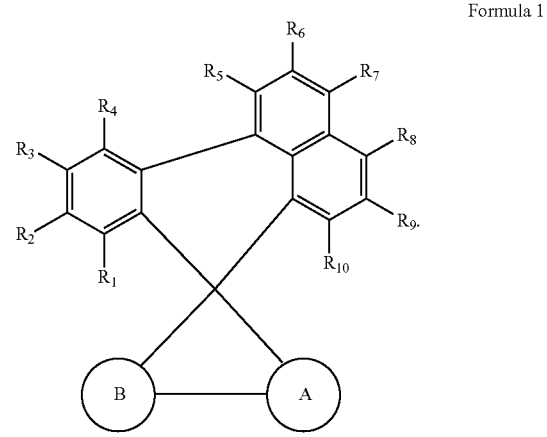

Formula 1

22 Claims, 6 Drawing Sheets

LUMINESCENCE DEVICE AND AMINE COMPOUND FOR ORGANIC ELECTROLUMINESCENCE DEVICE

CROSS-REFERENCE TO RELATED APPLICATION

This application claims priority to and the benefit of Korean Patent Application No. 10-2020-0136728, filed on Oct. 21, 2020, the entire content of which is hereby incorporated by reference.

BACKGROUND

One or more aspects of embodiments of the present disclosure herein relate to a luminescence device and an amine compound for an organic electroluminescence device.

Recently, the development of an organic electroluminescence display as an image display is being actively conducted. Unlike liquid crystal display apparatuses and/or the like, the organic electroluminescence display is a self-luminescent display apparatus in which holes and electrons injected from a first electrode and a second electrode recombine in an emission layer, and thus a luminescent material including an organic compound in the emission layer emits light to implement display of images.

In the application of an organic electroluminescence device to a display apparatus, there is a demand or desire for an organic electroluminescence device having a low driving voltage, high luminous efficiency, and a long service life (lifespan), and the development of materials for an organic electroluminescence device capable of stably (or suitably) attaining such characteristics is being continuously conducted.

SUMMARY

One or more aspects of embodiments of the present disclosure are directed toward a luminescence device and an amine compound for an organic electroluminescence device, and more particularly, toward a luminescence device having high efficiency and an amine compound included in a hole transport region of the luminescence device.

One or more embodiments of the present disclosure provide an amine compound represented by Formula 1 below:

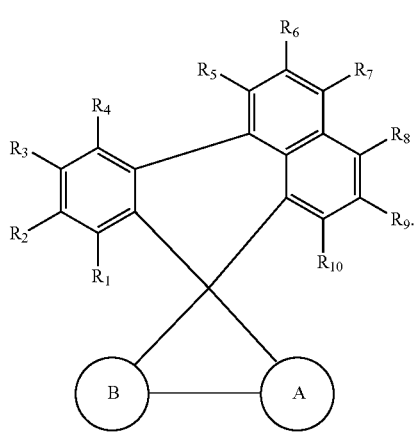

Formula 1

In Formula 1 above, $R_1$ to $R_{10}$ may each independently be a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, at least one among $R_1$ to $R_{10}$ is represented by Formula 2 below, and ring A and ring B may each independently be represented by Formula 3 or Formula 4 below, but are represented by different formulae.

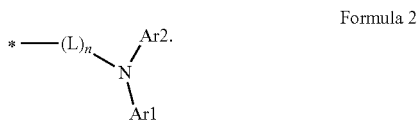

Formula 2

In Formula 2 above, L may be a direct linkage (e.g., a chemical bond such as a single bond), a substituted or unsubstituted arylene group having 6 to 30 ring-forming carbon atoms, or a substituted or unsubstituted heteroarylene group having 2 to 30 ring-forming carbon atoms; n may be an integer of 0 to 3, and Ar1 and Ar2 may each independently be a substituted or unsubstituted aryl group having 6 to 30 ring-forming carbon atoms, or a substituted or unsubstituted heteroarylene group having 2 to 30 ring-forming carbon atoms.

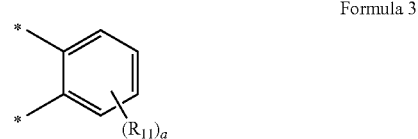

Formula 3

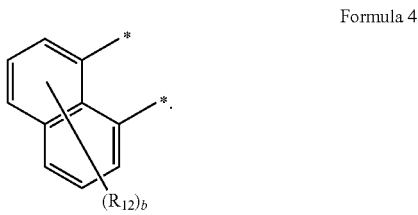

Formula 4

In Formula 3 and Formula 4 above, $R_{11}$ and $R_{12}$ may each independently be a hydrogen atom, a deuterium atom, a halogen atom, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms; a may be an integer of 0 to 4; and b may be an integer of 0 to 6.

In one or more embodiments, Formula 1 above may be represented by Formula 5 or Formula 6 below:

Formula 5

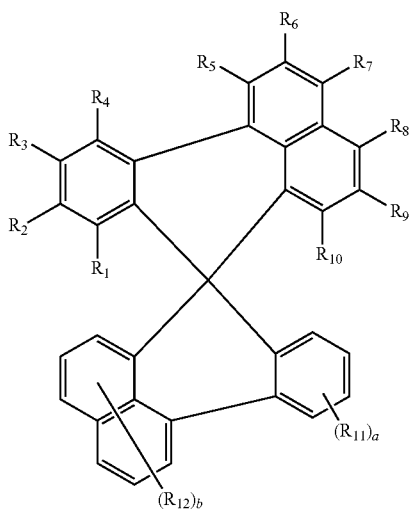

Formula 6

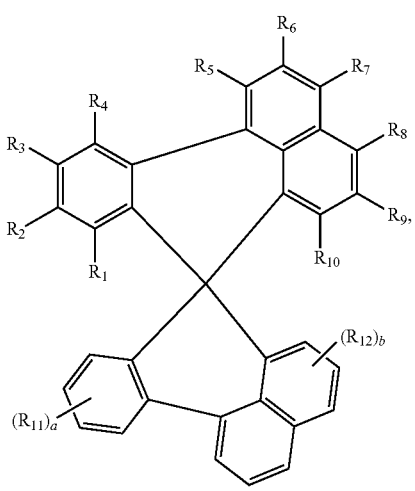

wherein, in Formula 5 and Formula 6 above,

R₁ to R₁₂, a, and b are the same as defined in Formula 1, Formula 3, and Formula 4.

In one or more embodiments, the amine compound may be a monoamine compound.

In one or more embodiments, Formula 5 above may be represented by Formula 7-1 below:

Formula 7-1

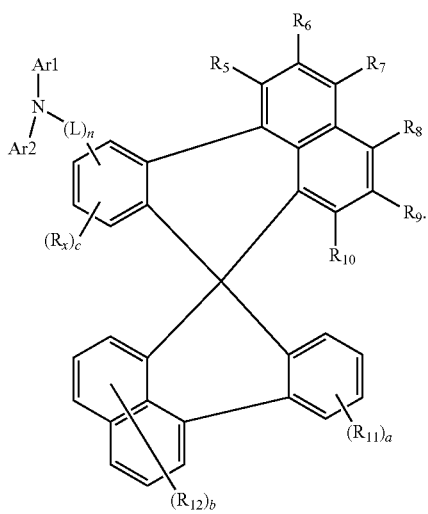

In Formula 7-1 above, Rx, and $R_5$ to $R_{10}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms; c may be an integer of 0 to 3; L may be a direct linkage, a substituted or unsubstituted arylene group having 6 to 30 ring-forming carbon atoms, or a substituted or unsubstituted heteroarylene group having 2 to 30 ring-forming carbon atoms; n may be an integer of 0 to 3; Ar1 and Ar2 may each independently be a substituted or unsubstituted aryl group having 6 to 30 ring-forming carbon atoms, or a substituted or unsubstituted heteroaryl group having 2 to 30 ring-forming carbon atoms; and $R_{11}$, $R_{12}$, a, and b are the same as defined in Formula 5.

In one or more embodiments, Formula 5 above may be represented by Formula 7-2 or Formula 7-3 below:

Formula 7-2

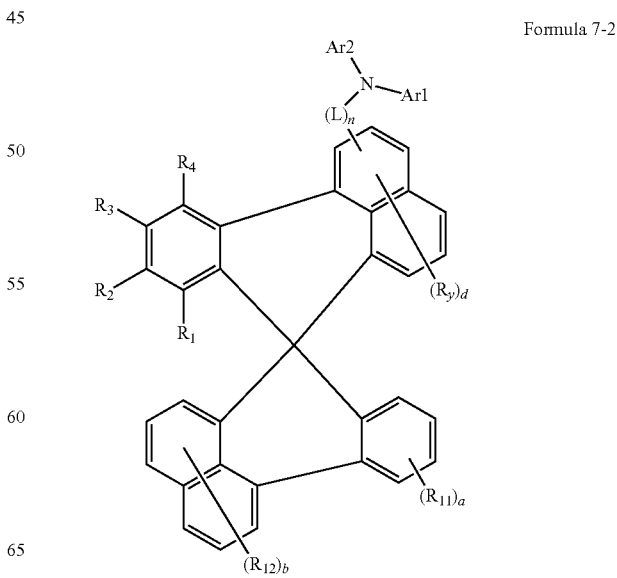

-continued

Formula 7-3

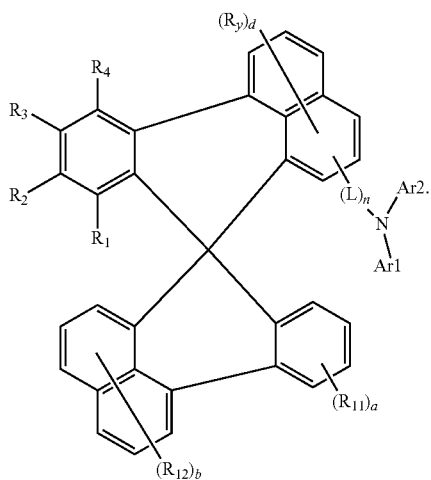

Formula 8-2

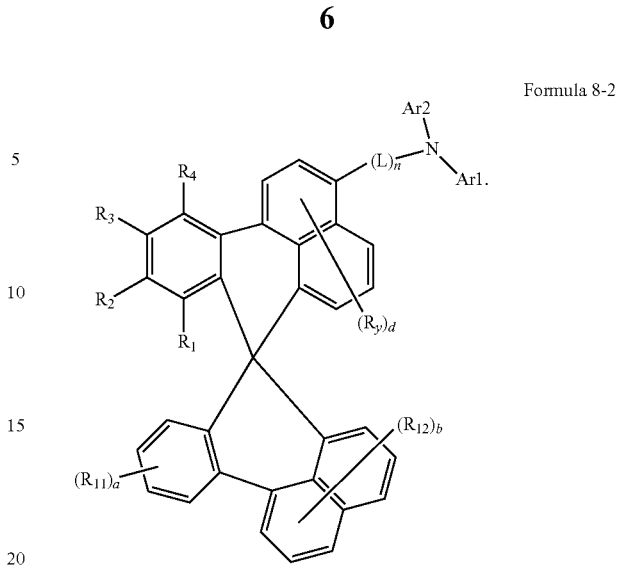

In Formula 7-2 and Formula 7-3 above, Ry, and $R_1$ to $R_4$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms; d may be an integer of 0 to 3; L may be a direct linkage, a substituted or unsubstituted arylene group having 6 to 30 ring-forming carbon atoms, or a substituted or unsubstituted heteroarylene group having 2 to 30 ring-forming carbon atoms; n may be an integer of 0 to 3; Ar1 and Ar2 may each independently be a substituted or unsubstituted aryl group having 6 to 30 ring-forming carbon atoms, or a substituted or unsubstituted heteroaryl group having 2 to 30 ring-forming carbon atoms; and $R_{11}$, $R_{12}$, a, and b are the same as defined in Formula 5.

In one or more embodiments, Formula 7-1 above may be represented by Formula 8-1 below:

Formula 8-1

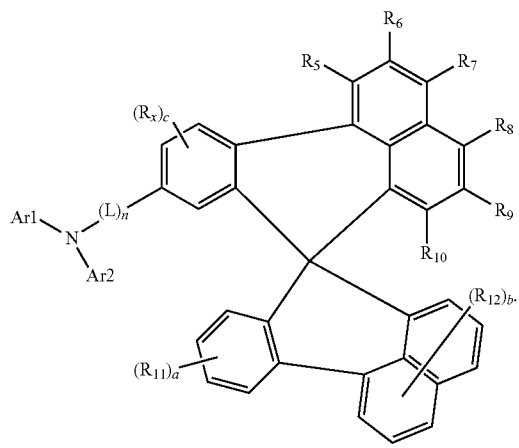

In Formula 8-1 above, Rx, $R_5$ to $R_{12}$, L, Ar1, Ar2, a to c, and n are the same as defined in Formula 7-1.

In one or more embodiments, Formula 7-2 above may be represented by Formula 8-2 below:

In Formula 8-2 above, Ry, $R_1$ to $R_{12}$, L, Ar1, Ar2, a, b, d, and n are the same as defined in Formula 7-2.

In one or more embodiments, Formula 6 above may be represented by Formula 9-1 below:

Formula 9-1

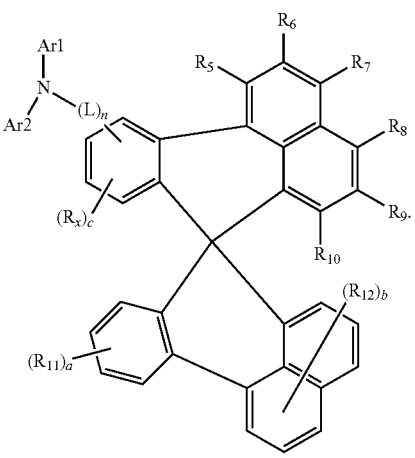

In Formula 9-1 above, Rx, and $R_5$ to $R_{10}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms; c may be an integer of 0 to 3; L may be a direct linkage, a substituted or unsubstituted arylene group having 6 to 30 ring-forming carbon atoms, or a substituted or unsubstituted heteroarylene group having 2 to 30 ring-forming carbon atoms; n may be an integer of 0 to 3; Ar1 and Ar2 may each independently be a substituted or unsubstituted aryl group having 6 to 30 ring-forming carbon atoms, or a substituted or unsubstituted heteroaryl group having 2 to 30 ring-forming carbon atoms; and $R_{11}$, $R_{12}$, a, and b are the same as defined in Formula 6.

In one or more embodiments, Formula 6 above may be represented by Formula 9-2 or Formula 9-3 below:

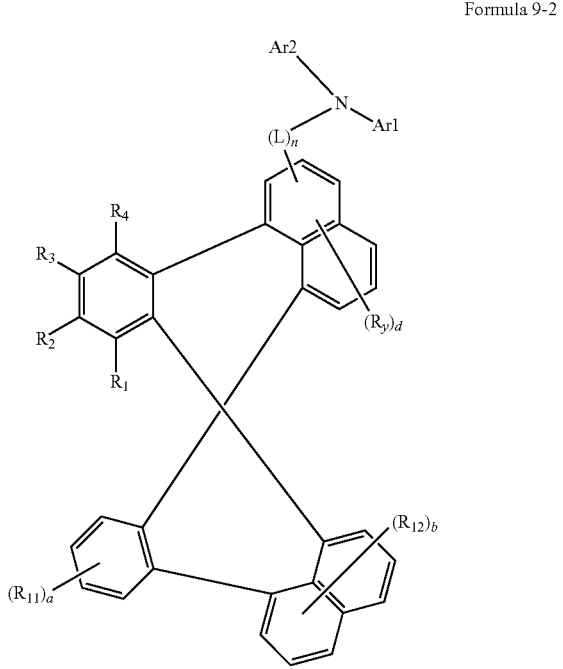

Formula 9-2

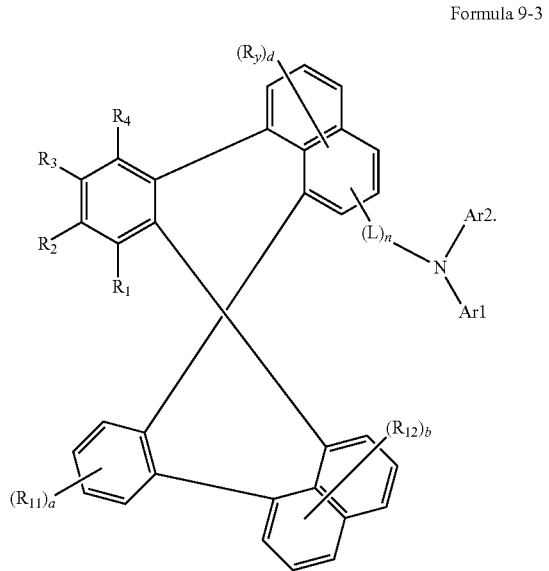

Formula 9-3

In Formula 9-2 and Formula 9-3 above, Ry, and $R_1$ to $R_4$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms; d may be an integer of 0 to 5; L may be a direct linkage, a substituted or unsubstituted arylene group having 6 to 30 ring-forming carbon atoms, or a substituted or unsubstituted heteroarylene group having 2 to 30 ring-forming carbon atoms; n may be an integer of 0 to 3; Ar1 and Ar2 may each independently be a substituted or unsubstituted aryl group having 6 to 30 ring-forming carbon atoms, or a substituted or unsubstituted heteroaryl group having 2 to 30 ring-forming carbon atoms; and $R_{11}$, $R_{12}$, a, and b are the same as defined in Formula 6.

In one or more embodiments, Formula 9-1 above may be represented by Formula 10-1 below:

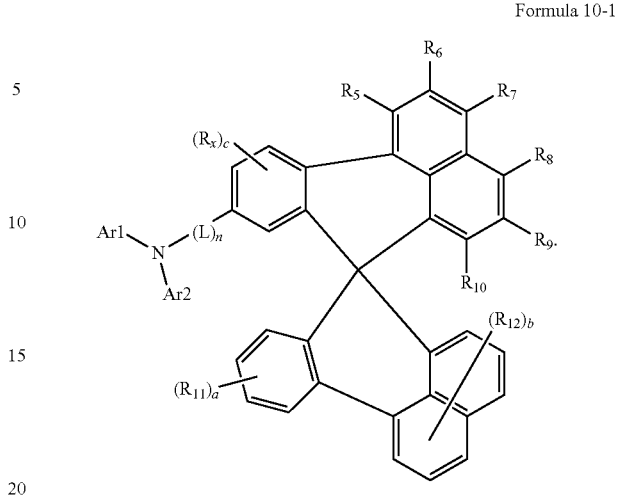

Formula 10-1

In Formula 10-1 above, Rx, $R_5$ to $R_{12}$, L, Ar1, Ar2, a to c, and n are the same as defined in Formula 9-1.

In one or more embodiments, Formula 9-2 above may be represented by Formula 10-2 below:

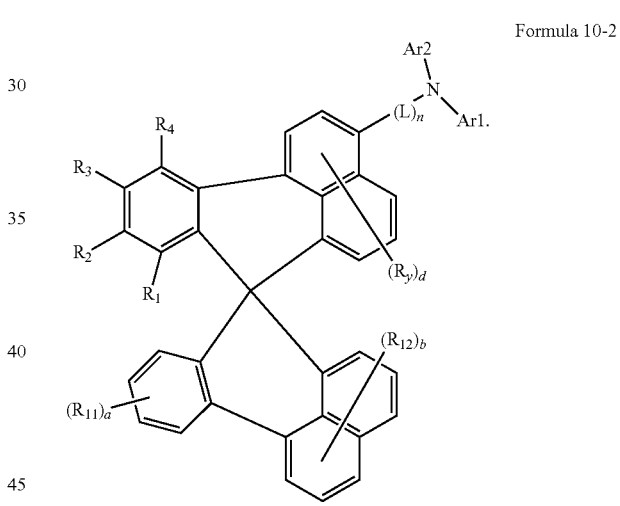

Formula 10-2

In Formula 10-2 above, Ry, $R_1$ to $R_{12}$, L, Ar1, Ar2, a, b, d, and n are the same as defined in Formula 9-2.

In an amine compound of one or more embodiments, n may be 1, and L may be a direct linkage.

In one or more embodiments, the amine compound represented by Formula 1 may be at least one selected from among the compounds represented in Compound Group 1 hereinbelow.

In one or more embodiments of the present disclosure, a luminescence device includes a first electrode, a hole transport region disposed (e.g., positioned) on the first electrode, an emission layer disposed on the hole transport region, an electron transport region disposed on the emission layer, and a second electrode disposed on the electron transport region, wherein the hole transport region includes the amine compound according to one or more embodiments.

In one or more embodiments, the hole transport region may include a hole injection layer disposed on the first electrode, and a hole transport layer disposed on the hole injection layer, and the hole transport layer or the hole injection layer may include the amine compound according to one or more embodiments.

In one or more embodiments, the hole transport region may include an electron blocking layer disposed on the hole transport layer.

BRIEF DESCRIPTION OF THE FIGURES

The accompanying drawings are included to provide a further understanding of the present disclosure, and are incorporated in and constitute a part of this specification. The drawings illustrate embodiments of the present disclosure and, together with the description, serve to explain principles of the present disclosure. In the drawings.

DETAILED DESCRIPTION

Figure 1:
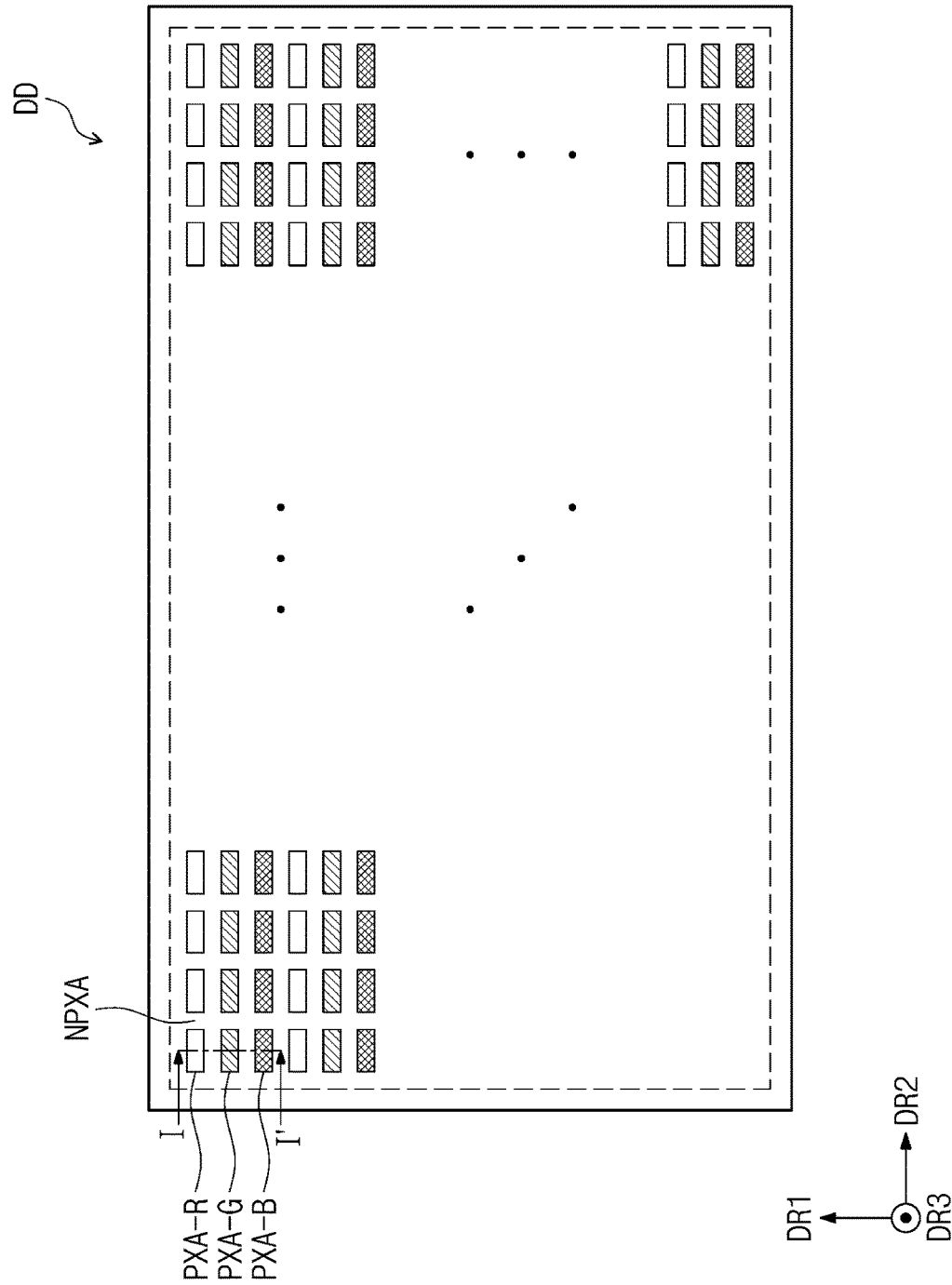
FIG. 1 is a plan view of a display apparatus according to one or more embodiments of the present disclosure.

The present disclosure may be modified in many alternate forms, and thus specific embodiments will be provided as examples in the drawings and described in more detail. It should be understood, however, that this description is not intended to limit the present disclosure to the particular forms disclosed, but rather, is intended to cover all modifications, equivalents, and alternatives falling within the spirit and scope of the present disclosure.

When explaining each of the drawings, like reference numbers are used for referring to like elements. In the accompanying drawings, the dimensions of each structure are exaggeratingly illustrated for clarity of the present disclosure. It will be understood that, although the terms "first," "second," etc. may be used herein to describe various elements, these elements should not be limited by these terms. These terms are only used to distinguish one element from another. For example, a first element may be referred to as a second element, and, similarly, the second element may be referred to as the first element, without departing from the scope of the present disclosure. The terms of a singular form may include plural forms unless the context clearly indicates otherwise.

In the present application, it will be understood that the terms "comprise" or "have" specify the presence of a feature, a fixed number, a step, a process, an element, a component, or a combination thereof disclosed in the specification, but do not exclude the possibility of presence or addition of one or more other features, fixed numbers, steps, processes, elements, components, or combination thereof.

In the present application, when a layer, a film, a region, or a plate is referred to as being "above" or "in an upper portion of" another layer, film, region, or plate, it can be not only directly on the layer, film, region, or plate (without any intervening elements therebetween), but one or more intervening layers, films, regions, or plates may also be present. Similarly, when a layer, a film, a region, or a plate is referred to as being "below," "in a lower portion of" another layer, film, region, or plate, it can be not only directly under the layer, film, region, or plate (without any intervening elements therebetween), but one or more intervening layers, films, regions, or plates may also be present. In addition, it will be understood that when a layer, a film, a region, or a plate is referred to as being "on" another layer, film, region, or plate, it can be not only disposed (e.g., positioned) on the layer, film, region, or plate, but also disposed under the layer, film, region, or plate.

As used herein, the terms "use," "using," and "used" may be considered synonymous with the terms "utilize," "utilizing," and "utilized," respectively.

As used herein, expressions such as "at least one of", "one of", and "selected from", when preceding a list of elements, modify the entire list of elements and do not modify the individual elements of the list.

As used herein, the term "and/or" includes any and all combinations of one or more of the associated listed items. Further, the use of "may" when describing embodiments of the present disclosure refers to "one or more embodiments of the present disclosure".

As used herein, the terms "substantially", "about", and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Hereinafter, embodiments of the present disclosure will be described with reference to the accompanying drawings.

Figure 2:
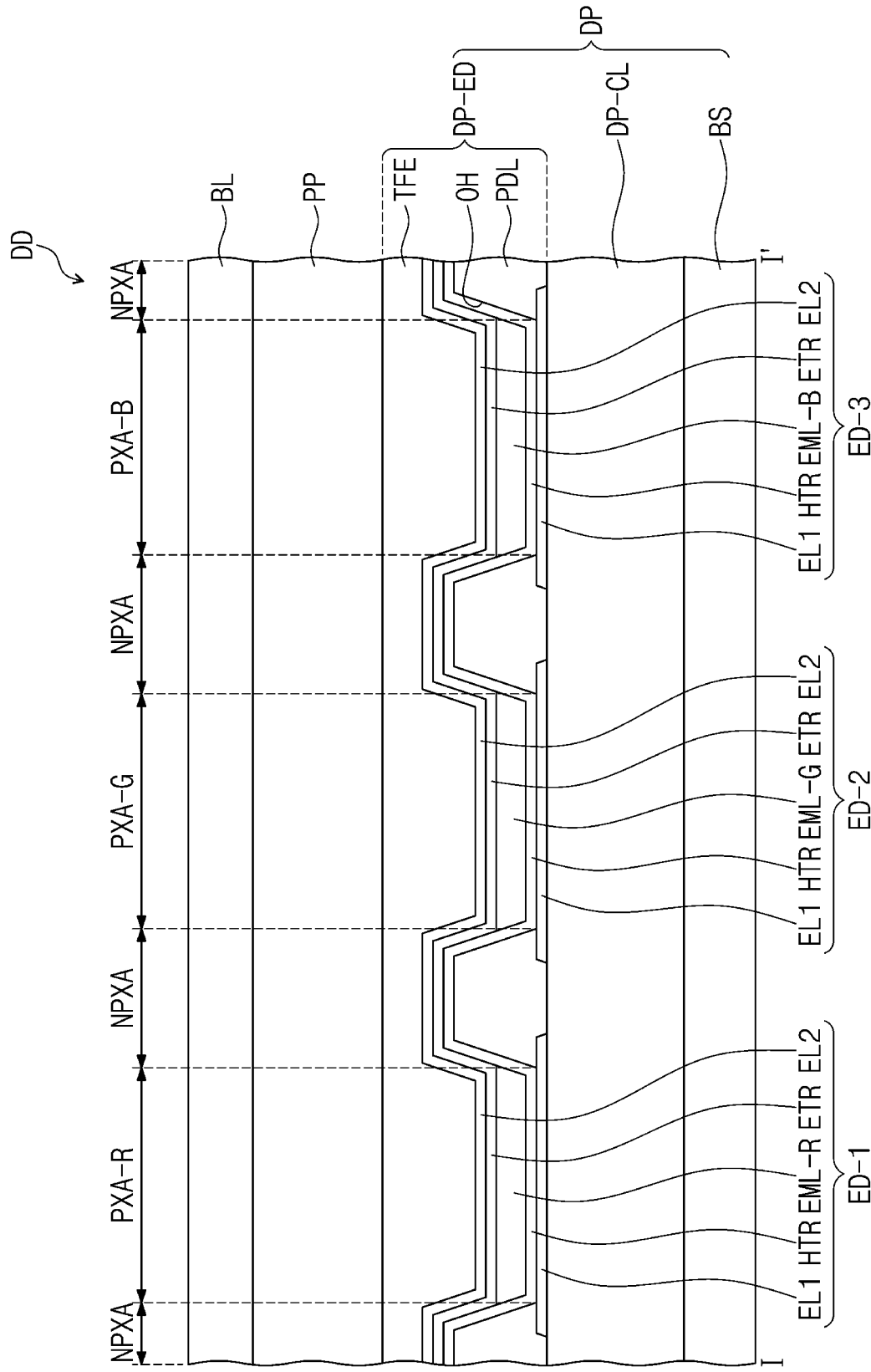
FIG. 2 is a cross-sectional view of a display apparatus according to one or more embodiments of the present disclosure.

FIG. 1 is a plan view illustrating one or more embodiments of a display apparatus DD. FIG. 2 is a cross-sectional view of the display apparatus DD of the embodiment. FIG. 2 is a cross-sectional view illustrating a part taken along line I-I' of FIG. 1.

The display apparatus DD may include a display panel DP and an optical layer PP disposed on the display panel DP. The display panel DP includes luminescence devices ED-1, ED-2, and ED-3. The display apparatus DD may include a plurality of luminescence devices ED-1, ED-2, and ED-3. The optical layer PP may be disposed on the display panel DP and control reflected light in the display panel DP due to external light. The optical layer PP may include, for example, a polarization layer or a color filter layer. In one or more embodiments, the optical layer PP may be omitted from the display apparatus DD of one or more embodiments.

The display panel DP may include a base layer BS, a circuit layer DP-CL provided on the base layer BS, and a display device layer DP-ED. The display device layer DP-ED may include a pixel defining film PDL, the luminescence devices ED-1, ED-2, and ED-3 disposed between portions of the pixel defining film PDL, and an encapsulation layer TFE disposed on the luminescence devices ED-1, ED-2, and ED-3.

The base layer BS may be a member which provides a base surface on which the display device layer DP-ED is disposed. The base layer BS may be a glass substrate, a metal substrate, and/or a plastic substrate, etc. However, the embodiments of the present disclosure are not limited thereto, and the base layer BS may be an inorganic layer, an organic layer, or a composite material layer (e.g., including an inorganic material and an organic material).

In one or more embodiments, the circuit layer DP-CL is disposed on the base layer BS, and the circuit layer DP-CL may include a plurality of transistors. Each of the transistors may include a control electrode, an input electrode, and an output electrode. For example, the circuit layer DP-CL may include a switching transistor and a driving transistor in order to drive the luminescence devices ED-1, ED-2, and ED-3 of the display device layer DP-ED.

Each of the luminescence devices ED-1, ED-2, and ED-3 may have a structure of a luminescence device ED of one or more embodiments according to FIGS. 3 to 6, which will be described below. Each of the luminescence devices ED-1, ED-2 and ED-3 may include a first electrode EL1, a hole transport region HTR, emission layers EML-R, EML-G and EML-B, an electron transport region ETR, and a second electrode EL2.

FIG. 2 illustrates one or more embodiments in which the emission layers EML-R, EML-G, and EML-B of the luminescence devices ED-1, ED-2, and ED-3 are positioned in the respective openings OH defined in the pixel defining film PDL, and the hole transport region HTR, the electron transport region ETR, and the second electrode EL2 are provided as a common layer in all of the luminescence devices ED-1, ED-2, and ED-3. However, the embodiments of the present disclosure are not limited thereto, and in one or more embodiments, the hole transport region HTR and the electron transport region ETR may be provided by being patterned inside the opening hole OH defined in the pixel defining film PDL. For example, the hole transport region HTR, the emission layers EML-R, EML-G, and EML-B, and the electron transport region ETR in one or more embodiments may be provided by being patterned in an inkjet printing method.

The encapsulation layer TFE may cover the luminescence devices ED-1, ED-2 and ED-3. The encapsulation layer TFE may seal the display device layer DP-ED (e.g., may have the sealing function in the display device layer DP-ED). The encapsulation layer TFE may be a thin film encapsulation layer. The encapsulation layer TFE may be formed by laminating one layer or a plurality of layers. The encapsulation layer TFE includes at least one insulation layer. The encapsulation layer TFE according to one or more embodiments may include at least one inorganic film (hereinafter, an encapsulation-inorganic film). The encapsulation layer TFE according to one or more embodiments may include at least one organic film (hereinafter, an encapsulation-organic film) and at least one encapsulation-inorganic film.

The encapsulation-inorganic film protects the display device layer DP-ED from moisture/oxygen, and the encapsulation-organic film protects the display device layer DP-ED from foreign substances such as dust particles. The encapsulation-inorganic film may include silicon nitride, silicon oxynitride, silicon oxide, titanium oxide, aluminum oxide, and/or the like, but the embodiments of the present disclosure are not particularly limited thereto. The encapsulation-organic film may include an acrylic-based compound, an epoxy-based compound, and/or the like. The encapsulation-organic film may include a photopolymerizable organic material, but the embodiments of the present disclosure are not particularly limited thereto.

The encapsulation layer TFE may be disposed on the second electrode EL2 and may be disposed filling the opening hole OH.

Referring to FIGS. 1 and 2, the display apparatus DD may include a non-light emitting region NPXA and light emitting regions PXA-R, PXA-G and PXA-B. The light emitting regions PXA-R, PXA-G and PXA-B each may be a region which emits (or is to emit) light generated from the luminescence devices ED-1, ED-2 and ED-3, respectively. The light emitting regions PXA-R, PXA-G, and PXA-B may be spaced apart from each other on a plane (e.g., in a plan view).

Each of the light emitting regions PXA-R, PXA-G, and PXA-B may be a region divided by pixel defining film PDL. The non-light emitting regions NPXA may be regions between the adjacent light emitting regions PXA-R, PXA-G, and PXA-B, which correspond to portions of the pixel defining film PDL. In one or more embodiments, each of the light emitting regions PXA-R, PXA-G, and PXA-B may correspond to a pixel. The pixel defining film PDL may separate the luminescence devices ED-1, ED-2, and ED-3. The emission layers EML-R, EML-G and EML-B of the luminescence devices ED-1, ED-2 and ED-3 may be disposed in openings OH defined by the pixel defining film PDL and separated from each other.

The light emitting regions PXA-R, PXA-G and PXA-B may be divided into a plurality of groups according to the color of light generated (or to be generated) from the plurality of luminescence devices ED-1, ED-2 and ED-3. In the display apparatus DD of one or more embodiments shown in FIGS. 1 and 2, three light emitting regions PXA-R, PXA-G, and PXA-B which emit (or are to emit) red light, green light, and blue light, respectively are exemplarily illustrated. For example, the display apparatus DD of one or more embodiments may include the red light emitting region PXA-R, the green light emitting region PXA-G, and the blue light emitting region PXA-B, which are different.

In the display apparatus DD according to one or more embodiments, the plurality of luminescence devices ED-1, ED-2 and ED-3 may emit light in different wavelength regions. For example, in one or more embodiments, the display apparatus DD may include the first luminescence device ED-1 that emits (or is to emit) red light, the second luminescence device ED-2 that emits (or is to emit) green light, and the third luminescence device ED-3 that emits (or is to emit) blue light. For example, the red light emitting region PXA-R, the green light emitting region PXA-G, and the blue light emitting region PXA-B of the display apparatus DD may correspond to the first luminescence device ED-1, the second luminescence device ED-2, and the third luminescence device ED-3, respectively.

However, the embodiments of the present disclosure are not limited thereto, and the first to the third luminescence devices ED-1, ED-2, and ED-3 may emit light in the same wavelength range or at least one luminescence device may emit light in a wavelength range different from the others. For example, the first to third luminescence devices ED-1, ED-2, and ED-3 may all emit blue light.

The light emitting regions PXA-R, PXA-G, and PXA-B in the display apparatus DD according to one or more embodiments may be arranged in a stripe form. Referring to FIG. 1, the plurality of red light emitting regions PXA-R may be arranged with each other along a second directional axis DR2, the plurality of green light emitting regions PXA-G may be arranged with each other along the second directional axis DR2, and the plurality of blue light emitting regions PXA-B may be arranged with each other along the second directional axis DR2. In addition, a red light emitting region PXA-R, a green light emitting region PXA-G, and a blue light emitting region PXA-B may be alternately arranged in this order along a first directional axis DR1.

FIGS. 1 and 2 illustrate that all the light emitting regions PXA-R, PXA-G, and PXA-B have similar area, but the embodiments of the present disclosure are not limited thereto, and the light emitting regions PXA-R, PXA-G, and PXA-B may have different areas from each other according to a wavelength range of the emitted light. In this case, the areas of the light emitting regions PXA-R, PXA-G, and PXA-B may refer to areas thereof when viewed on a plane defined by the first directional axis DR1 and the second directional axis DR2 (e.g., in a plan view).

The arrangement form of the light emitting regions PXA-R, PXA-G, and PXA-B is not limited to the feature illustrated in FIG. 1, and the order in which the red light emitting region PXA-R, the green light emitting region PXA-G, and the blue light emitting region PXA-B are arranged may be variously suitably combined and provided according to characteristics of a display quality required in the display apparatus DD. For example, the arrangement form of the light emitting regions PXA-R, PXA-G, and PXA-B may be a PenTile®/PENTILE® arrangement form (PENTILE® is a registered trademark owned by Samsung Display Co., Ltd.) or a diamond arrangement form.

In one or more embodiments, the areas of the light emitting regions PXA-R, PXA-G, and PXA-B may be different from each other. For example, in one or more embodiments, the area of the green light emitting region PXA-G may be smaller than that of the blue light emitting region PXA-B, but the embodiments of the present disclosure are not limited thereto.

Hereinafter, FIGS. 3 to 6 are cross-sectional views schematically illustrating luminescence devices according to one or more embodiments. Each of the luminescence devices ED according to embodiments may include a first electrode EL1, a hole transport region HTR, an emission layer EML, an electron transport region ETR, and a second electrode EL2 that are sequentially stacked.

The luminescence device ED of one or more embodiments may include a monoamine compound of one or more embodiments, which will be described below, in the hole transport region HTR disposed between the first electrode EL1 and the second electrode EL2. However, the embodiments are not limited thereto, and the organic electroluminescence device 10 may include the monoamine compound not only in the hole transport region HTR but also in the emission layer EML and/or electron transport region ETR, which are/is among a plurality of functional layers disposed between the first electrode EL1 and the second electrode EL2, or in the capping layer CPL disposed on the second electrode EL2.

Figure 3:
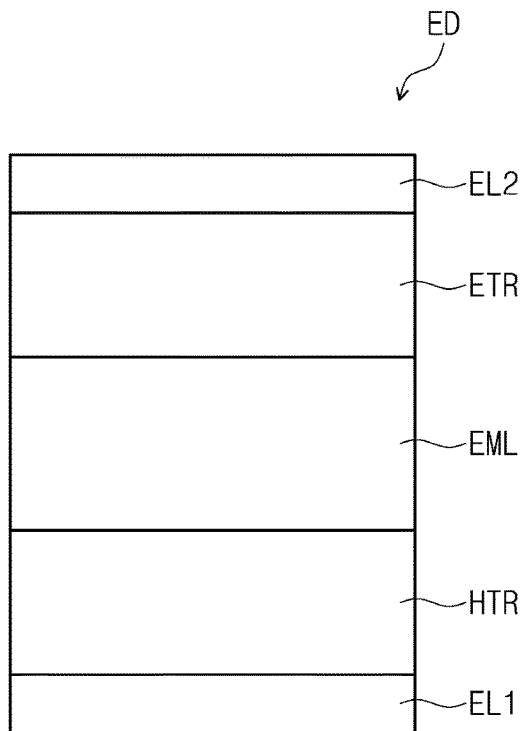
FIG. 3 is a cross-sectional view schematically illustrating a luminescence device according to one or more embodiments of the present disclosure.
Figure 4:
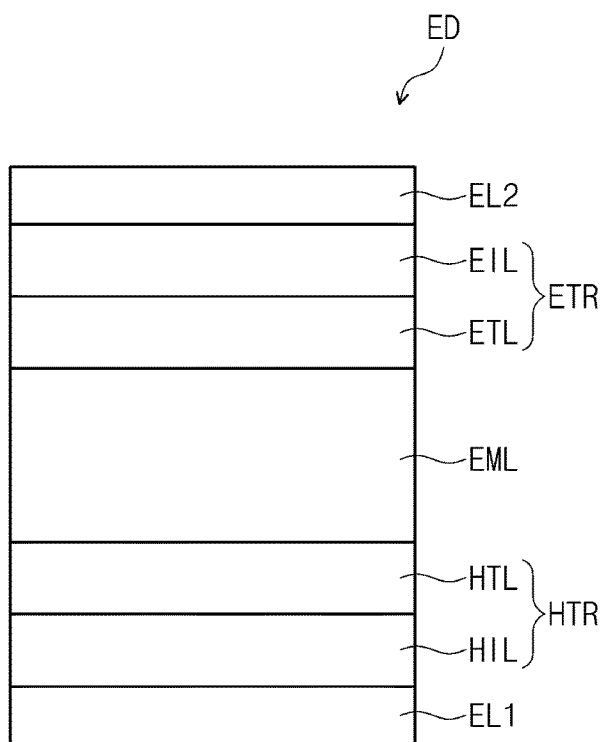
FIG. 4 is a cross-sectional view schematically illustrating a luminescence device according to one or more embodiments of the present disclosure.
Figure 5:
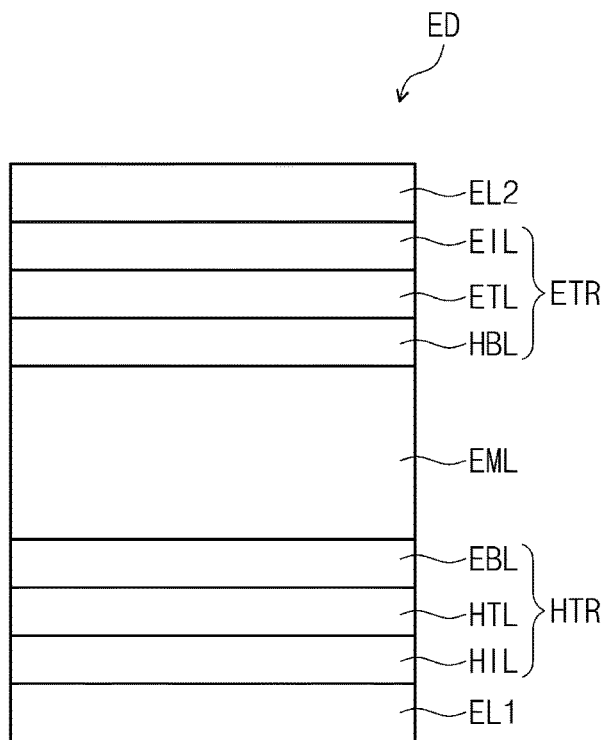
FIG. 5 is a cross-sectional view schematically illustrating a luminescence device according to one or more embodiments of the present disclosure.
Figure 6:
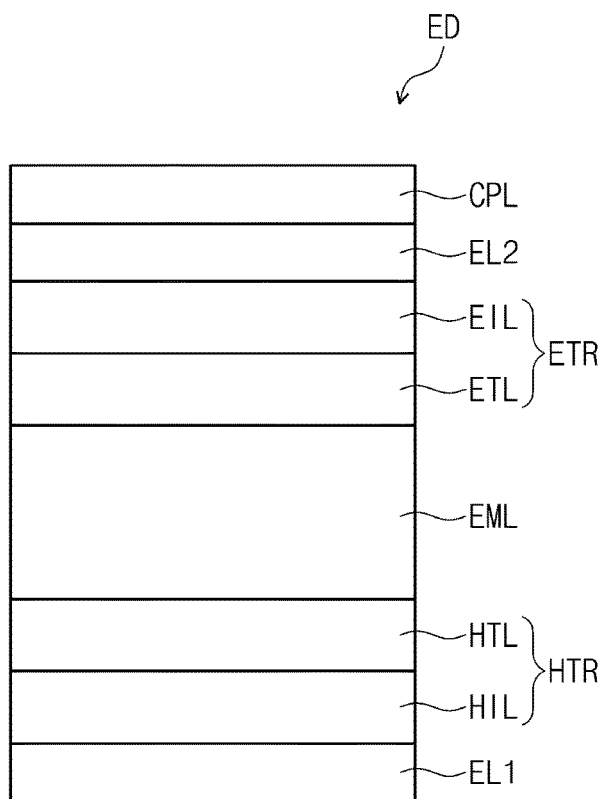
FIG. 6 is a cross-sectional view schematically illustrating a luminescence device according to one or more embodiments of the present disclosure.

Compared to FIG. 3, FIG. 4 illustrates a cross-sectional view of a luminescence device ED of one or more embodiments, in which a hole transport region HTR includes a hole injection layer HIL and a hole transport layer HTL, and an electron transport region ETR includes an electron injection layer EIL and an electron transport layer ETL. In one or more embodiments, compared to FIG. 3, FIG. 5 illustrates a cross-sectional view of a luminescence device ED of one or more embodiments, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared to FIG. 4, FIG. 6 illustrates a cross-sectional view of a luminescence device ED of one or more embodiments including a capping layer CPL disposed on a second electrode EL2.

The first electrode EL1 has conductivity. The first electrode EL1 may be formed of a metal alloy or any suitable conductive compound. The first electrode EL1 may be an anode or a cathode. However, the embodiments of the present disclosure are not limited thereto. In one or more embodiments, the first electrode EL1 may be a pixel electrode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and/or indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In one or more embodiments, the first electrode EL1 may have a multilayer structure including a reflective layer or a transflective layer formed of any of the above-described materials, and a transparent conductive layer formed of ITO, IZO, ZnO, ITZO, etc. For example, the first electrode EL1 may have a three-layer structure of ITO/Ag/ITO, but the embodiments of the present disclosure are not limited thereto. The thickness of the first electrode EL1 may be from about 700 Å to about 10,000 Å. For example, the thickness of the first electrode EL1 may be from about 1,000 Å to about 3,000 Å.

The hole transport region HTR is provided on the first electrode EL1. The hole transport region HTR may include at least one selected from the group consisting of a hole injection layer HIL, a hole transport layer HTL, a hole buffer layer, and an electron blocking layer EBL. The thickness of the hole transport region HTR may be, for example, from about 50 Å to about 15,000 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of the hole injection layer HIL or the hole transport layer HTL, or may have a single layer structure formed of a hole injection material and a hole transport material. In one or more embodiments, the hole transport region HTR may have a single layer structure formed of a plurality of different materials, or a structure in which a hole injection layer HIL/hole transport layer HTL, a hole injection layer HIL/hole transport layer HTL/hole buffer layer, a hole injection layer HIL/hole buffer layer, a hole transport layer HTL/hole buffer layer, or a hole injection layer HIL/hole transport layer HTL/electron blocking layer EBL are stacked in the stated order from the first electrode EL1, but the embodiments of the present disclosure are not limited thereto.

The hole transport region HTR in the luminescence device ED of one or more embodiments includes a monoamine compound according to one or more embodiments of the present disclosure.

As used herein, the term "substituted or unsubstituted" herein may refer to a functional group or a substituent that is unsubstituted or that is substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In one or more embodiments, each of the substituents exemplified above may itself be substituted or unsubstituted. For example, a biphenyl group may be interpreted as an aryl group or a phenyl group substituted with a phenyl group.

In the description, the term "bonded to an adjacent group to form a ring" may indicate that one (e.g., a functional group or a substituent) is bonded to an adjacent group to form a substituted or unsubstituted hydrocarbon ring, or a substituted or unsubstituted heterocycle. The hydrocarbon ring includes an aliphatic hydrocarbon ring and an aromatic hydrocarbon ring. The heterocycle includes an aliphatic heterocycle and an aromatic heterocycle. Rings formed by being bonded to an adjacent group may be monocyclic or polycyclic. In one or more embodiments, the rings formed by being bonded to each other may be connected to another ring to form a spiro structure.

In the description, the term "an adjacent group" may refer to a pair of substituent groups where the first substituent is connected to an atom which is directly connected to another atom substituted with the second substituent; a pair of substituent groups connected to the same atom; or a pair of substituent groups where the first substituent is sterically positioned at the nearest position to the second substituent. For example, two methyl groups in 1,2-dimethylbenzene may be interpreted as mutually "adjacent groups" and two ethyl groups in 1,1-diethylcyclopentane may be interpreted as mutually "adjacent groups".

In the specification, examples of the halogen atom may include a fluorine atom, a chlorine atom, a bromine atom, and/or an iodine atom.

In the specification, the alkyl group may be a linear, branched or cyclic alkyl group. The number of carbon atoms in the alkyl group may be 1 to 50, 1 to 30, 1 to 20, 1 to 10, or 1 to 6. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but the embodiments of the present disclosure are not limited thereto.

In the specification, an alkenyl group may refer to a hydrocarbon group including at least one carbon double bond in the middle and/or at the terminal of an alkyl group having 2 or more carbon atoms in its main hydrocarbon chain. The alkenyl group may be linear or branched. The carbon number is not specifically limited, but may be 2 to 30, 2 to 20 or 2 to 10. Examples of the alkenyl group include a vinyl group, a 1-butenyl group, a 1-pentenyl group, a 1,3-butadienyl aryl group, a styrenyl group, a styrylvinyl group, etc., without limitation.

In the specification, an alkynyl group may refer to a hydrocarbon group including at least one carbon triple bond in the middle and/or at the terminal of an alkyl group having 2 or more carbon atoms in its main hydrocarbon chain. The alkynyl group may be linear or branched. The carbon number is not specifically limited, but may be 2 to 30, 2 to 20 or 2 to 10. Examples of the alkynyl group include an ethynyl group, a propynyl group, etc., without limitation.

In the specification, a hydrocarbon ring group may be any functional group or substituent derived from an aliphatic hydrocarbon ring, or any functional group or substituent derived from an aromatic hydrocarbon ring. The number of ring-forming carbon atoms in the hydrocarbon ring group may be 5 to 60, 5 to 30, or 5 to 20.

The aryl group as used herein may refer to any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but the embodiment of the present disclosure is not limited thereto.

In the specification, the fluorenyl group may be substituted, and two substituents may be combined with each other to form a spiro structure. Examples of cases where the fluorenyl group is substituted are as follows. However, the embodiments of the present disclosure are not limited thereto:

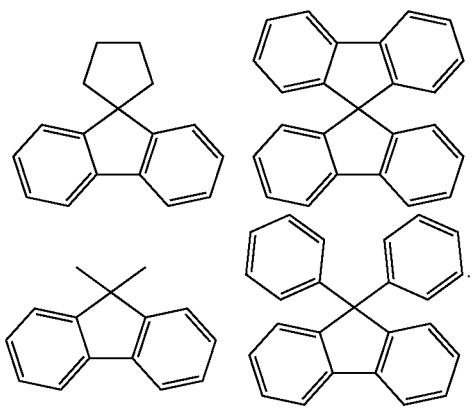

In the specification, a heterocyclic group may refer to any functional group or substituent derived from a ring containing at least one selected from the group consisting of B, O, N, P, Si, and S as a heteroatom. The heterocyclic group includes an aliphatic heterocyclic group and an aromatic heterocyclic group. The aromatic heterocyclic group may be a heteroaryl group. The aliphatic heterocycle (e.g., aliphatic heterocyclic group) and aromatic heterocycle (e.g., aromatic heterocyclic group) may each independently be monocyclic or polycyclic.

In the specification, the heterocyclic group may include at least one selected from the group consisting of B, O, N, P, Si and S as a heteroatom. If the heterocyclic group includes two or more heteroatoms, the two or more heteroatoms may be the same or different. The heterocyclic group may be a monocyclic heterocyclic group or a polycyclic heterocyclic group and has the concept including a heteroaryl group. The ring-forming carbon number (e.g., the number of ring-forming carbon atoms) of the heterocyclic group may be 2 to 30, 2 to 20, or 2 to 10.

In the specification, the aliphatic heterocyclic group may include at least one selected from the group consisting of B, O, N, P, Si, and S as a heteroatom. The number of ring-forming carbon atoms in the aliphatic heterocyclic group may be 2 to 30, 2 to 20, or 2 to 10. Examples of the aliphatic heterocyclic group include an oxirane group, a pyran group, a pyrrolidine group, a piperidine group, a tetrahydrofuran group, a tetrahydrothiophene group, a thiane group, a tetrahydropyran group, a 1,4-dioxane group, etc., but the embodiments of the present disclosure are not limited thereto.

In the specification, the heteroaryl group may include at least one selected from the group consisting of B, O, N, P, Si, and S as a heteroatom. When the heteroaryl group contains two or more hetero atoms, the two or more hetero atoms may be the same as or different from each other. The heteroaryl group may be a monocyclic heteroaryl group or polycyclic heteroaryl group. The number of ring-forming carbon atoms in the heteroaryl group may be 2 to 30, 2 to 20, or 2 to 10.

Examples of the heteroaryl group may include a thiophene group, a furan group, a pyrrole group, an imidazole group, a triazole group, a pyridine group, a bipyridine group, a pyrimidine group, a triazine group, a triazole group, an acridine group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazole group, a thiadiazole group, a phenothiazine group, a dibenzosilole group, a dibenzofuran group, etc., but the embodiments of the present disclosure are not limited thereto.

In the specification, the number of carbon atoms in an amine group is not specifically limited, but may be 1 to 30. The amine group may include an alkyl amine group, an aryl amine group and/or a heteroaryl amine group. Examples of the amine group include a methylamine group, a dimethylamine group, a phenylamine group, a diphenylamine group, a naphthylamine group, a 9-methyl-anthracenylamine group, etc., but the embodiments of the present disclosure are not limited thereto.

In the specification, the above description with respect to the aryl group is applied to an arylene group except that the arylene group is a divalent group.

In the specification, the above description with respect to the heteroaryl group is applied to a heteroarylene group except that the heteroarylene group is a divalent group.

In the specification, "-*" herein means a position to be connected (e.g., a bonding site).

The amine compound according to one or more embodiments of the present disclosure is represented by Formula 1 below:

Formula 1

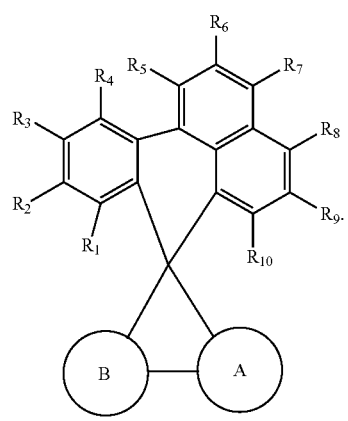

In Formula 1, $R_1$ to $R_{10}$ may each independently be a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, provided that at least one among $R_1$ to $R_{10}$ is represented by Formula 2 below.

In Formula 1, ring A and ring B may each independently be represented by Formula 3 or Formula 4 below, provided that ring A and ring B are represented by different formulae (e.g., have different chemical structures). For example, when ring A is represented by Formula 3 below, ring B may be represented by Formula 4 below. When ring A is represented by Formula 4 below, ring B may be represented by Formula 3 below.

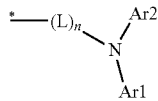

Formula 2

In Formula 2, L may be a direct linkage, a substituted or unsubstituted arylene group having 6 to 30 ring-forming carbon atoms, or a substituted or unsubstituted heteroarylene group having 2 to 30 ring-forming carbon atoms.

In Formula 2, n may be an integer of 0 to 3. When n is 2 or more, a plurality of L's may be the same as or different from each other.

In Formula 2, Ar1 and Ar2 may each independently be a substituted or unsubstituted aryl group having 6 to 30 ring-forming carbon atoms, or a substituted or unsubstituted heteroaryl group having 2 to 30 ring-forming carbon atoms.

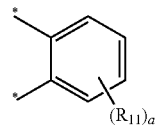

Formula 3

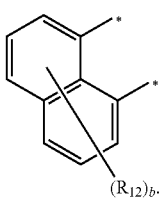

Formula 4

In Formula 3 and Formula 4, $R_{11}$ and $R_{12}$ may each independently be a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 3 and Formula 4, a may be an integer of 0 to 4, and b may be an integer of 0 to 6. When a is 2 or more, a plurality of $R_{11}$'s may be the same as or different from each other, and when b is 2 or more, a plurality of $R_{12}$'s may be the same as or different from each other.

In one or more embodiments, only one among $R_1$ to $R_{10}$ in Formula 1 may be represented by Formula 2. In one or more other embodiments, the amine compound represented by Formula 1 may not include an amine group other than the amine group represented by Formula 2 (e.g., may include the amine group represented by Formula 2 as the only amine group). For example, the amine compound represented by Formula 1 may be a monoamine compound.

In one or more embodiments, Formula 1 may be represented by Formula 5 or Formula 6 below:

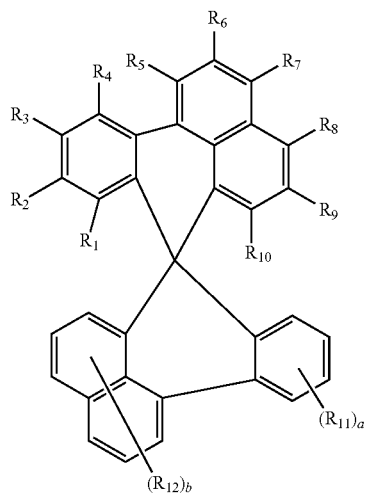

Formula 5

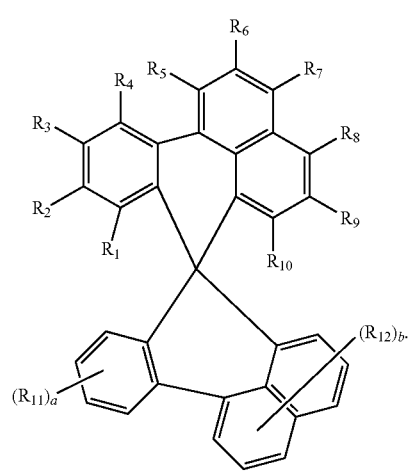

Formula 6

In Formula 5 and Formula 6, $R_1$ to $R_{12}$, a, and b are the same as defined in Formula 1, Formula 3, and Formula 4.

In one or more embodiments, Formula 5 may be represented by Formula 7-1 below:

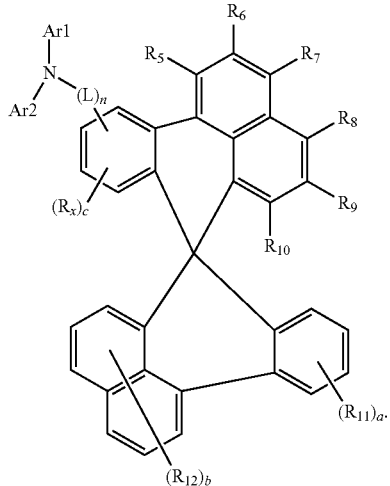

Formula 7-1

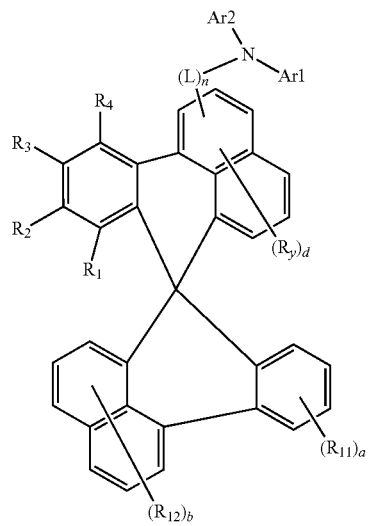

Formula 7-2

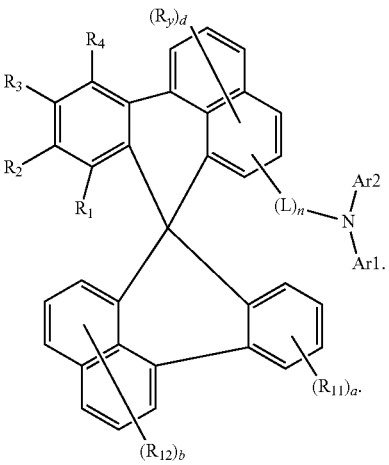

Formula 7-3

In Formula 7-1, Rx, and $R_5$ to $R_{10}$ may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 7-1, c may be an integer of 0 to 3, and when c is 2 or more, a plurality of Rx's are the same as or different from each other.

In Formula 7-1, L may be a direct linkage, a substituted or unsubstituted arylene group having 6 to 30 ring-forming carbon atoms, or a substituted or unsubstituted heteroarylene group having 2 to 30 ring-forming carbon atoms.

In Formula 7-1, n may be an integer of 0 to 2, and when n is 2 or more, a plurality of L's are the same as or different from each other.

In Formula 7-1, Ar1 and Ar2 may each independently be a substituted or unsubstituted aryl group having 6 to 30 ring-forming carbon atoms, or a substituted or unsubstituted heteroaryl group having 2 to 30 ring-forming carbon atoms.

In Formula 7-1, $R_{11}$, $R_{12}$, a and b are the same as defined in Formula 5.

In one or more embodiments, Formula 5 may be represented by Formula 7-2 or Formula 7-3 below:

In Formula 7-2 and Formula 7-3, Ry and $R_1$ to $R_4$ may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 7-2 and Formula 7-3, d may be an integer of 0 to 5, and when d is 2 or more, a plurality of Ry's are the same as or different from each other.

In Formula 7-2 and Formula 7-3, L may be a direct linkage, a substituted or unsubstituted arylene group having 6 to 30 ring-forming carbon atoms, or a substituted or unsubstituted heteroarylene group having 2 to 30 ring-forming carbon atoms.

In Formula 7-2 and Formula 7-3, n may be an integer of 0 to 3, and when n is 2 or more, a plurality of L's are the same as or different from each other.

In Formula 7-2 and Formula 7-3, Ar1 and Ar2 may be each independently a substituted or unsubstituted aryl group having 6 to 30 ring-forming carbon atoms, or a substituted or unsubstituted heteroaryl group having 2 to 30 ring-forming carbon atoms.

In Formula 7-2 and Formula 7-3, $R_{11}$, $R_{12}$, a and b are the same as defined in Formula 5.

In one or more embodiments, Formula 7-1 may be represented by Formula 8-1 below:

Formula 8-1

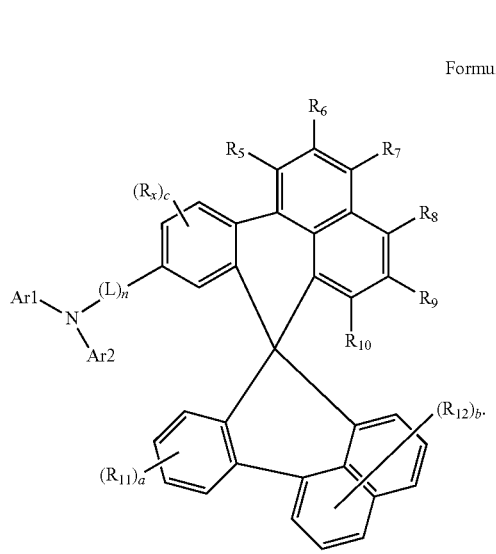

In Formula 8-1, Rx, $R_5$ to $R_{12}$, L, Ar1, Ar2, a to c, and n are the same as defined in Formula 7-1.

In one or more embodiments, Formula 7-2 may be represented by Formula 8-2 below:

Formula 8-2

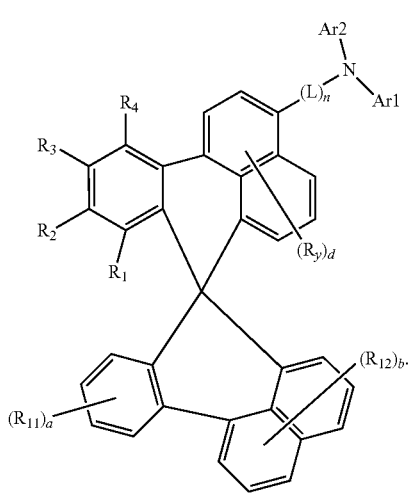

In Formula 8-2, Ry, $R_1$ to $R_4$, $R_{11}$, $R_{12}$, L, Ar1, Ar2, a, b, d, and n are the same as defined in Formula 7-2.

In one or more embodiments, Formula 6 may be represented by Formula 9-1 below:

Formula 9-1

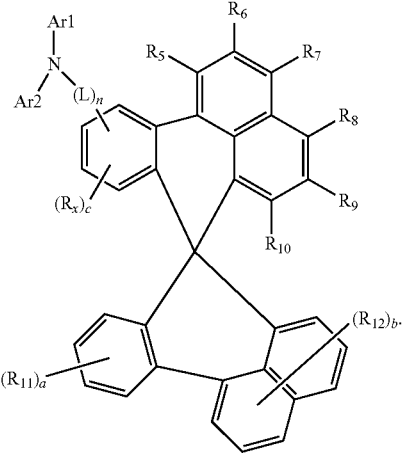

In Formula 9-1, Rx, and $R_5$ to $R_{10}$ may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 9-1, c may be an integer of 0 to 3, and when c is 2 or more, a plurality of Rx's are the same as or different from each other.

In Formula 9-1, L may be a direct linkage, a substituted or unsubstituted arylene group having 6 to 30 ring-forming carbon atoms, or a substituted or unsubstituted heteroarylene group having 2 to 30 ring-forming carbon atoms.

In Formula 9-1, n may be an integer of 0 to 2, and when n is 2 or greater, a plurality of L's are the same as or different from each other.

In Formula 9-1, Ar1 and Ar2 may each independently be a substituted or unsubstituted aryl group having 6 to 30 ring-forming carbon atoms, or a substituted or unsubstituted heteroaryl group having 2 to 30 ring-forming carbon atoms.

In Formula 9-1, $R_{11}$, $R_{12}$, a and b are the same as defined in Formula 6.

In one or more embodiments, Formula 6 may be represented by Formula 9-2 or Formula 9-3 below:

Formula 9-2

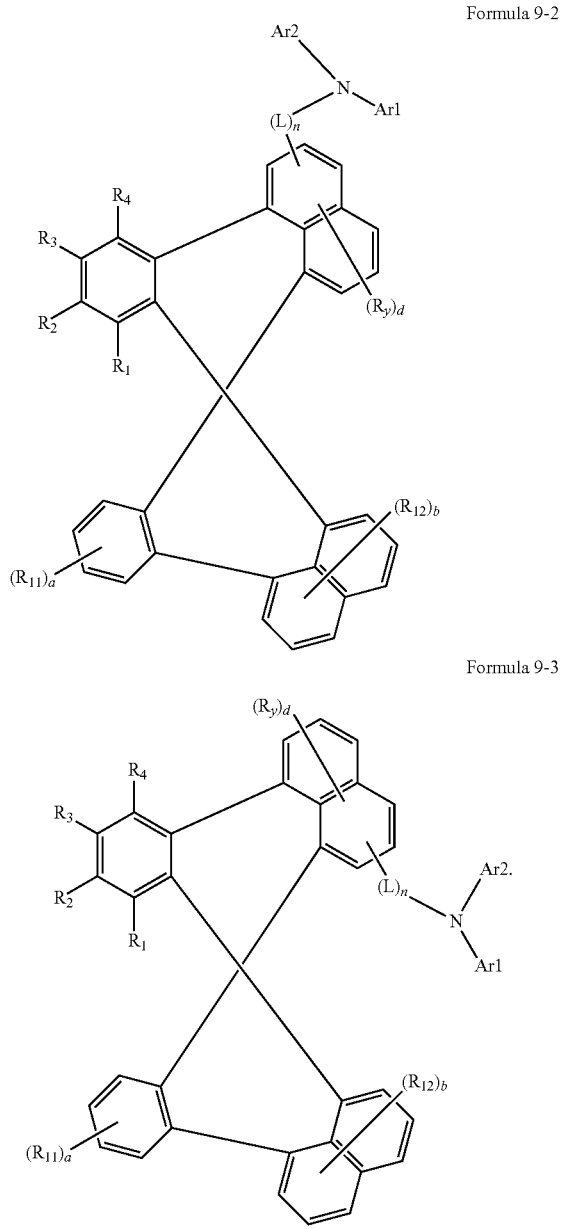

Formula 9-3

In Formula 9-2 and Formula 9-3, Ar1 and Ar2 may be each independently a substituted or unsubstituted aryl group having 6 to 30 ring-forming carbon atoms, or a substituted or unsubstituted heteroaryl group having 2 to 30 ring-forming carbon atoms.

In Formula 9-2 and Formula 9-3, $R_{11}$, $R_{12}$, a and b are the same as defined in Formula 6.

In one or more embodiments, Formula 9-1 may be represented by Formula 10-1 below:

Formula 10-1

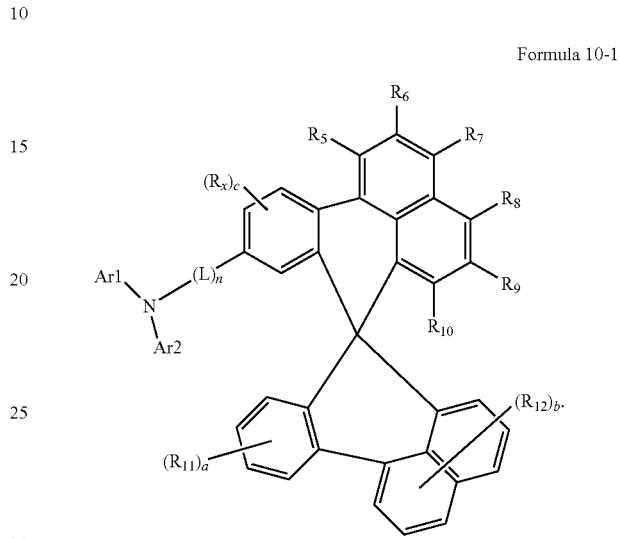

In Formula 10-1, Rx, $R_5$ to $R_{12}$, L, Ar1, Ar2, a to c, and n are the same as defined in Formula 9-1.

In one or more embodiments, Formula 9-2 may be represented by Formula 10-2 below:

Formula 10-2

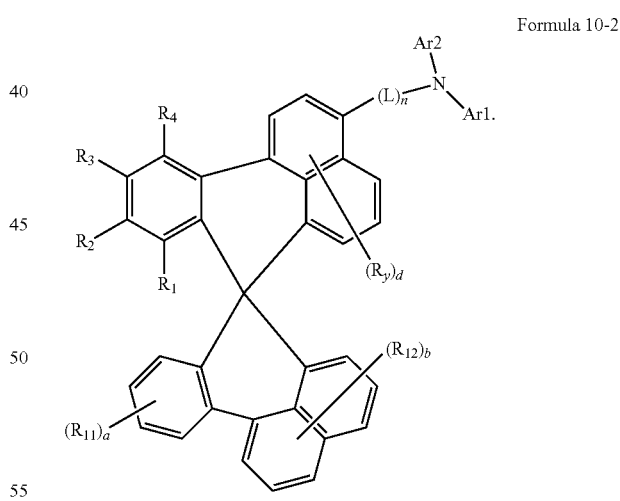

In Formula 10-2, Ry, $R_1$ to $R_4$, $R_{11}$, $R_{12}$, L, Ar1, Ar2, a, b, d, and n are the same as defined in Formula 9-2.

In one or more embodiments, in any one formula among Formula 1 to Formula 10-2, n may be 1, and L may be a direct linkage.

The amine compound represented by Formula 1 according to one or more embodiments of the present disclosure may be any one selected from among the compounds represented by Compound Group 1 below. However, the embodiments of the present disclosure are not limited thereto:

In Formula 9-2 and Formula 9-3, Ry and $R_1$ to $R_4$ may be each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula 9-2 and Formula 9-3, d may be an integer of 0 to 5, and when d is 2 or more, a plurality of Ry's are the same as or different from each other.

In Formula 9-2 and Formula 9-3, L may be a direct linkage, a substituted or unsubstituted arylene group having 6 to 30 ring-forming carbon atoms, or a substituted or unsubstituted heteroarylene group having 2 to 30 ring-forming carbon atoms.

In Formula 9-2 and Formula 9-3, n may be an integer of 0 to 3, and when n is 2 or more, a plurality of L's are the same as or different from each other.

Compound Group 1
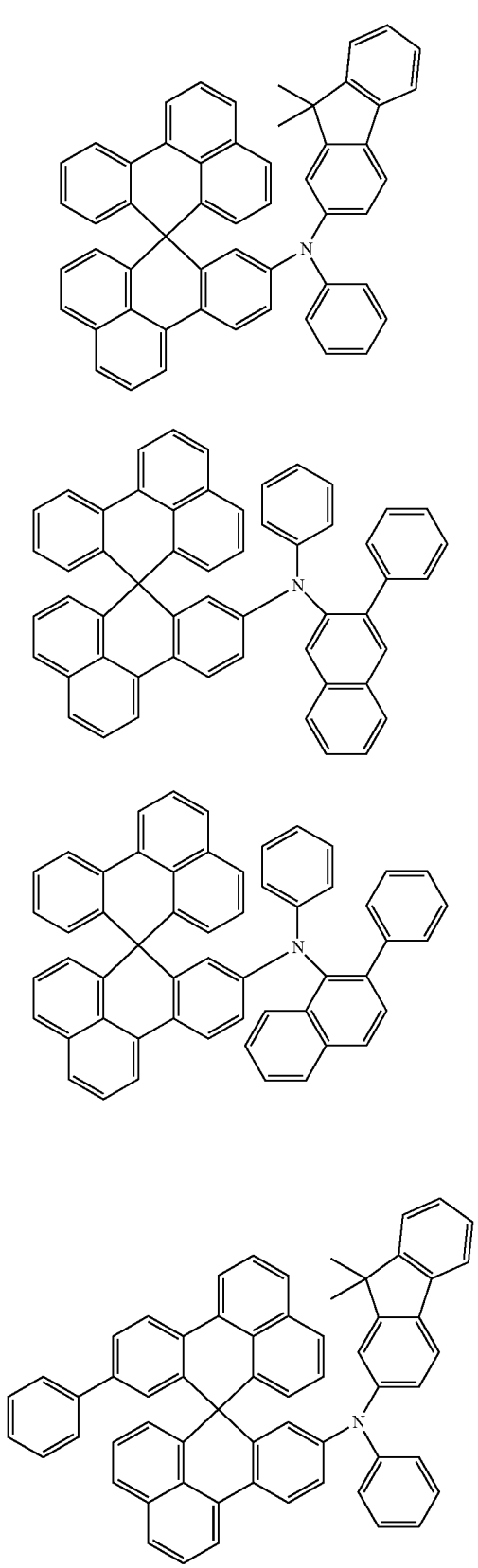
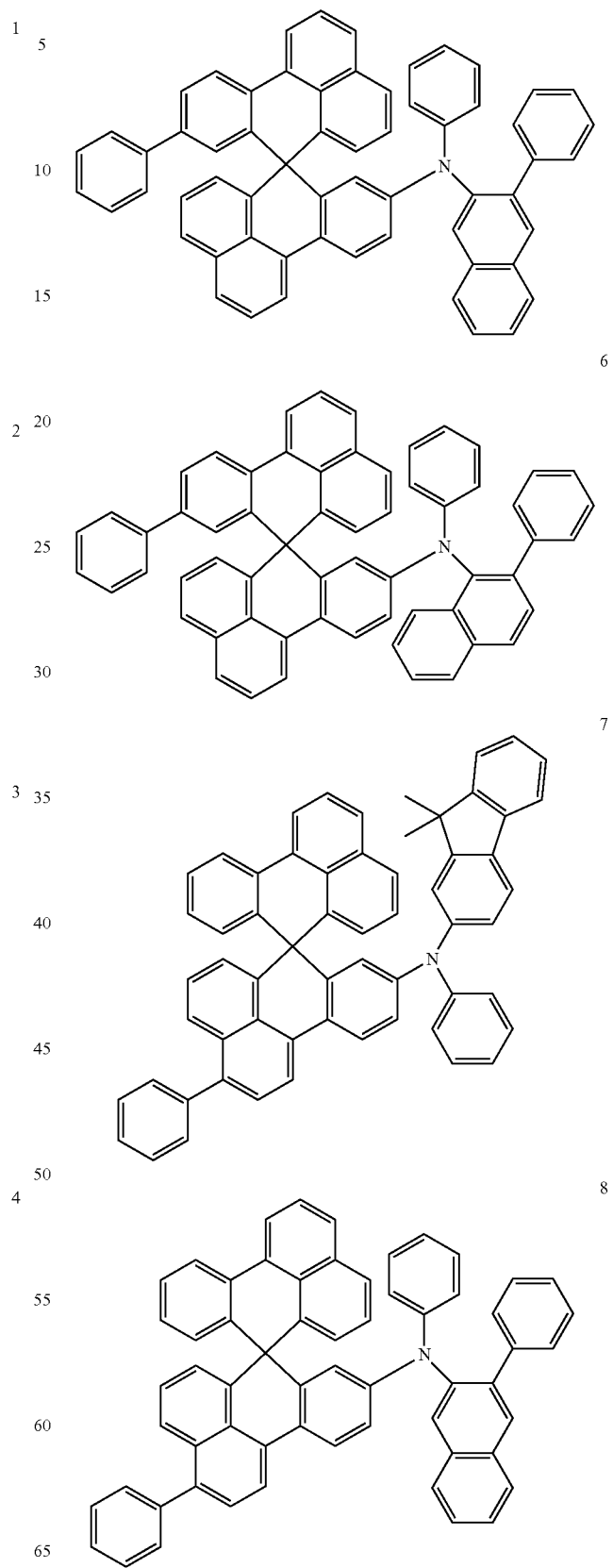

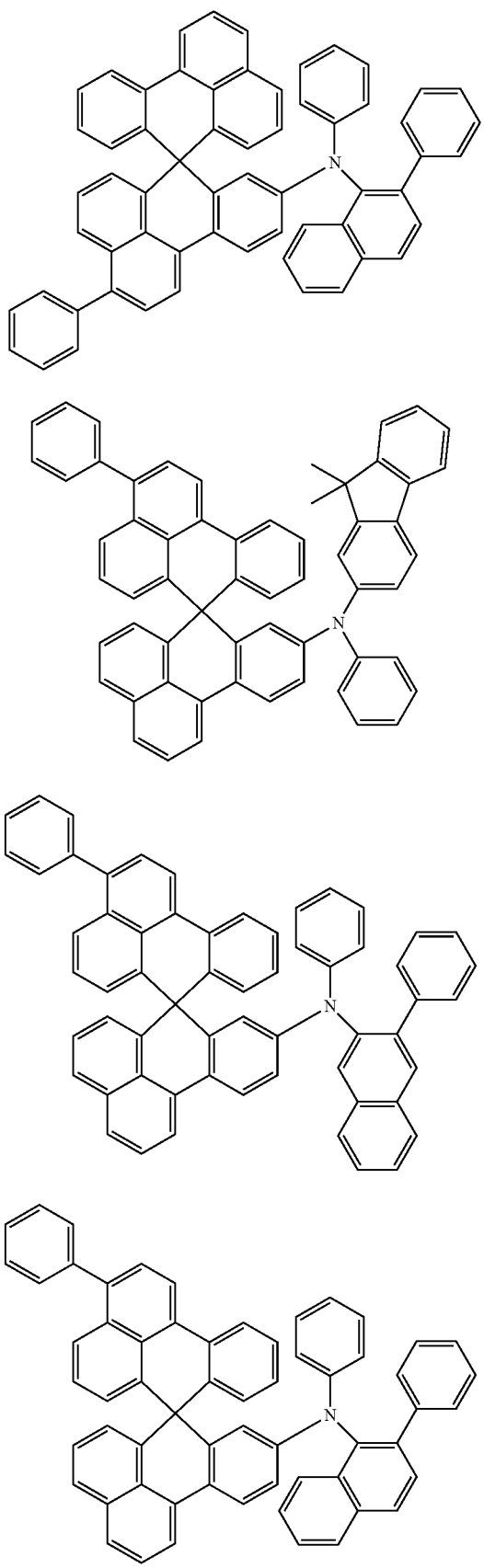
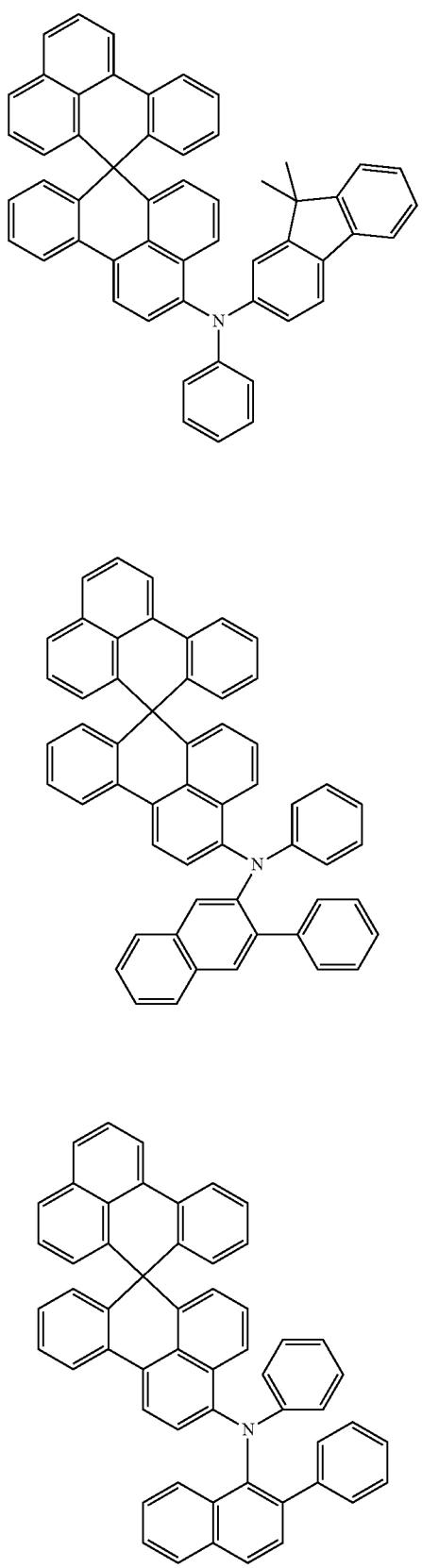

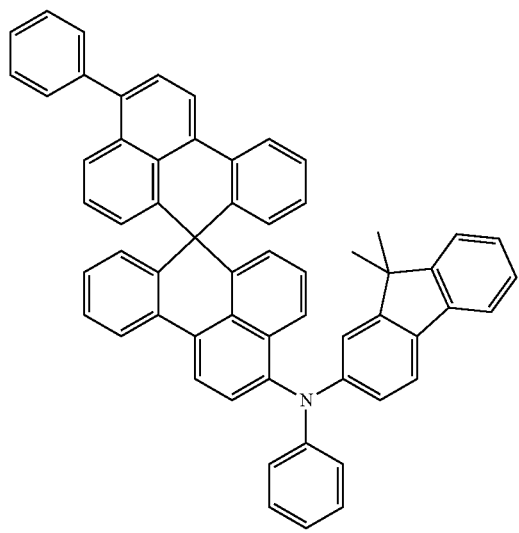
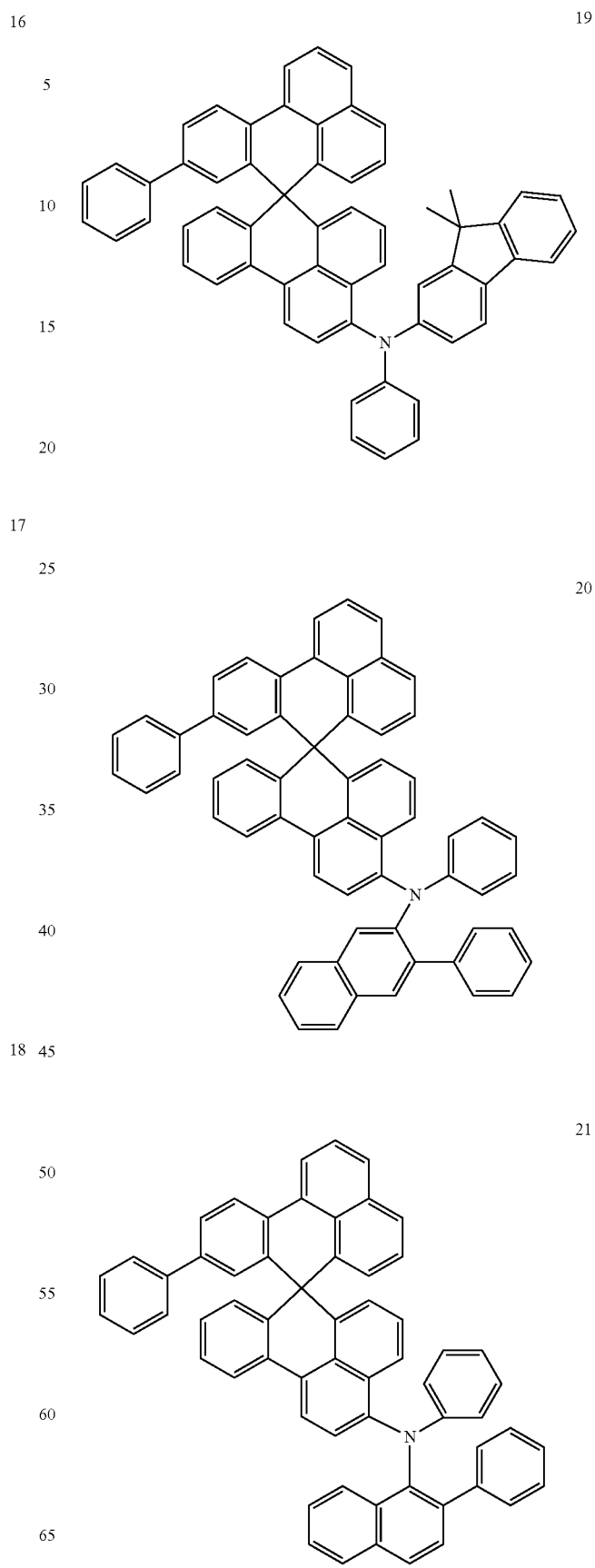

22
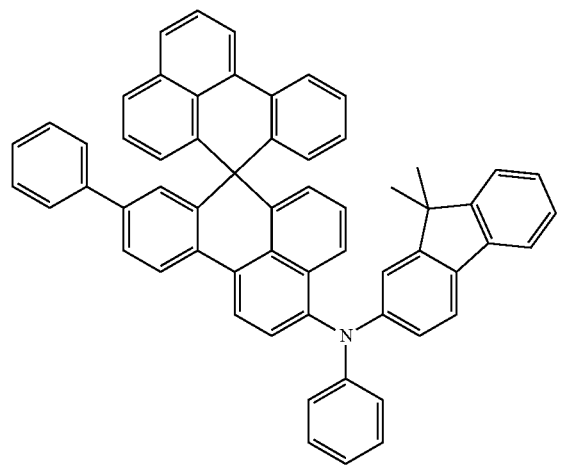
23
25
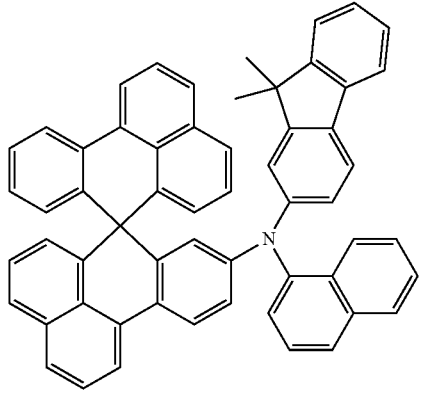
26
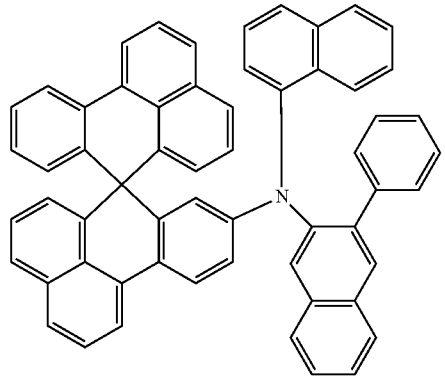
27
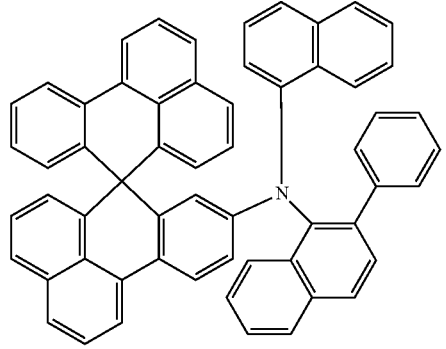
24
28
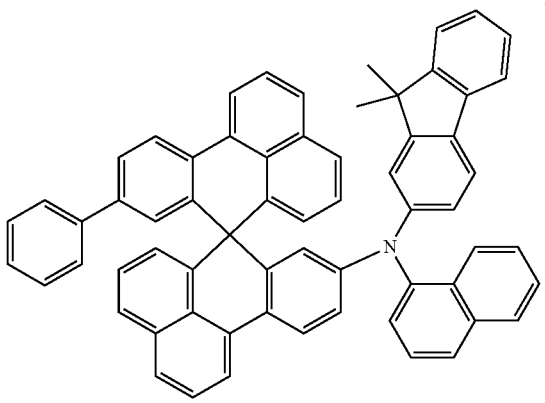

29
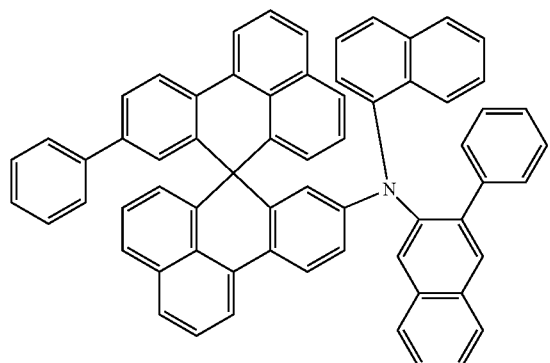
30
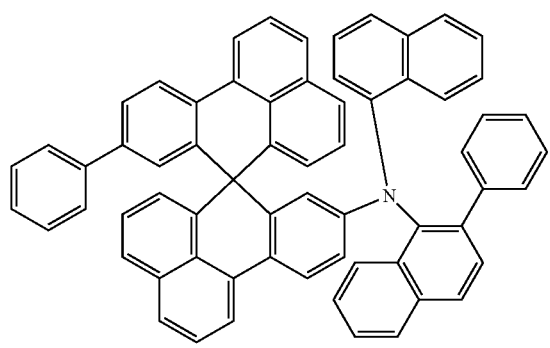
31
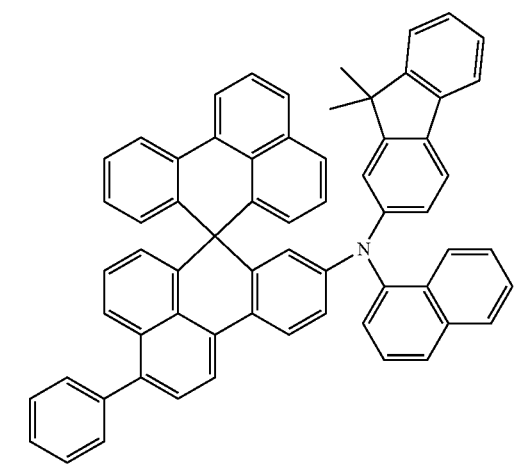
32
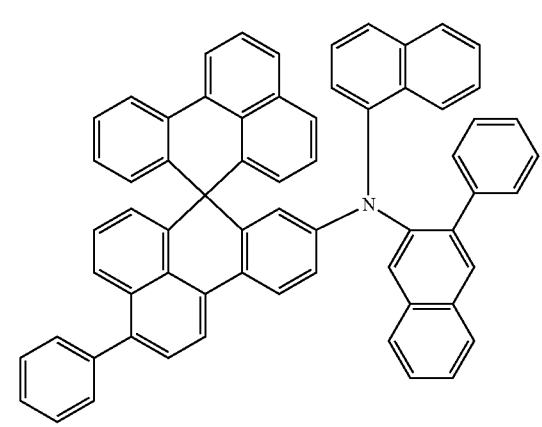
33
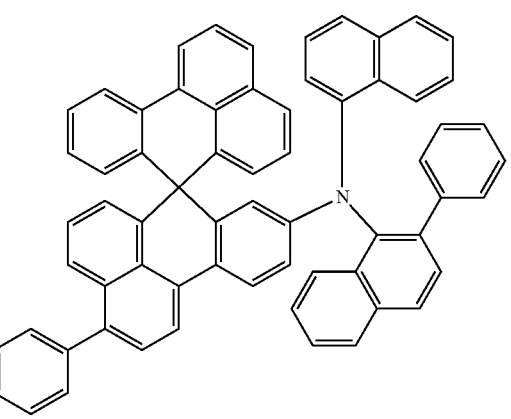
34
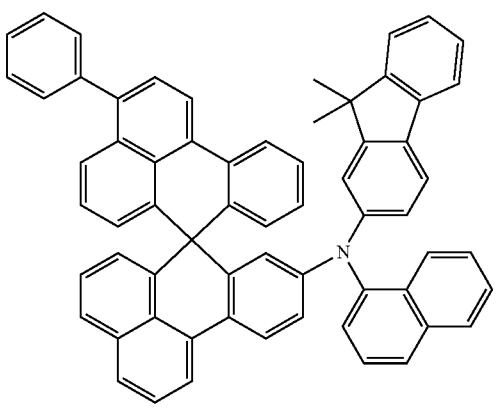
35
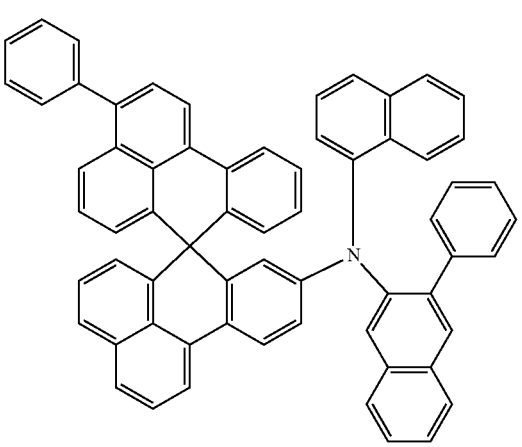

36
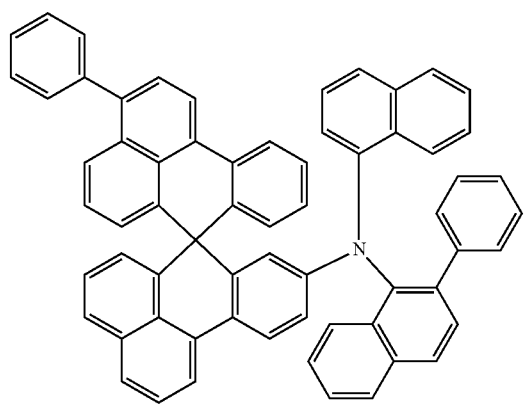
37
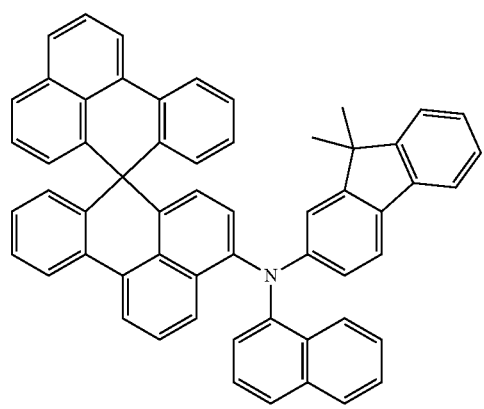
38
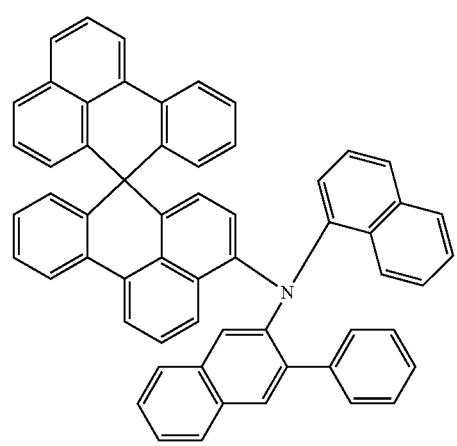
39
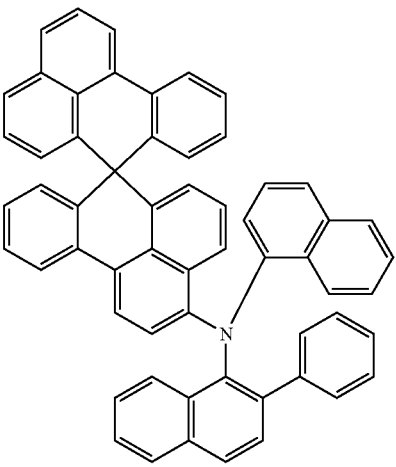
40
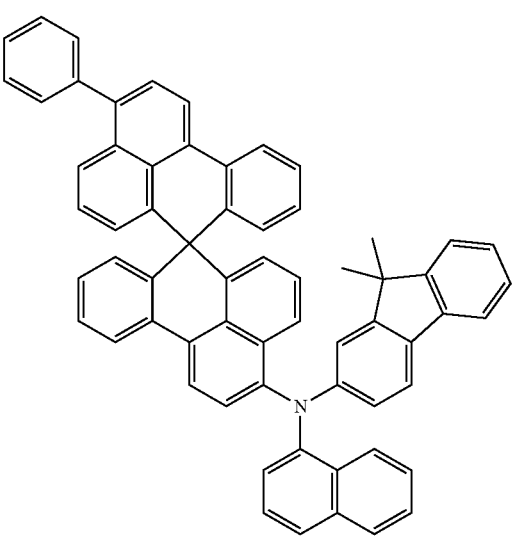
41
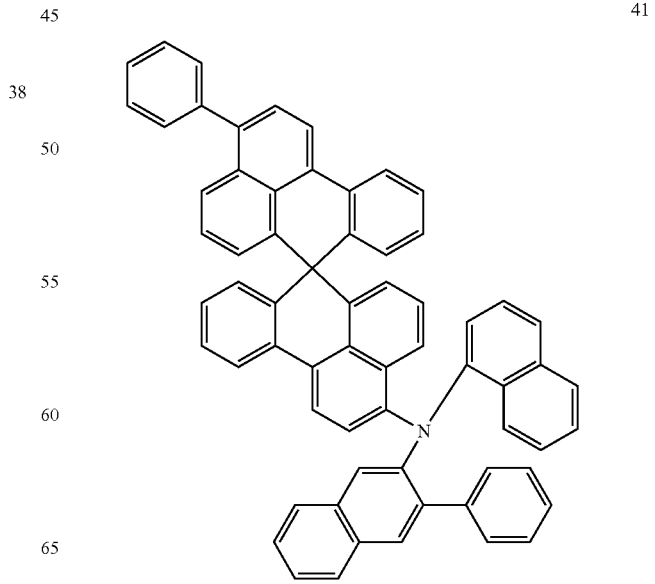

-continued

42

43

44

-continued

45

46

47

48
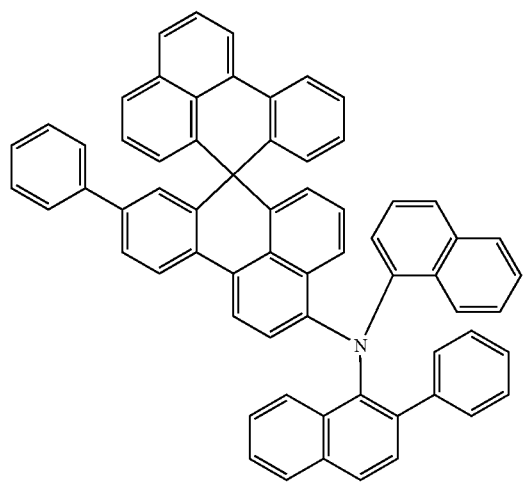
49
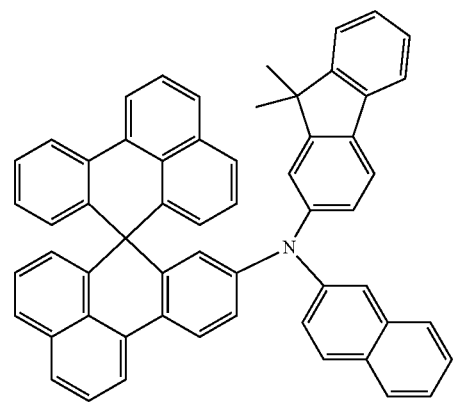
50
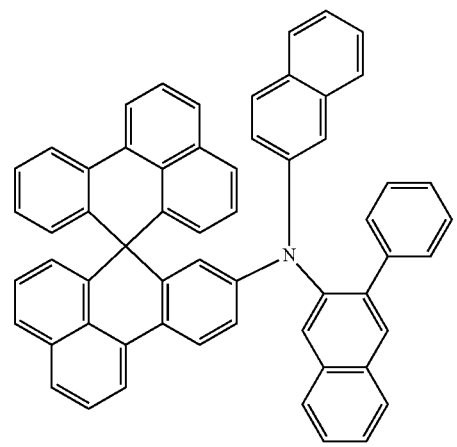
51
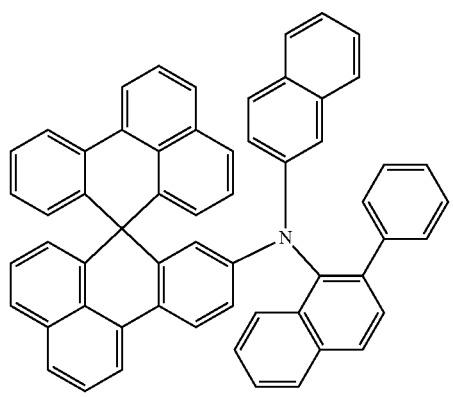
52
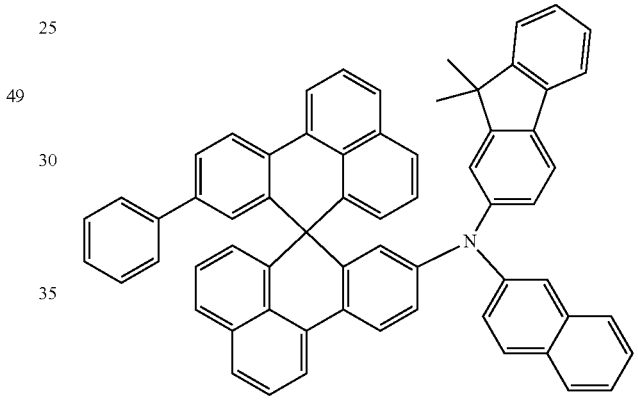
53
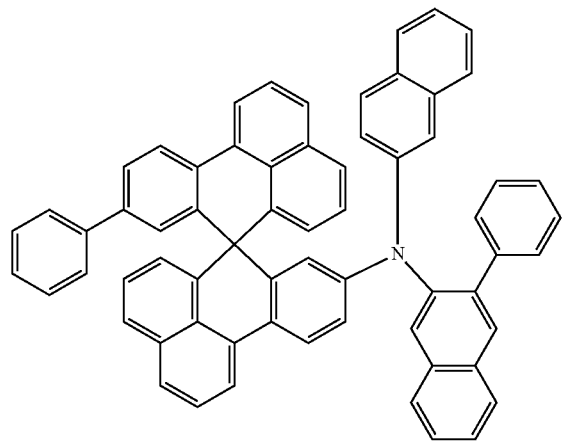

54
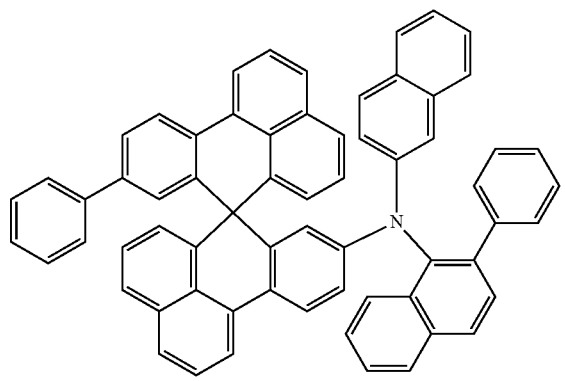
55
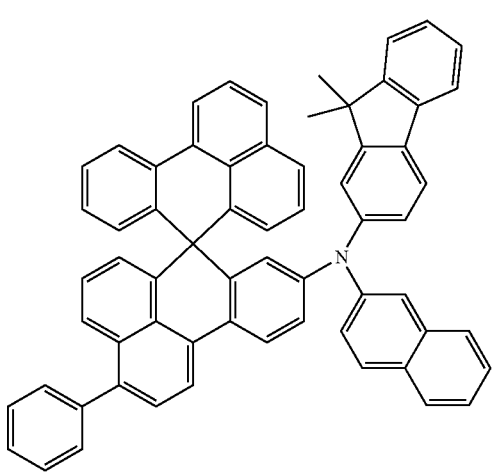
56
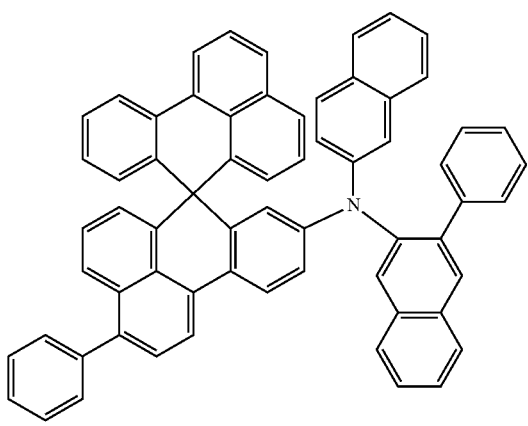
57
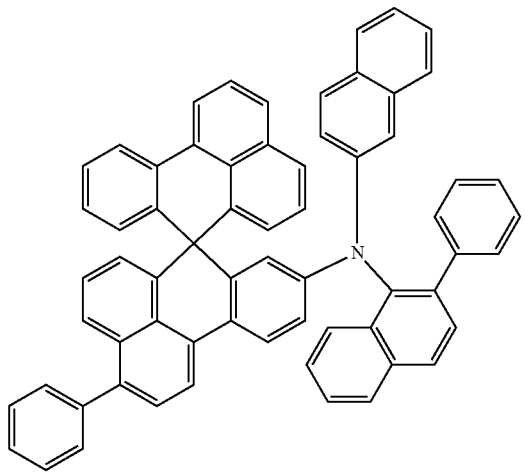
58
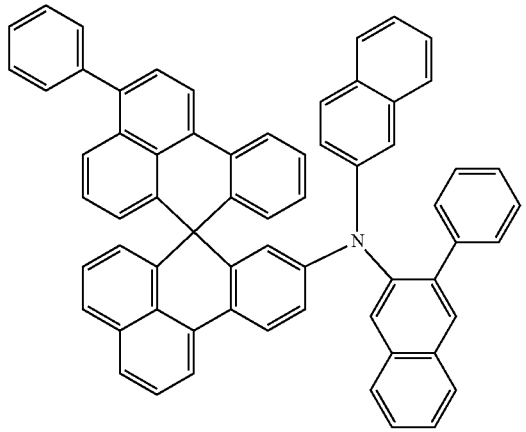
59

45
-continued
60
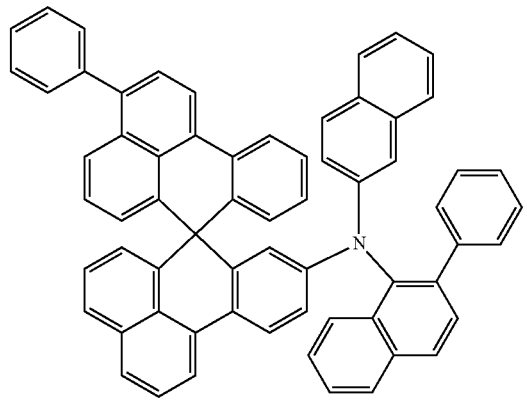
61
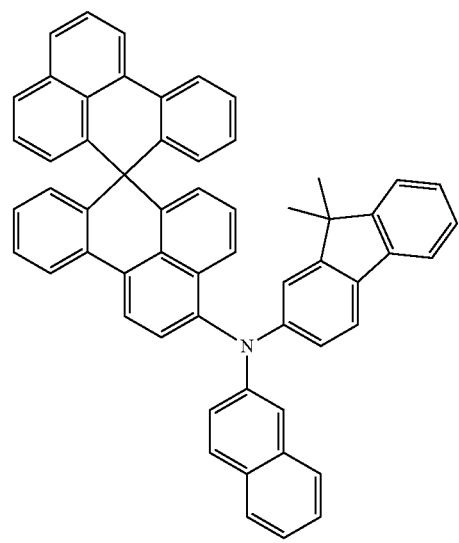
62
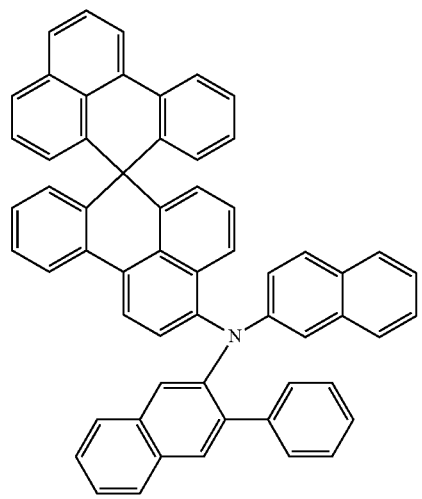
46
-continued
63
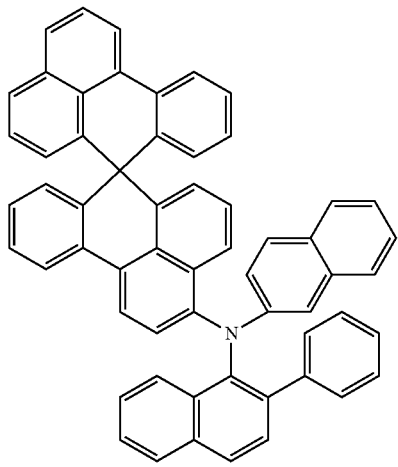
64
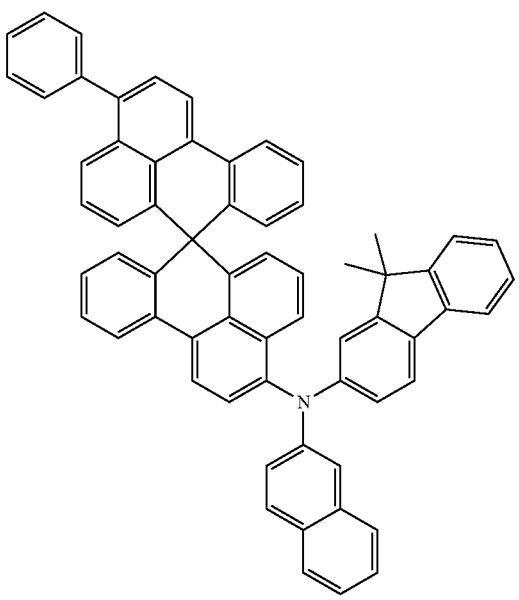
65
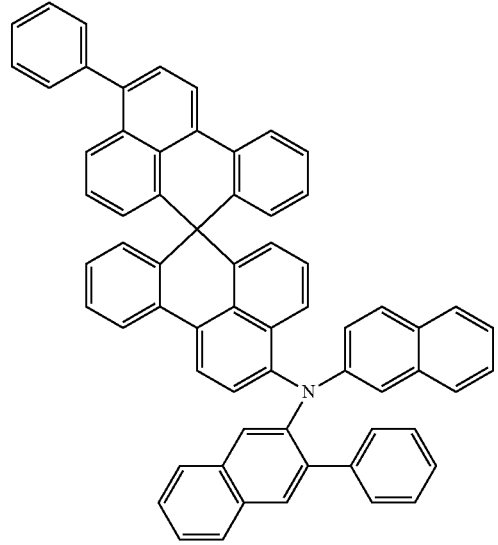

66
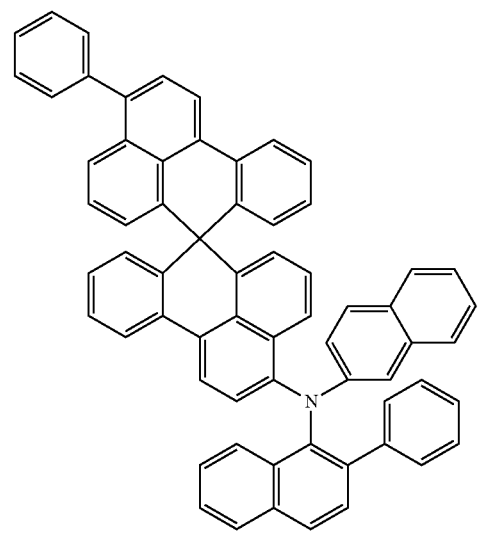
67
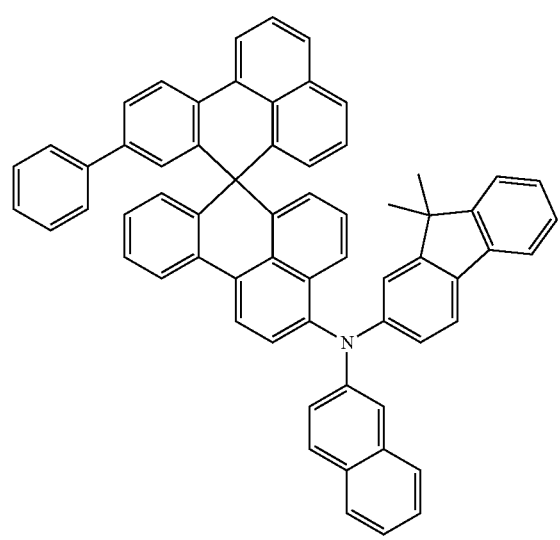
68
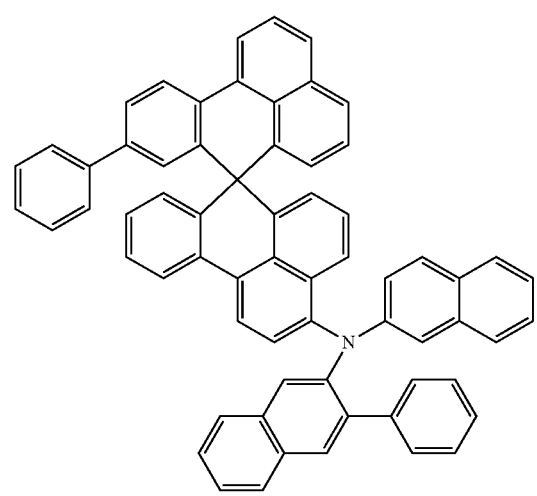
69
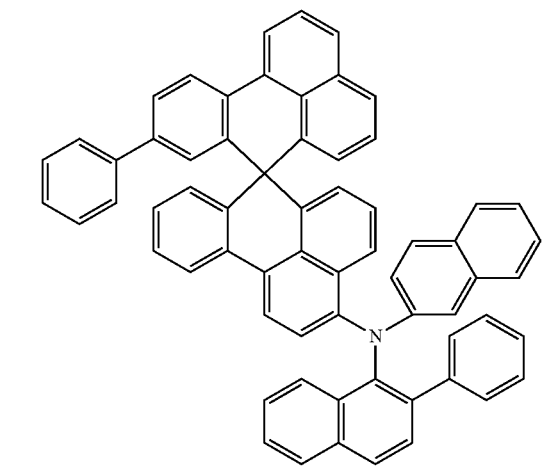
70
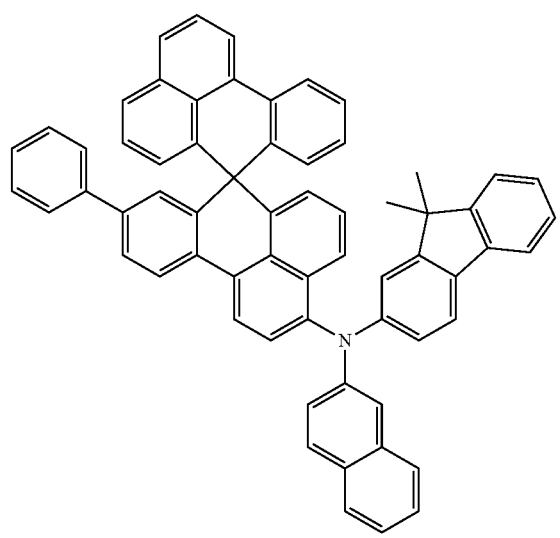
71
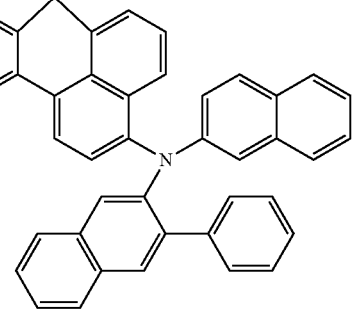

72
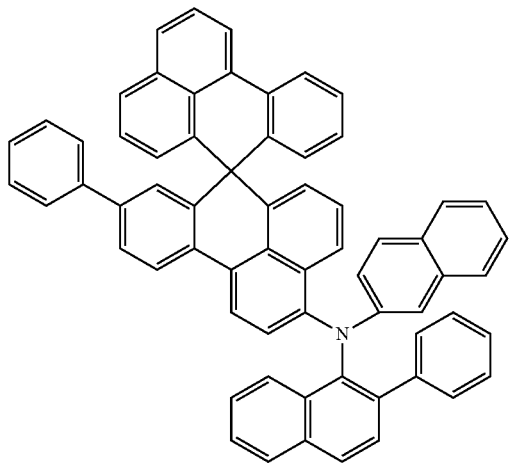
73
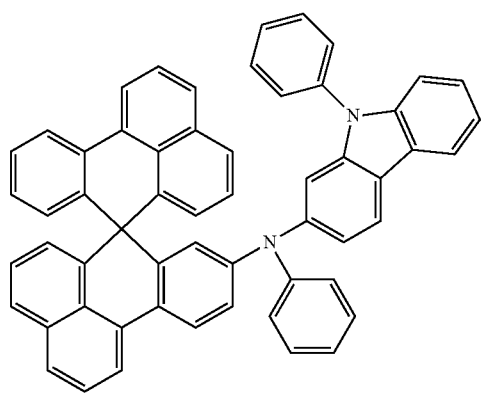
74
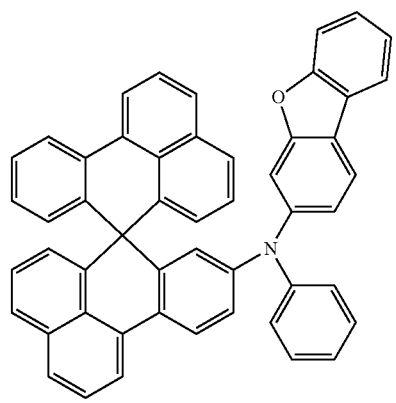
75
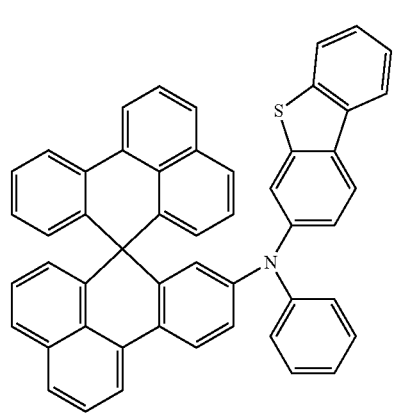
76
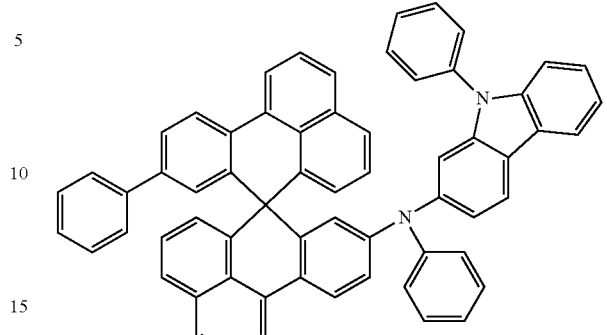
77
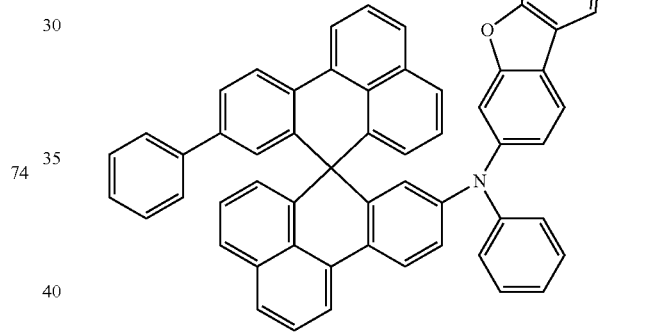
78
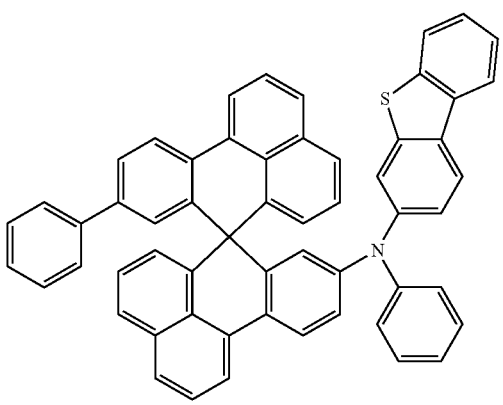

79
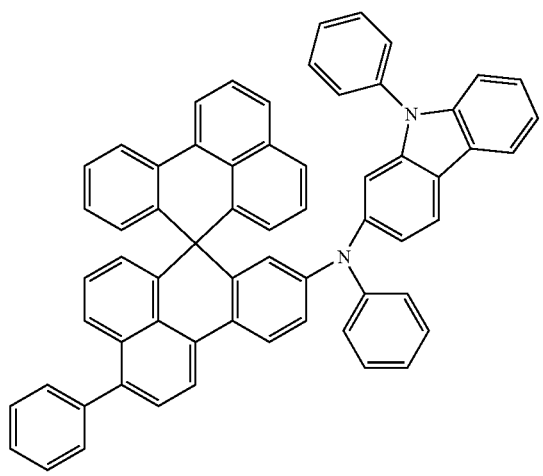
80
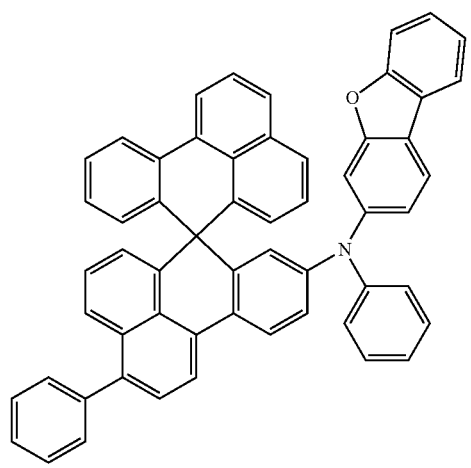
81
82
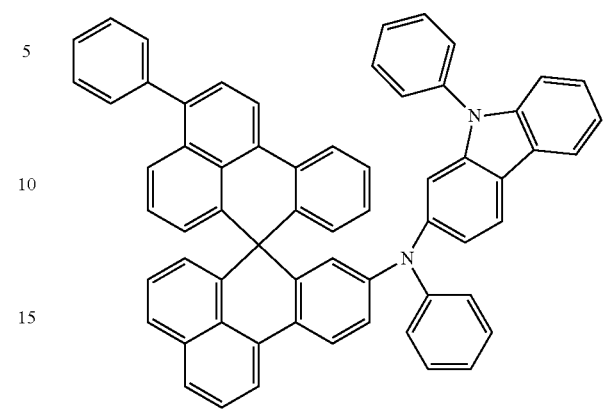
83
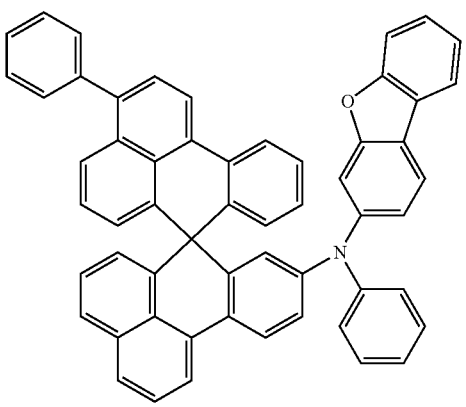
84
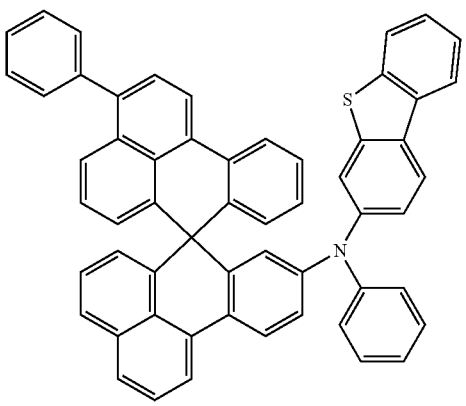

85
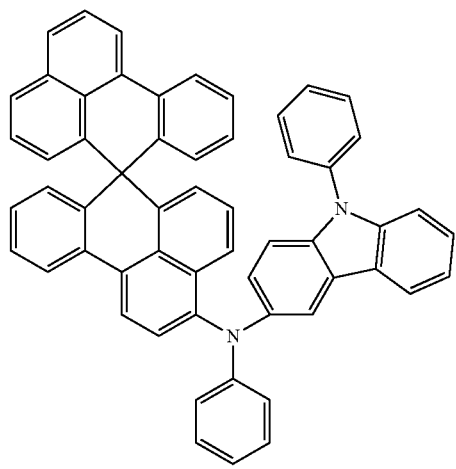
86
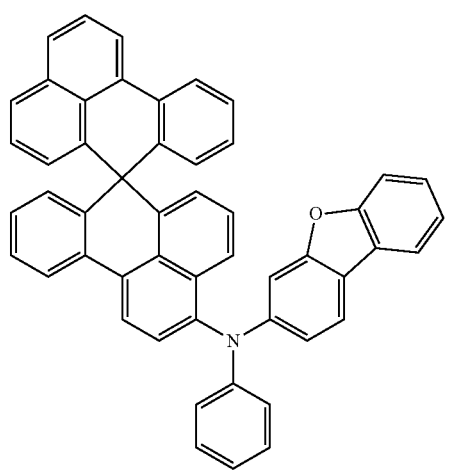
87
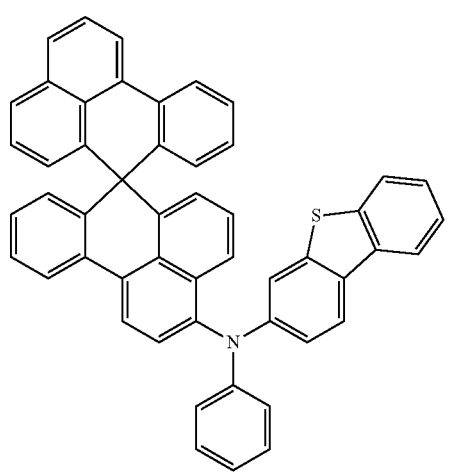
88
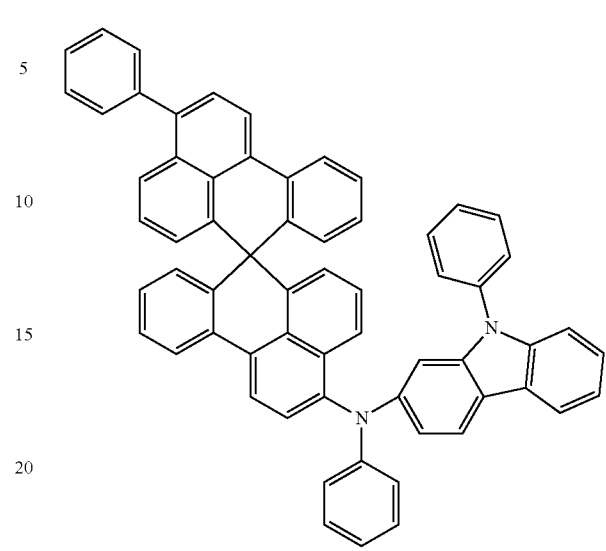
89
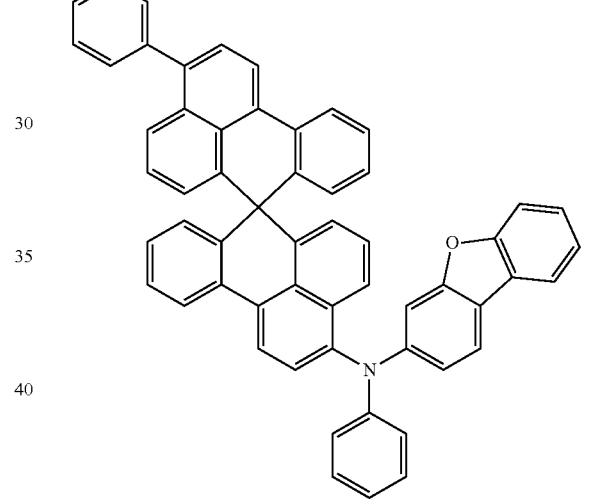
90
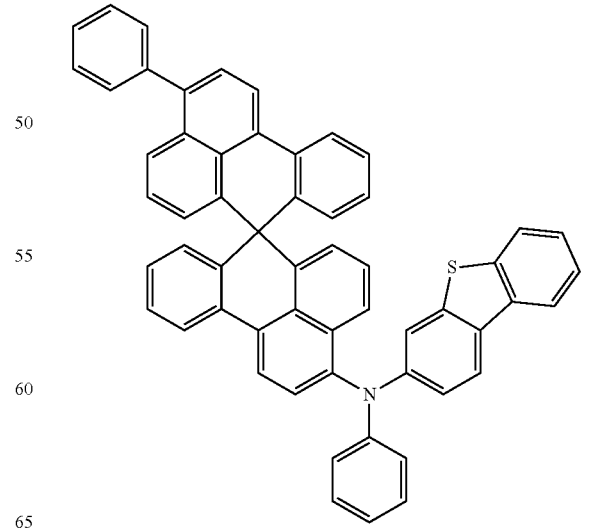

91
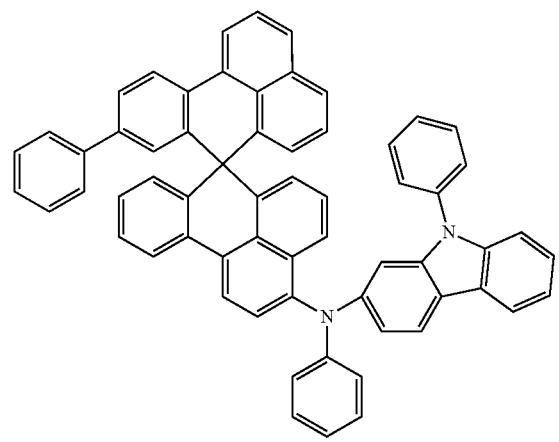
92
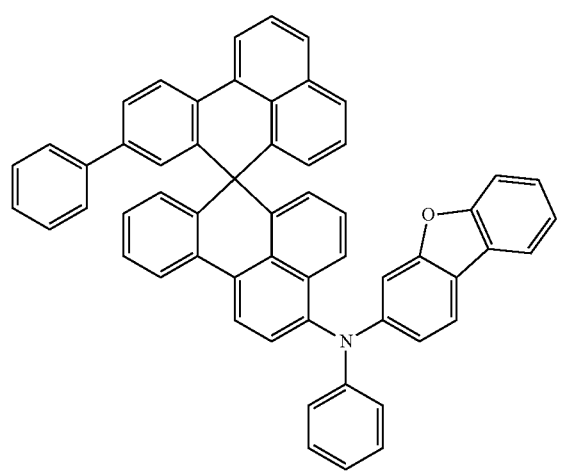
93
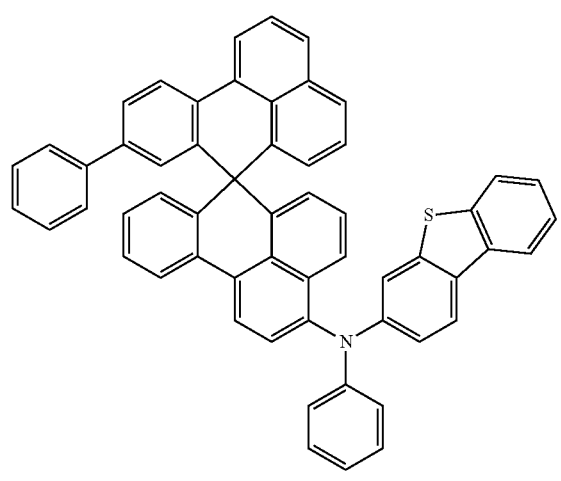
94
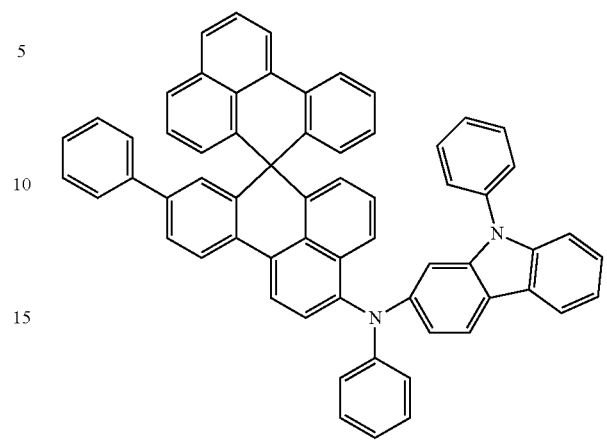
95
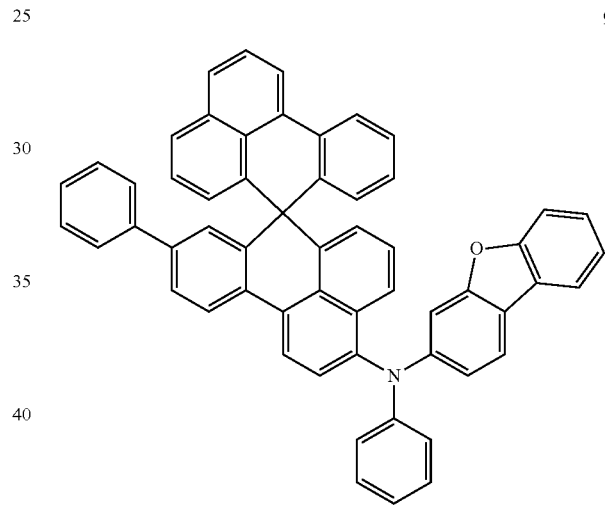
96
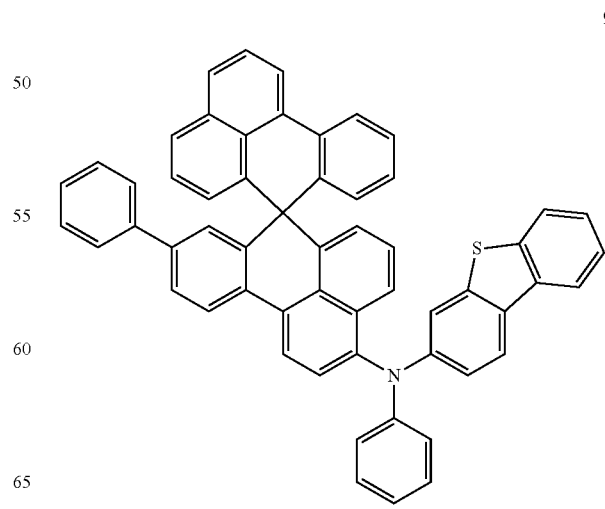

97
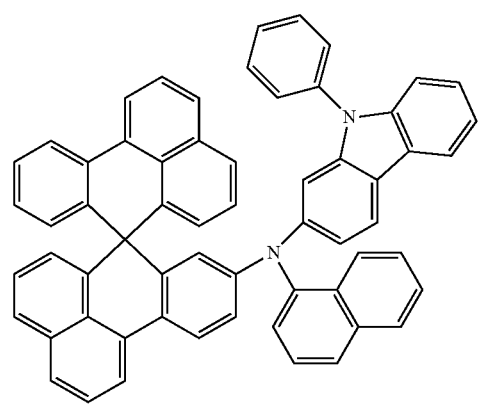
98
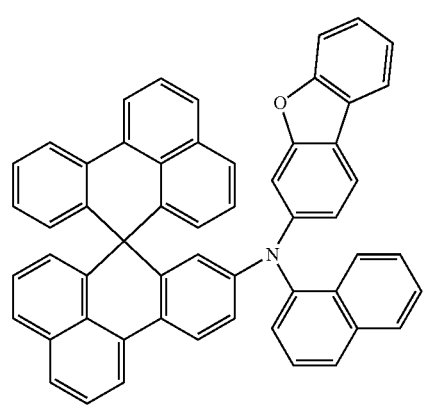
99
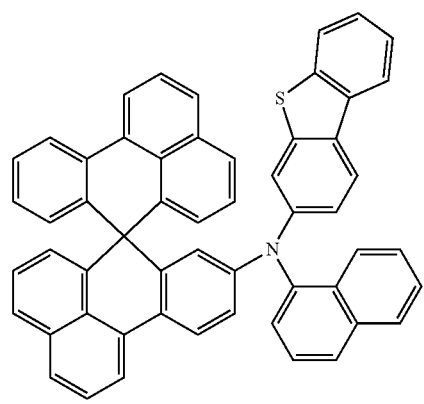
100
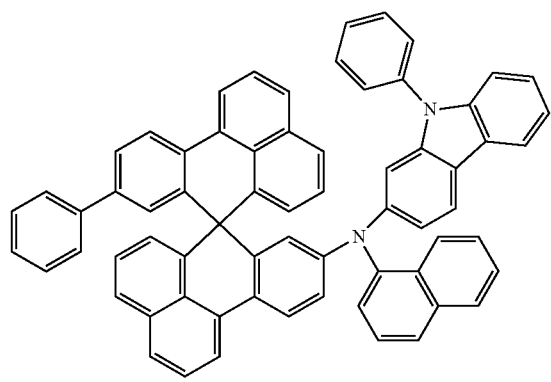
101
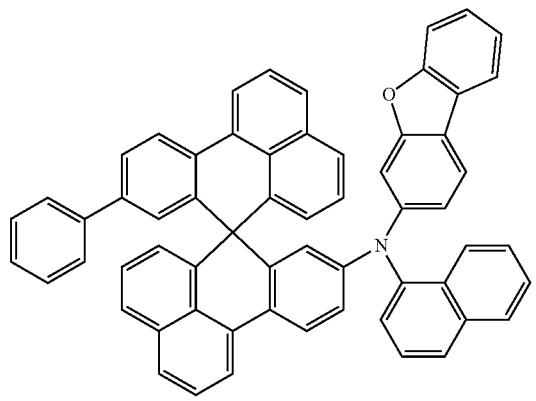
102
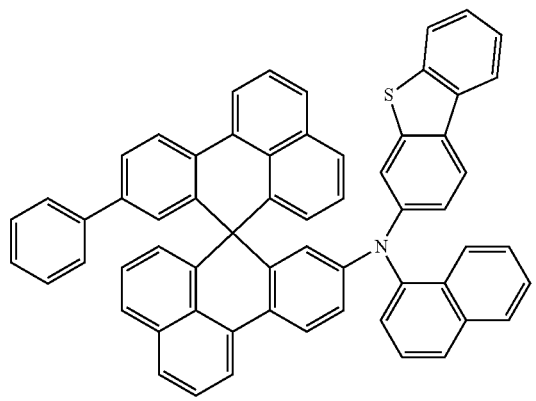
103
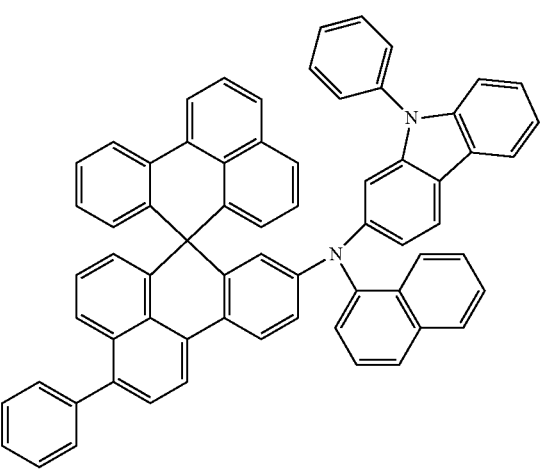

-continued
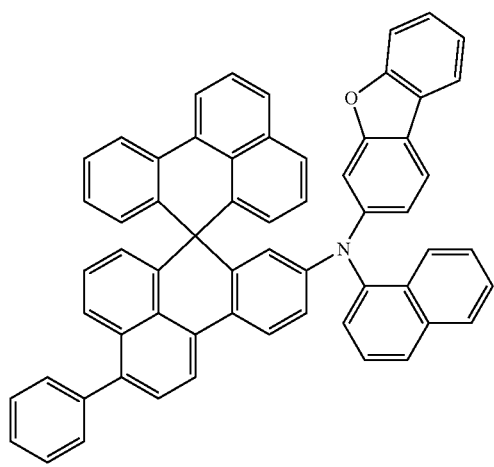
104
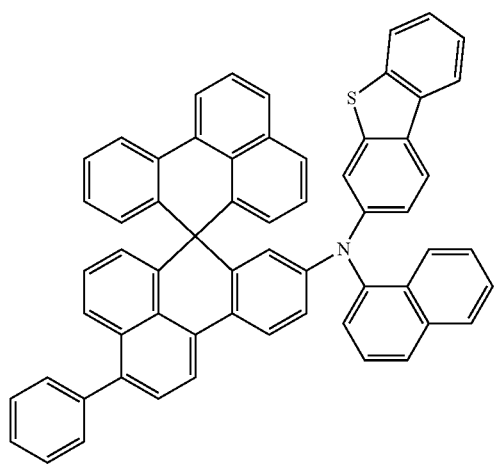
105
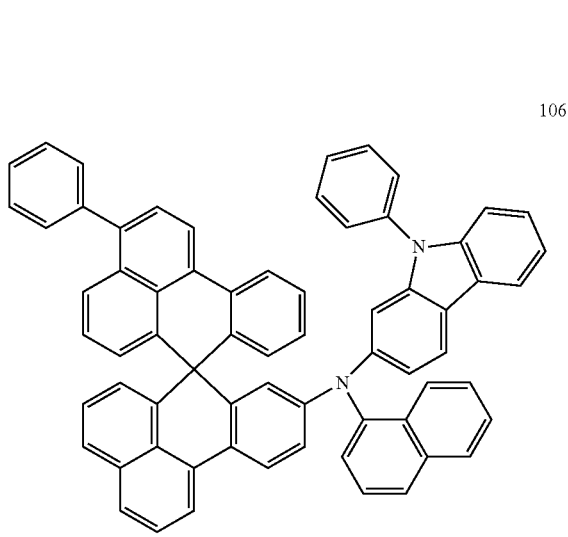
106
-continued
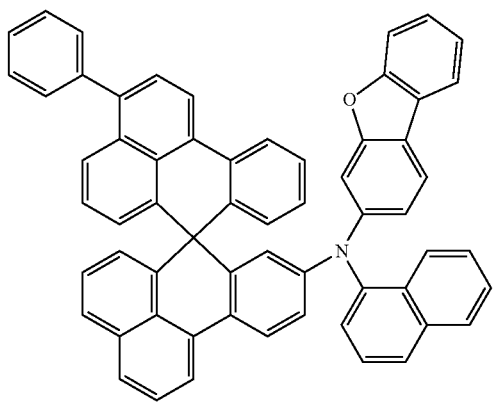
107
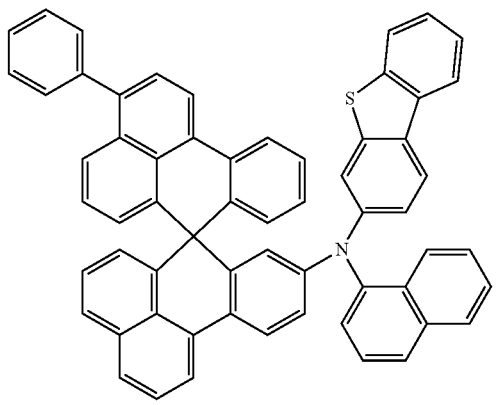
108
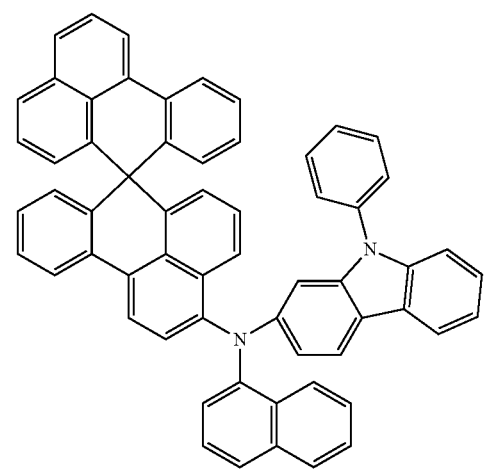
109

110
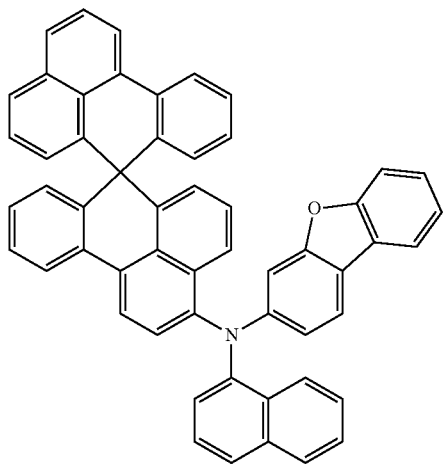
111
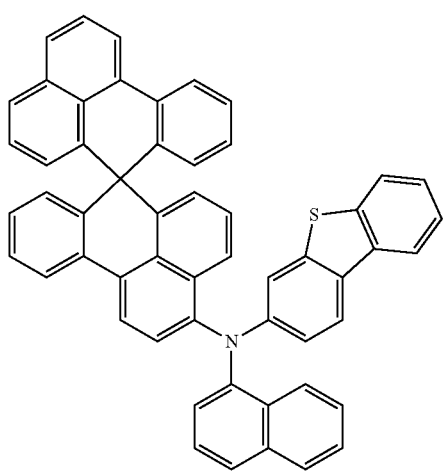
112
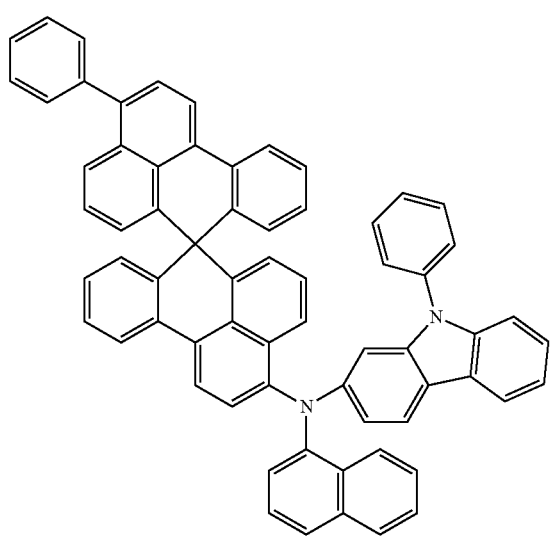
113
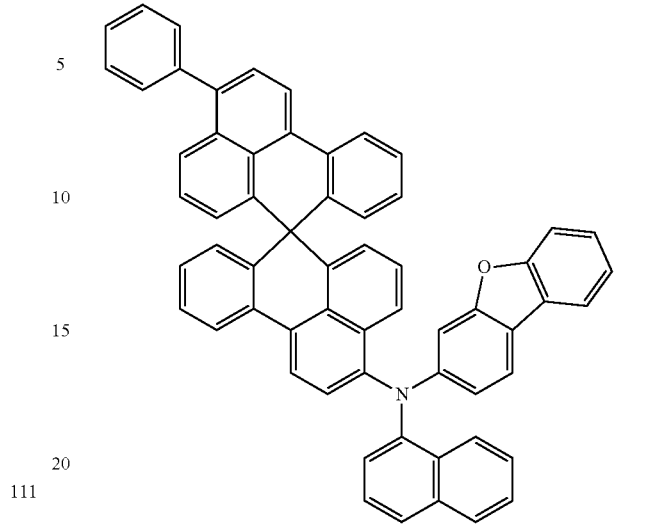
114
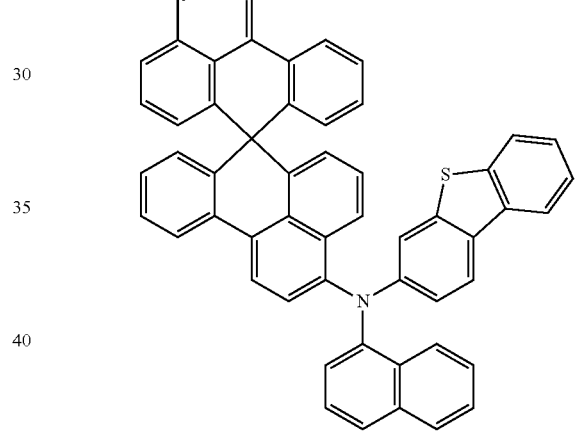
115
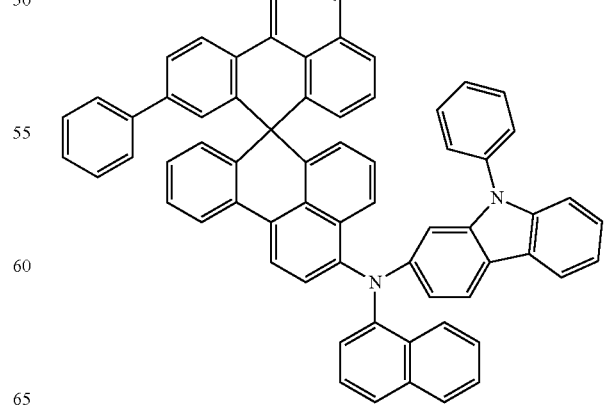

116
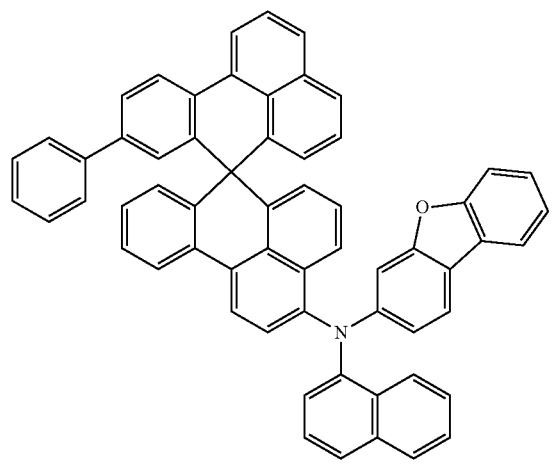
117
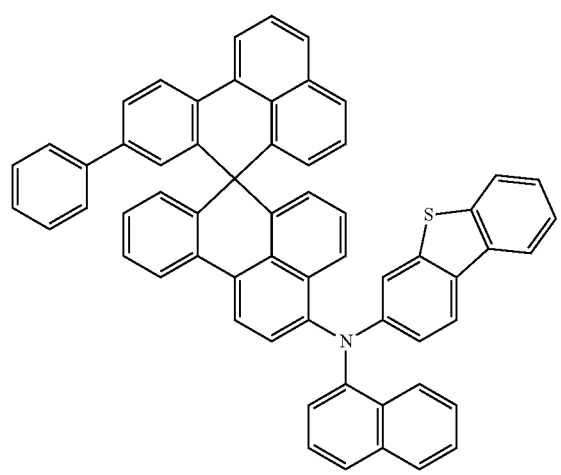
118
119
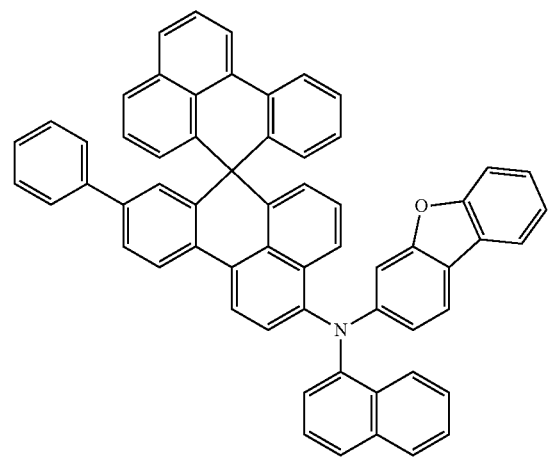
120
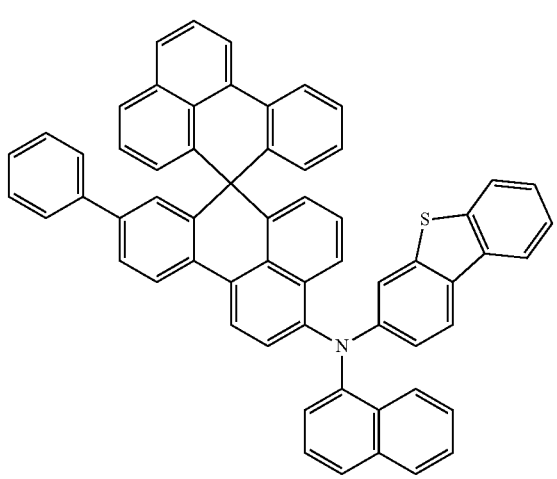
121
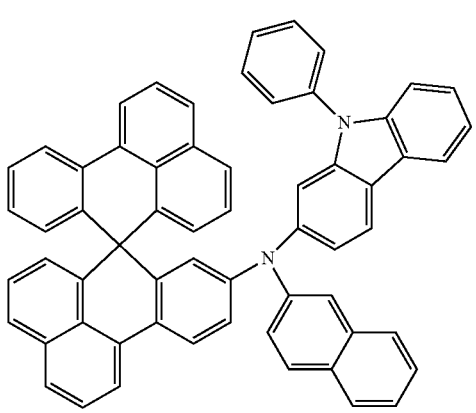

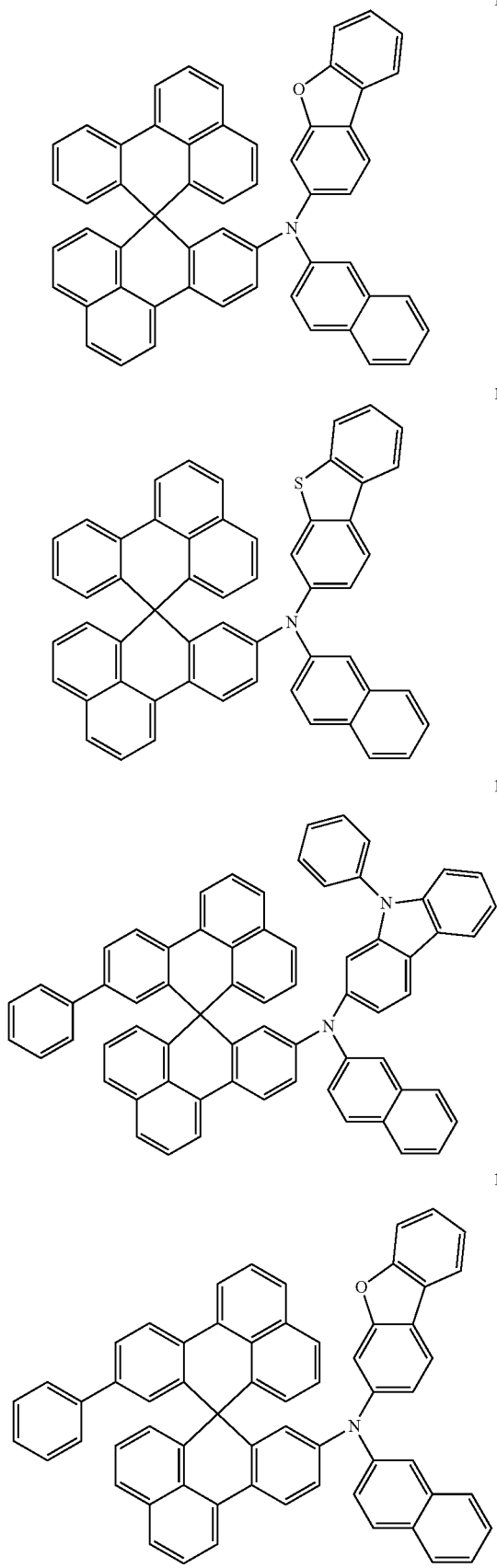
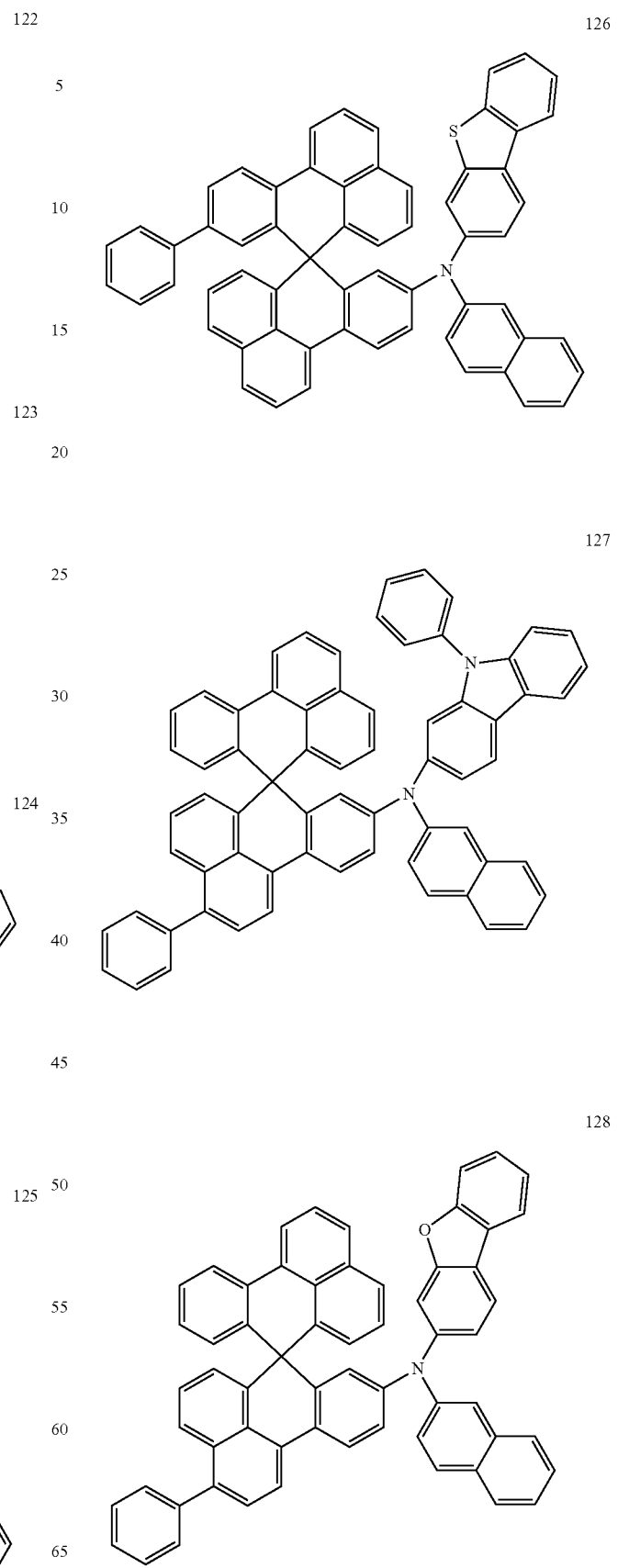

129
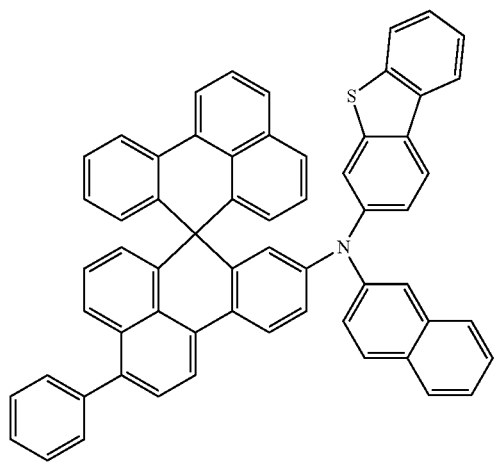
130
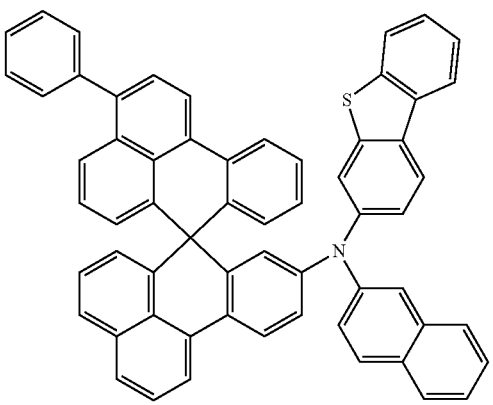
131
132
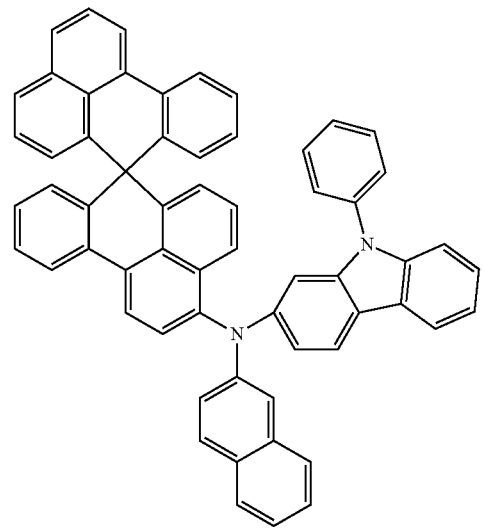
133
134
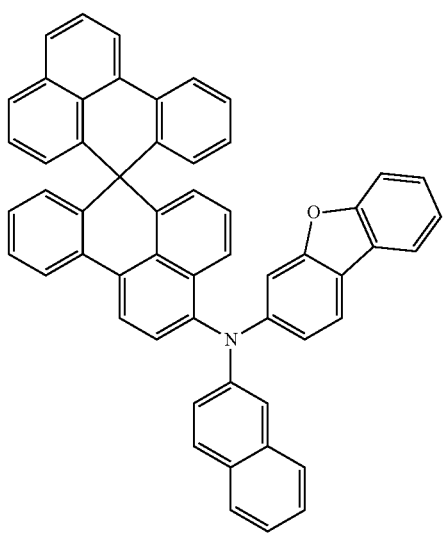

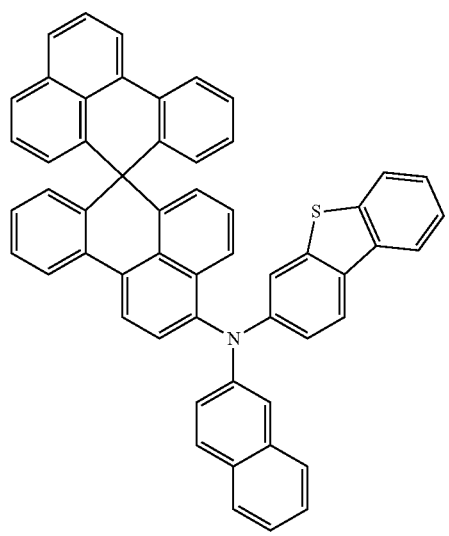
135
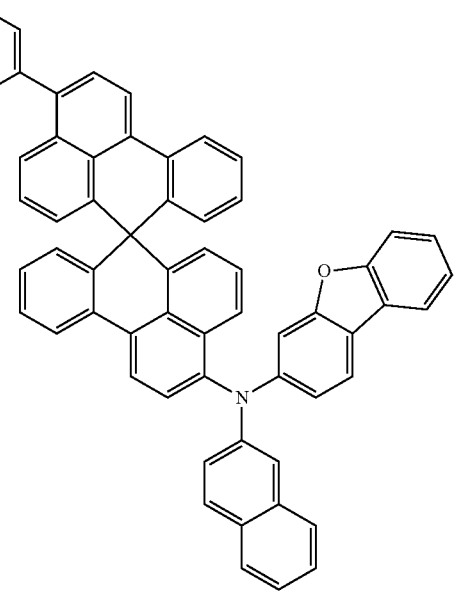
137
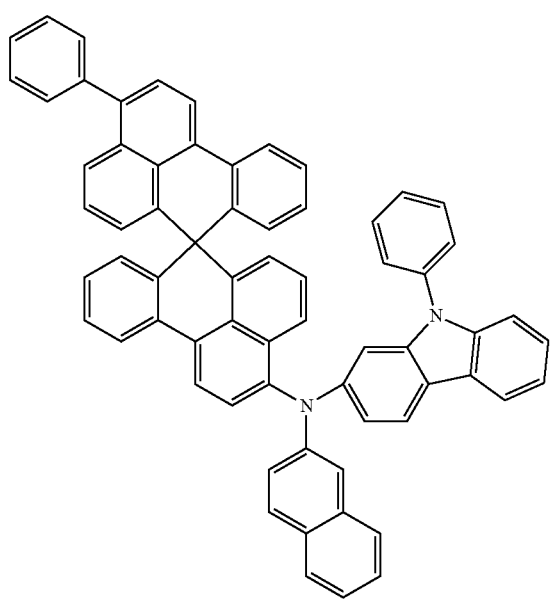
136
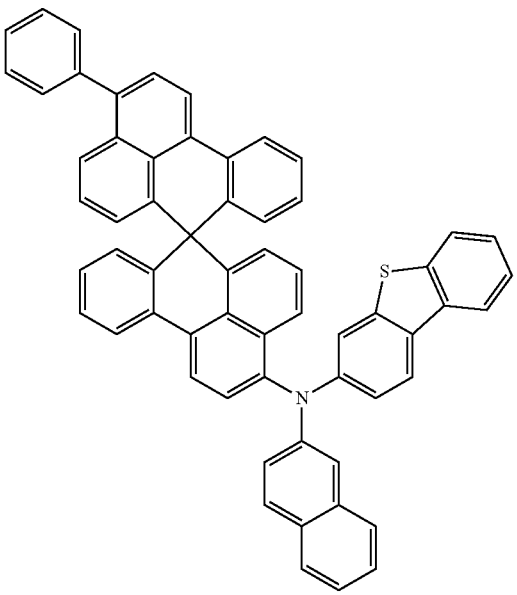
138

139
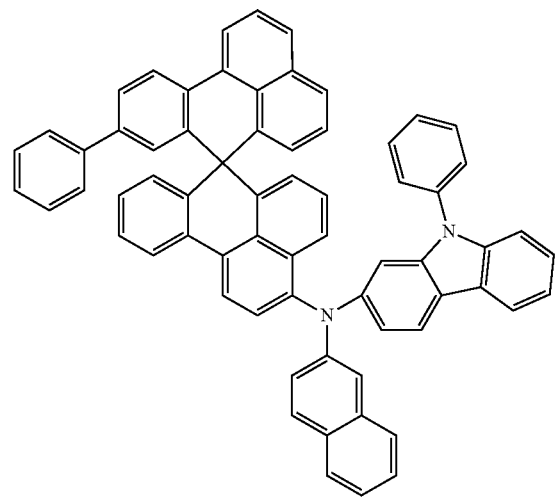
140
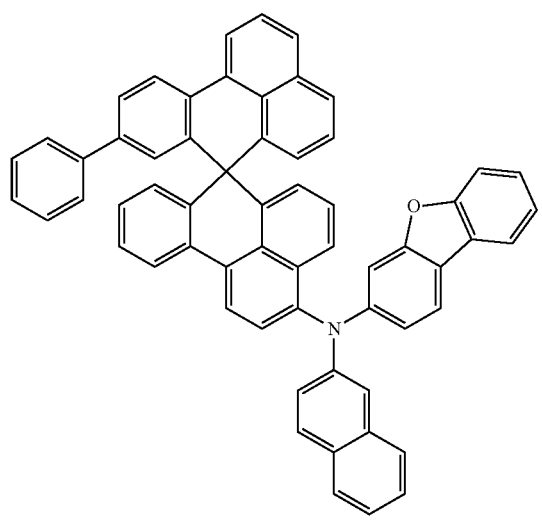
141
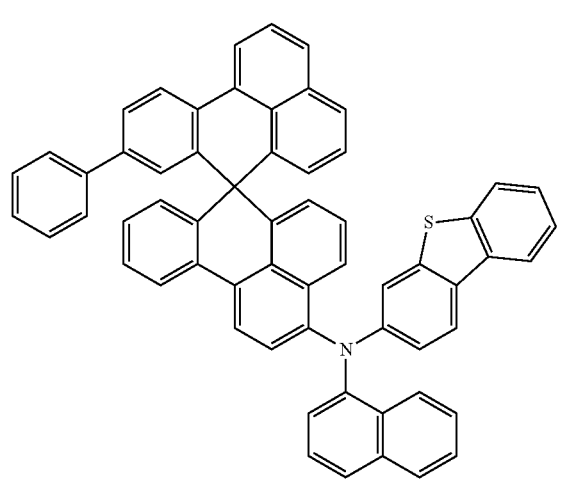
142
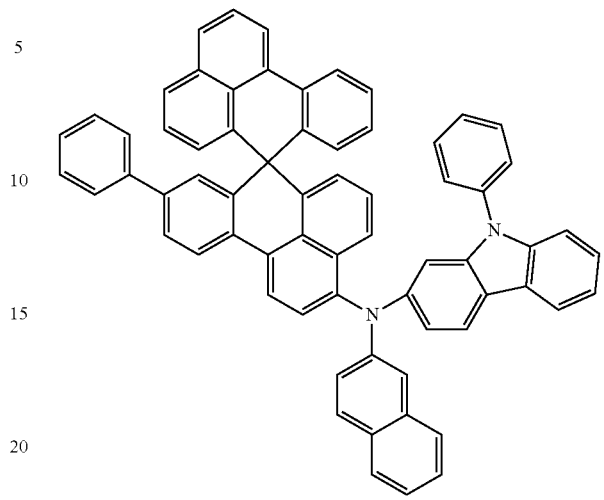
143
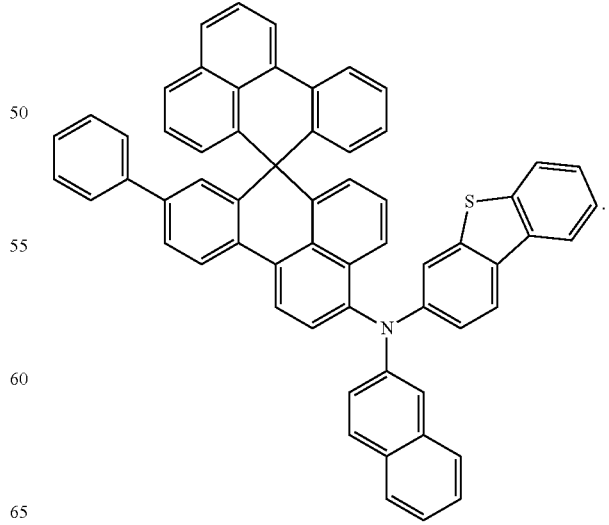
144

A luminescence device ED according to one or more embodiments of the present disclosure will be described with reference to FIGS. 3 to 6.

As described above, the hole transport region HTR includes an amine compound according to one or more embodiments of the present disclosure as described above. For example, the hole transport region HTR includes the amine compound represented by Formula 1.

When the hole transport region HTR is a multilayer structure having a plurality of layers, any one layer of the plurality of layers may include the amine compound represented by Formula 1. For example, the hole transport region HTR may include the hole injection layer HIL disposed on the first electrode EL1 and the hole transport layer HTL disposed on the hole injection layer, and the hole transport layer HTL or the hole injection layer HIL may include the amine compound represented by Formula 1. However, the embodiments of the present disclosure are not limited thereto, and for example, the hole transport region HTR may include the electron blocking layer EBL disposed on the hole transport layer HTL, and the electron blocking layer EBL may include the amine compound represented by Formula 1.

The hole transport region HTR may include one or two or more of the amine compounds represented by Formula 1. For example, the hole transport region HTR may include at least one selected from among the compounds represented by Compound Group 1 as described above.

The hole transport region HTR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

The hole transport region HTR may further include a compound represented by Formula H-1 below:

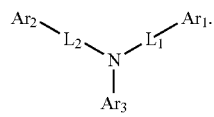

Formula H-1

In Formula H-1 above, $L_1$ and $L_2$ may be each independently a direct linkage, a substituted or unsubstituted arylene group having 6 to 30 ring-forming carbon atoms, or a substituted or unsubstituted heteroarylene group having 2 to 30 ring-forming carbon atoms. In Formula H-1, $Ar_1$ and $Ar_2$ may be each independently a substituted or unsubstituted aryl group having 6 to 30 ring-forming carbon atoms, or a substituted or unsubstituted heteroaryl group having 2 to 30 ring-forming carbon atoms. In one or more embodiments, in Formula H-1, $Ar_3$ may be a substituted or unsubstituted aryl group having 6 to 30 ring-forming carbon atoms, or a substituted or unsubstituted heteroaryl group having 2 to 30 ring-forming carbon atoms.

The compound represented by Formula H-1 above may be a monoamine compound. In one or more embodiments, the compound represented by Formula H-1 above may be a diamine compound in which at least one among $Ar_1$ to $Ar_3$ includes the amine group as a substituent. In one or more embodiments, the compound represented by Formula H-1 above may be a carbazole-based compound including a substituted or unsubstituted carbazole group in at least one of $Ar_1$ or $Ar_2$, or a fluorene-based compound including a substituted or unsubstituted fluorene group in at least one of $Ar_1$ or $Ar_2$.

The compound represented by Formula H-1 may be represented by any one among the compounds of Compound Group H below. However, the compounds listed in Compound Group H below are examples, and the compounds represented by Formula H-1 are not limited to those represented by Compound Group H below:

Compound Group H

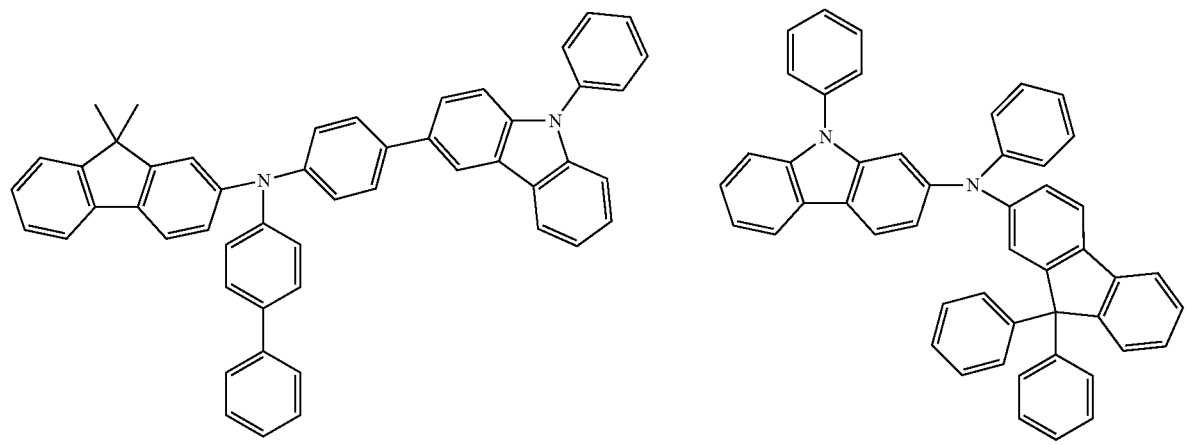

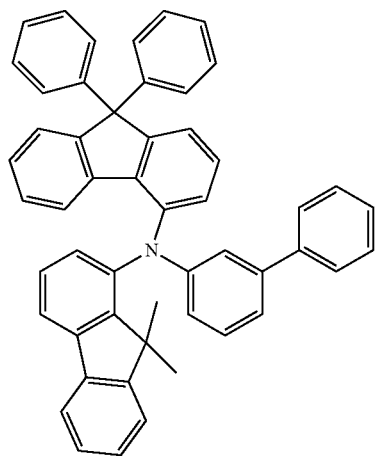
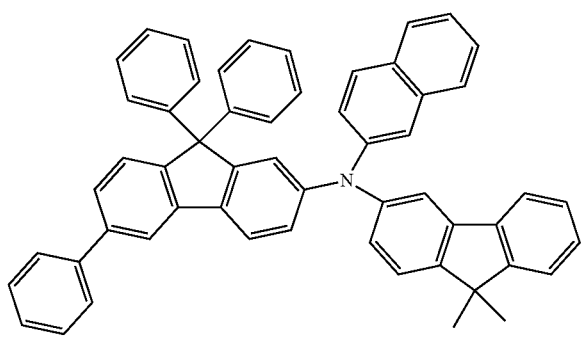
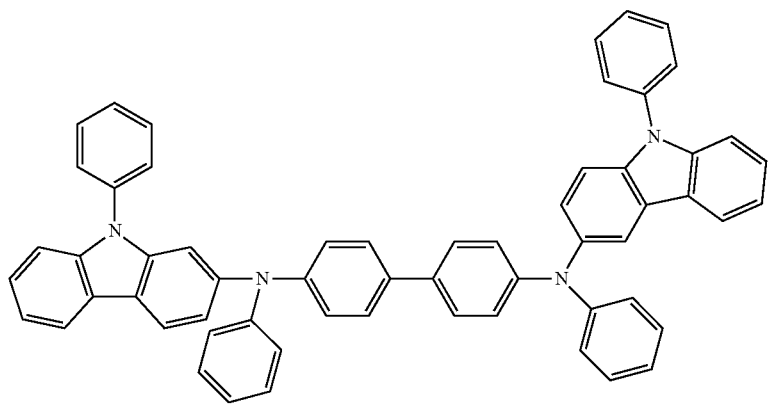
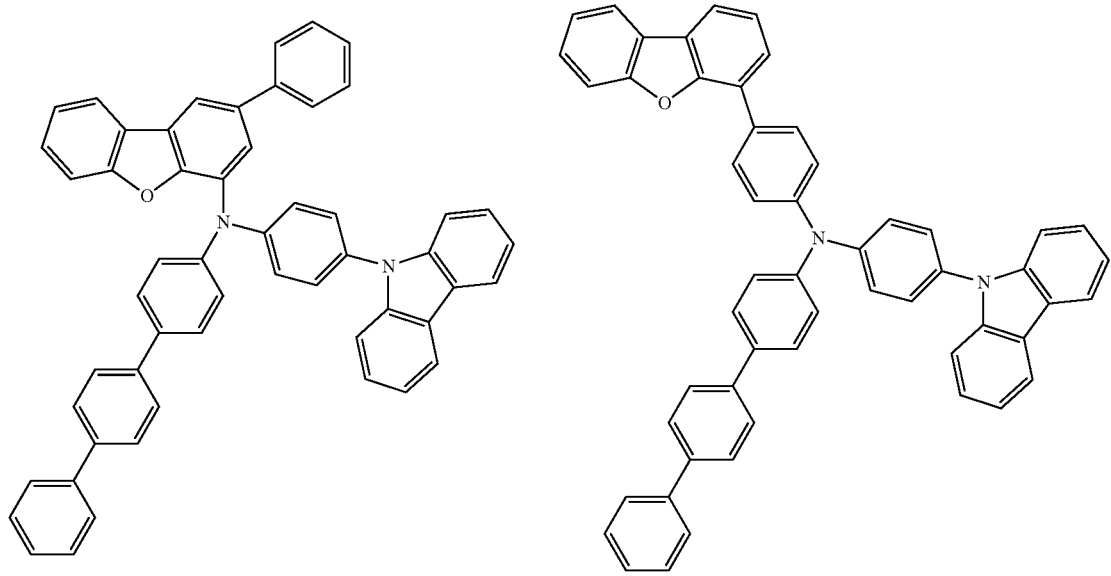

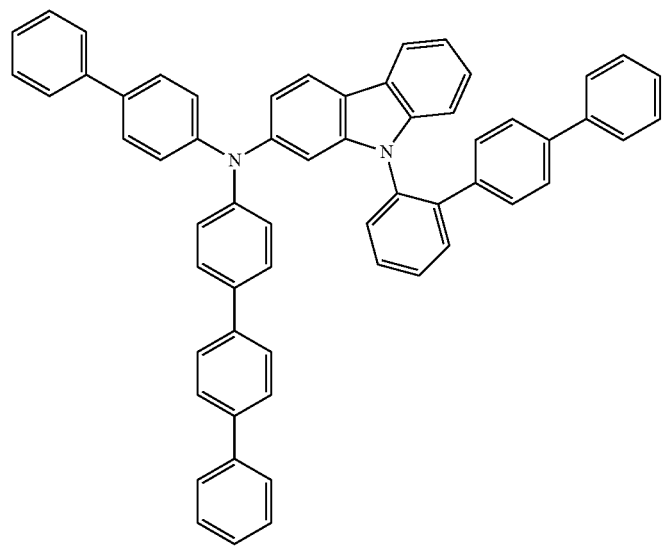
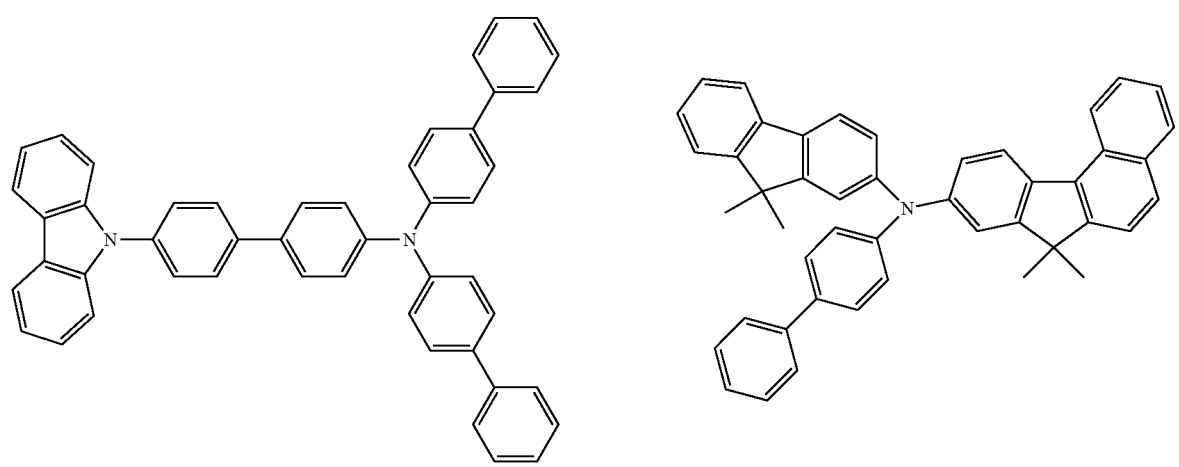
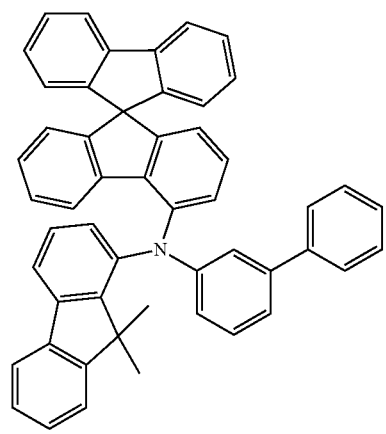
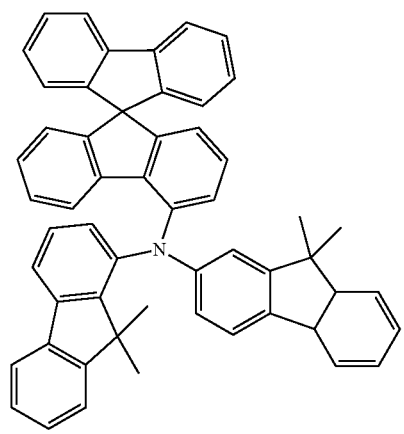

-continued
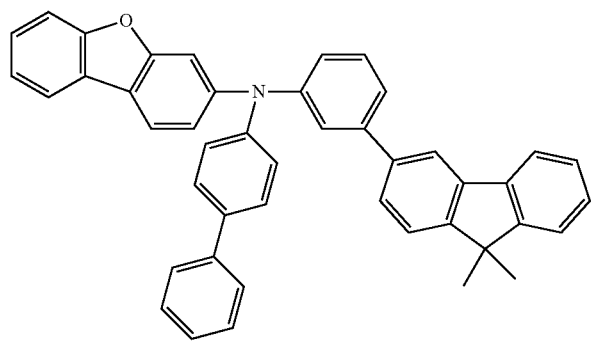
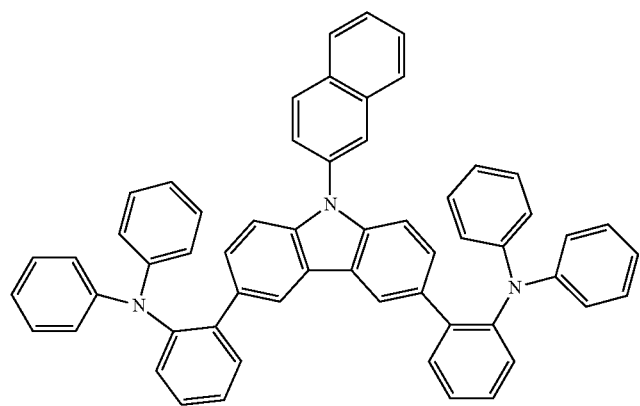
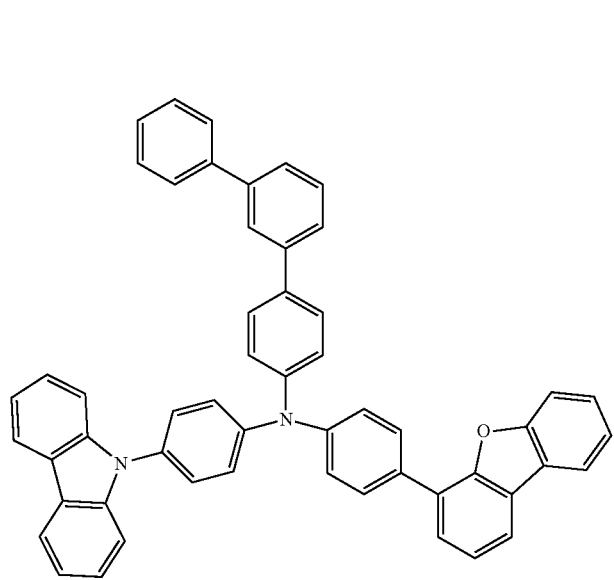
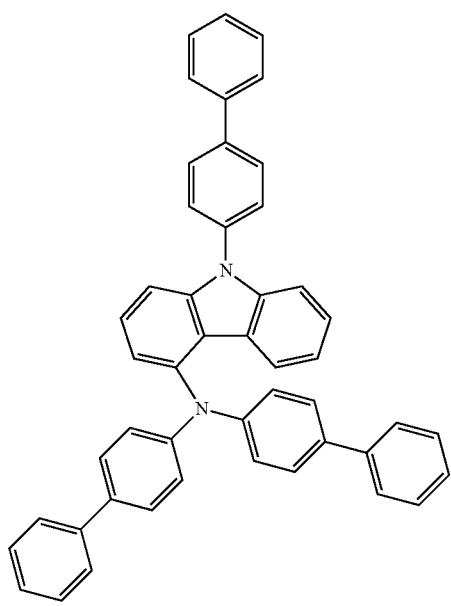

-continued

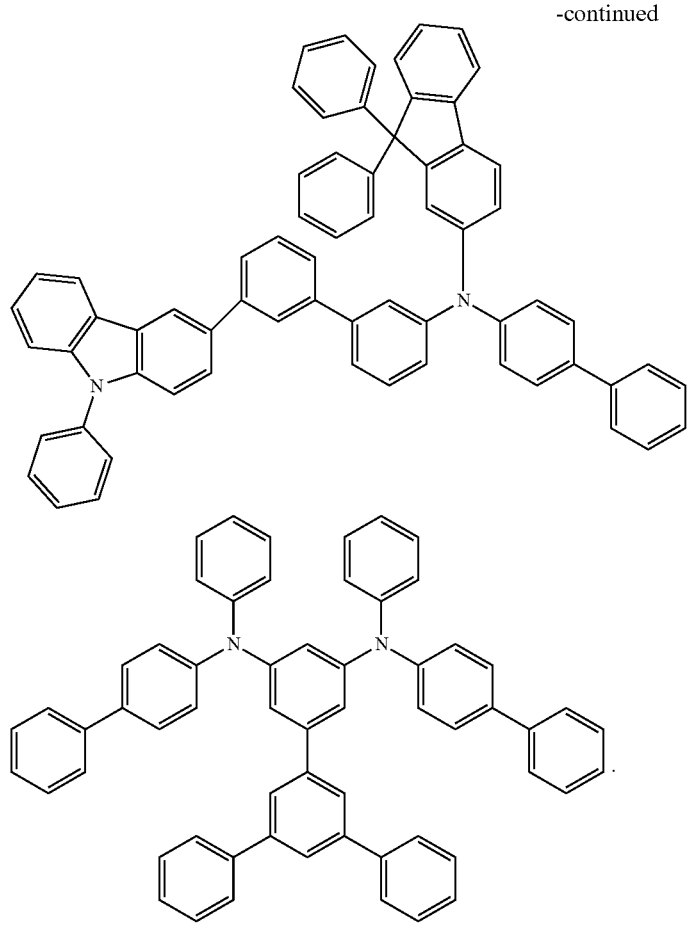

The hole transport region HTR may further include a phthalocyanine compound (such as copper phthalocyanine), $N^1,N^{1'}$-([1,1'-biphenyl]-4,4'-diyl)bis($N^1$-phenyl-$N^4,N^4$-di-m-tolylbenzene-1,4-diamine) (DNTPD), 4,4', 4"-[tris(3-methylphenyl)phenylamino] triphenylamine (m-MTDATA), 4,4'4"-tris(N,N-diphenylamino)triphenylamine (TDATA), 4,4', 4"-tris[N(1-naphthyl)-N-phenylamino]-triphenylamine (1-TNATA), 4,4', 4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-I-yl)-N,N'-diphenyl-benzidine (NPB), triphenylamine-containing polyetherketone (TPAPEK), 4-isopropyl-4'-methyldiphenyliodonium [tetrakis(pentafluorophenyl) borate], dipyrazino[2,3-f: 2', 3'-h]quinoxaline-2,3,6,7,10,11-hexacarbonitrile (HATCN), etc.

The hole transport region HTR may further include, for example, carbazole derivatives (such as N-phenyl carbazole and/or polyvinyl carbazole), fluorene derivatives, N,N'-bis(3-methylphenyl)-N,N'-diphenyl-[1,1-biphenyl]-4,4'-diamine (TPD), triphenylamine derivatives (such as 4,4', 4"-tris(N-carbazolyl)triphenylamine (TCTA)), N,N'-di(naphthalene-I-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The hole transport region HTR may further include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc.

The hole transport region HTR may include the above-described compound of the hole transport region in at least one of a hole injection layer HIL, a hole transport layer HTL, or an electron blocking layer EBL. The thickness of the hole transport region HTR may be from about 100 Å to about 10,000 Å, for example, from about 100 Å to about 5,000 Å. When the hole transport region HTR includes the hole injection layer HIL, the hole injection layer HIL may have, for example, a thickness of about 30 Å to about 1,000 Å. When the hole transport region HTR includes the hole transport layer HTL, the hole transport layer HTL may have a thickness of about 30 Å to about 1,000 Å. When the hole transport region HTR includes the electron blocking layer EBL, the electron blocking layer EBL may have a thickness of about 10 Å to about 1,000 Å. If the thicknesses of the hole transport region HTR, the hole injection layer HIL, the hole transport layer HTL and the electron blocking layer EBL satisfy the above-described respective ranges, satisfactory or suitable hole transport characteristic may be achieved without a substantial increase in a driving voltage.

As described above, the hole transport region HTR may further include at least one selected from the group consisting of the hole buffer layer and the electron blocking layer EBL, in addition to the hole injection layer HIL and the hole transport layer HTL. The hole buffer layer may compensate a resonance distance according to the wavelength of light emitted from the emission layer EML, and may thus increase light emission efficiency. Any of the materials which may be included in the hole transport region HTR may be used as materials to be included in the hole buffer layer. The electron blocking layer EBL is a layer that serves to prevent or reduce the injection of electrons from the electron transport region ETR to the hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed of a single material, a single layer formed of a plurality of different materials, or a multilayer structure having a plurality of layers formed of a plurality of different materials.

In the luminescence device ED of one or more embodiments, the emission layer EML may include a material selected from the group consisting of anthracene derivatives, pyrene derivatives, fluoranthene derivatives, chrysene derivatives, dehydrobenzanthracene derivatives, and triphenylene derivatives. For example, the emission layer EML may include anthracene derivative(s) and/or pyrene derivative(s).

In each luminescence device ED of embodiments illustrated in FIGS. 3 to 6, the emission layer EML may include a host and a dopant, and the emission layer EML may include a compound represented by Formula E-1 below. The compound represented by Formula E-1 below may be used as a fluorescence host material.

Formula E-1

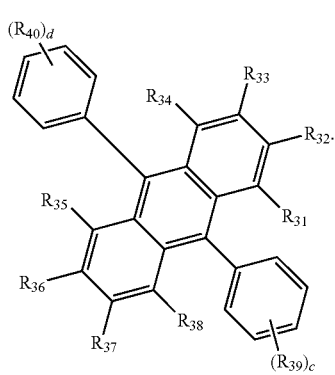

In Formula E-1, $R_{31}$ to $R_{40}$ may be each independently a hydrogen atom, a deuterium atom, a halogen atom, a substituted or unsubstituted silyl group, a substituted or unsubstituted alkyl group having 1 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. Any of $R_{31}$ to $R_{40}$ may be bonded to an adjacent group to form a saturated hydrocarbon ring or an unsaturated hydrocarbon ring.

In Formula E-1, c and d may be each independently an integer of 0 to 5.

Formula E-1 may be represented by any one among Compound E1 to Compound E19 below:

E1
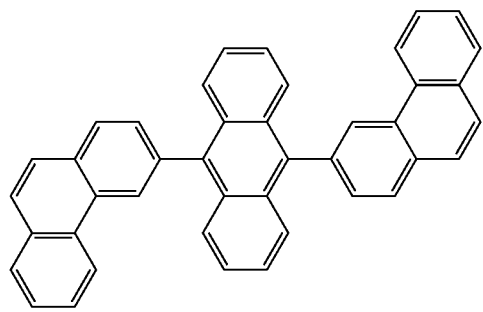

E2
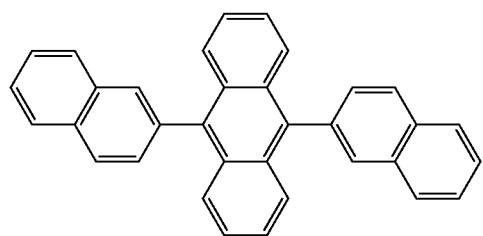

E3
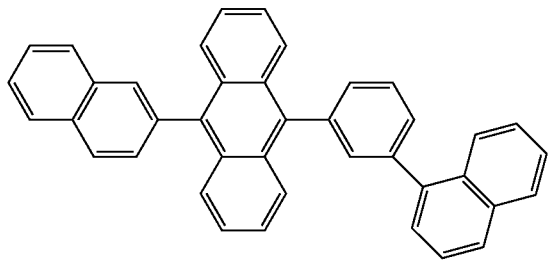

E4
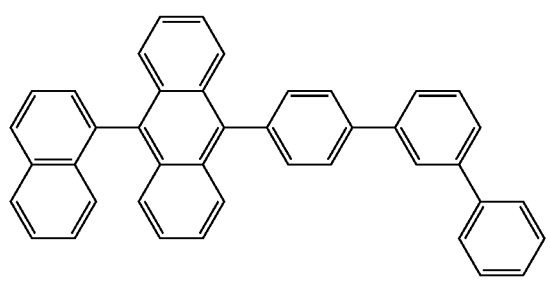

E5
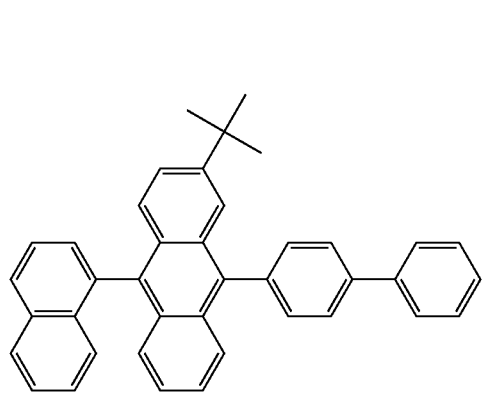

E6
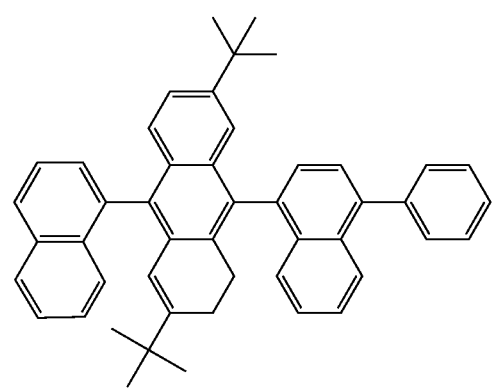
E7
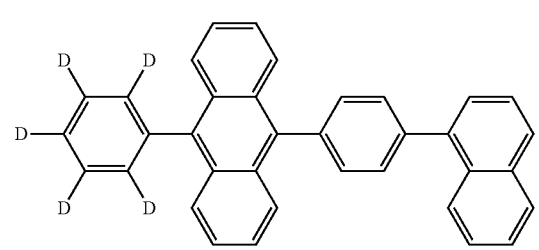
E8
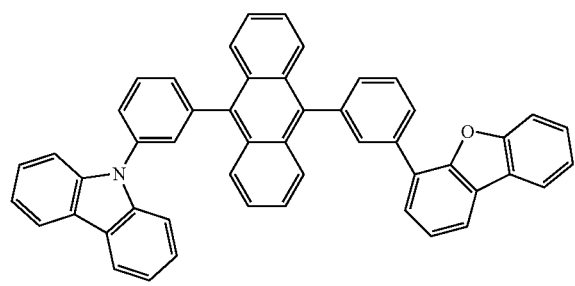
E9
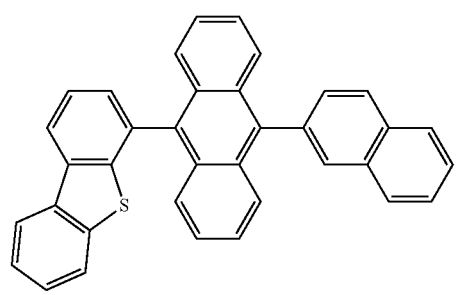
E10
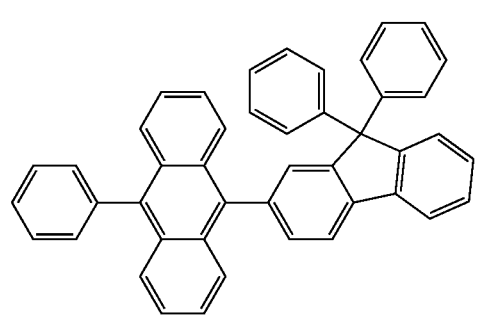
E11
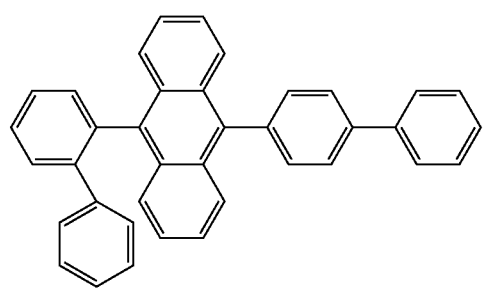
E12
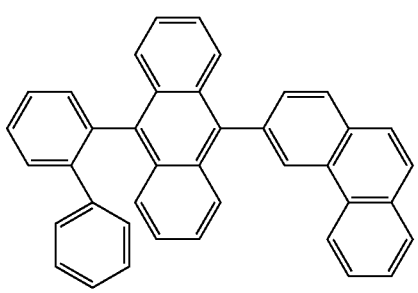
E13
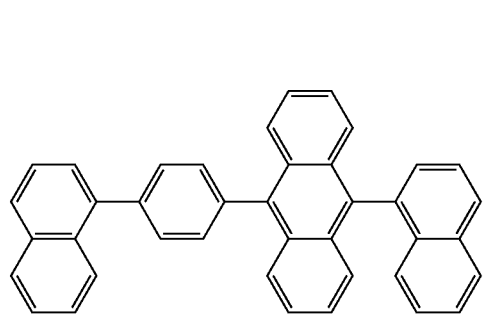
E14
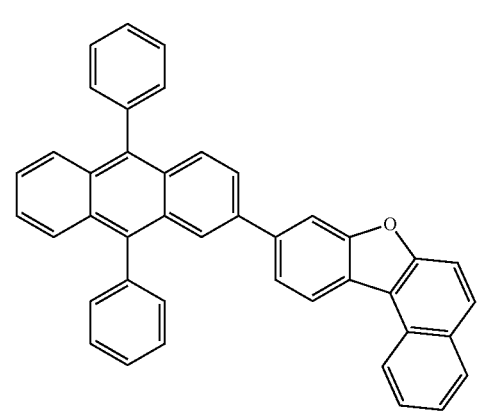

E15

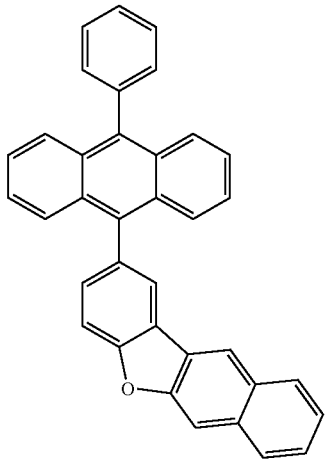

E16

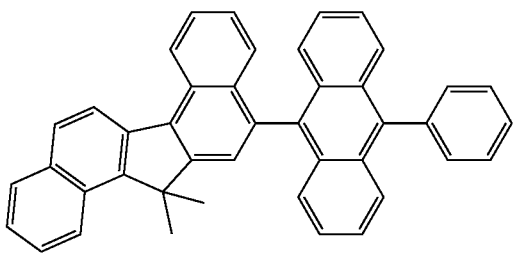

E17

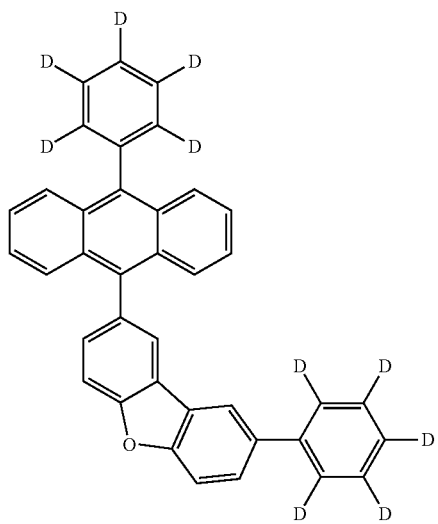

E18

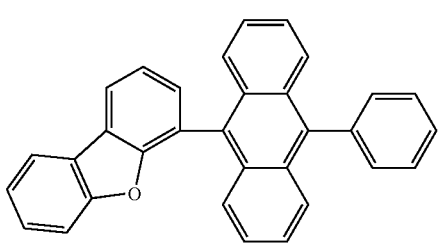

E19

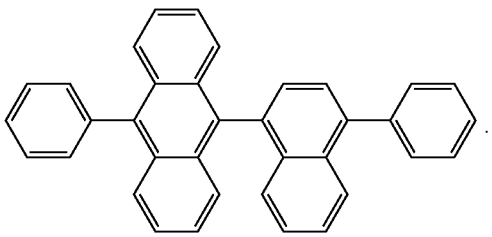

In one or more embodiments, the emission layer EML may include a compound represented by Formula E-2a or Formula E-2b below. The compound represented by Formula E-2a or Formula E-2b below may be used as a phosphorescence host material.

Formula E-2a

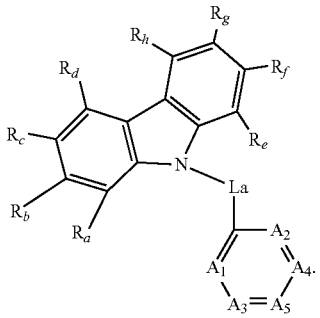

In Formula E-2a, $L_a$ may be a direct linkage, or a substituted or unsubstituted arylene group having 6 to 30 ring-forming carbon atoms. In one or more embodiments, in Formula E-2a, $A_1$ to $A_5$ may be each independently N or $CR_i$. $R_a$ to $R_i$ may be each independently a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. Any of $R_a$ to $R_i$ may be bonded to an adjacent group to form a hydrocarbon ring or a heterocycle containing N, O, S, etc. as a ring-forming atom.

In Formula E-2a, two or three selected from among $A_1$ to $A_5$ may be N, and the rest may be $CR_i$.

Formula E-2b $$(Cbz_1)\!\!-\!\!L_b\!\!-\!\!(Cbz_2).$$

In Formula E-2b, Cbz1 and Cbz2 may be each independently an unsubstituted carbazole group, or a carbazole group substituted with an aryl group having 6 to 30 ring-forming carbon atoms. $L_b$ may be a direct linkage, or a substituted or unsubstituted arylene group having 6 to 30 ring-forming carbon atoms.

The compound represented by Formula E-2a or Formula E-2b may be represented by any one among the compounds of Compound Group E-2 below. However, the compounds listed in Compound Group E-2 below are examples, and the compound represented by Formula E-2a or Formula E-2b is not limited to those represented by Compound Group E-2 below.
Compound Group E-2
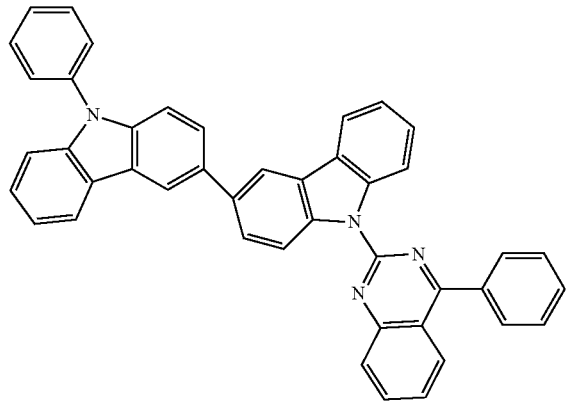
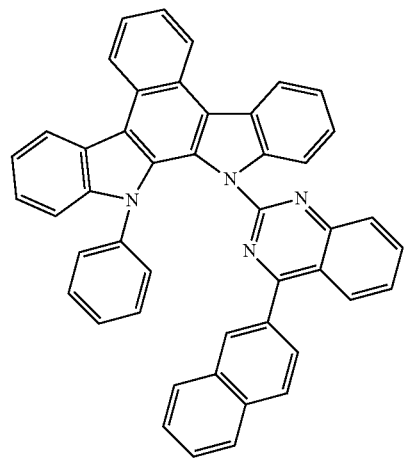
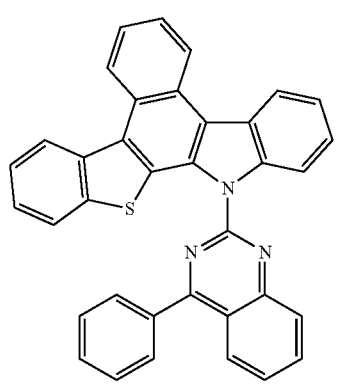
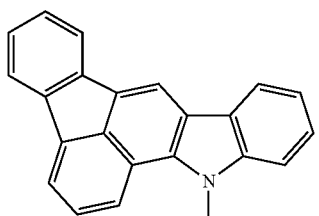
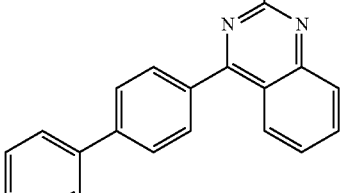
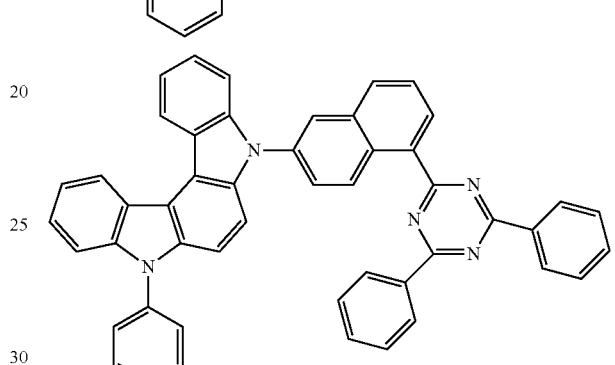
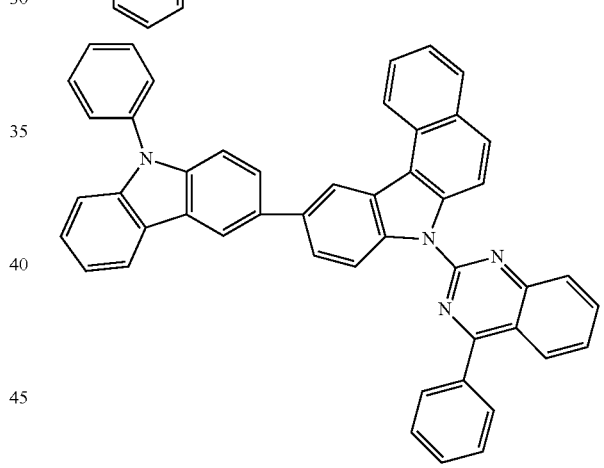
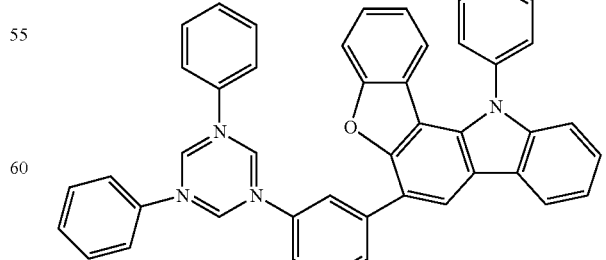

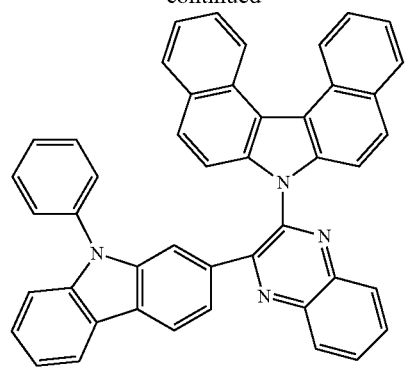
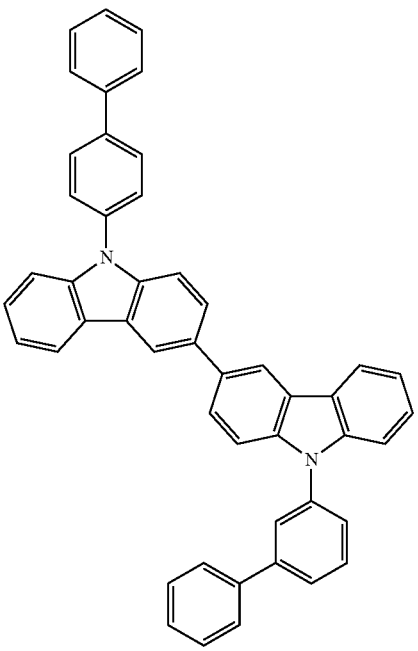
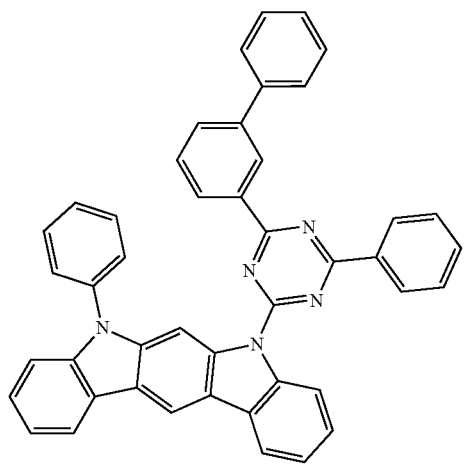
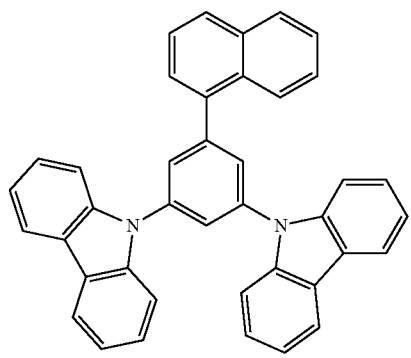
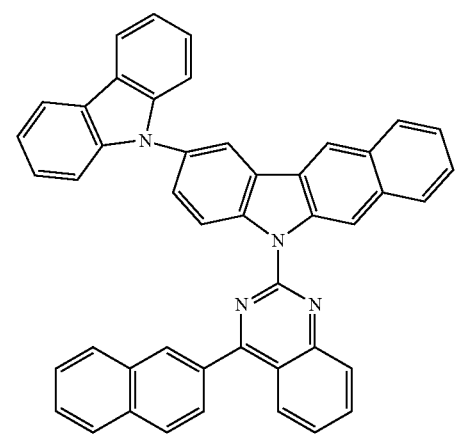
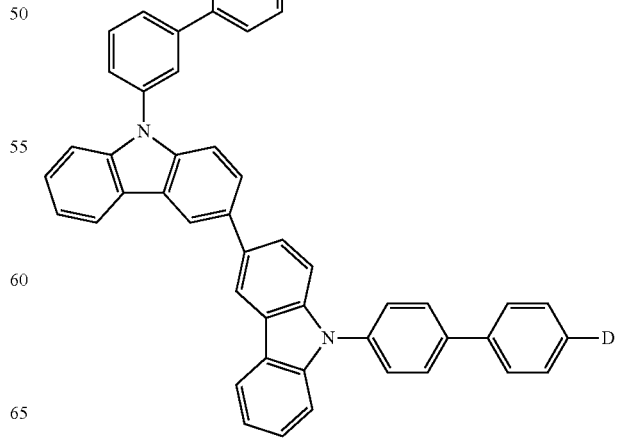

93
-continued
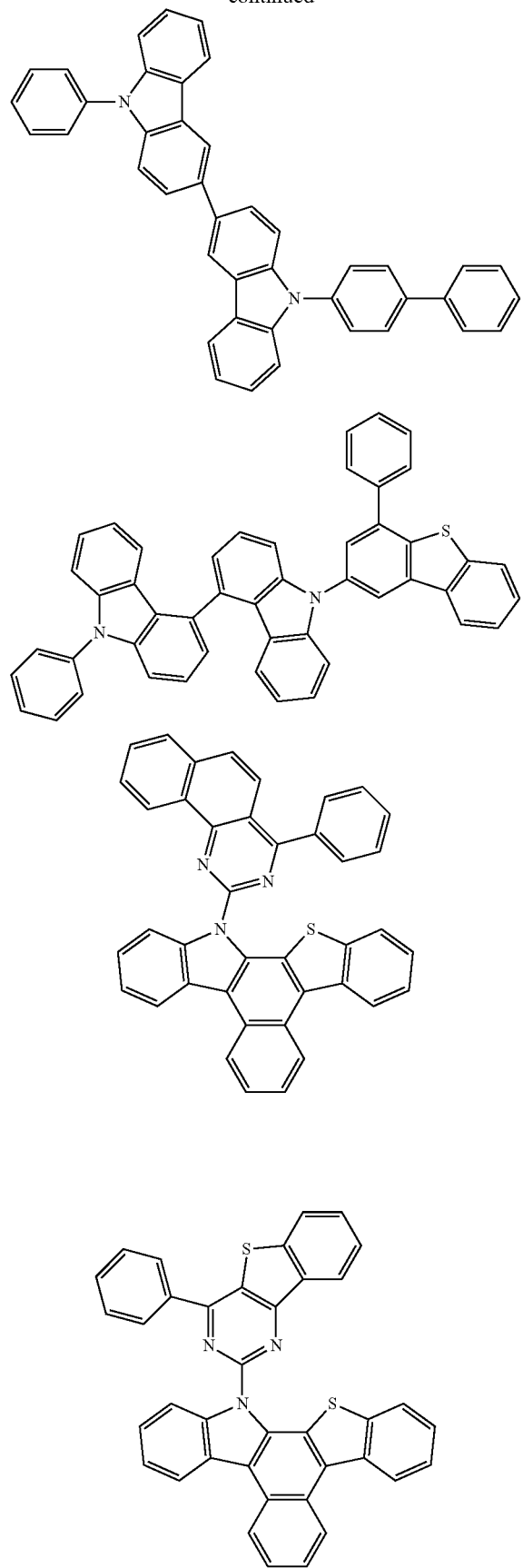
94
-continued
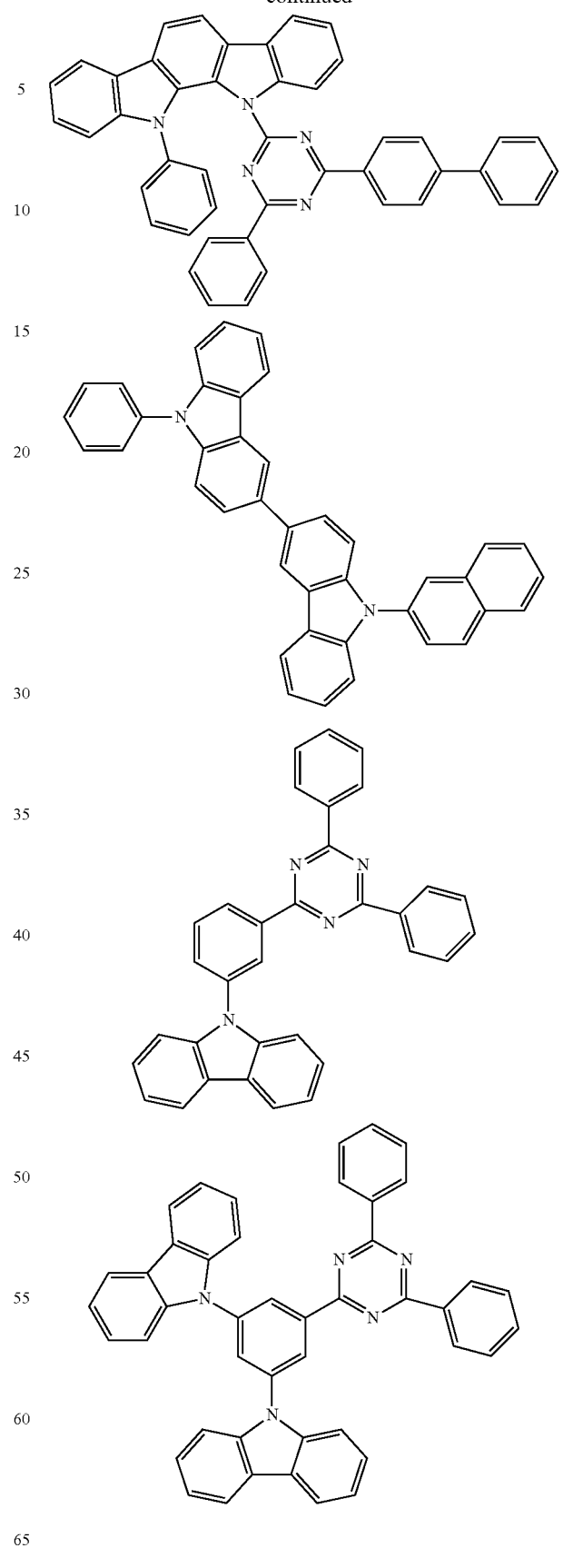

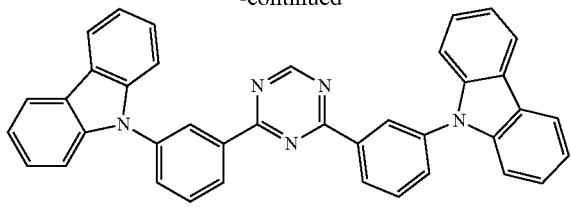

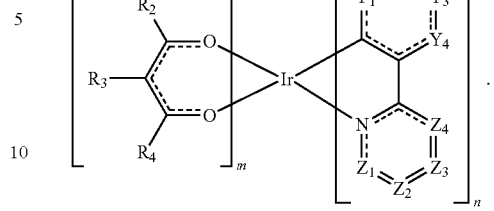

Formula M-a

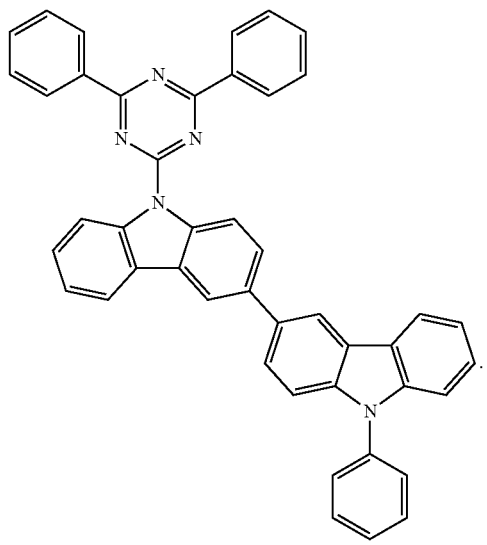

In Formula M-a above, $Y_1$ to $Y_4$ and $Z_1$ to $Z_4$ may be each independently $CR_1$ or N; $R_1$ to $R_4$ may be each independently a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula M-a, m is 0 or 1, and n is 2 or 3. In Formula M-a, when m is 0, n is 3, and when m is 1, n is 2.

The compound represented by Formula M-a may be used as a red phosphorescence dopant or a green phosphorescence dopant.

The emission layer EML may further include any suitable material as a host material. For example, the emission layer EML may include, as a host material, at least one selected from the group consisting of bis[2-(diphenylphosphino) phenyl] ether oxide (DPEPO), 4,4'-bis(N-carbazol-9-yl)-1, 1'-biphenyl (CBP), 1,3-bis(carbazol-9-yl)benzene (mCP), 2,8-bis(diphenyl phosphoryl)dibenzo[b,d]furan (PPF), 4,4', 4"-tris(carbazol-9-yl)-triphenylamine (TCTA), and 1,3,5-tris (1-phenyl-1H-benzo[d]imidazole-2-yl)benzene (TPBi). However, the embodiments of the present disclosure are not limited thereto, and for example, tris(8-hydroxyquinolino) aluminum (Alq3), poly(n-vinylcabazole) (PVK), 9,10-di (naphtha lene-2-yl)anthracene (ADN), 2-tert-butyl-9,10-di (naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis(triphenyls ilyl)benzene (UGH2), hexaphenylcyclotrisiloxane (DP-SiO3), octaphenylcyclotetra siloxane (DPSiO4), etc. may be used as a host material.

The emission layer EML may include a compound represented by Formula M-a or Formula M-b below. The compound represented by Formula M-a or Formula M-b below may be used as a phosphorescence dopant material.

The compound represented by Formula M-a may be represented by any one among Compound M-a1 to Compound M-a19 below. However, Compounds M-a1 to M-a19 below are examples, and the compound represented by Formula M-a is not limited to those represented by Compounds M-a1 to M-a19 below.

M-a1

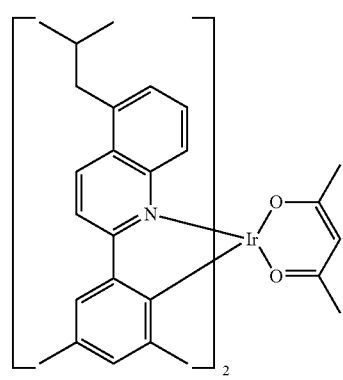

M-a2
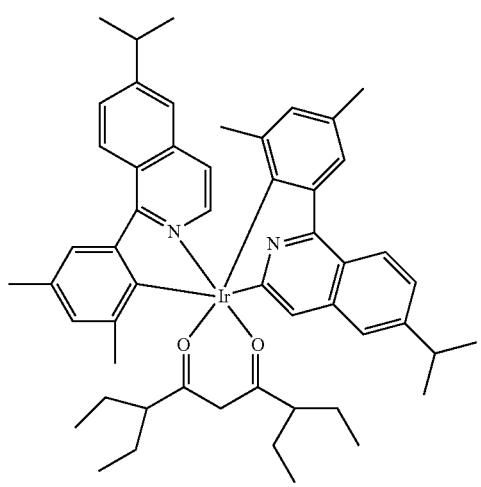
M-a3
M-a4
M-a5
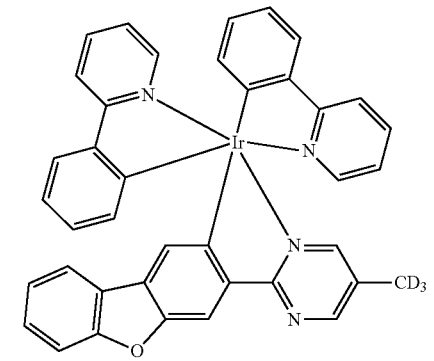
M-a6
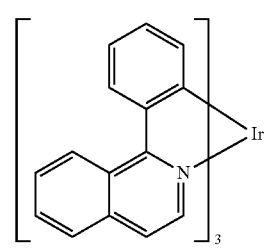
M-a7
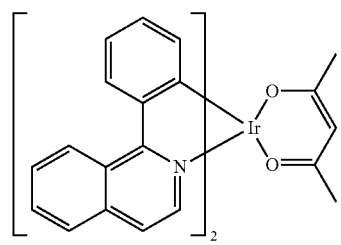
M-a8
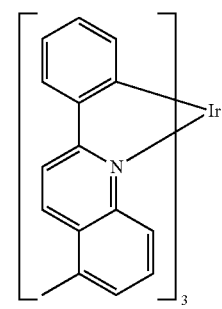
M-a9
M-a10
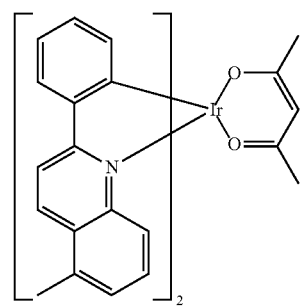

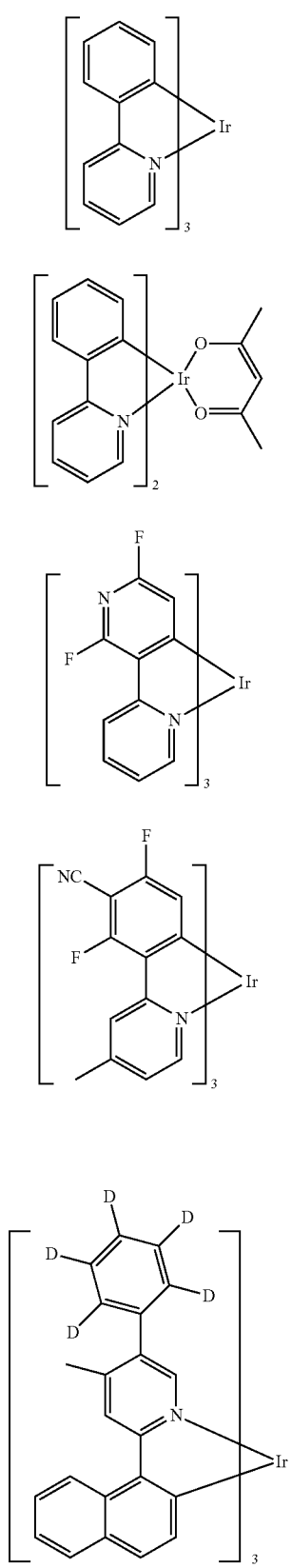
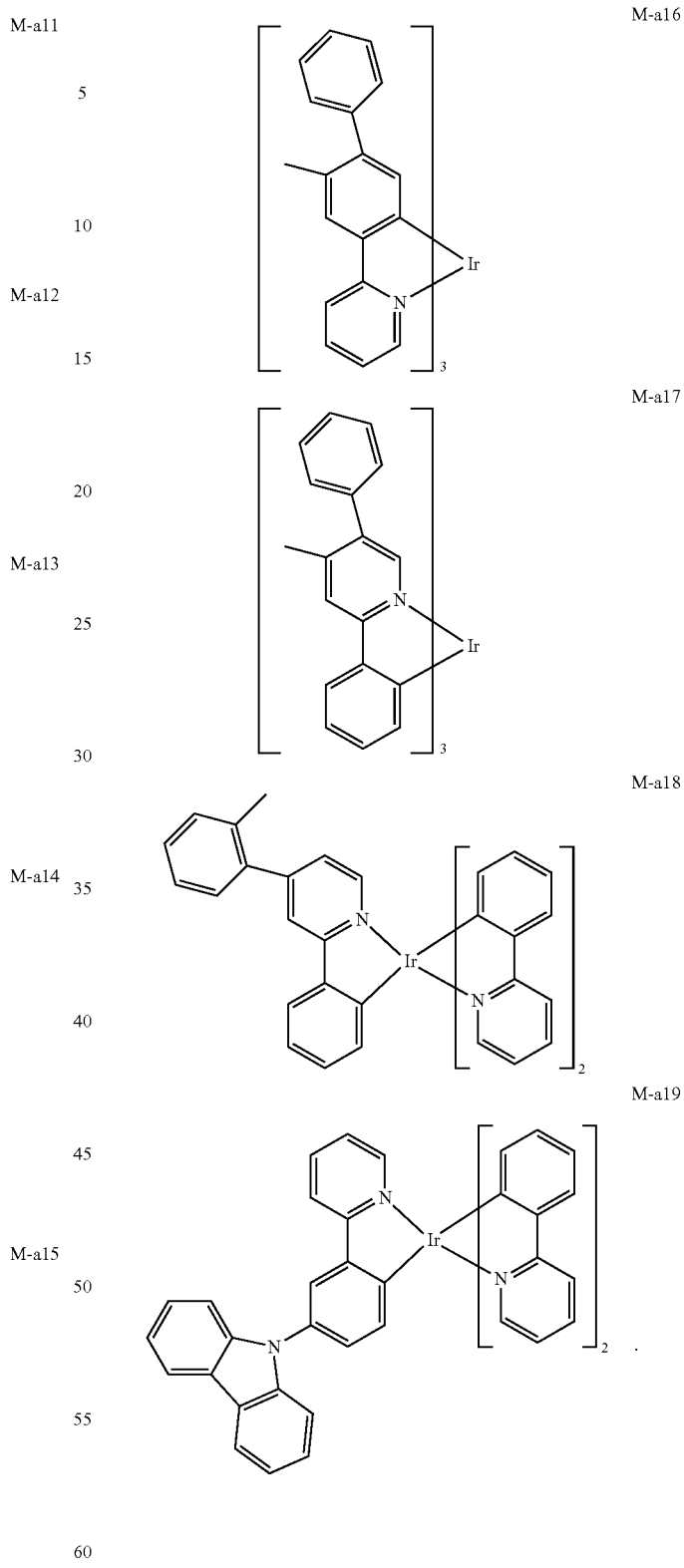
Compound M-a1 and Compound M-a2 may be used as a red dopant material, and Compound M-a3 and Compound M-a4 may be used as a green dopant material.

101

Formula M-b

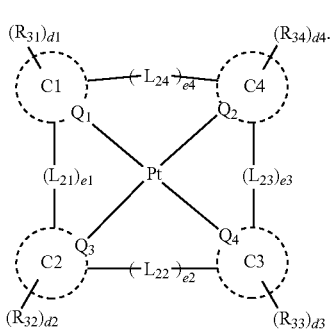

In Formula M-b, $Q_1$ to $Q_4$ may each independently be C or N; and $C_1$ to $C_4$ may each independently be a substituted or unsubstituted hydrocarbon ring having 5 to 30 ring-forming carbon atoms, or a substituted or unsubstituted heterocycle having 2 to 30 ring-forming carbon atoms. $L_{21}$ to $L_{24}$ may each independently be a direct linkage,

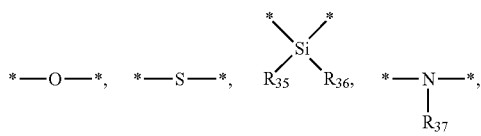

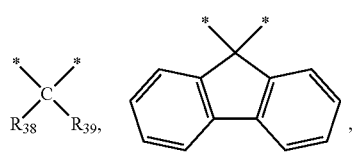

a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms; and e1 to e4 may each independently be 0 or 1. $R_{31}$ to $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring, and d1 to d4 may each independently be an integer of 0 to 4.

The compound represented by Formula M-b may be used as a blue phosphorescence dopant or a green phosphorescence dopant.

The compound represented by Formula M-b may be represented by any one among the compounds below. However, the compounds below are examples, and the compound represented by Formula M-b is not limited to those represented by the compounds below.

102

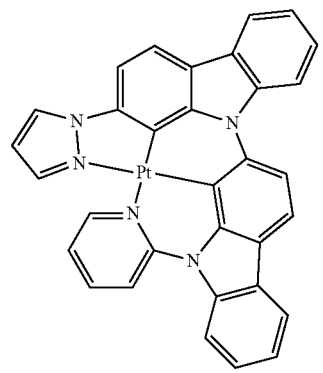

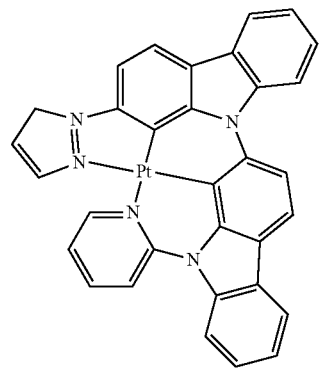

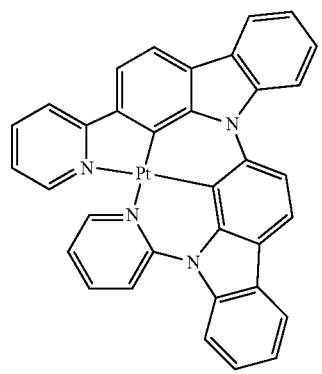

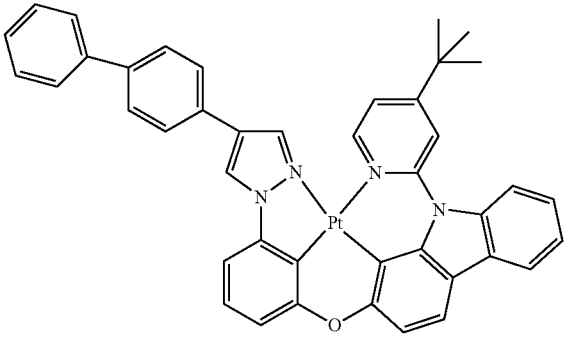

103
-continued

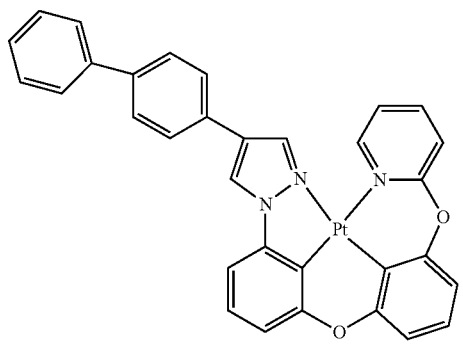

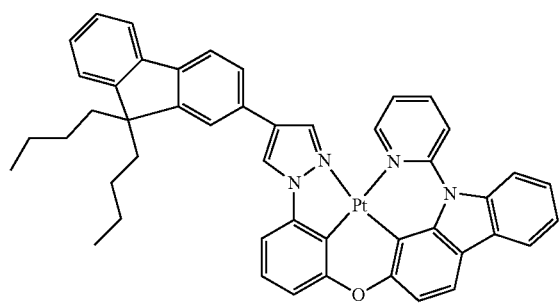

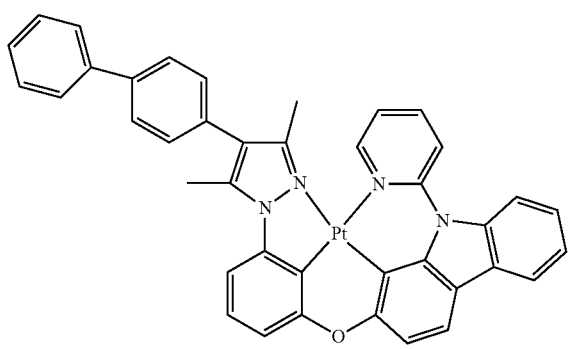

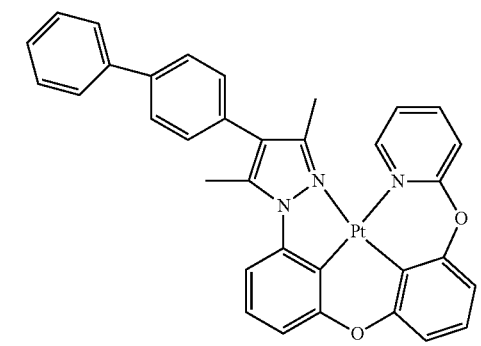

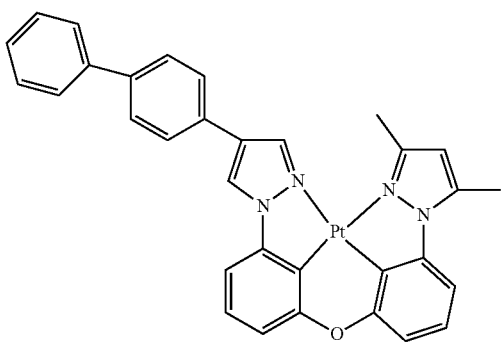

104
-continued

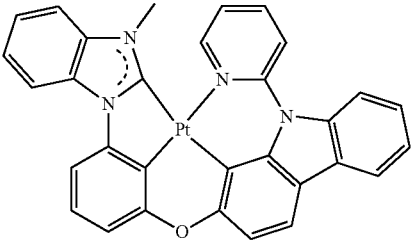

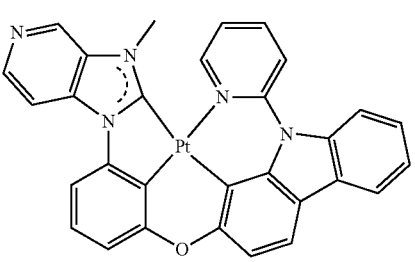

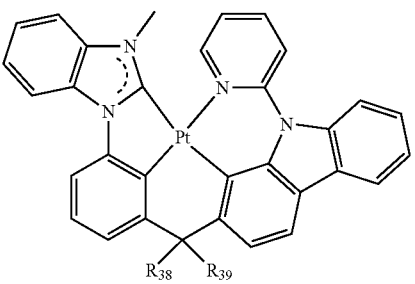

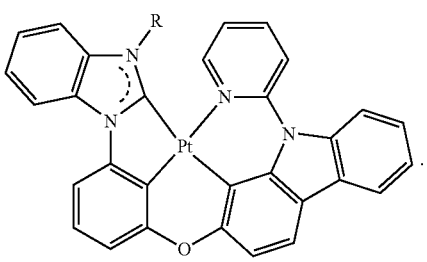

In the compounds included in the emission layer EML, R-substituents, $R_{38}$, and $R_{39}$ may be each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

The emission layer EML may include a compound represented by any one among Formula F-a to Formula F-c below. The compound represented by Formula F-a or Formula F-c below may be used as a fluorescence dopant material.

Formula F-a

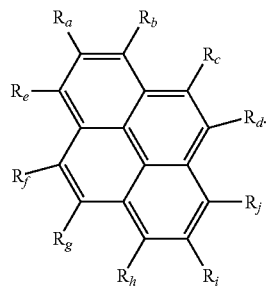

In Formula F-a, two selected from among $R_a$ to $R_j$ may each independently be substituted with *—$NAr_1Ar_2$. The others, which are not substituted with *—$NAr_1Ar_2$, among $R_a$ to $R_j$ may be each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In *—$NAr_1Ar_2$, $Ar_1$, and $Ar_2$ may be each independently a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group containing O or S as a ring-forming atom.

Formula F-b

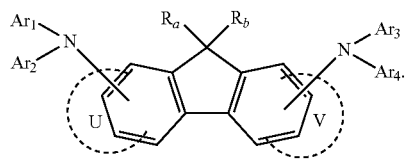

In Formula F-b, $R_a$ and $R_b$ may be each independently a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-b, U and V may be each independently a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may be each independently 0 or 1. For example, in Formula F-b, when the number of U or V is 1, one ring forms a condensed ring at a part described as U or V, and when the number of U or V is 0, a ring described as U or V is not present. For example, when the number of U is 0 and the number of V is 1, or when the number of U is 1 and the number of V is 0, the condensed ring having a fluorene core of Formula F-b may be a four-ring cyclic compound (e.g., a benzofluorene moiety). In one or more embodiments, when each number of U and V is 0, the condensed ring of Formula F-b may be a three-ring cyclic compound (e.g., a fluorene moiety). In one or more embodiments, when each number of U and V is 1, the condensed ring having a fluorene core of Formula F-b may be a five-ring cyclic compound (e.g., a dibenzofluorene moiety).

Formula F-c

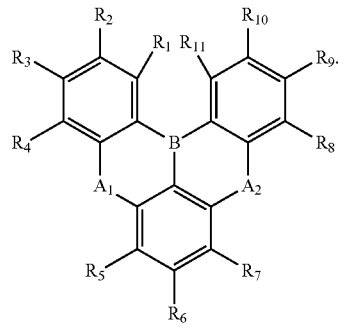

In Formula F-c, $A_1$ and $A_2$ may be each independently O, S, Se, or $NR_m$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $R_1$ to $R_{11}$ may be each independently a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

In Formula F-c, $A_1$ and $A_2$ may each independently be bonded to substituents of an adjacent ring to form a condensed ring. For example, when $A_1$ and $A_2$ are each independently $NR_m$, $A_1$ may be bonded to $R_4$ or $R_5$ to form a ring. In one or more embodiments, $A_2$ may be bonded to $R_7$ or $R_8$ to form a ring.

In one or more embodiments, the emission layer EML may include, as dopant material(s), styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino) styryl)naphthalen-2-yl)vinyl)phenyl)-N-phenylbenzenamine (N-BDAVBi)), perylene and/or the derivatives thereof (e.g., 2,5,8,11-tetra-t-butylperylene (TBP)), pyrene and/or the derivatives thereof (e.g., 1-dipyrene, 1,4-dipyrenylbenzene, and/or 1,4-bis(N,N-diphenylamino)pyrene), etc.

The emission layer EML may include a suitable phosphorescence dopant material. For example, a metal complex including iridium (Ir), platinum (Pt), osmium (Os), aurum (Au), titanium (Ti), zirconium (Zr), hafnium (Hf), europium (Eu), terbium (Tb), and/or thulium (Tm) may be used as a phosphorescence dopant. For example, iridium(III) bis(4,6-difluorophenylpyridinato-N,C2') (Firpic), bis(2,4-difluorophenylpyridinato)-tetrakis(1-pyrazolyl)borate iridium(III) (Fir6), and/or platinum octaethyl porphyrin (PtOEP) may be used as a phosphorescence dopant. However, the embodiments of the present disclosure are not limited thereto.

The emission layer EML may include a quantum dot material. The core of the quantum dot may be selected from among a Group II-VI compound, a Group III-V compound, a Group IV-VI compound, a Group IV element, a Group IV compound, and a combination thereof.

A Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound such as $In_2S3$ and/or $In_2Se_3$; a ternary compound such as $InGaS_3$ and/or $InGaSe_3$; or any combination thereof.

A Group I-III-VI compound may be selected from the group consisting of a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, and a mixture thereof; and a quaternary compound such as $AgInGaS_2$ and/or $CuInGaS_2$.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof; and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. The Group III-V compound may further include a Group II metal. For example, InZnP, etc. may be selected as a Group III-II-V compound.

The Group IV-VI compound may be selected from the group consisting of a binary compound selected from the group consisting of SnS, SnSe, SnTe, PbS, PbSe, PbTe, and a mixture thereof; a ternary compound selected from the group consisting of SnSeS, SnSeTe, SnSTe, PbSeS, PbSeTe, PbSTe, SnPbS, SnPbSe, SnPbTe, and a mixture thereof; and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

A binary compound, a ternary compound, and/or a quaternary compound may be present in particles in a uniform concentration distribution, or may be present in the same particle in a partially different concentration distribution. In one or more embodiments, the quantum dot may have a core/shell structure in which one quantum dot surrounds another quantum dot. An interface between the core and the shell may have a concentration gradient in which the concentration of an element present in the shell becomes lower towards the center.

In some embodiments, a quantum dot may have the above-described core-shell structure including a core having nanocrystals and a shell surrounding (e.g., around) the core. The shell of the quantum dot may serve as a protection layer to prevent or reduce the chemical deformation of the core so as to maintain semiconductor properties, and/or a charging layer to impart electrophoresis properties to the quantum dot. The shell may be a single layer or a multilayer. An interface between the core and the shell may have a concentration gradient in which the concentration of an element present in the shell becomes lower towards the center. An example of the shell of the quantum dot may include a metal a metal oxide, a non-metal oxide, a semiconductor compound, or a combination thereof.

For example, the metal or non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $CO_3O_4$, and/or NiO; and/or a ternary compound such as $MgAl_2O_4$, $CoFe_2O_4$, $NiFe_2O_4$, and/or $CoMn_2O_4$, but the embodiments of the present disclosure are not limited thereto.

In one or more embodiments, the semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but the embodiments of the present disclosure are not limited thereto.

The quantum dot may have a full width of half maximum (FWHM) of a light emission wavelength spectrum of about 45 nm or less, for example about 40 nm or less, or about 30 nm or less, and color purity or color reproducibility may be improved in any of the above ranges. In one or more embodiments, light emitted through such a quantum dot is emitted in all directions, and thus a wide viewing angle may be improved.

In one or more embodiments, although the form of a quantum dot is not particularly limited as long as it is a suitable form, for example, a quantum dot in the form of spherical, pyramidal, multi-arm, and/or cubic nanoparticles, nanotubes, nanowires, nanofibers, nanoparticles, etc. may be used.

The quantum dot may control the color of emitted light according to the particle size thereof. Accordingly, the quantum dot may have various light emission colors such as blue, red, and/or green.

In each luminescence device ED of embodiments illustrated in FIGS. 3 to 6, the electron transport region ETR is provided on the emission layer EML. The electron transport region ETR may include at least one selected from the group consisting of the hole blocking layer HBL, the electron transport layer ETL, and the electron injection layer EIL, but the embodiments of the present disclosure are not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of the electron injection layer EIL or the electron transport layer ETL, or may have a single layer structure formed of an electron injection material and an electron transport material. In one or more embodiments, the electron transport region ETR may have a single layer structure formed of a plurality of different materials, or may have a structure in which an electron transport layer ETL/ electron injection layer EIL, or a hole blocking layer HBL/ electron transport layer ETL/electron injection layer EIL are stacked in the stated order from the emission layer EML, but the embodiments of the present disclosure are not limited thereto. The electron transport region ETR may have a thickness, for example, from about 300 Å to about 1,500 Å.

The electron transport region ETR may be formed by using one or more suitable methods such as a vacuum deposition method, a spin coating method, a cast method, a Langmuir-Blodgett (LB) method, an inkjet printing method, a laser printing method, a laser induced thermal imaging (LITI) method, etc.

The electron transport layer ETL may include a compound represented by Formula ET-1 below:

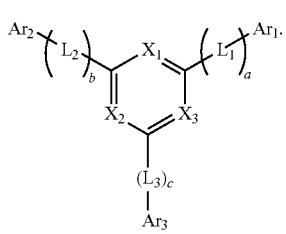

Formula ET-1

In Formula ET-1, at least one among $X_1$ to $X_3$ is N, and the rest are $CR_a$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $Ar_1$ to $Ar_3$ may be each independently a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may be each independently an integer of 0 to 10. In Formula ET-1, $L_1$ to $L_3$ may be each independently a direct linkage, a substituted or unsubstituted arylene group having 6 to 30 ring-forming carbon atoms, or a substituted or unsubstituted heteroarylene group having 2 to 30 ring-forming carbon atoms. When a to c are each independently an integer of 2 or more, the respective $L_1$ to $L_3$ may be each independently a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, the embodiments of the present disclosure are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate ($Bebq_2$), 9,10-di(naphthalene-2-yl)anthracene (ADN), 1,3-Bis[3,5-di(pyridin-3-yl)phenyl]benzene (BmPyPhB), or a mixture thereof.

In one or more embodiments, the electron transport region ETR may include a metal halide (such as LiF, NaCl, CsF, RbCl, RbI, CuI, and/or KI), a lanthanide metal (such as Yb), and/or a co-deposited material of the metal halide and the lanthanide metal. For example, the electron transport region ETR may include KI:Yb, RbI:Yb, etc. as a co-deposited material. In one or more embodiments, the electron transport region ETR may be formed using a metal oxide such as $Li_2O$ and/or BaO, or 8-hydroxyl-lithium quinolate (Liq), etc., but the embodiments of the present disclosure are not limited thereto. The electron transport region ETR may also be formed of a mixture material of an electron transport material and an insulating organometallic salt. The organometallic salt may be a material having an energy band gap of about 4 eV or more. For example, the organometallic salt may include metal acetates, metal benzoates, metal acetoacetates, metal acetylacetonates, and/or metal stearates, but the embodiments of the present disclosure are not limited thereto.

The electron transport region ETR may include any of the above-described compounds of the electron transport region in at least one selected from the group consisting of the electron injection layer EIL, the electron transport layer ETL, and the hole blocking layer HBL.

When the electron transport region ETR includes the electron transport layer ETL, the electron transport layer ETL may have a thickness of about 100 Å to about 1,000 Å, for example, about 150 Å to about 500 Å. If the thickness of the electron transport layer ETL satisfies any of the aforementioned ranges, satisfactory or suitable electron transport characteristics may be obtained without a substantial increase in driving voltage. When the electron transport region ETR includes the electron injection layer EIL, the electron injection layer EIL may have a thickness of about 1 Å to about 100 Å, for example, about 3 Å to about 90 Å. If the thickness of the electron injection layer EIL satisfies any of the above-described ranges, satisfactory or suitable electron injection characteristics may be obtained without a substantial increase in driving voltage.

The second electrode EL2 is provided on the electron transport region ETR. The second electrode EL2 may be a common electrode. The second electrode EL2 may be a cathode or an anode, but the embodiments of the present disclosure are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is the transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, or a compound or mixture thereof (e.g., AgMg, AgYb, and/or MgAg). In one or more embodiments, the second electrode EL2 may have a multi-layer structure including a reflective layer or a transflective layer formed of any of the above-described materials, and a transparent conductive layer formed of ITO, IZO, ZnO, ITZO, etc. For example, the second electrode EL2 may include any of the above-described metal materials, combination of at least two metal materials of the above-described metal materials, oxide(s) of the above-described metal materials, and/or the like.

In one or more embodiments, the second electrode EL2 may be connected with an auxiliary electrode. If the second electrode EL2 is connected with the auxiliary electrode, the resistance of the second electrode EL2 may decrease.

In one or more embodiments, the capping layer CPL may further be disposed on the second electrode EL2 of the luminescence device ED of one or more embodiments. The capping layer CPL may include a multilayer or a single layer.

In one or more embodiments, the capping layer CPL may be an organic layer or an inorganic layer. For example, when the capping layer CPL includes an inorganic material, the inorganic material may include an alkaline metal compound such as LiF, an alkaline earth metal compound such as $MgF_2$, SiON, $SiN_x$, and/or SiOy, etc.

For example, when the capping layer CPL includes an organic material, the organic material may include α-NPD, NPB, TPD, m-MTDATA, $Alq_3$, CuPc, N4,N4,N4',N4'-tetra(biphenyl-4-yl)biphenyl-4,4'-diamine (TPD15), 4,4', 4"-tris(carbazol sol-9-yl)triphenylamine (TCTA), etc.; an epoxy resin; and/or acrylate such as methacrylate. However, the embodiments of the present disclosure are not limited thereto, and the organic material may also include any of Compounds P1 to P5 below:

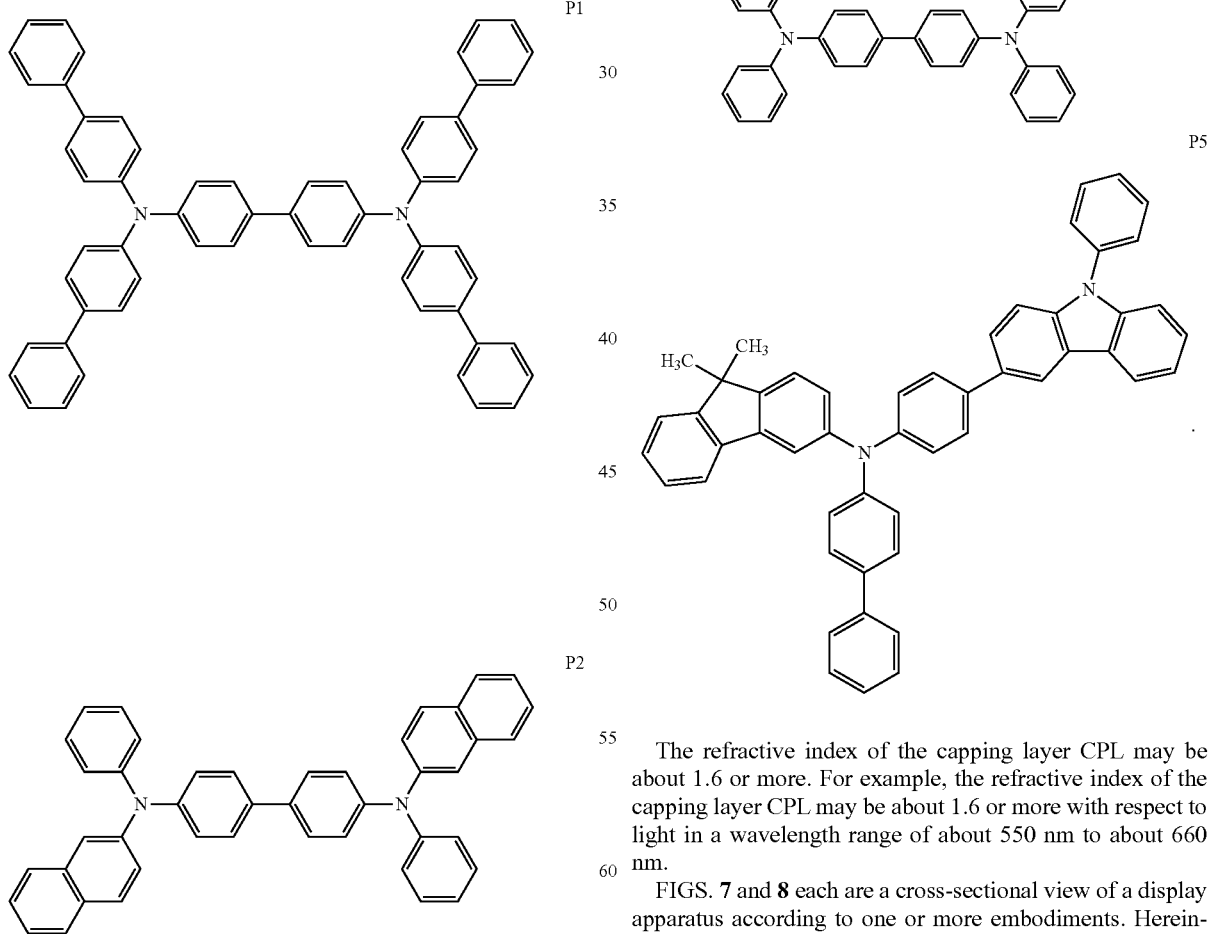

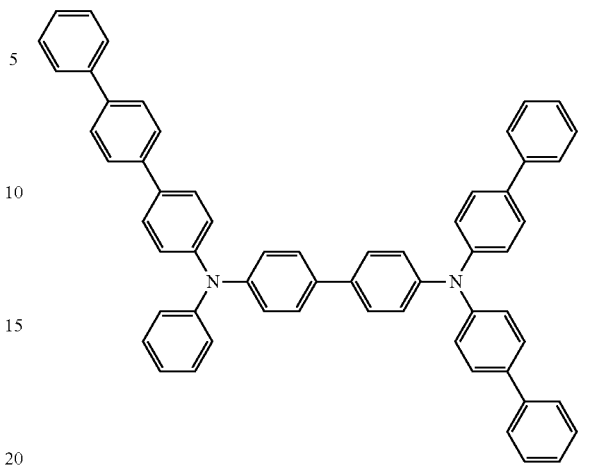

The refractive index of the capping layer CPL may be about 1.6 or more. For example, the refractive index of the capping layer CPL may be about 1.6 or more with respect to light in a wavelength range of about 550 nm to about 660 nm.

Figure 7:
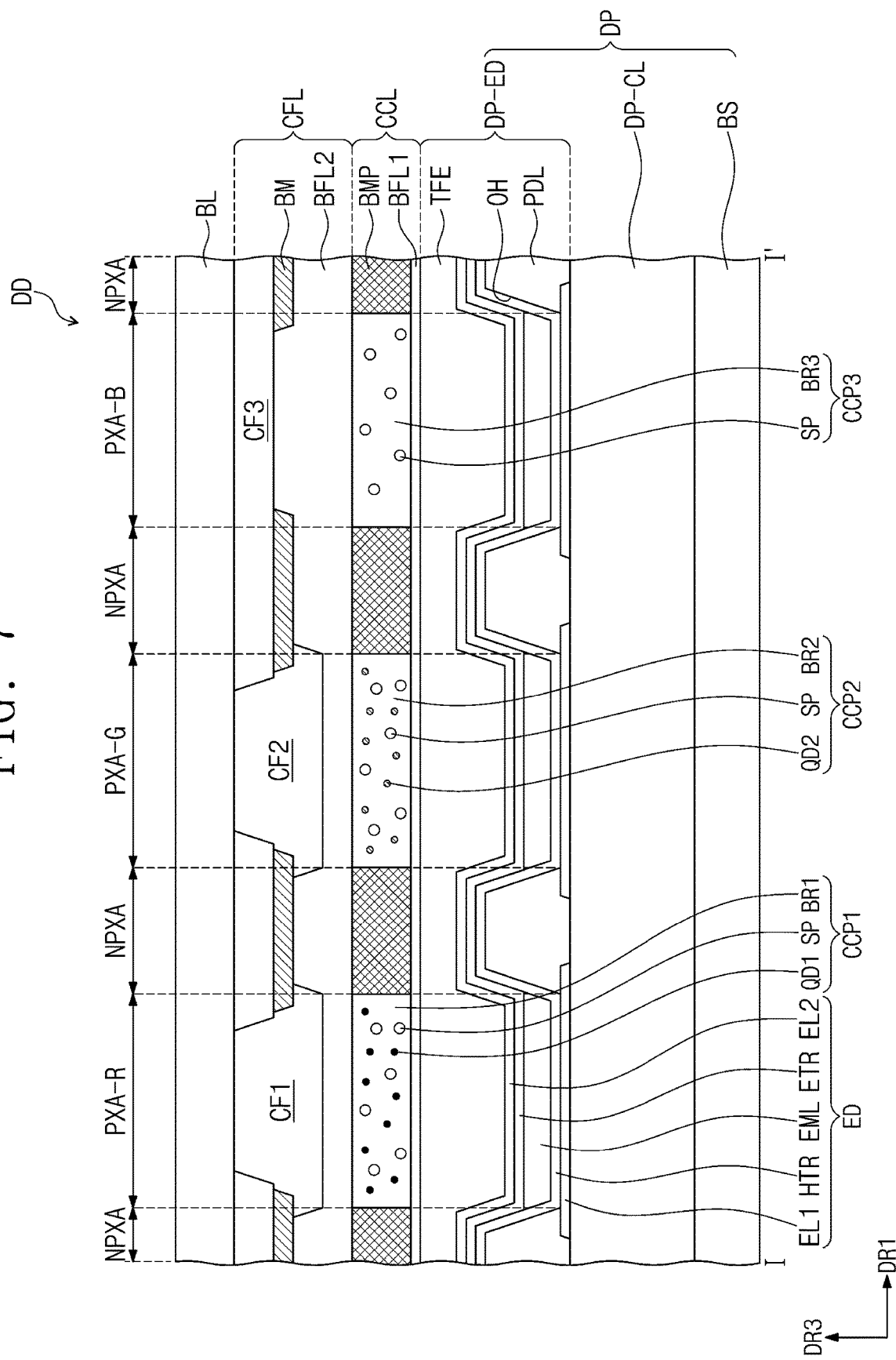
FIG. 7 is a cross-sectional view of a display apparatus according to one or more embodiments of the present disclosure.
Figure 8:
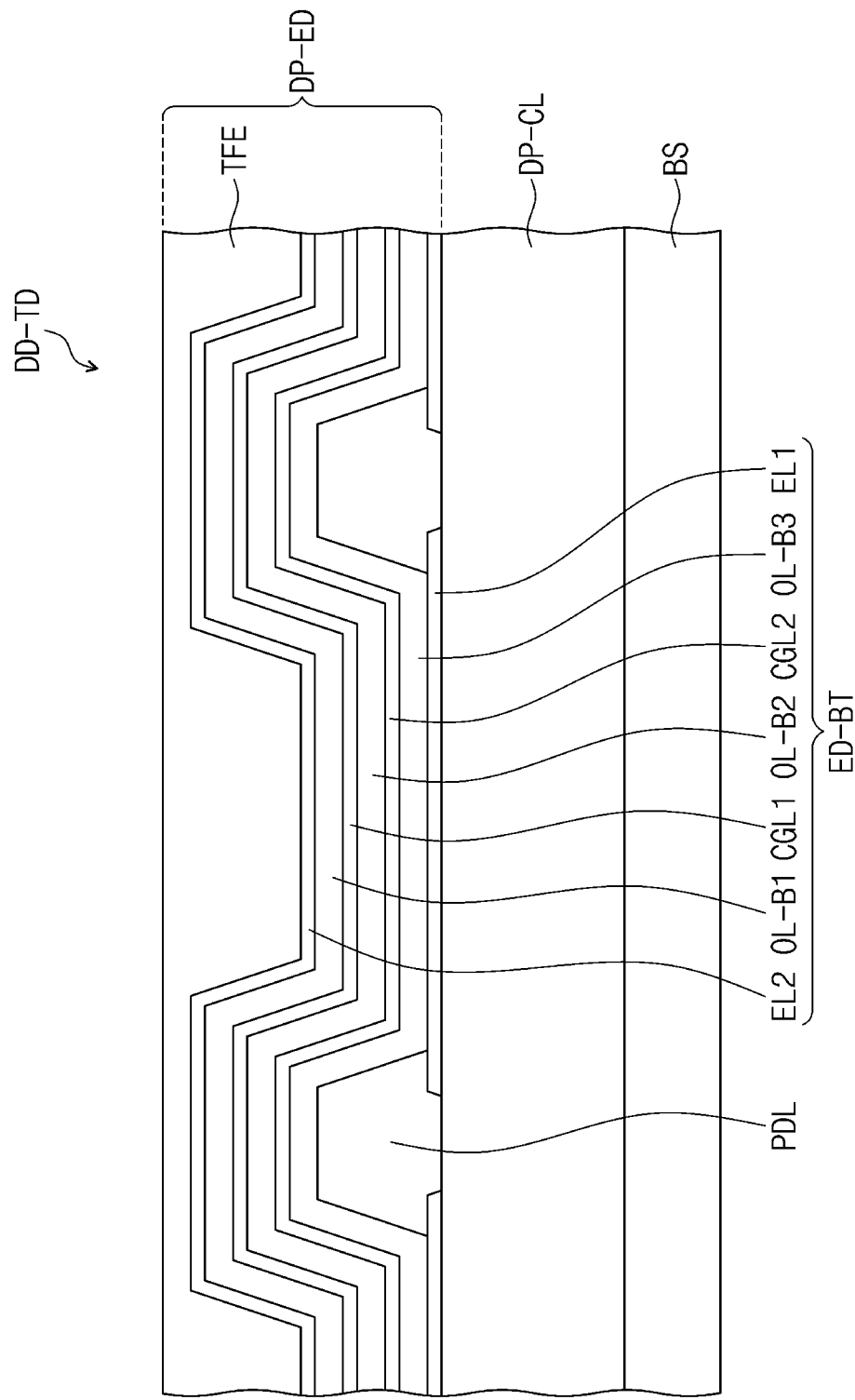
FIG. 8 is a cross-sectional view of a display apparatus according to one or more embodiments of the present disclosure.

FIGS. 7 and 8 each are a cross-sectional view of a display apparatus according to one or more embodiments. Hereinafter, in describing the display apparatus of one or more embodiments with reference to FIGS. 7 and 8, the features which have already been described in FIGS. 1 to 6 are not described again, but the differences will be mainly described.

Referring to FIG. 7, the display apparatus DD according to one or more embodiments may include a display panel DP including a display device layer DP-ED, a light control layer CCL disposed on the display panel DP, and a color filter layer CFL.

In one or more embodiments illustrated in FIG. 7, the display panel DP may include a base layer BS, a circuit layer DP-CL provided on the base layer BS, and the display device layer DP-ED, and the display device layer DP-ED may include a luminescence device ED.

The luminescence device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. In one or more embodiments, the structures of the luminescence devices of FIGS. 4 to 6 as described above may be equally applied to the structure of the luminescence device ED shown in FIG. 7.

Referring to FIG. 7, the emission layer EML may be disposed in an opening OH defined in a pixel defining film PDL. For example, the emission layer EML, which is divided by the pixel defining film PDL and provided corresponding to each light emitting regions PXA-R, PXA-G, and PXA-B, may emit light in the same wavelength range. In the display apparatus DD of one or more embodiments, the emission layer EML may emit blue light. In one or more embodiments, the emission layer EML may be provided as a common layer in (e.g., through) the entire light emitting regions PXA-R, PXA-G, and PXA-B.

The light control layer CCL may be disposed on the display panel DP. The light control layer CCL may include a light conversion body. The light conversion body may be a quantum dot, a phosphor, and/or the like. The light conversion body may emit provided light by converting the wavelength thereof. For example, the light control layer CCL may be a layer containing the quantum dot or a layer containing the phosphor.

The light control layer CCL may include a plurality of light control units CCP1, CCP2 and CCP3. The light control units CCP1, CCP2, and CCP3 may be spaced apart from one another (in a plan view).

Referring to FIG. 7, divided patterns BMP may be disposed between the light control units CCP1, CCP2 and CCP3 which are spaced apart from each other, but the embodiments of the present disclosure are not limited thereto. FIG. 7 illustrates that the divided patterns BMP do not overlap the light control units CCP1, CCP2 and CCP3, but at least a portion of the edges of the light control units CCP1, CCP2 and CCP3 may be defined (e.g., overlap) the divided patterns BMP.

The light control layer CCL may include a first light control unit CCP1 containing a first quantum dot QD1, which converts (or is to convert) first color light provided from the luminescence device ED into second color light, a second light control unit CCP2 containing a second quantum dot QD2 which converts (or is to convert) the first color light into third color light, and a third light control unit CCP3 which transmits (or is to transmit) the first color light.

In one or more embodiments, the first light control unit CCP1 may provide red light that is the second color light, and the second light control unit CCP2 may provide green light that is the third color light. The third light control unit CCP3 may transmit blue light that is the first color light provided in the luminescence device ED. For example, the first quantum dot QD1 may be a red quantum dot, and the second quantum dot QD2 may be a green quantum dot. The same description as provided above may be applied with respect to the quantum dots QD1 and QD2.

In one or more embodiments, the light control layer CCL may further include a scatterer SP. The first light control unit CCP1 may include the first quantum dot QD1 and the scatterer SP, the second light control unit CCP2 may include the second quantum dot QD2 and the scatterer SP, and the third light control unit CCP3 may not include any quantum dot but include the scatterer SP.

The scatterer SP may be inorganic particles. For example, the scatterer SP may include at least one selected from the group consisting of $TiO_2$, ZnO, $Al_2O_3$, $SiO_2$, and hollow silica. The scatterer SP may include any one of $TiO_2$, ZnO, $Al_2O_3$, $SiO_2$, or hollow silica, or may be a mixture of at least two materials selected from among $TiO_2$, ZnO, $Al_2O_3$, $SiO_2$, and hollow silica.

The light control layer CCL may include a barrier layer BFL1. The barrier layer BFL1 may serve to prevent or reduce the penetration of moisture and/or oxygen (hereinafter, referred to as 'moisture/oxygen'). The barrier layer BFL1 may be disposed on the light control units CCP1, CCP2, and CCP3 to block or reduce the light control units CCP1, CCP2 and CCP3 from being exposed to moisture/oxygen. The barrier layer BFL1 may cover the light control units CCP1, CCP2, and CCP3. In one or more embodiments, the barrier layer BFL2 may be provided between the light control units CCP1, CCP2, and CCP3 and the color filter layer CFL.

The barrier layers BFL1 and BFL2 may include at least one inorganic layer. For example, the barrier layers BFL1 and BFL2 may each independently include an inorganic material. For example, the barrier layers BFL1 and BFL2 may include a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride, any suitable metal thin film which secures a transmittance, etc. In one or more embodiments, the barrier layers BFL1 and BFL2 may each independently further include an organic film. The barrier layers BFL1 and BFL2 may each independently be formed of a single layer or a plurality of layers.

In the display apparatus DD of one or more embodiments, the color filter layer CFL may be disposed on the light control layer CCL. For example, the color filter layer CFL may be directly disposed on the light control layer CCL. In this case, the barrier layer BFL2 may be omitted.

The color filter layer CFL may include a light shielding unit BM and filters CF1, CF2, and CF3. The color filter layer CFL may include a first filter CF1 configured to transmit the second color light, a second filter CF2 configured to transmit the third color light, and a third filter CF3 configured to transmit the first color light. For example, the first filter CF1 may be a red filter, the second filter CF2 may be a green filter, and the third filter CF3 may be a blue filter. The filters CF1, CF2, and CF3 each may include a polymeric photosensitive resin and a pigment and/or dye. The first filter CF1 may include a red pigment and/or dye, the second filter CF2 may include a green pigment and/or dye, and the third filter CF3 may include a blue pigment and/or dye. However, the embodiments of the present disclosure are not limited thereto, and the third filter CF3 may not include a pigment or dye. The third filter CF3 may include a polymeric photosensitive resin and may not include a pigment or dye. The third filter CF3 may be transparent. The third filter CF3 may be formed of a transparent photosensitive resin.

Furthermore, in one or more embodiments, the first filter CF1 and the second filter CF2 may be a yellow filter. The first filter CF1 and the second filter CF2 may not be separated, but may be provided as one filter.

The light shielding unit BM may be a black matrix. The light shielding unit BM may include an organic light shielding material or an inorganic light shielding material containing a black pigment and/or dye. The light shielding unit BM may prevent or reduce light leakage, and may separate boundaries between the adjacent filters CF1, CF2, and CF3. In one or more embodiments, the light shielding unit BM may be formed of a blue filter.

The first to third filters CF1, CF2, and CF3 may be disposed corresponding to the red light emitting region PXA-R, the green light emitting region PXA-G, and the blue light emitting region PXA-B, respectively.

A base substrate BL may be disposed on the color filter layer CFL. The base substrate BL may be a member which provides a base surface in which the color filter layer CFL, the light control layer CCL, and/or the like are disposed. The base substrate BL may be a glass substrate, a metal substrate, a plastic substrate, etc. However, the embodiments of the present disclosure are not limited thereto, and the base substrate BL may be an inorganic layer, an organic layer, or a composite material layer (e.g., including an inorganic material and an organic material). In one or more embodiments, the base substrate BL may be omitted.

FIG. 8 is a cross-sectional view illustrating a part of a display apparatus according to one or more embodiments. FIG. 8 illustrates a cross-sectional view of a part corresponding to the display panel DP of FIG. 7. In the display apparatus DD-TD of one or more embodiments, the luminescence device ED-BT may include a plurality of light emitting structures OL-B1, OL-B2, and OL-B3. The luminescence device ED-BT may include a first electrode EL1 and a second electrode EL2 which face each other, and the plurality of light emitting structures OL-B1, OL-B2, and OL-B3 sequentially stacked in the thickness direction between the first electrode EL1 and the second electrode EL2. The light emitting structures OL-B1, OL-B2, and OL-B3 each may include an emission layer EML (FIG. 7) and a hole transport region HTR and an electron transport region ETR disposed with the emission layer EML (FIG. 7) therebetween.

For example, the luminescence device ED-BT included in the display apparatus DD-TD of one or more embodiments may be a luminescence device having a tandem structure and including a plurality of emission layers.

In one or more embodiments illustrated in FIG. 8, each light emitted from each of the light emitting structures OL-B1, OL-B2, and OL-B3 may be blue light. However, the embodiments of the present disclosure are not limited thereto, and the light emitted from each of the light emitting structures OL-B1, OL-B2, and OL-B3 may be in a wavelength range different from each other. For example, the luminescence device ED-BT (including the plurality of light emitting structures OL-B1, OL-B2, and OL-B3 each of which emit light in a wavelength range different from each other) may emit white light.

A charge generation layer CGL may be disposed between the neighboring light emitting structures OL-B1, OL-B2, and OL-B3. For example, the charge generation layer CGL may include a first charge generation layer CGL1 between the light emitting structures OL-B1 and OL-B2, and a second charge generation layer CGL2 between the light emitting structures OL-B2 and OL-B3. The charge generation layer CGL may include a p-type charge generation layer and/or an n-type charge generation layer.

Hereinafter, the present disclosure will be described in more detail with reference to Examples and Comparative Examples. Examples below are only illustrations for assisting the understanding of the present disclosure, and the scope of the present disclosure is not limited thereto.

SYNTHETIC EXAMPLES

An amine compound according to one or more embodiments of the present disclosure may be synthesized, for example, as follows. However, a synthetic method of the amine compound according to one or more embodiments of the present disclosure is not limited thereto.

1. Synthesis of Compound 1

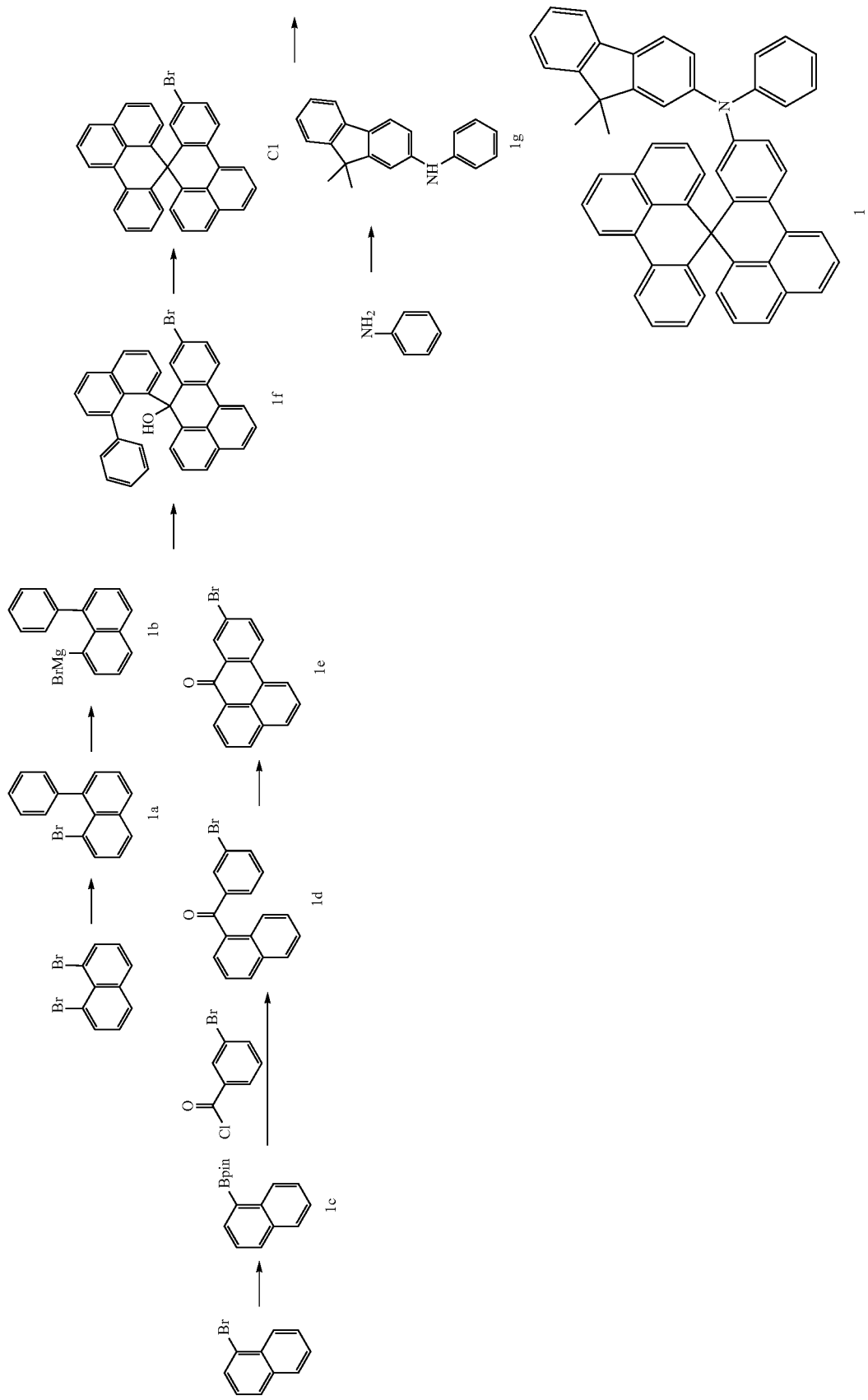

1-1. (Synthesis of Intermediate 1a)

1,8-dibromonaphthalene (1.0 eq.), phenylboronic acid (1.0 eq.), tetrakis(triphenylphosphine)palladium (0.05 eq.), and potassium carbonate (2.0 eq.) were dissolved in THF:H$_2$O which has a volume ratio of about 4:1, and then the mixture was stirred at about 90° C. for about 12 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 1a. (yield: 62%)

1-2. (Synthesis of Intermediate 1c)

1-bromonaphthalene (1.0 eq.), bis(pinacolato)diboron (2.0 eq.), potassium acetate (4.0 eq.), and palladium acetate (0.05 eq.) were dissolved in 1,4-dioxane, and then the mixture was stirred at about 80° C. for about 3 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 1c. (yield: 85%)

1-3. (Synthesis of Intermediate 1d)

Intermediate 1c (1.0 eq.), 3-bromobenzoyl chloride (1.5 eq.), tetrakis(triphenylphosphine)palladium (0.05 eq.), and potassium carbonate (2.0 eq.) were dissolved in THF:H$_2$O which has a volume ratio of about 4:1, and then the mixture was stirred at about 80° C. for about 12 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 1d. (yield: 66%)

1-4. (Synthesis of Intermediate 1e)

Intermediate 1d (1.0 eq.), palladium acetate (0.01 eq.), and silver(I) oxide (1.5 eq.) were dissolved in trifluoroacetic acid, and then the mixture was stirred at about 130° C. for about 36 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 1e. (yield: 70%)

1-5. (Synthesis of Intermediate 1b and Intermediate 1f)

Anhydrous diethyl ether was added dropwise to Intermediate 1a (1.0 eq.), magnesium (5.0 eq.), and dichloroethane (0.01 eq.), and then the mixture was stirred at about 40° C. for about 1 hour in a nitrogen atmosphere to produce a solution of Intermediate 1 b. After the solution of Intermediate 1 b was cooled to about 0° C., the cooled solution was slowly added dropwise to a solution of Intermediate 1e that is dissolved in THF, and then the mixture was stirred at about 40° C. for about 1 hour. After cooling, an ammonium chloride solution was slowly added dropwise thereto, and the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 1f. (yield: 75%)

1-6. (Synthesis of Intermediate C1)

Intermediate 1f (1.0 eq.) was dissolved in acetic acid:hydrochloric acid which has a volume ratio of about 9:1, and then the mixture was stirred at about 80° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate C1. (yield: 69%)

1-7. (Synthesis of Intermediate 1g)

2-bromo-9,9-dimethyl-9H-fluorene (1 eq.), aniline (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene, and then the mixture was stirred at about 80° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 1g. (yield: 85%)

1-8. Synthesis of Compound 1

Intermediate C1 (1.0 eq.), Intermediate 1g (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Compound 1. (yield: 82%)

2. Synthesis of Compound 2

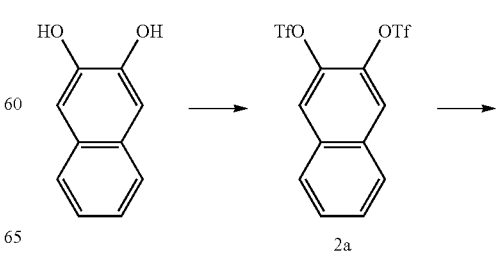

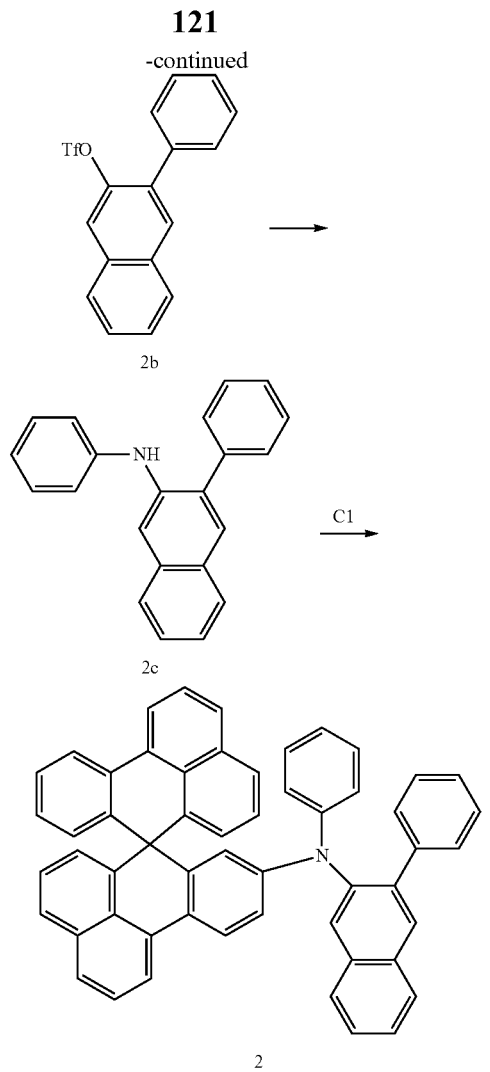

organic layer was purified by column chromatography to obtain Intermediate 2b. (yield: 85%)

2-3. (Synthesis of Intermediate 2c)

Intermediate 2b (1.0 eq.), aniline (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene and then the mixture was stirred at about 80° C. for about 2 hours in a nitrogen atmosphere. After cooling, the resulting product was washed three times with ethyl acetate and water, and then an organic layer was obtained. The obtained organic layer was dried over $MgSO_4$, and then dried at reduced pressure. The dried organic layer was purified by column chromatography to obtain Intermediate 2c. (yield: 75%)

2-4. Synthesis of Compound 2

Intermediate C1 (1.0 eq.), Intermediate 2c (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then the mixture was stirred at about 100° C. for about 2 hours in a nitrogen atmosphere. After cooling, the resulting product was washed three times with ethyl acetate and water, and then an organic layer was obtained. The obtained organic layer was dried over $MgSO_4$, and then dried at reduced pressure. The dried organic layer was purified by column chromatography to obtain Compound 2. (yield: 80%)

3. Synthesis of Compound 4

2-1. (Synthesis of Intermediate 2a)

2,3-dihydroxynaphthalene (1.0 eq.) and triethylamine (6.0 eq.) were dissolved in dichloromethane and cooled to about 0° C. in a nitrogen atmosphere, and then trifluoromethanesulfonic anhydride (3.0 eq.) was slowly added dropwise thereto. The mixture was stirred at room temperature for about 3 hours in a nitrogen atom. The resulting product was washed three times with ethyl acetate and water, and then an organic layer was obtained. The obtained organic layer was dried over $MgSO_4$, and then dried at reduced pressure. The dried organic layer was purified by column chromatography to obtain Intermediate 2a. (yield: 85%)

2-2. (Synthesis of Intermediate 2b)

Intermediate 2a (1.0 eq.), phenylboronic acid (1.0 eq.), tetrakis(triphenylphosphine)palladium (0.05 eq.), and potassium carbonate (2.0 eq.) were dissolved in $THF:H_2O$ which has a volume ratio of about 4:1, and then the mixture was stirred at about 80° C. for about 12 hours in a nitrogen atmosphere. After cooling, the resulting product was washed three times with ethyl acetate and water, and then an organic layer was obtained. The obtained organic layer was dried over $MgSO_4$, and then dried at reduced pressure. The dried

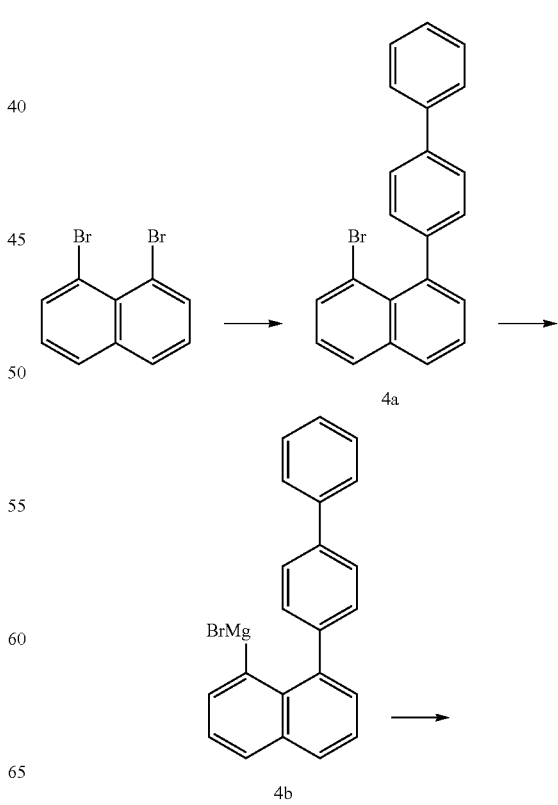

-continued

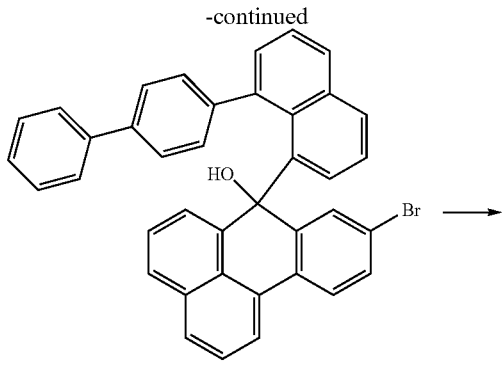

4c

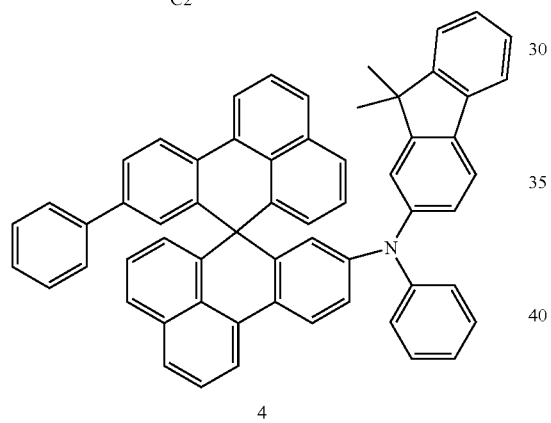

C2

4

3-1. (Synthesis of Intermediate 4a)

1,8-dibromonaphthalene (1.0 eq.), [1,1'-biphenyl]-4-ylboronic acid (1.0 eq.), tetrakis(triphenylphosphine)palladium (0.05 eq.), and potassium carbonate (2.0 eq.) were dissolved in THF:H$_2$O which has a volume ratio of about 4:1, and then the mixture was stirred at about 80° C. for about 12 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 4a. (yield: 65%)

3-2. (Synthesis of Intermediate 1b and Intermediate 4c)

Anhydrous diethyl ether was added dropwise to Intermediate 4a (1.0 eq.), magnesium (5.0 eq.), and dichloroethane (0.01 eq.), and then the mixture was stirred at about 40° C. for about 1 hour in a nitrogen atmosphere to produce a solution of Intermediate 4b. After the solution of Intermediate 4b was cooled to about 0° C., the cooled solution was slowly added dropwise to a solution of Intermediate 1e that is dissolved in THF, and then the mixture was stirred at about 40° C. for about 1 hour. After cooling, an ammonium chloride solution was slowly added dropwise thereto, and the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 4c. (yield: 75%)

3-3. (Synthesis of Intermediate C2)

Intermediate 4c (1.0 eq.) was dissolved in acetic acid: hydrochloric acid which has a volume ratio of about 9:1, and then the mixture was stirred at about 80° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate C2. (yield: 69%)

3-4. Synthesis of Compound 4

Intermediate C2 (1.0 eq.), Intermediate 1a (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Compound 4. (yield: 79%)

4. Synthesis of Compound 5

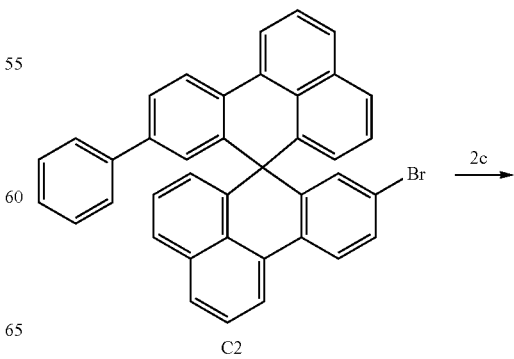

C2

-continued

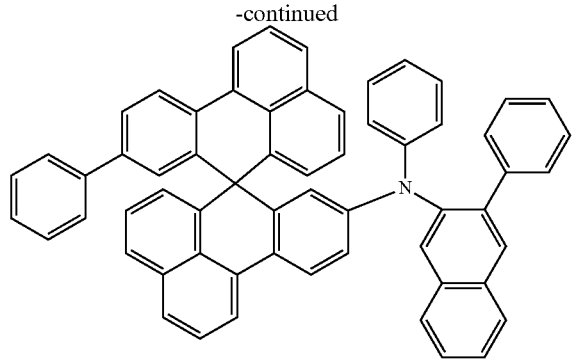

5

Intermediate C2 (1.0 eq.), Intermediate 2c (1.1 eq.), tris(dibenzylideneacetone) dipalladium (0) (0.05 eq.), tri-tert-butylphosphine (0.10 eq.), and sodium tert-butoxide (2.0 eq.) were dissolved in toluene, and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$^4$, and then dried at reduced pressure. The dried organic layer was purified by column chromatography to obtain Compound 5. (yield: 75%) 5. Synthesis of Compound 10

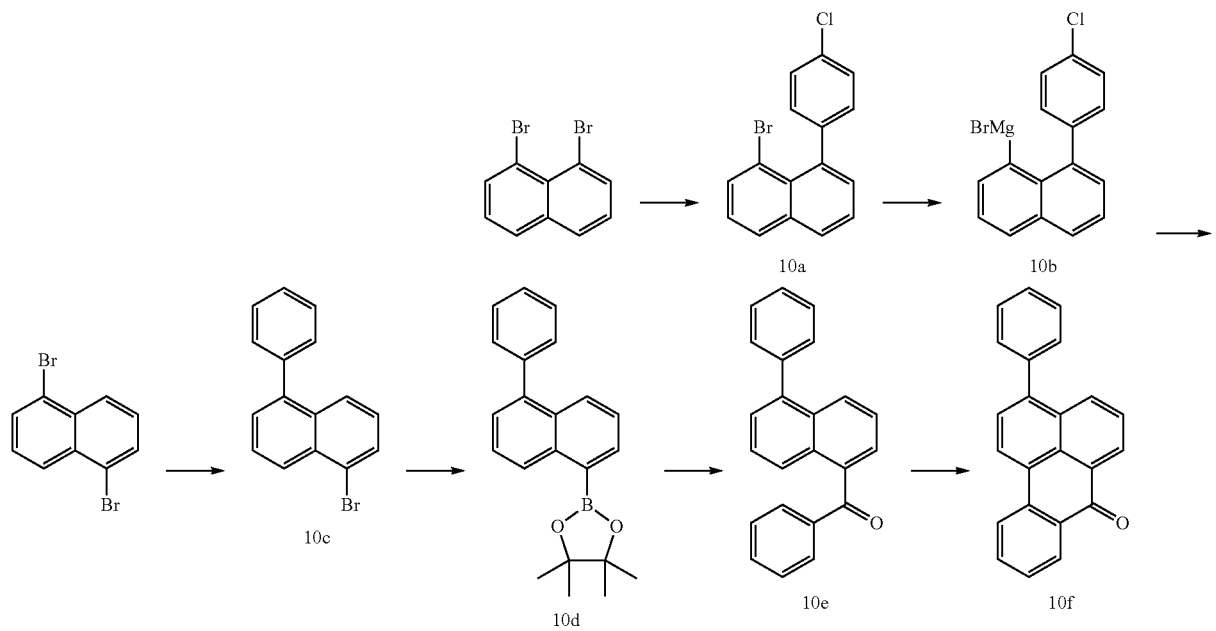

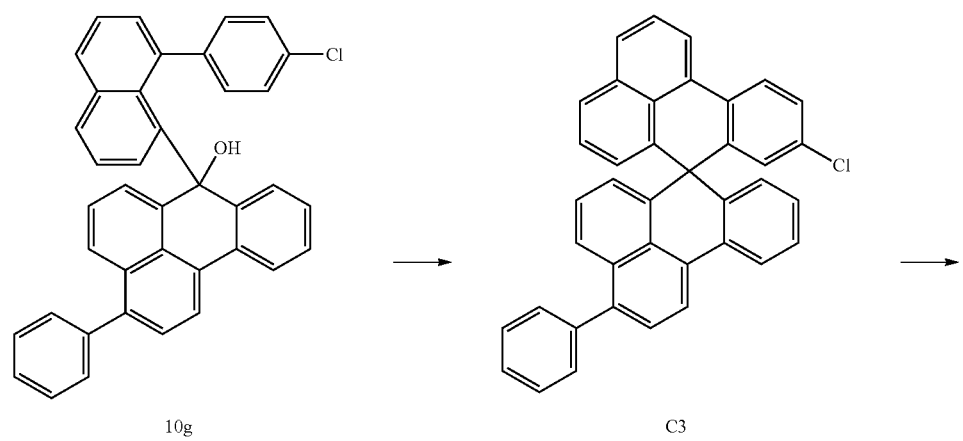

-continued

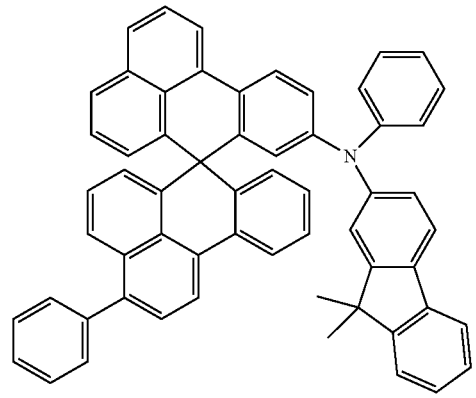

10

5-1. (Synthesis of Intermediate 10a)

1,8-dibromonaphthalene (1.0 eq.), 4-chlorophenylboronic acid (1.0 eq.), tetrakis(triphenylphosphine)palladium (0.05 eq.), and potassium carbonate (2.0 eq.) were dissolved in THF:H$_2$O which has a volume ratio of about 4:1, and then the mixture was stirred at about 90° C. for about 12 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 10a. (yield: 62%)

5-2. (Synthesis of Intermediate 10c)

1,5-dibromonaphthalene (1.0 eq.), phenylboronic acid (1.0 eq.), tetrakis(triphenylphosphine)palladium (0.05 eq.), and potassium carbonate (2.0 eq.) were dissolved in toluene/EtOH:H$_2$O which has a volume ratio of about 4:1:1, and then the mixture was stirred at about 100° C. for about 12 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 10c. (yield: 68%)

5-3. (Synthesis of Intermediate 10d)

Intermediate 10c (1.0 eq.), bis(pinacolato)diboron (2.5 eq.), potassium acetate (5.0 eq.), and palladium acetate (0.05 eq.) were dissolved in 1,4-dioxane, and then the mixture was stirred at about 80° C. for about 3 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 10d. (yield: 81%)

5-4. (Synthesis of Intermediate 10e)

Intermediate 10d (1.0 eq.), benzoyl chloride (1.5 eq.), tetrakis(triphenylphosphine)palladium (0.05 eq.), and potassium carbonate (2.0 eq.) were dissolved in THF:H$_2$O which has a volume ratio of about 4:1, and then the mixture was stirred at about 80° C. for about 12 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 10e. (yield: 60%)

5-5. (Synthesis of Intermediate 10f)

Intermediate 10e (1.0 eq.), palladium acetate (0.01 eq.), and silver(I) oxide (1.5 eq.) were dissolved in trifluoroacetic acid, and then the mixture was stirred at about 130° C. for about 36 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 10f. (yield: 70%)

5-6. (Synthesis of Intermediate 1b and Intermediate 10g)

Anhydrous diethyl ether was added dropwise to Intermediate 10a (1.0 eq.), magnesium (5.0 eq.), and dichloroethane (0.01 eq.), and then the mixture was stirred at about 40° C. for about 1 hour in a nitrogen atmosphere to produce a solution of Intermediate 10b. After the solution of Intermediate 10b was cooled to about 0° C., the cooled solution was slowly added dropwise to a solution of Intermediate 10f that is dissolved in THF, and then the mixture was stirred at about 40° C. for about 1 hour. After cooling, an ammonium chloride solution was slowly added dropwise thereto, and the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 10g. (yield: 65%)

5-7. (Synthesis of Intermediate C3)

Intermediate 10g (1.0 eq.) was dissolved in acetic acid: hydrochloric acid which has a volume ratio of about 9:1, and then the mixture was stirred at about 80° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate C3. (yield: 68%)

5-8. Synthesis of Compound 10

Intermediate C3 (1.0 eq.), Intermediate 1g (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Compound 10. (yield: 78%)

6. Synthesis of Compound 11

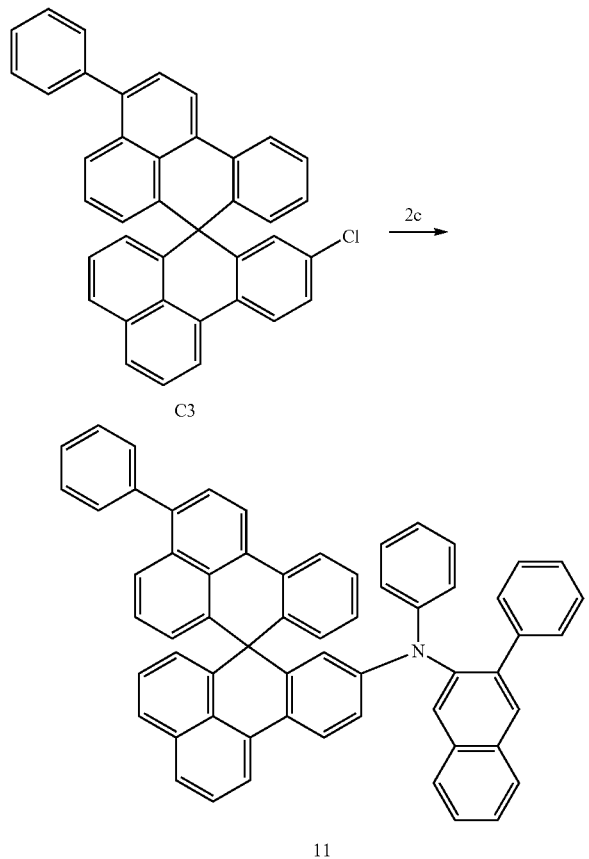

Intermediate C3 (1.0 eq.), Intermediate 2c (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Compound 11. (yield: 75%)

7. Synthesis of Compound 73

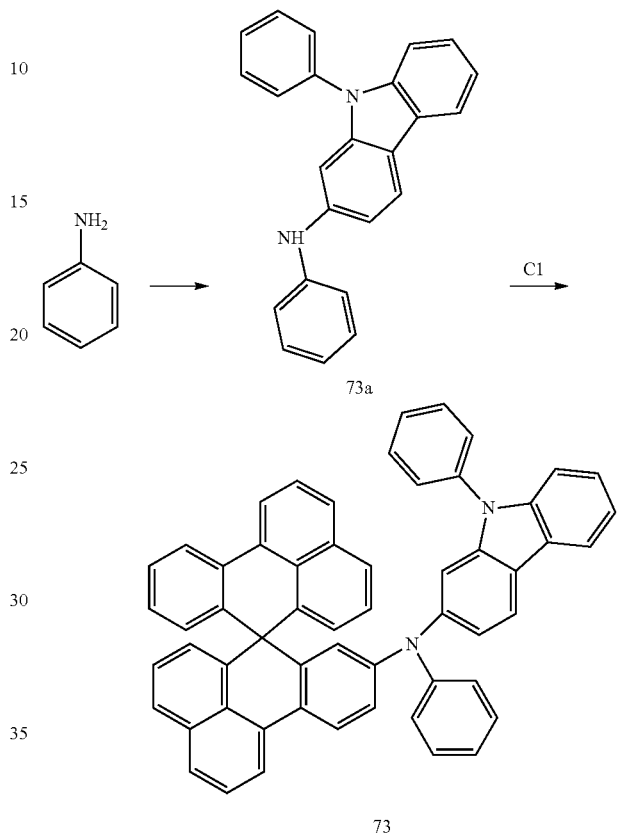

7-1. (Synthesis of Intermediate 73a)

Aniline (1.0 eq.), 2-bromo-9-phenyl-9H-carbazole (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 73a. (yield: 78%)

7-2. Synthesis of Compound 73

Intermediate C1 (1.0 eq.), Intermediate 73a (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Compound 73. (yield: 75%)

8. Synthesis of Compound 76

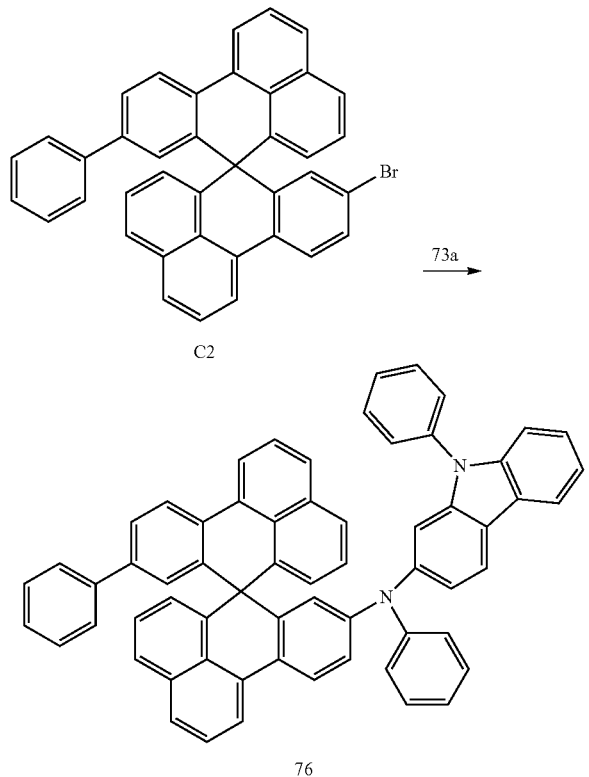

Intermediate C2 (1.0 eq.), Intermediate 73a (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Compound 76. (yield: 72%)

9. Synthesis of Compound 82

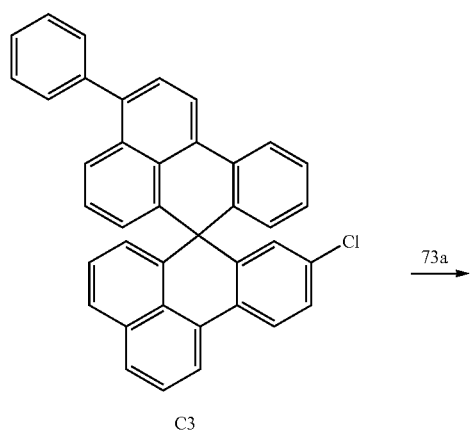

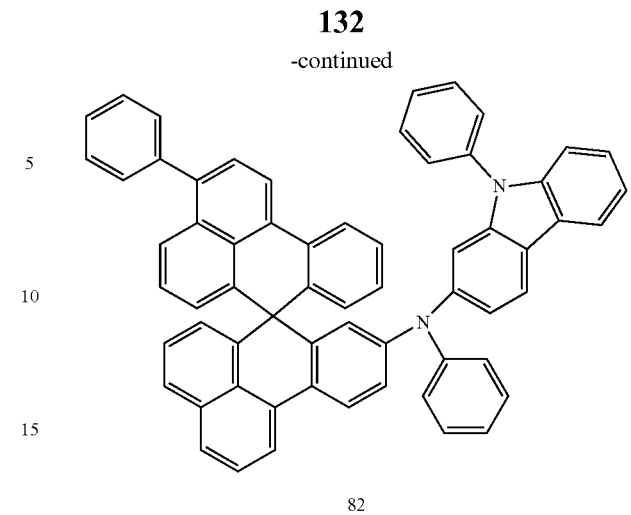

Intermediate C3 (1.0 eq.), Intermediate 73a (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Compound 82. (yield: 70%)

10. Synthesis of Compound 94

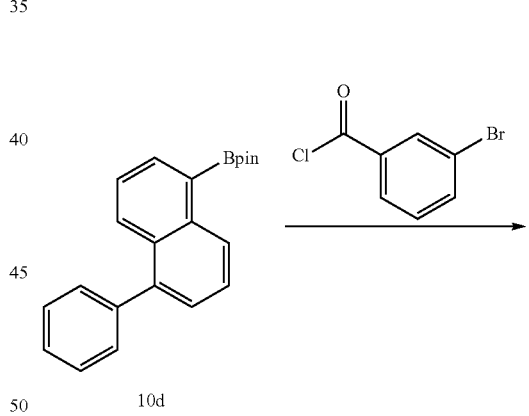

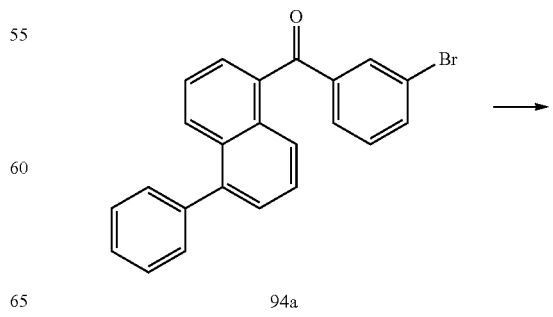

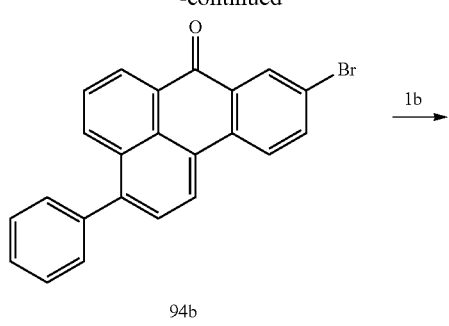

1b

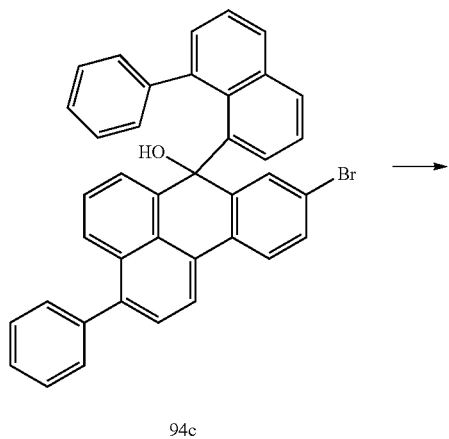

94b

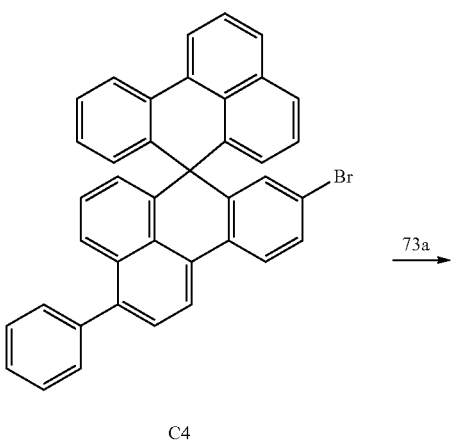

94c

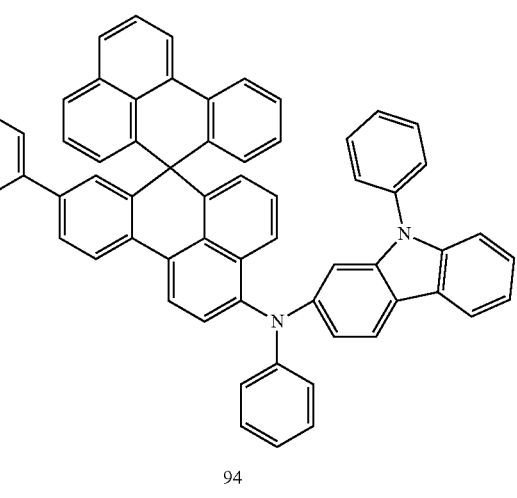

C4

94

10-1. (Synthesis of Intermediate 94a)

Intermediate 10d (1.0 eq.), 3-bromo benzoyl chloride (1.5 eq.), tetrakis(triphenylphosphine)palladium (0.05 eq.), and potassium carbonate (2.0 eq.) were dissolved in THF:H$_2$O which has a volume ratio of about 4:1, and then the mixture was stirred at about 80° C. for about 12 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 94a. (yield: 60%)

10-2. (Synthesis of Intermediate 94b)

Intermediate 94a (1.0 eq.), palladium acetate (0.01 eq.), and silver(I) oxide (1.5 eq.) were dissolved in trifluoroacetic acid, and then the mixture was stirred at about 130° C. for about 36 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 94b. (yield: 70%)

10-3. (Synthesis of Intermediate 1b and Intermediate 94c)

Anhydrous diethyl ether was added dropwise to Intermediate 1a (1.0 eq.), magnesium (5.0 eq.), and dichloroethane (0.01 eq.), and then the mixture was stirred at about 40° C. for about 1 hour in a nitrogen atmosphere to produce a solution of Intermediate 1 b. After the solution of Intermediate 1 b was cooled to about 0° C., the cooled solution was slowly added dropwise to a solution of Intermediate 94b that is dissolved in THF, and then the mixture was stirred at about 40° C. for about 1 hour. After cooling, an ammonium chloride solution was slowly added dropwise thereto, and the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate 94c. (yield: 65%)

10-4. (Synthesis of Intermediate C4)

Intermediate 94c (1.0 eq.) was dissolved in acetic acid: hydrochloric acid which has a volume ratio of about 9:1, and then the mixture was stirred at about 80° C. for about 2 hours in a nitrogen atmosphere. After cooling, the resulting product was washed three times with ethyl acetate and water, and then an organic layer was obtained. The obtained organic layer was dried over MgSO$_4$, and then dried at reduced pressure. The dried organic layer was purified by column chromatography to obtain Intermediate C4. (yield: 68%)

10-5. Synthesis of Compound 94

Intermediate C4 (1.0 eq.), Intermediate 73a (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then the mixture was stirred at about 90° C. for about 2 hours in a nitrogen atmosphere. After cooling, the resulting product was washed three times with ethyl acetate and water, and then an organic layer was obtained. The obtained organic layer was dried over MgSO₄, and then dried at reduced pressure. The dried organic layer was purified by column chromatography to obtain Compound 94. (yield: 75%)

DEVICE MANUFACTURING EXAMPLES

Organic electroluminescence devices were manufactured using (e.g., utilizing) Example Compounds and Comparative Example Compounds below as a hole transport region material:

Example Compounds

1
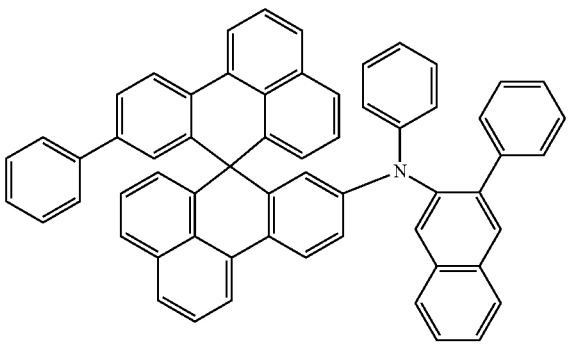

2
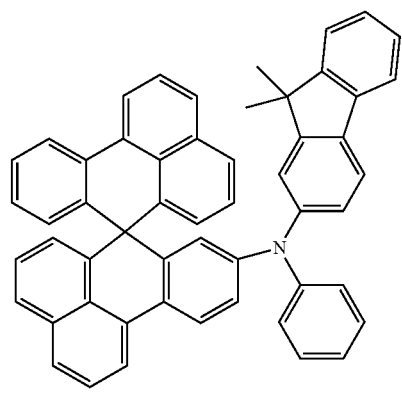

4
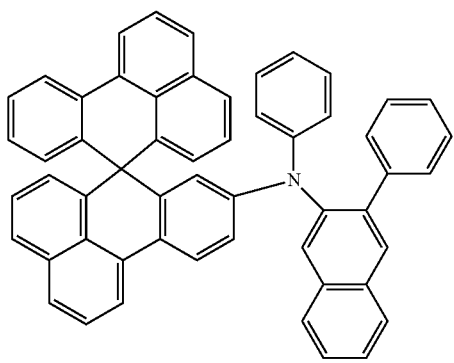

-continued

5
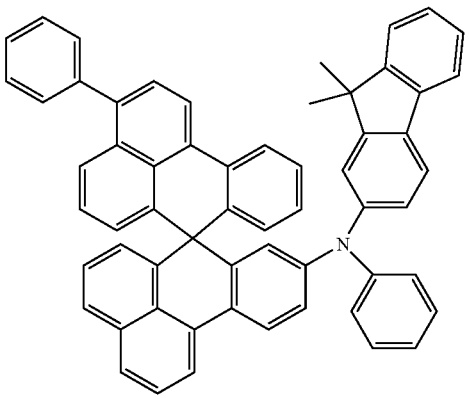

10
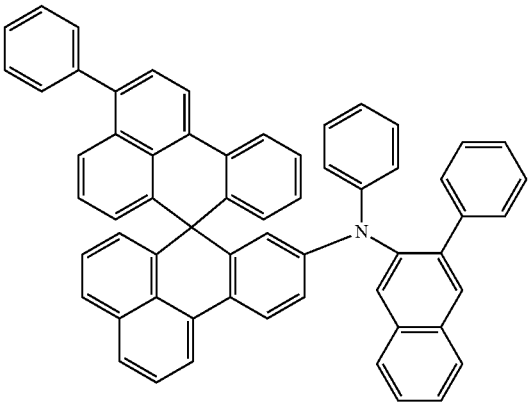

11
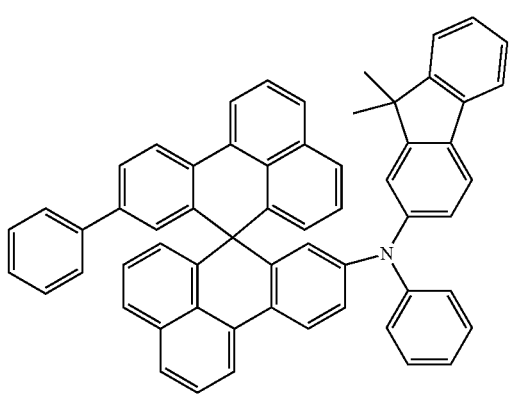

73
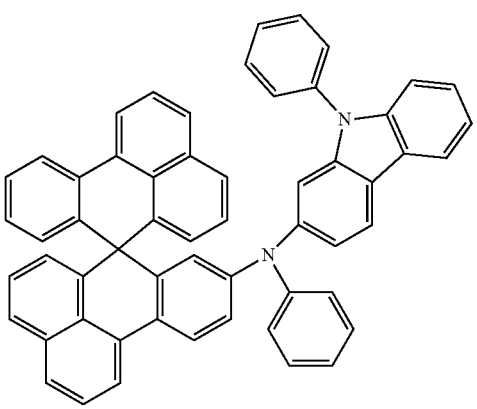

-continued

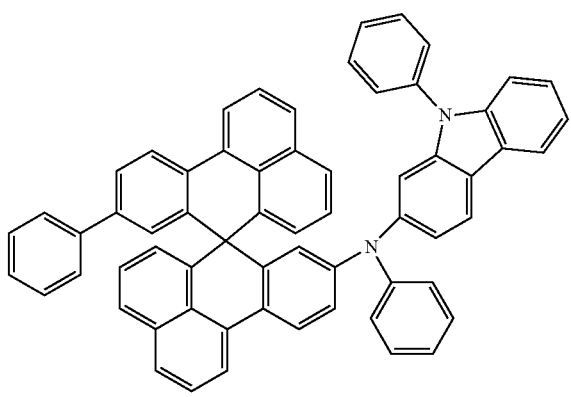

76

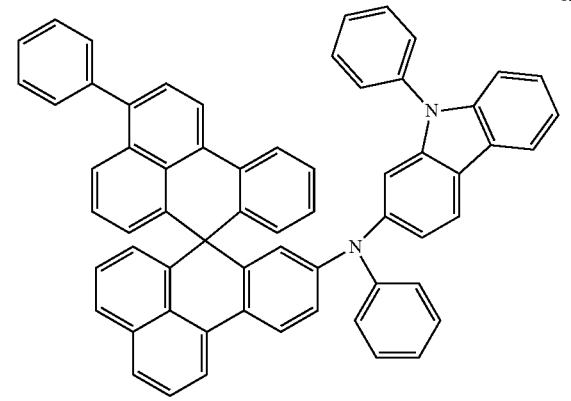

82

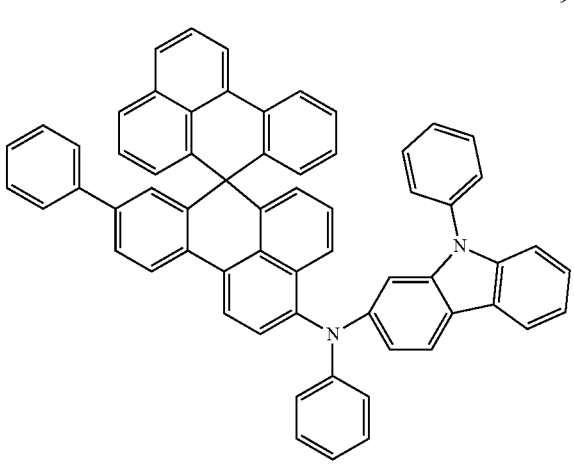

94

Comparative Example Compounds

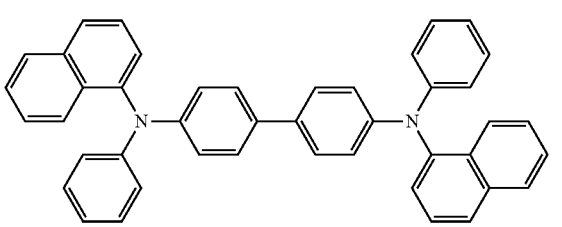

R1

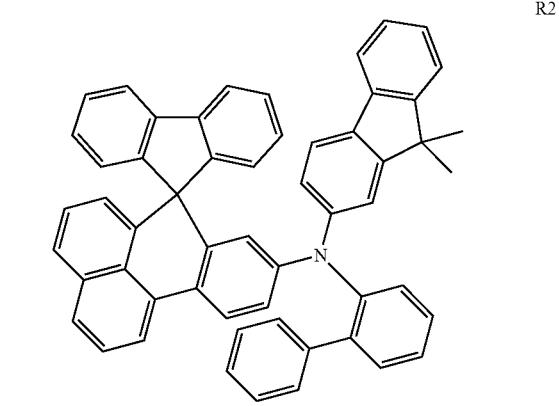

R2

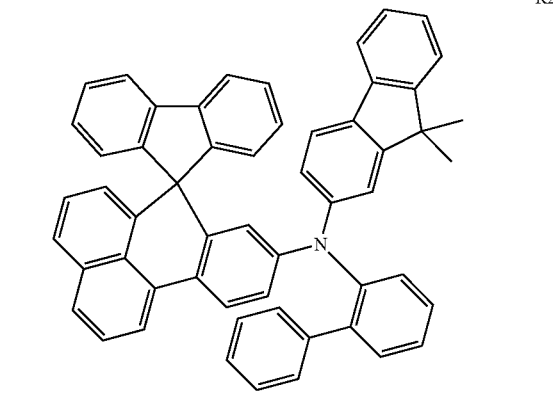

R3

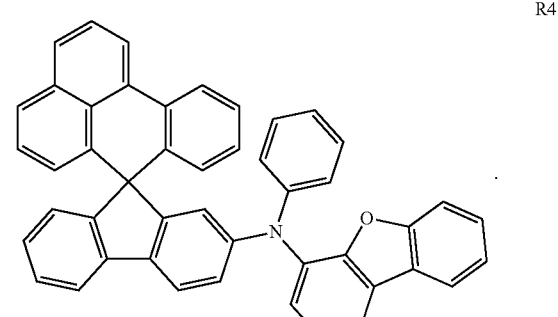

R4

The organic electroluminescence devices of Examples and Comparative Examples were manufactured by the following method. A 120 nm-thick ITO was patterned on a glass substrate, and then the glass substrate was washed with ultrapure water and treated with UV and ozone to form a first electrode. Then, 2-TNATA was deposited thereon to a thickness of about 60 nm, and Example Compounds or Comparative Example Compounds were respectively used to form a 30 nm-thick hole transport layer. Then, DPAVBi was doped to 9,10-di(naphthalen-2-yl)anthracene (DNA) by 2% to form a 30 nm-thick emission layer, a 30 nm-thick layer was formed with Alq$_3$ on the emission layer, and a 1 nm-thick layer was formed with LiF to form an electron transport region. Then, a 300 nm-thick second electrode was formed with aluminum (Al). Each layer was formed by a vacuum deposition method.

The measured values according to Examples 1 to 10 and Comparative Examples 1 to 4 are shown in Table 1 below. The luminous efficiencies were measured at 10 mA/cm$^2$, and the half service lives were tested (e.g., were test results performed) at 1.0 mA/cm$^2$.

TABLE 1

|  | Hole transport layer | Voltage (V) | Current density (mA/cm$^2$) | Brightness (cd/m$^2$) | Luminous efficiency (cd/A) | Service life LT50(h) |
|---|---|---|---|---|---|---|
| Example 1 | Example Compound 1 | 4.20 | 50 | 3650 | 7.3 | 359 |
| Example 2 | Example Compound 2 | 4.31 | 50 | 3701 | 7.402 | 360 |
| Example 3 | Example Compound 4 | 4.19 | 50 | 3764 | 7.528 | 369 |
| Example 4 | Example Compound 5 | 4.26 | 50 | 3720 | 7.44 | 370 |
| Example 5 | Example Compound 10 | 4.19 | 50 | 3771 | 7.542 | 371 |
| Example 6 | Example Compound 11 | 4.25 | 50 | 3723 | 7.446 | 378 |
| Example 7 | Example Compound 73 | 4.31 | 50 | 3705 | 7.41 | 355 |
| Example 8 | Example Compound 76 | 4.24 | 50 | 3733 | 7.466 | 363 |
| Example 9 | Example Compound 82 | 4.26 | 50 | 3731 | 7.462 | 361 |
| Example 10 | Example Compound 94 | 4.23 | 50 | 3741 | 7.482 | 367 |
| Comparative Example 1 | Comparative Example Compound R1 | 5.01 | 50 | 2645 | 5.29 | 258 |
| Comparative Example 2 | Comparative Example Compound R2 | 4.22 | 50 | 3601 | 7.202 | 234 |
| Comparative Example 3 | Comparative Example Compound R3 | 4.20 | 50 | 3600 | 7.220 | 320 |
| Comparative Example 4 | Comparative Example Compound R4 | 4.20 | 50 | 3645 | 7.421 | 324 |

Referring to Table 1 above, it may be confirmed that Examples 1 to 10 have each achieved a low voltage, a high brightness, a high efficiency, and a long service life compared to Comparative Examples 1 to 4.

The amine compounds according to examples of the present disclosure are used in the hole transport regions to achieve (e.g., to make contribution to) low driving voltages, high efficiencies, and long service lives of the organic electroluminescence devices. The amine compounds according to examples of the present disclosure are bonded to a 7,7'-spirobi[benzo[de]anthracene] structure. Without being bound by any particular theory, it is believed that the amine compounds according to examples of the present disclosure may have wide band values and high glass transition temperatures. Therefore, the hole transport property may be improved to thus increase exciton producing efficiency, thereby achieving high luminous efficiency.

The amine compounds according to examples of the present disclosure are used in the hole transport regions to achieve low driving voltages, high efficiencies, and long service lives of the organic electroluminescence devices.

The luminescence device according to one or more embodiments of the present disclosure has excellent efficiency.

The amine compound according to one or more embodiments of the present disclosure may be used as a material of the hole transport region of the luminescence device, and thereby the luminescence device may have improved efficiency.

Although the embodiments of the present disclosure are described herein, those with ordinary skill in the technical field to which the present disclosure pertains will understood that the present disclosure may be carried out in other specific forms without changing the technical idea or essential features. Therefore, the above-described embodiments are to be understood in all aspects as illustrative and not restrictive.

What is claimed is:

1. A luminescence device comprising:

a first electrode;

a hole transport region on the first electrode;

an emission layer on the hole transport region;

an electron transport region on the emission layer; and a second electrode on the electron transport region, wherein the hole transport region comprises an amine compound represented by Formula 1:

Formula 1

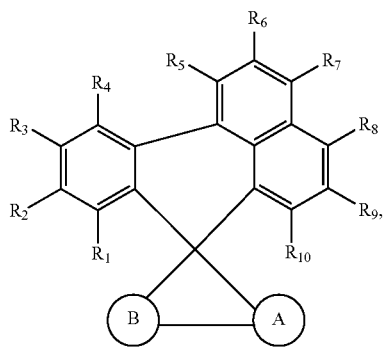

wherein, in Formula 1,
R$_1$ to R$_{10}$ are each independently a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms,
at least one among R$_1$ to R$_{10}$ is represented by Formula 2, and
ring A and ring B are each independently represented by Formula 3 or Formula 4, and are represented by different formulae:

Formula 2

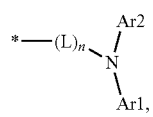

wherein, in Formula 2,
L is a direct linkage, a substituted or unsubstituted arylene group having 6 to 30 ring-forming carbon atoms, or a substituted or unsubstituted heteroarylene group having 2 to 30 ring-forming carbon atoms,
n is an integer of 0 to 3, and
Ar1 and Ar2 are each independently a substituted or unsubstituted aryl group having 6 to 30 ring-forming carbon atoms, or a substituted or unsubstituted heteroaryl group having 2 to 30 ring-forming carbon atoms:

Formula 3

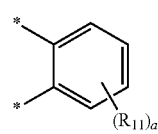

Formula 4

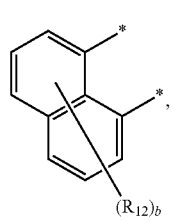

and
wherein, in Formula 3 and Formula 4,
R$_{11}$ and R$_{12}$ are each independently a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms,
a is an integer of 0 to 4, and
b is an integer of 0 to 6.

2. The luminescence device of claim 1, wherein the hole transport region comprises:
a hole injection layer on the first electrode; and
a hole transport layer on the hole injection layer, and
wherein the hole transport layer or the hole injection layer comprises the amine compound represented by Formula 1.

3. The luminescence device of claim 2, wherein the hole transport region further comprises an electron blocking layer on the hole transport layer.

4. The luminescence device of claim 1, wherein Formula 1 is represented by Formula 5 or Formula 6:

Formula 5

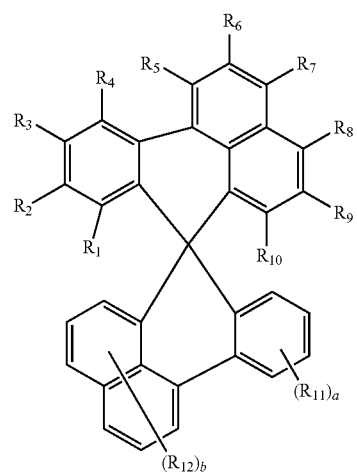

Formula 6

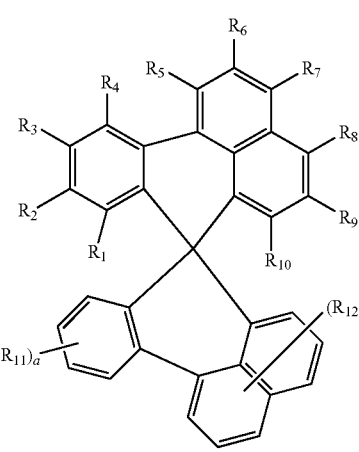

and
wherein, in Formula 5 and Formula 6,
R$_1$ to R$_{12}$, a, and b are the same as defined in Formula 1, Formula 3, and Formula 4.

5. The luminescence device of claim 4, wherein Formula 5 is represented by Formula 7-1:

Formula 7-1

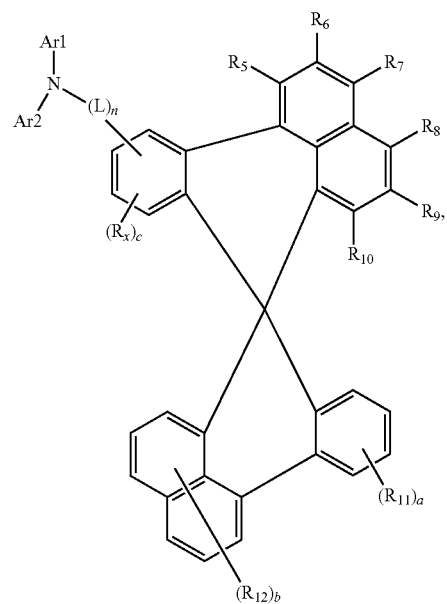

and wherein, in Formula 7-1, $R_x$, and $R_5$ to $R_{10}$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, c is an integer of 0 to 3, L is a direct linkage, a substituted or unsubstituted arylene group having 6 to 30 ring-forming carbon atoms, or a substituted or unsubstituted heteroarylene group having 2 to 30 ring-forming carbon atoms, n is an integer of 0 to 3, Ar1 and Ar2 are each independently a substituted or unsubstituted aryl group having 6 to 30 ring-forming carbon atoms, or a substituted or unsubstituted heteroaryl group having 2 to 30 ring-forming carbon atoms, and $R_{11}$, $R_{12}$, a, and b are the same as defined in Formula 5.

6. The luminescence device of claim 5, wherein Formula 7-1 is represented by Formula 8-1:

Formula 8-1

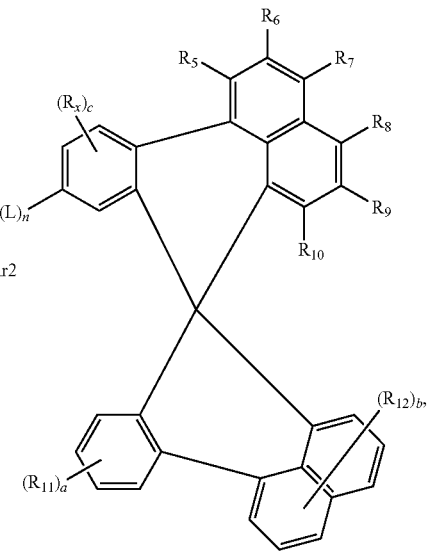

and wherein, in Formula 8-1, $R_x$, $R_5$ to $R_{12}$, L, Ar1, Ar2, a to c, and n are the same as defined in Formula 7-1.

7. The luminescence device of claim 4, wherein Formula 5 is represented by Formula 7-2 or Formula 7-3:

Formula 7-2

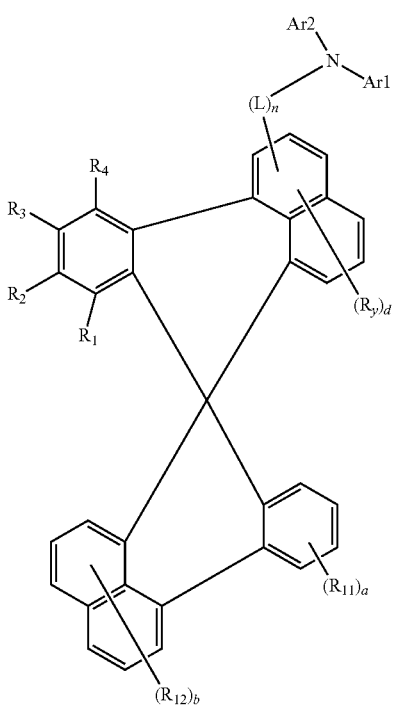

-continued

Formula 7-3

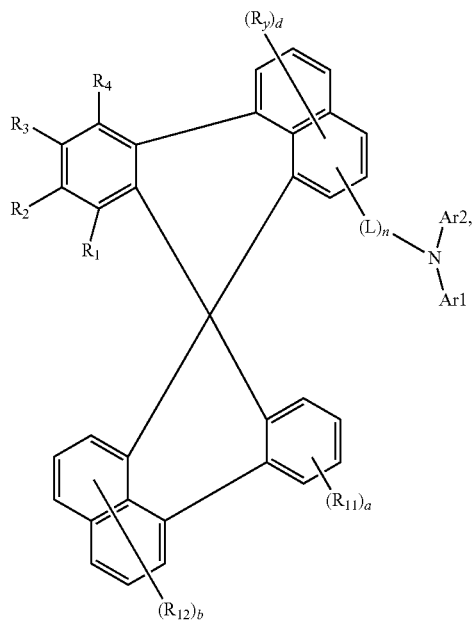

and wherein, in Formulae 7-2 and 7-3, $R_y$, and $R_1$ to $R_4$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, d is an integer of 0 to 5, L is a direct linkage, a substituted or unsubstituted arylene group having 6 to 30 ring-forming carbon atoms, or a substituted or unsubstituted heteroarylene group having 2 to 30 ring-forming carbon atoms, n is an integer of 0 to 3, Ar1 and Ar2 are each independently a substituted or unsubstituted aryl group having 6 to 30 ring-forming carbon atoms, or a substituted or unsubstituted heteroaryl group having 2 to 30 ring-forming carbon atoms, and $R_{11}$, $R_{12}$, a, and b are the same as defined in Formula 5.

8. The luminescence device of claim 7, wherein Formula 7-2 is represented by Formula 8-2:

Formula 8-2

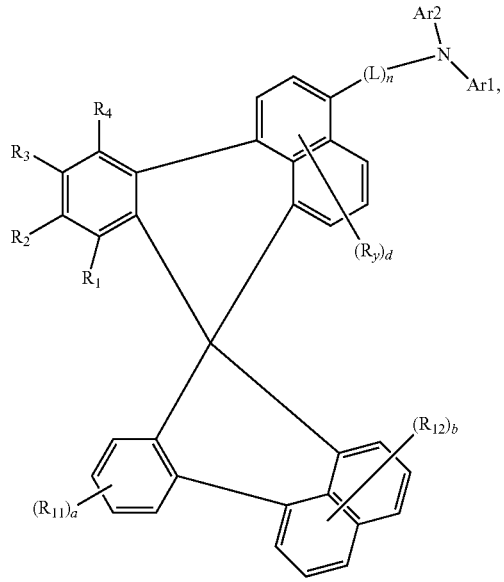

and wherein, in Formula 8-2, $R_y$, $R_1$ to $R_4$, $R_{11}$, $R_{12}$, L, Ar1, Ar2, a, b, d, and n are the same as defined in Formula 7-2.

9. The luminescence device of claim 4, wherein Formula 6 is represented by Formula 9-1:

Formula 9-1

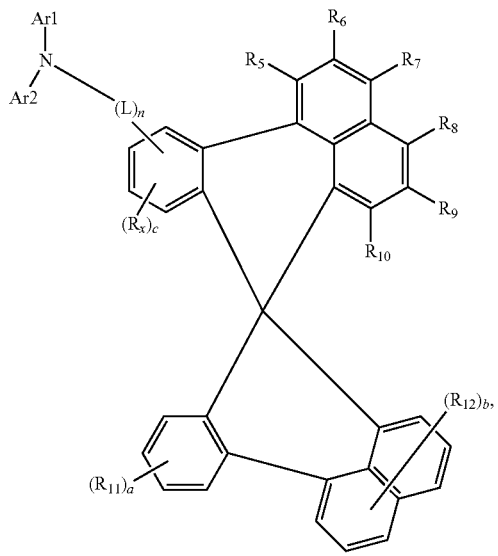

and wherein, in Formula 9-1, $R_x$, and $R_5$ to $R_{10}$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, c is an integer of 0 to 3, L is a direct linkage, a substituted or unsubstituted arylene group having 6 to 30 ring-forming carbon atoms, or a substituted or unsubstituted heteroarylene group having 2 to 30 ring-forming carbon atoms, n is an integer of 0 to 3, Ar1 and Ar2 are each independently a substituted or unsubstituted aryl group having 6 to 30 ring-forming carbon atoms, or a substituted or unsubstituted heteroaryl group having 2 to 30 ring-forming carbon atoms, and $R_{11}$, $R_{12}$, a, and b are the same as defined in Formula 6.

10. The luminescence device of claim 9, wherein Formula 9-1 is represented by Formula 10-1:

Formula 10-1

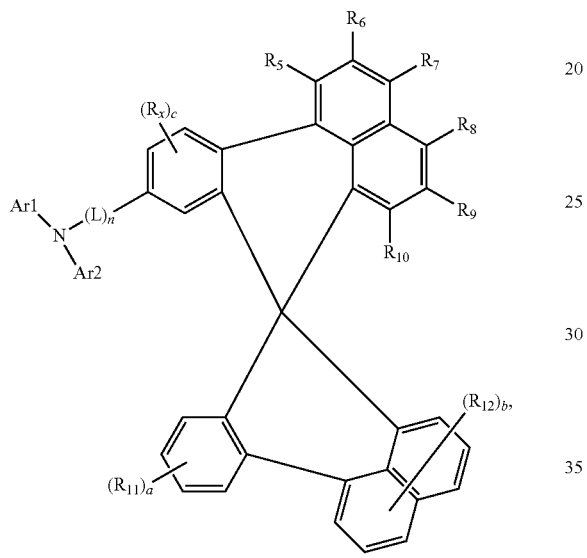

and wherein, in Formula 10-1, $R_x$, $R_5$ to $R_{12}$, L, Ar1, Ar2, a to c, and n are the same as defined in Formula 9-1.

11. The luminescence device of claim 4, wherein Formula 6 is represented by Formula 9-2 or Formula 9-3:

Formula 9-2

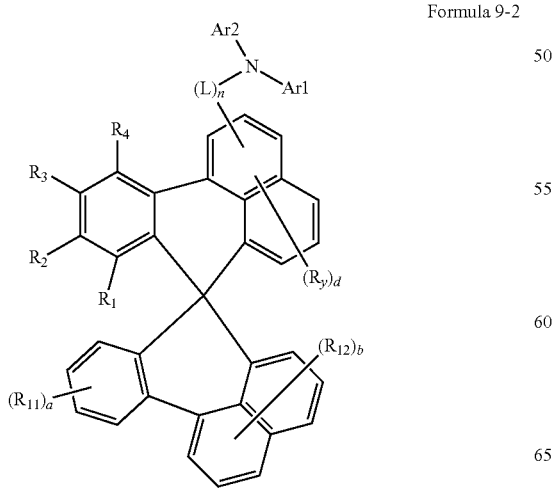

Formula 9-3

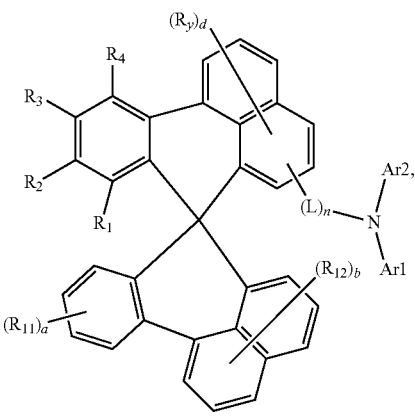

and wherein, in Formulae 9-2 and 9-3, $R_y$, and $R_1$ to $R_4$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, d is an integer of 0 to 5, L is a direct linkage, a substituted or unsubstituted arylene group having 6 to 30 ring-forming carbon atoms, or a substituted or unsubstituted heteroarylene group having 2 to 30 ring-forming carbon atoms, n is an integer of 0 to 3, Ar1 and Ar2 are each independently a substituted or unsubstituted aryl group having 6 to 30 ring-forming carbon atoms, or a substituted or unsubstituted heteroaryl group having 2 to 30 ring-forming carbon atoms, and $R_{11}$, $R_{12}$, a, and b are the same as defined in Formula 6.

12. The luminescence device of claim 11, wherein Formula 9-2 is represented by Formula 10-2:

Formula 10-2

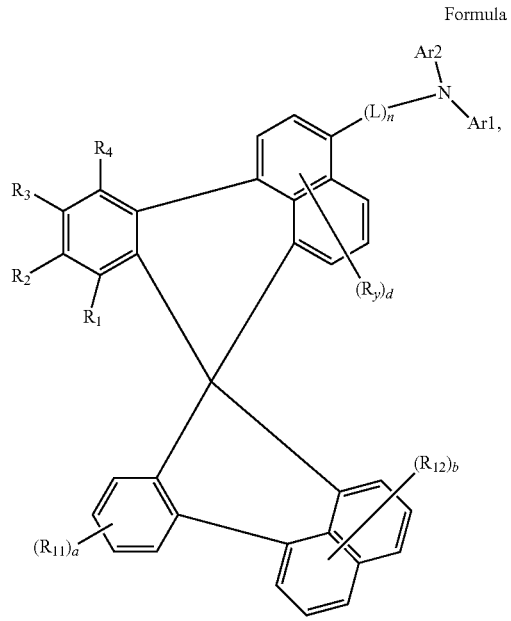

and wherein, in Formula 10-2, $R_y$, $R_1$ to $R_4$, $R_{11}$, $R_{12}$, L, Ar1, Ar2, a, b, d, and n are the same as defined in Formula 9-2.

13. The luminescence device of claim 1, wherein the amine compound is a monoamine compound.

14. The luminescence device of claim 1, wherein n is 1, and L is a direct linkage.

15. The luminescence device of claim 1, wherein the amine compound represented by Formula 1 is at least one selected from among compounds represented by Compound Group 1:

Compound Group 1

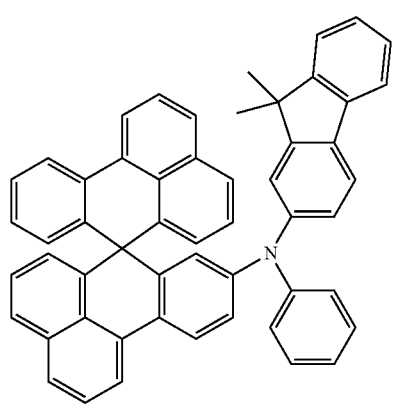

1

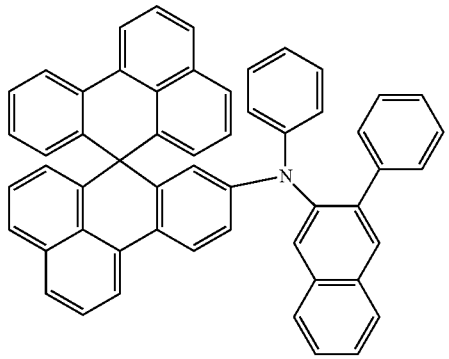

2

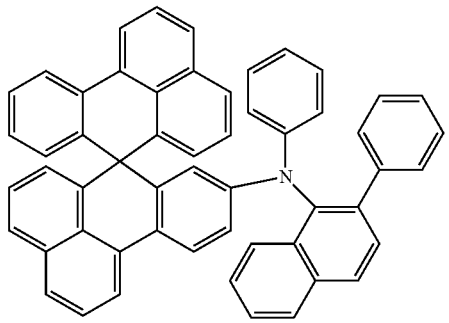

3

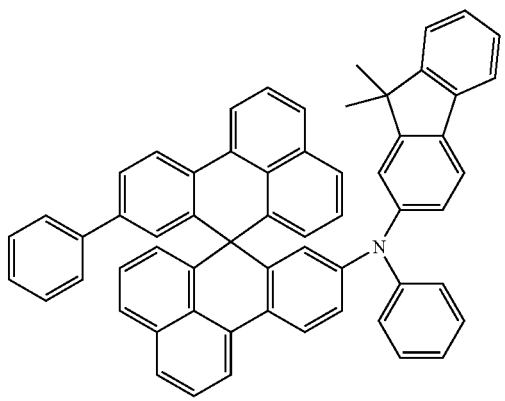

4

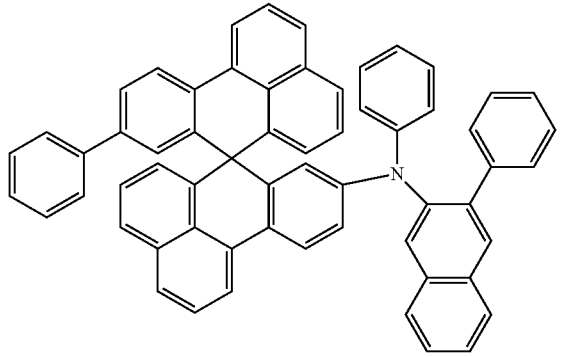

5

-continued
6
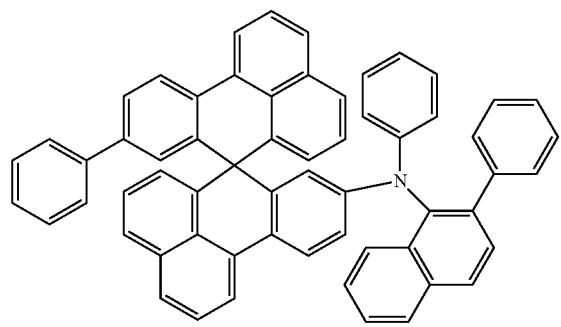
7
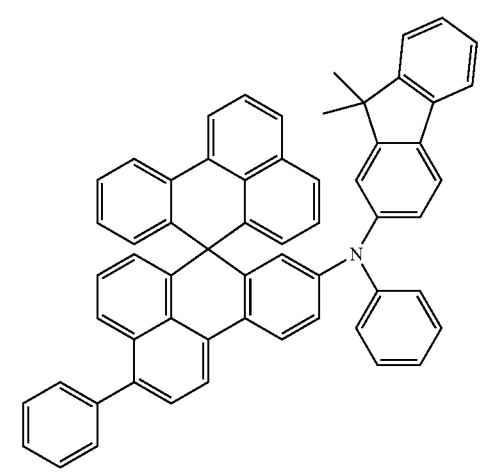
8
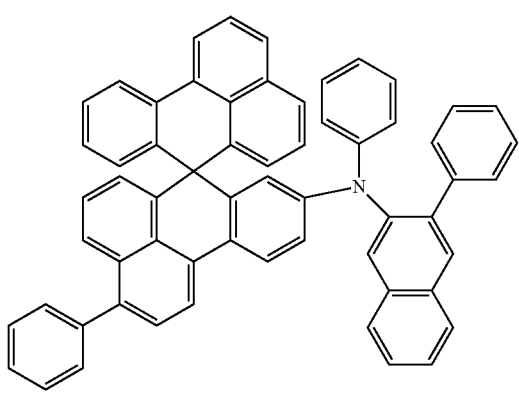
9
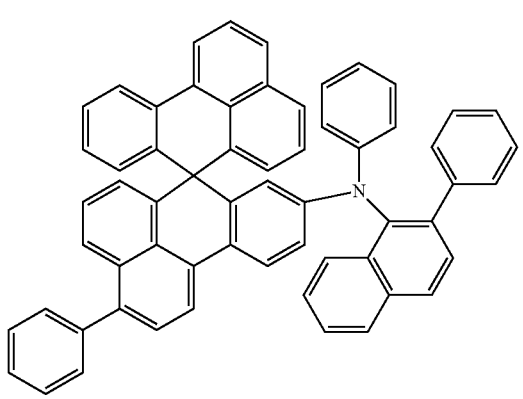
-continued
10
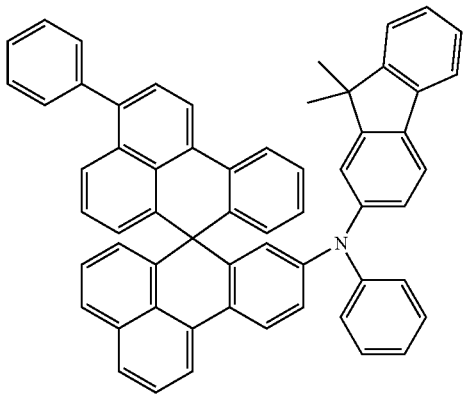
11
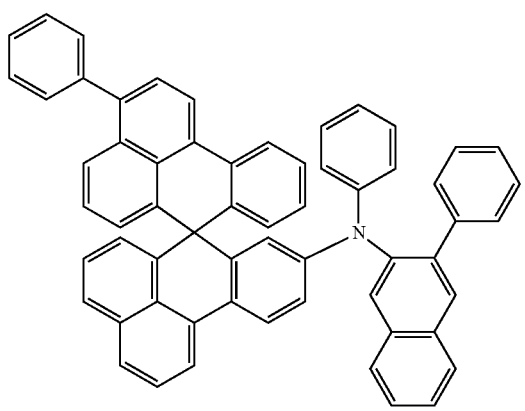
12
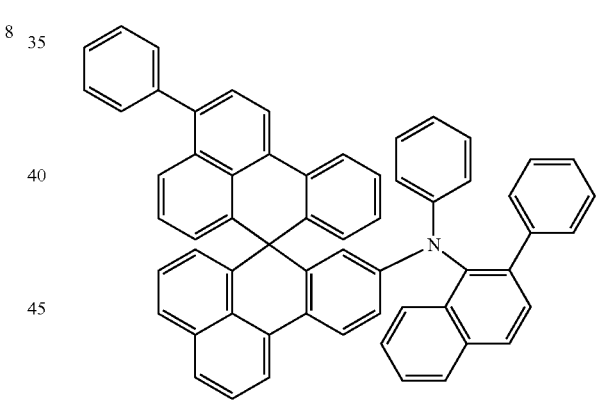
13
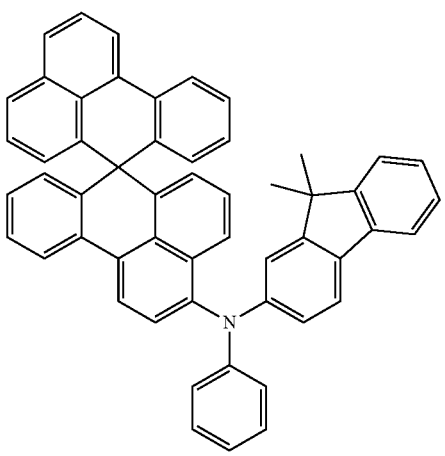

153
-continued
14
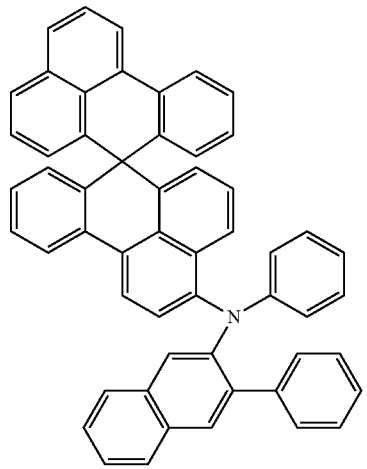
15
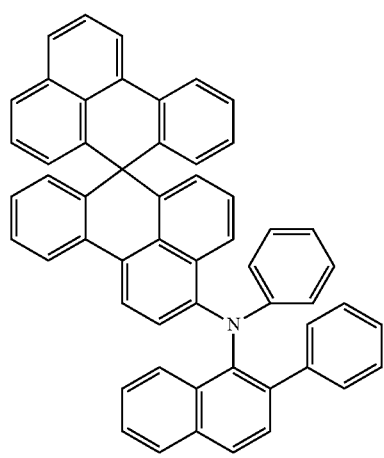
16
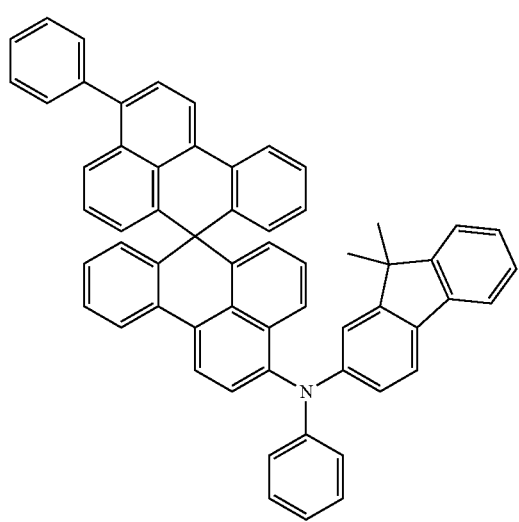
154
-continued
17
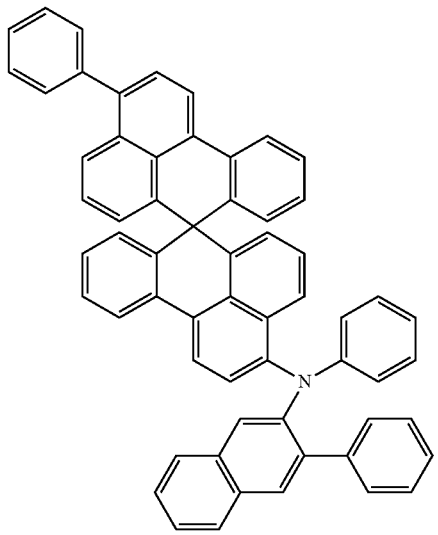
18
19

20
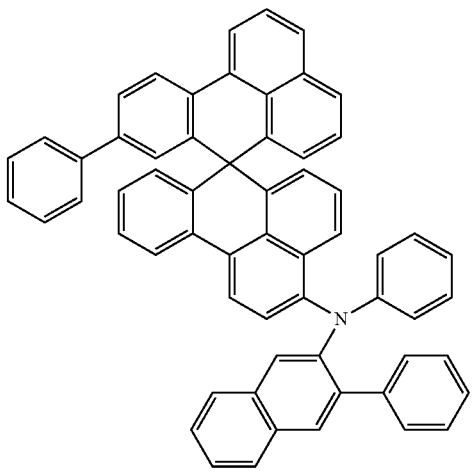
21
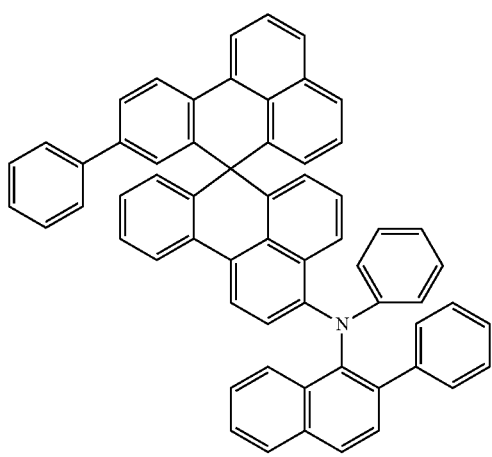
22
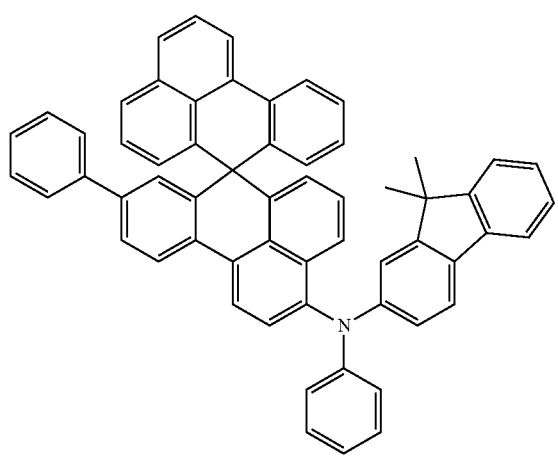
23
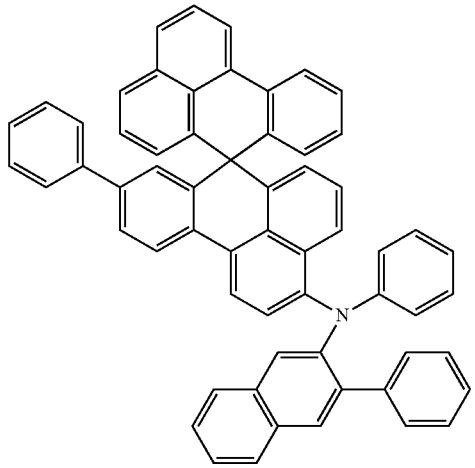
24
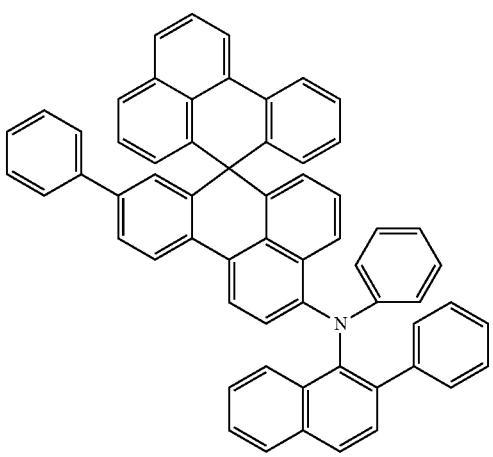
25
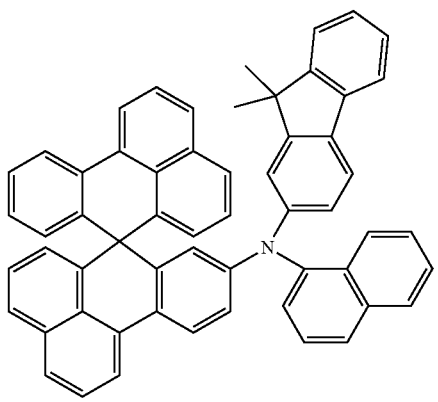

-continued
26
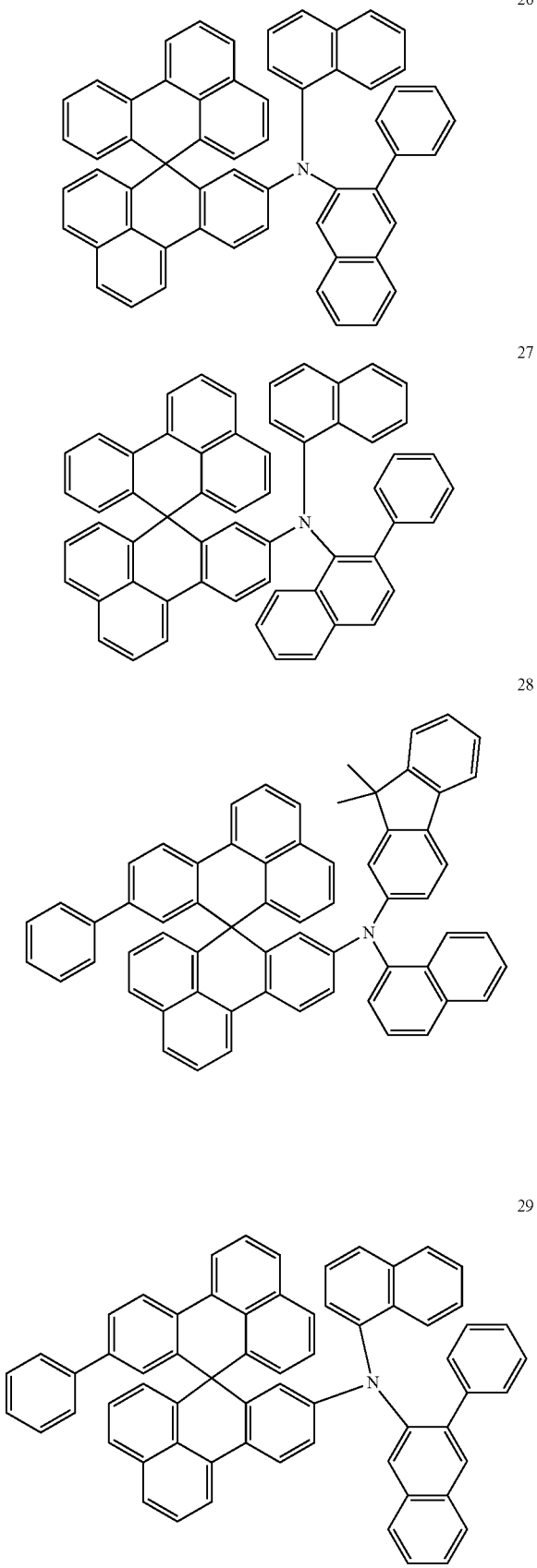
27
28
29
-continued
30
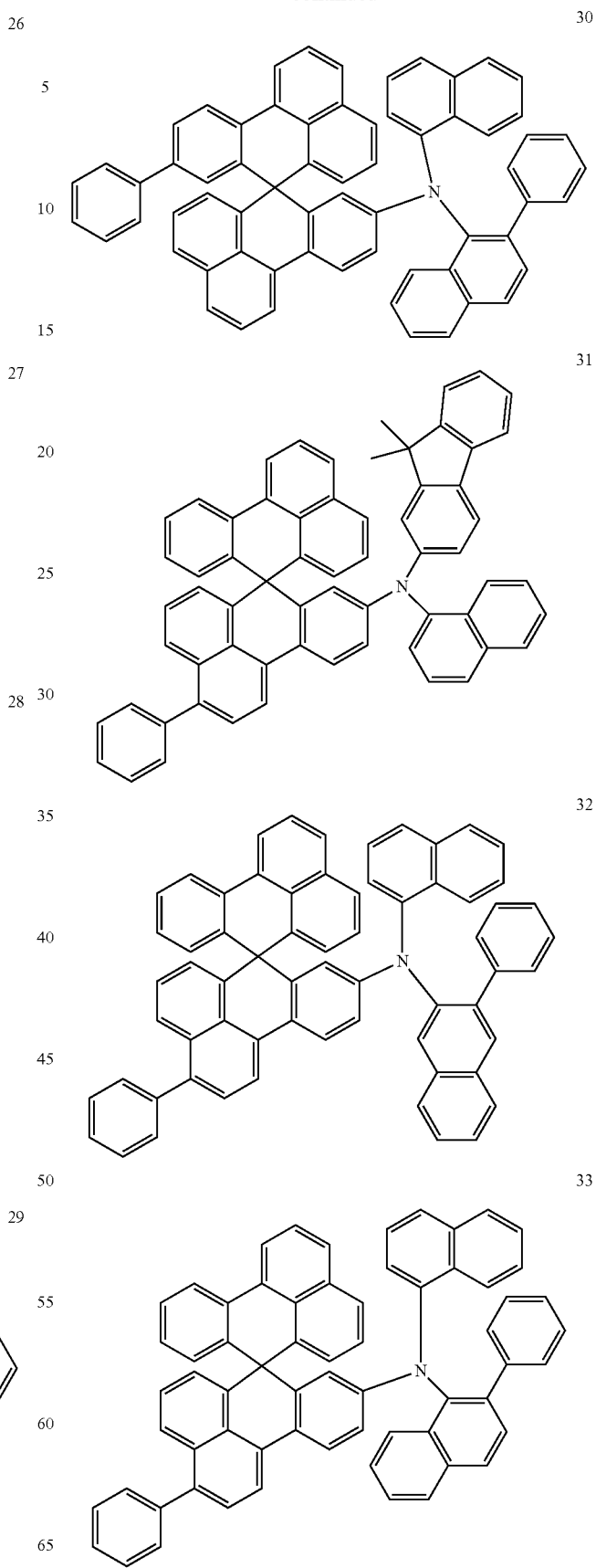
31
32
33

34
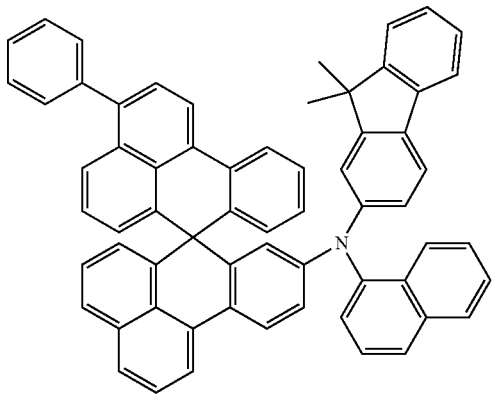
35
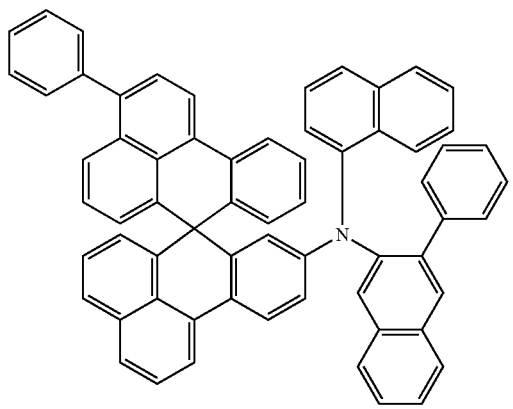
36
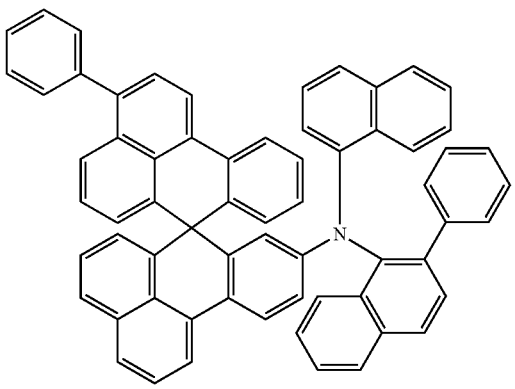
37
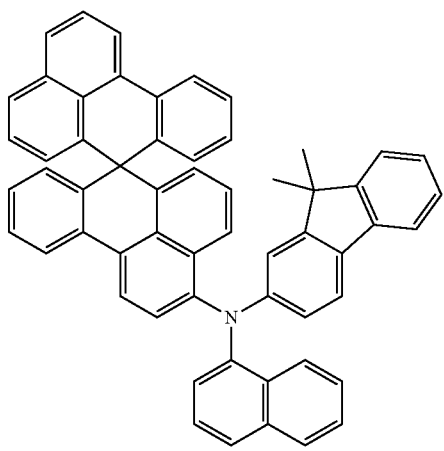
38
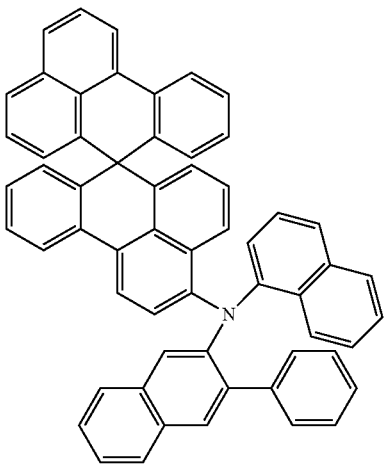
39
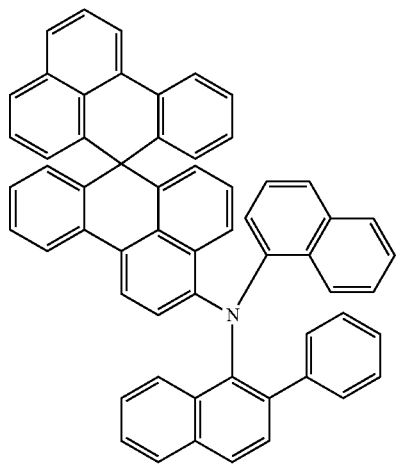
40
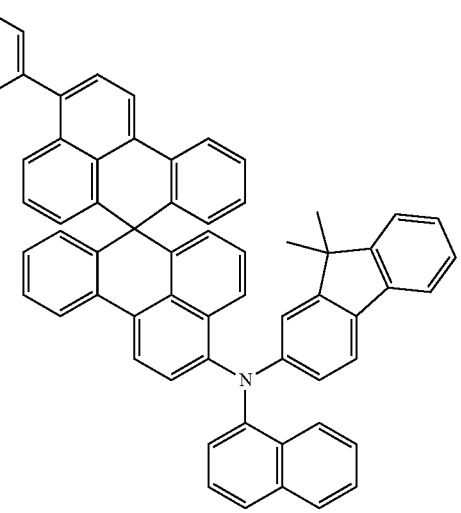

161
-continued
41
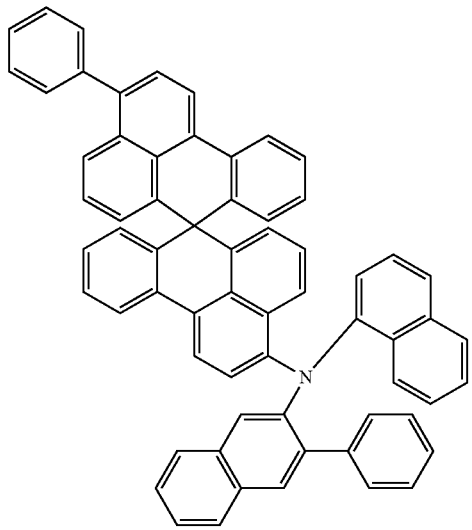
42
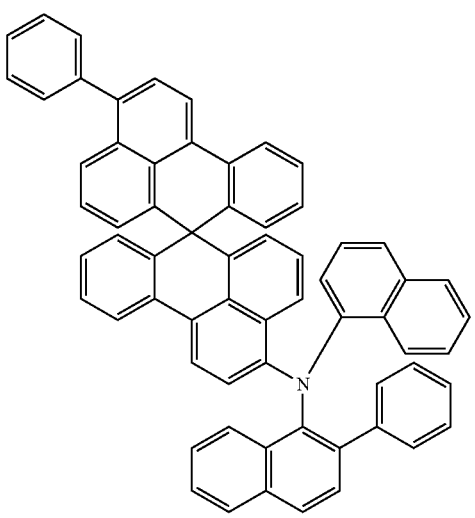
43
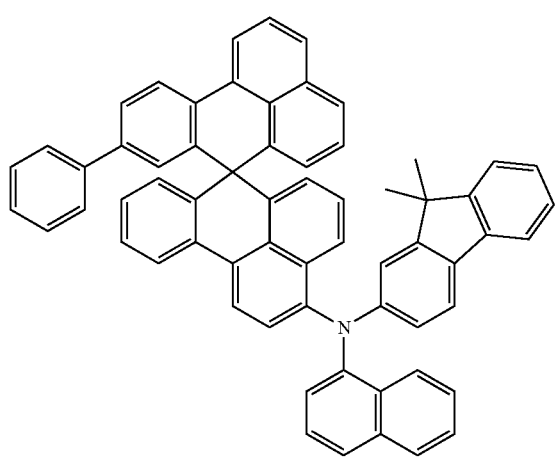
162
-continued
44
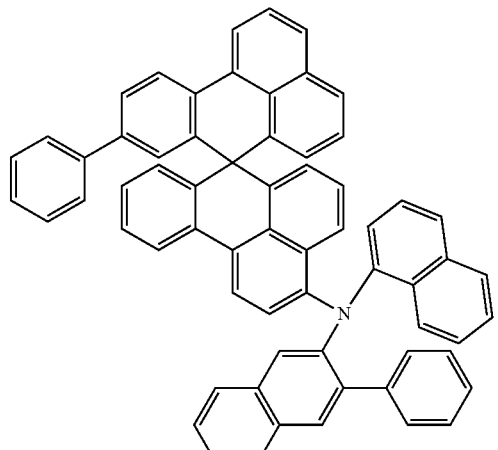
45
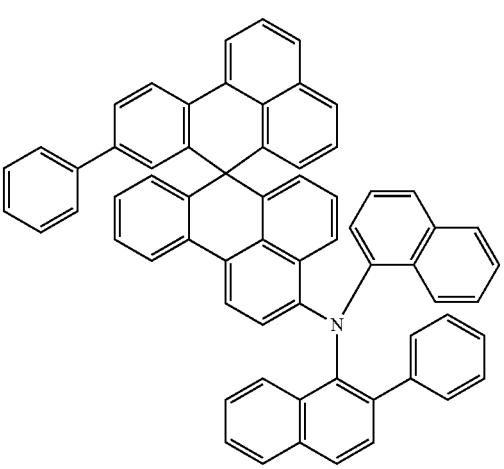
46
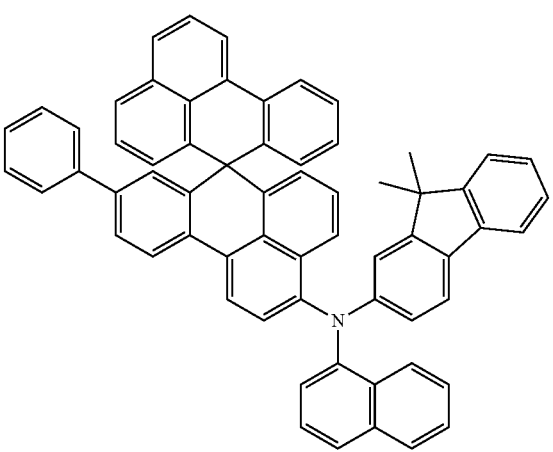

47
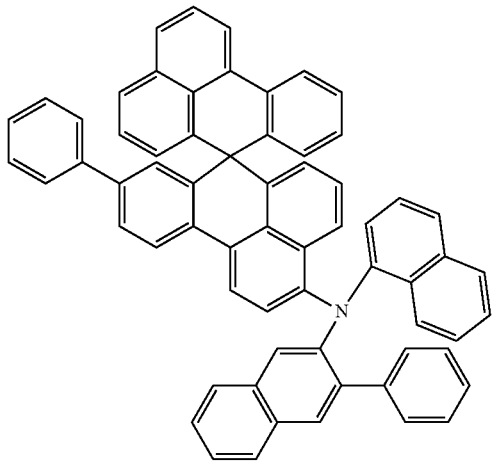
48
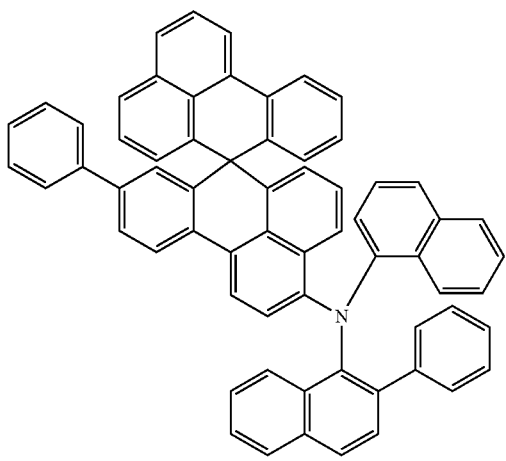
49
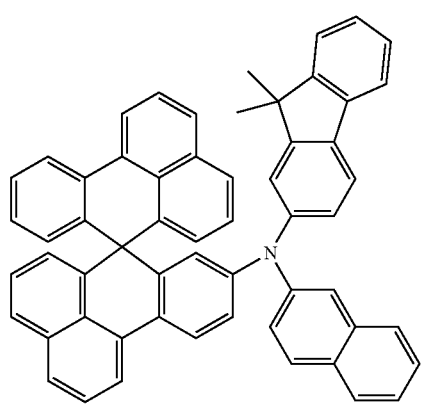
50
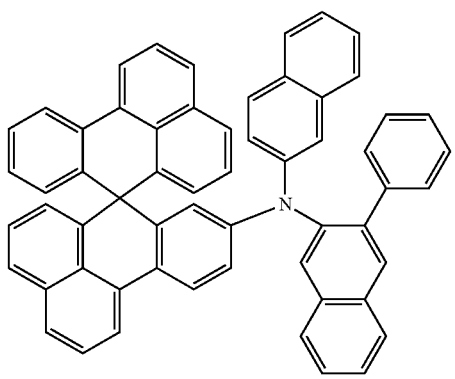
51
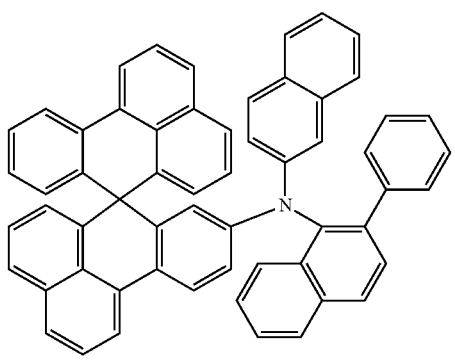
52
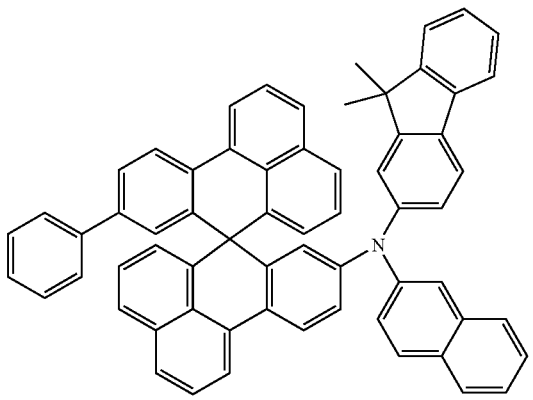
53
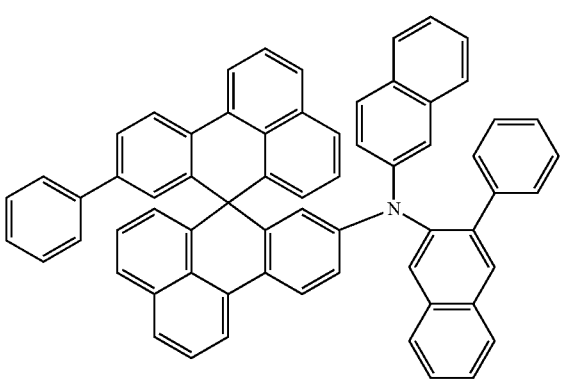

54
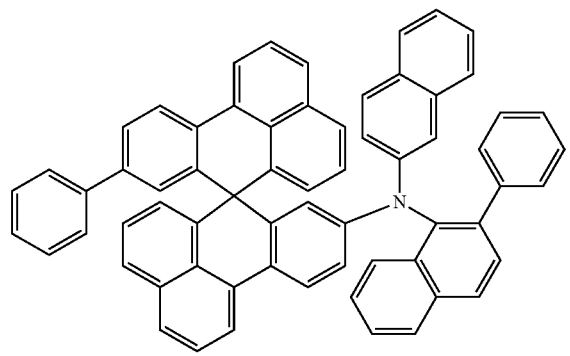
55
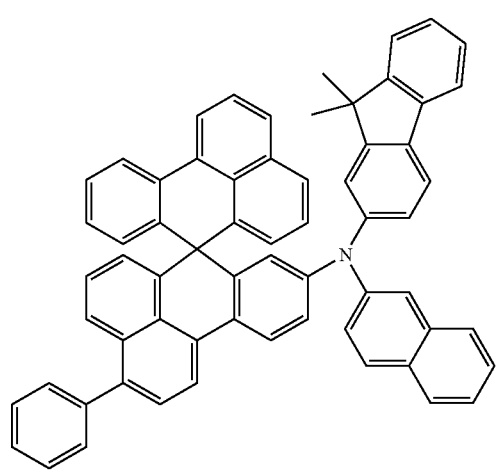
56
57
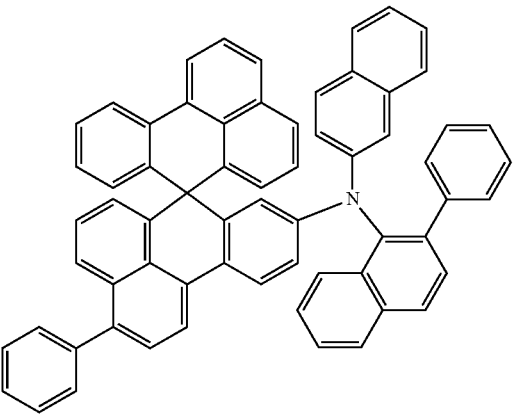
58
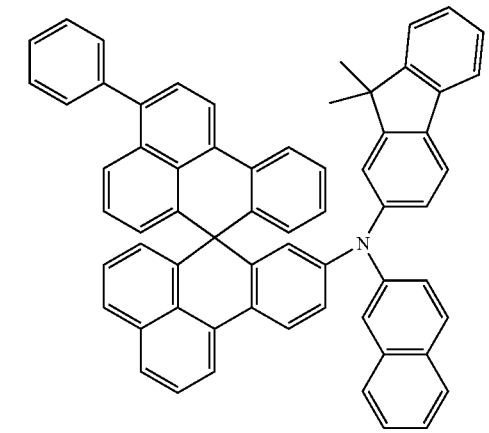
59
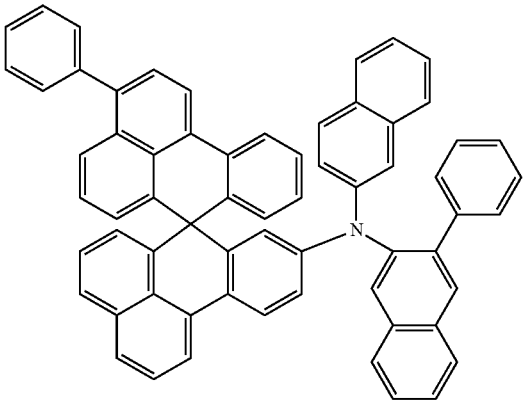
60
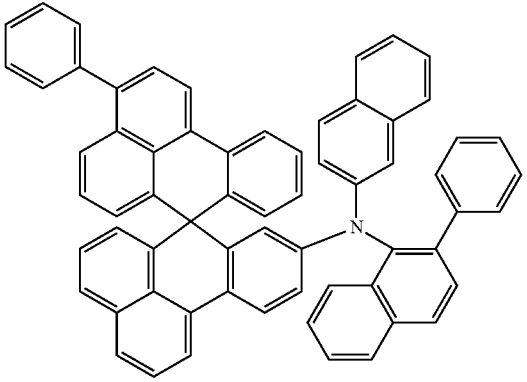

61
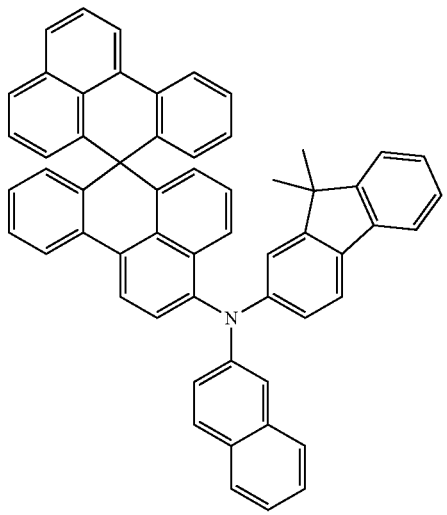
62
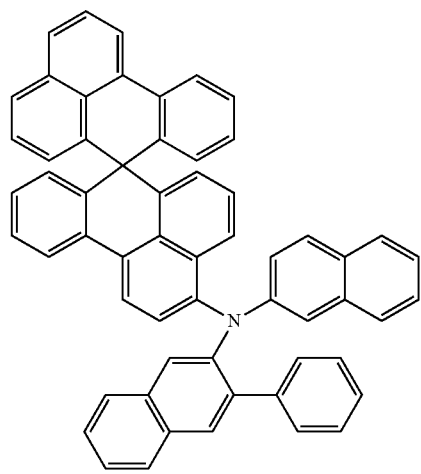
63
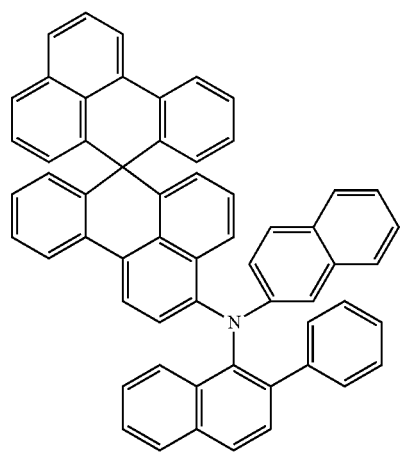
64
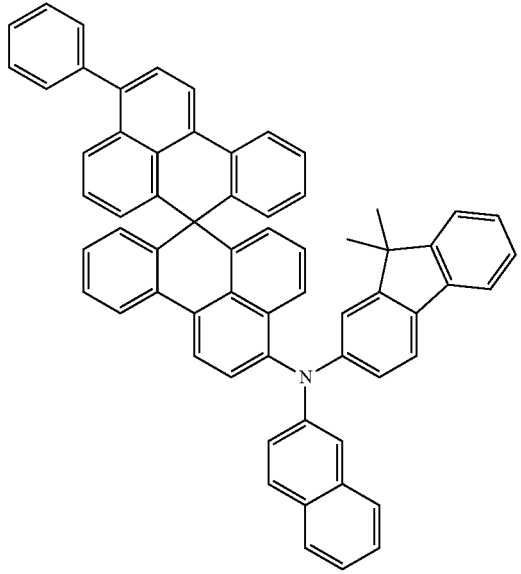
65
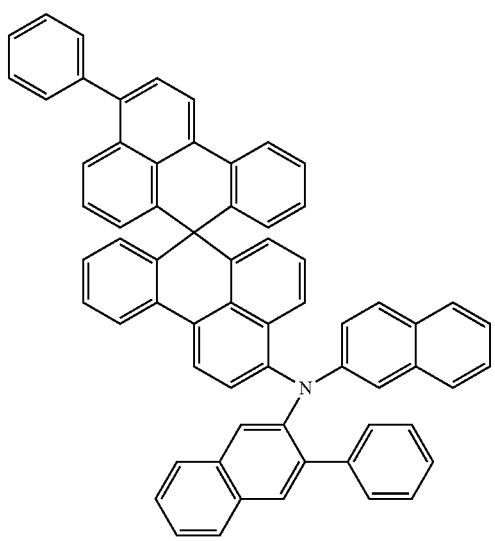
66
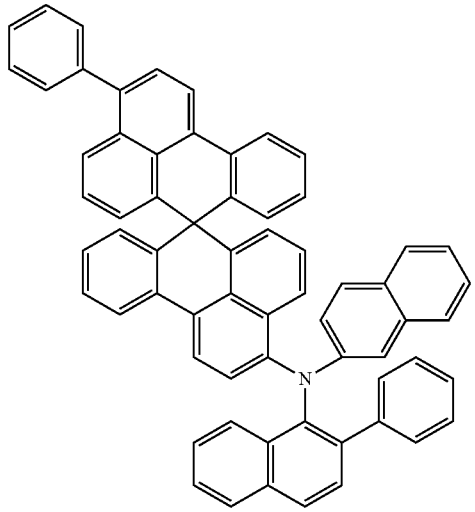

-continued
67
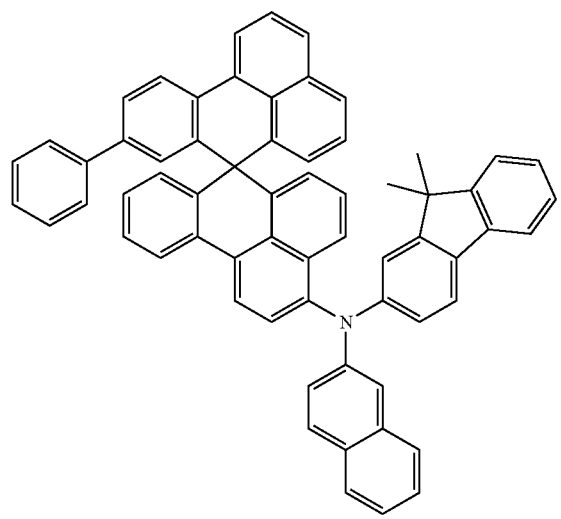
68
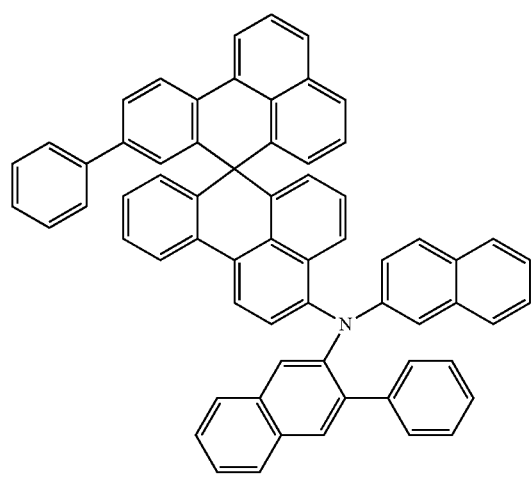
69
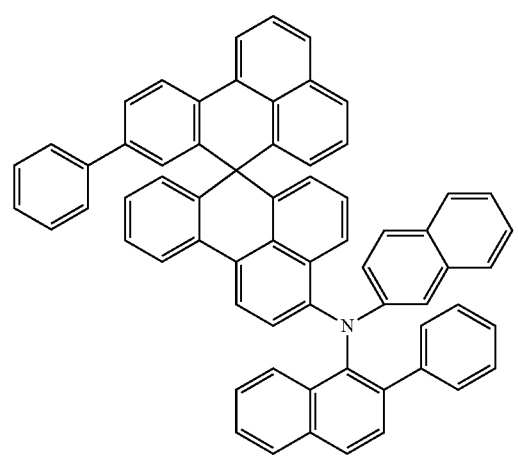
-continued
70
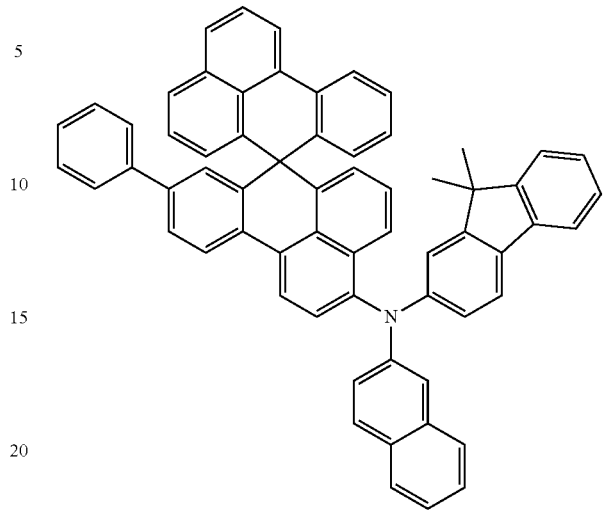
71
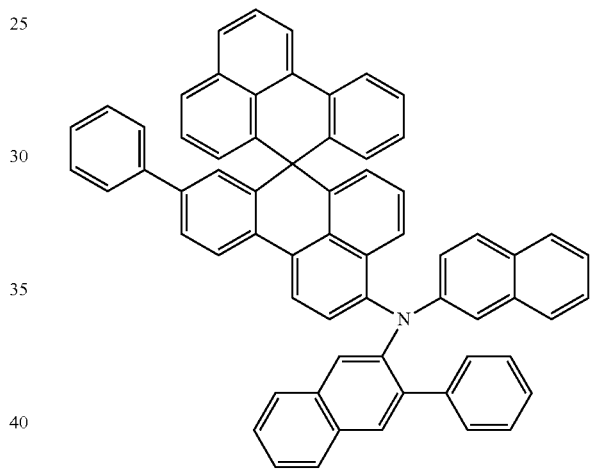
72
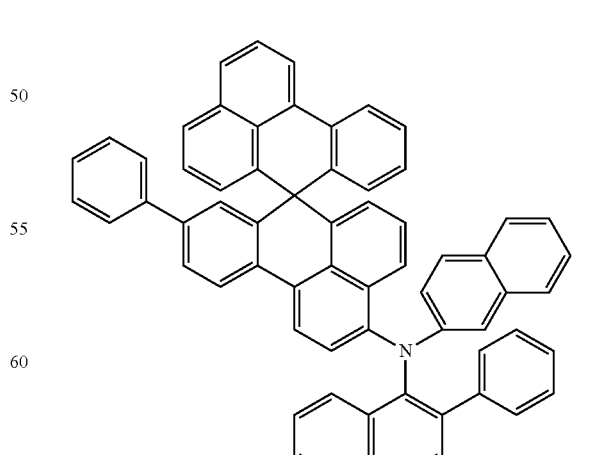

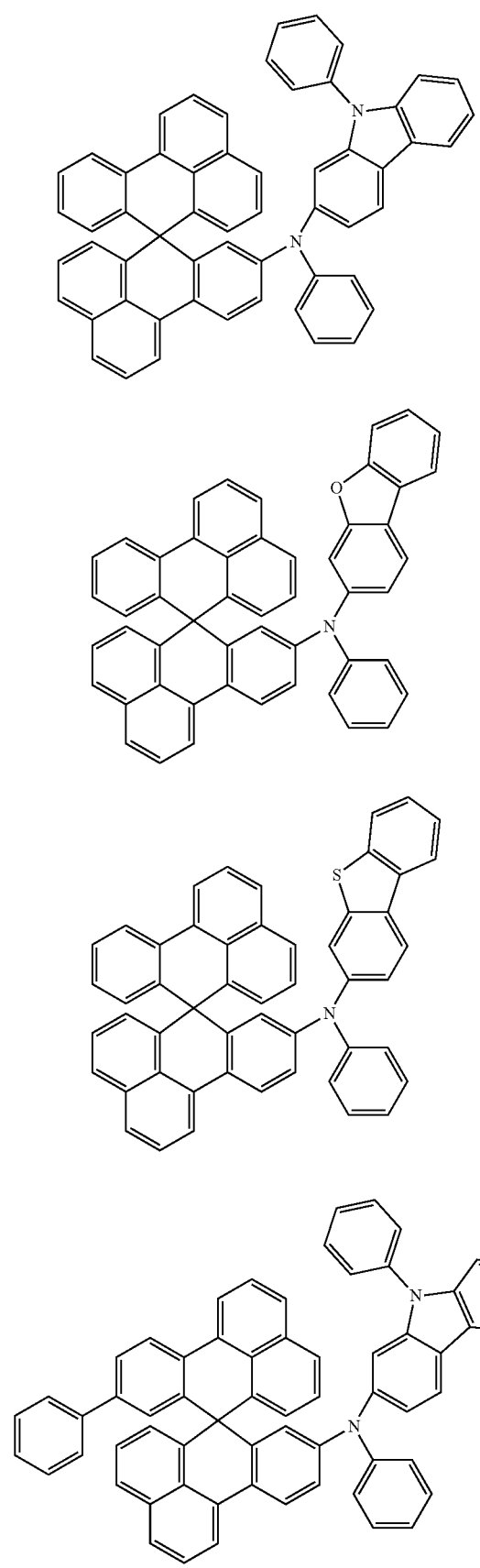
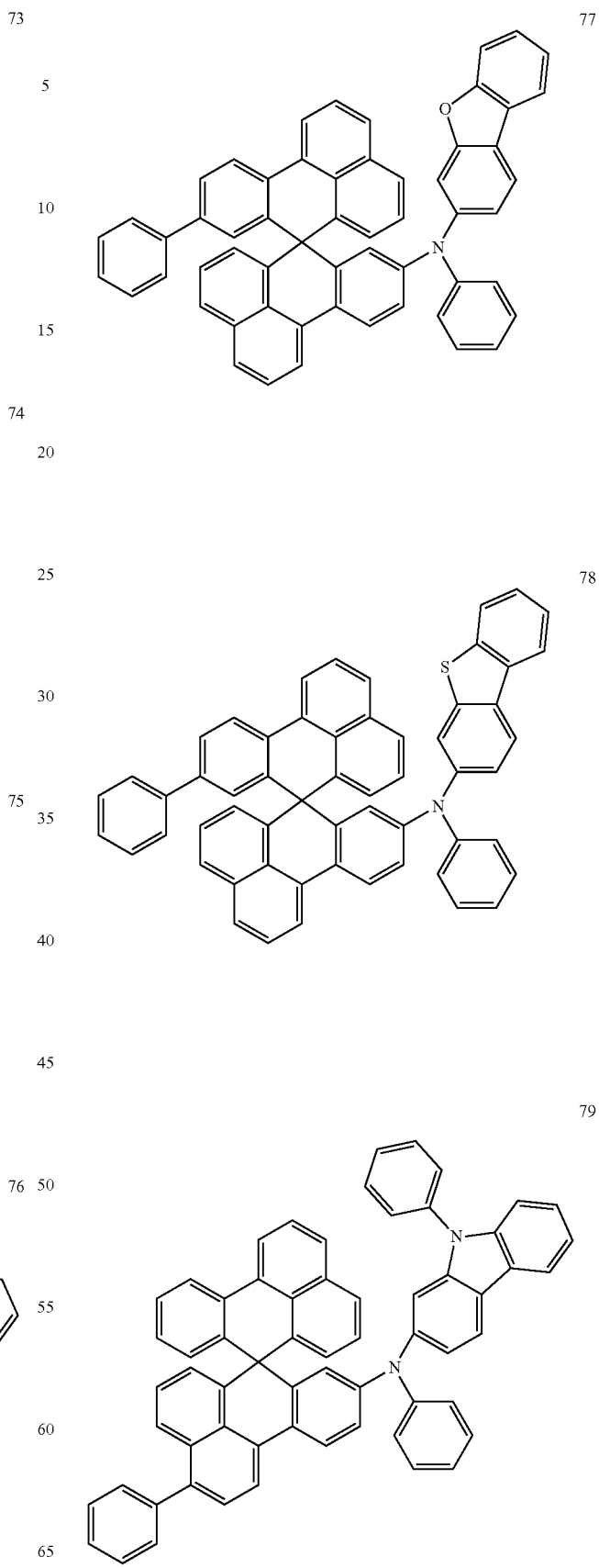

173
-continued
80
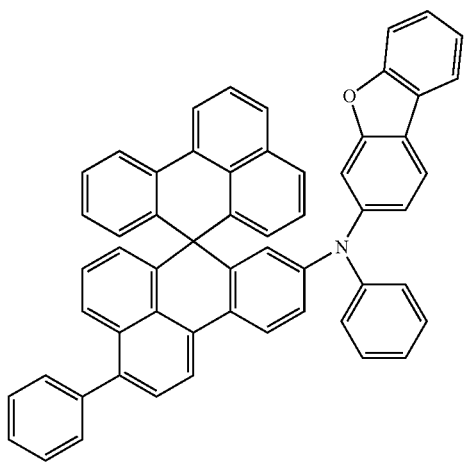
81
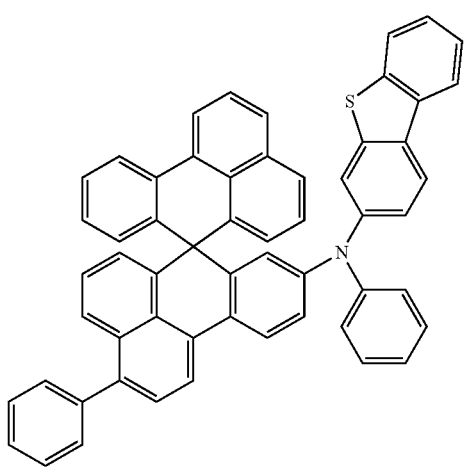
82
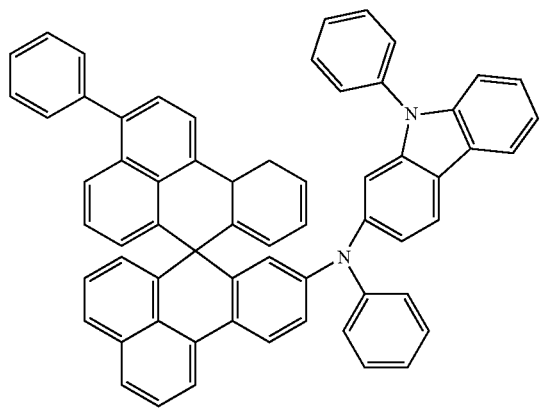
174
-continued
83
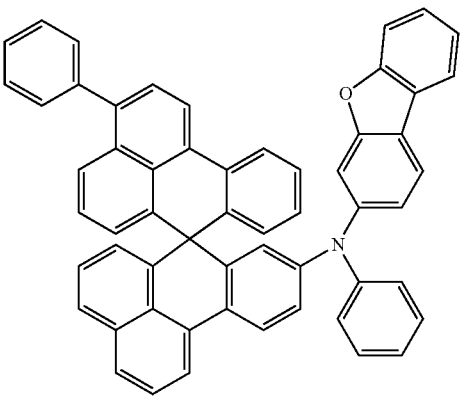
84
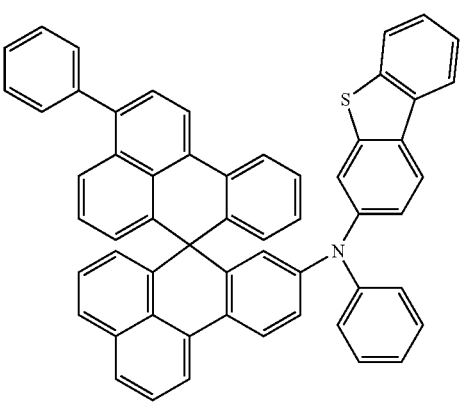
85
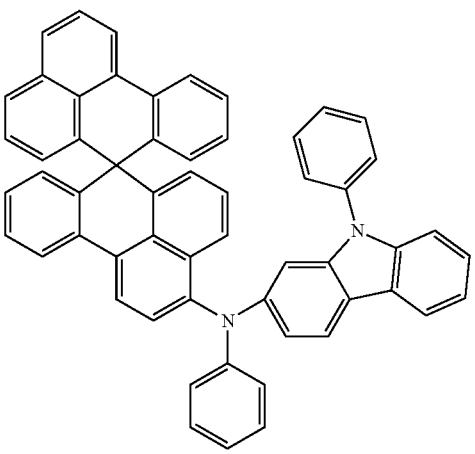

86
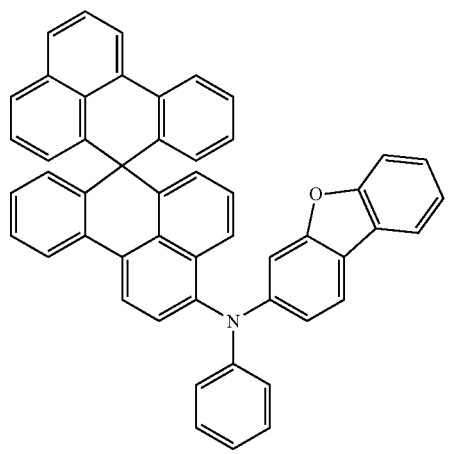
87
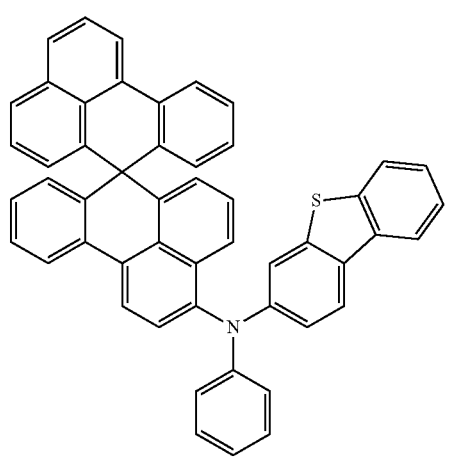
88
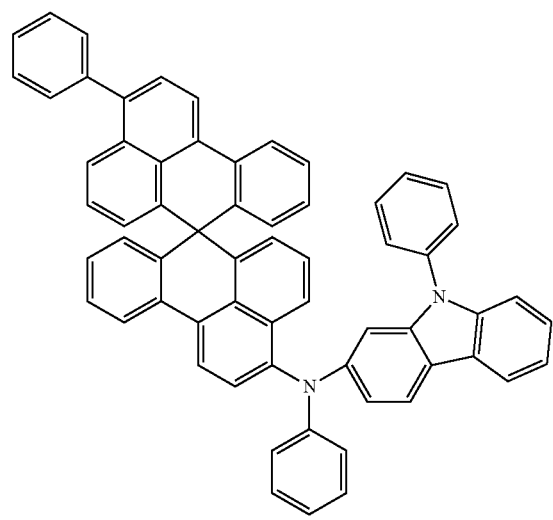
89
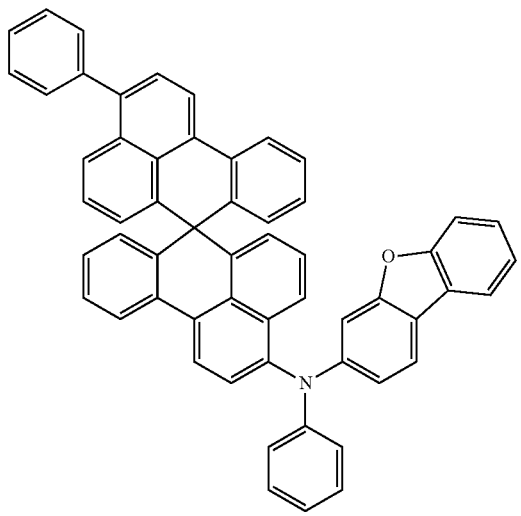
90
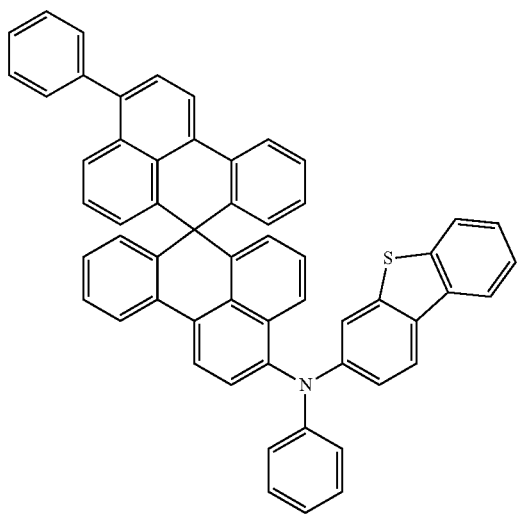
91
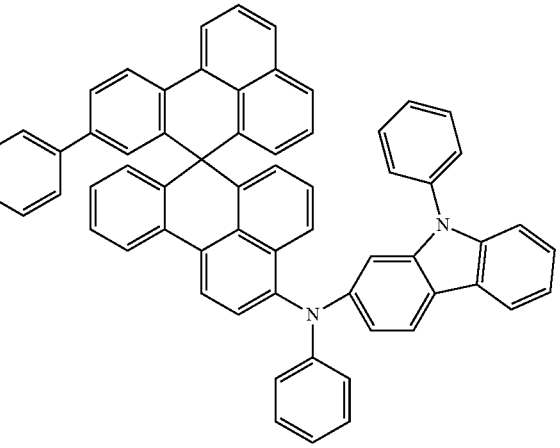

92
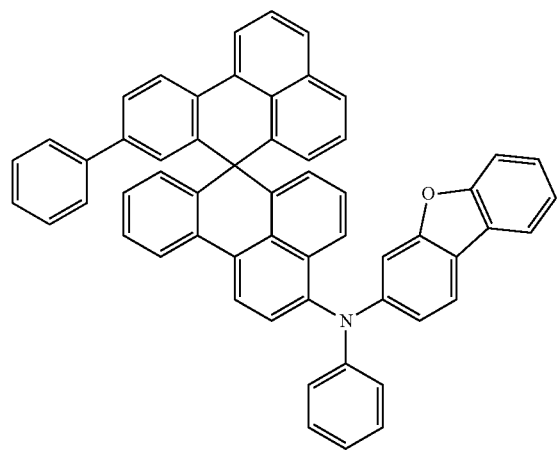
93
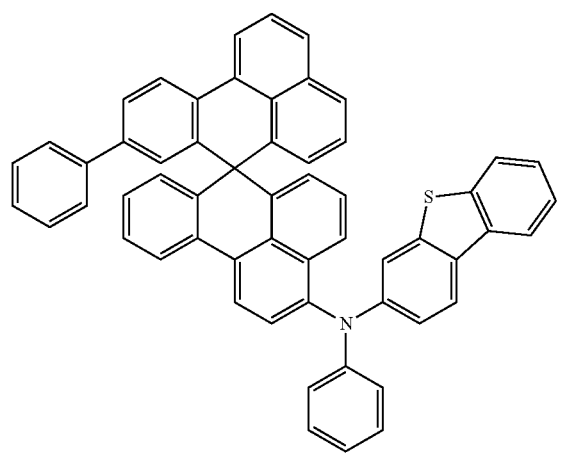
94
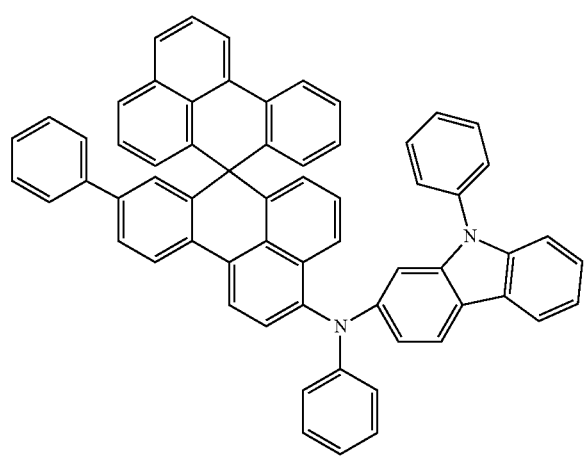
95
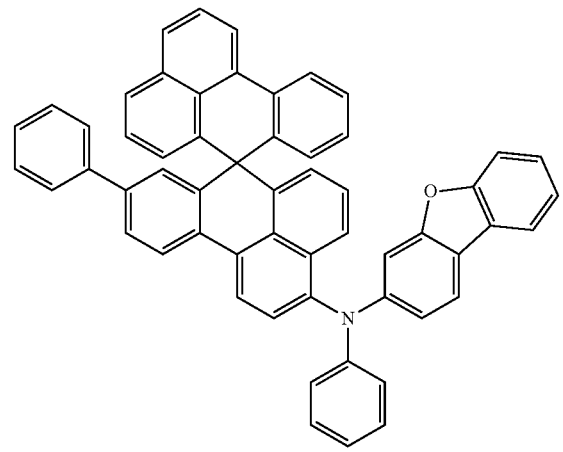
96
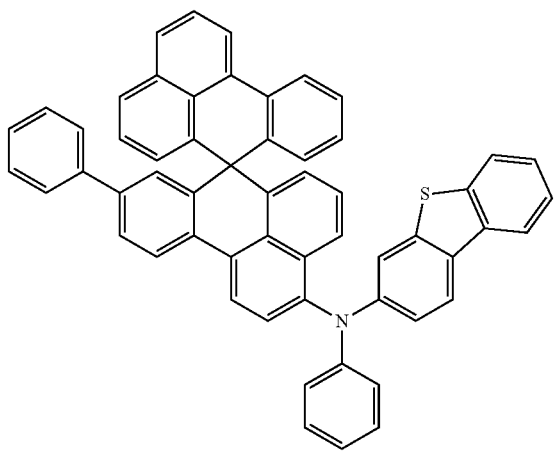
97
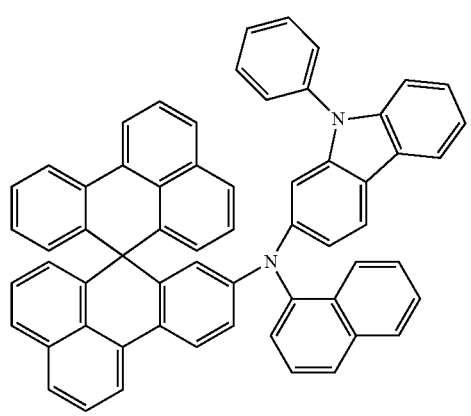

-continued
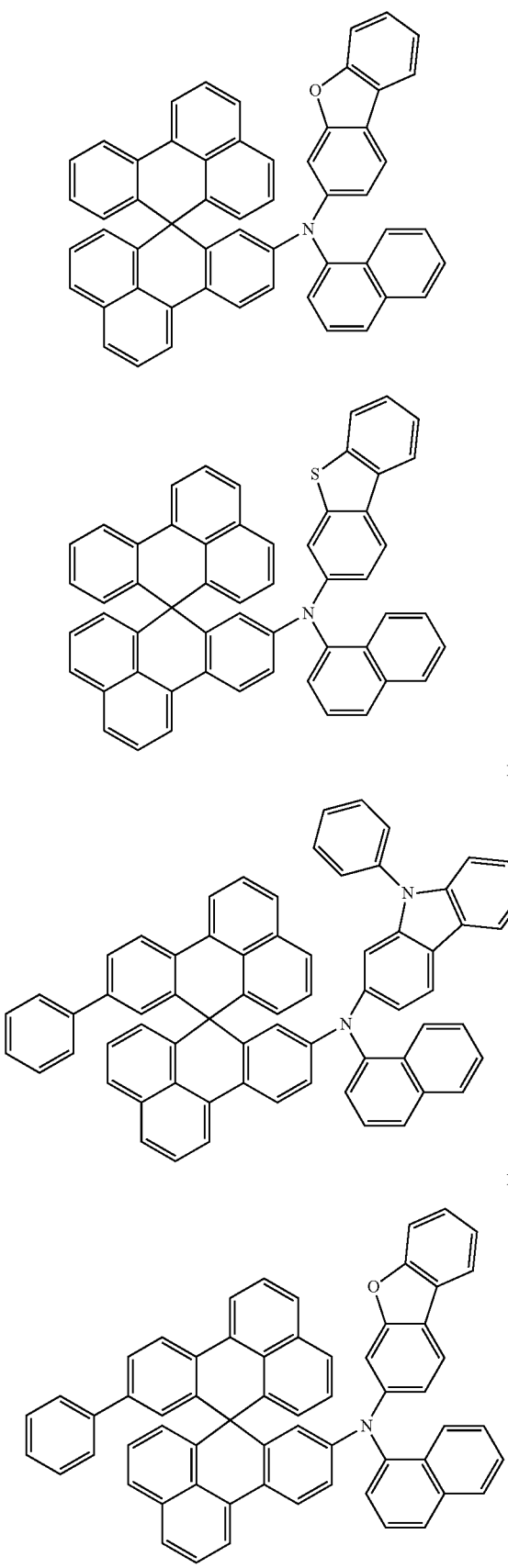
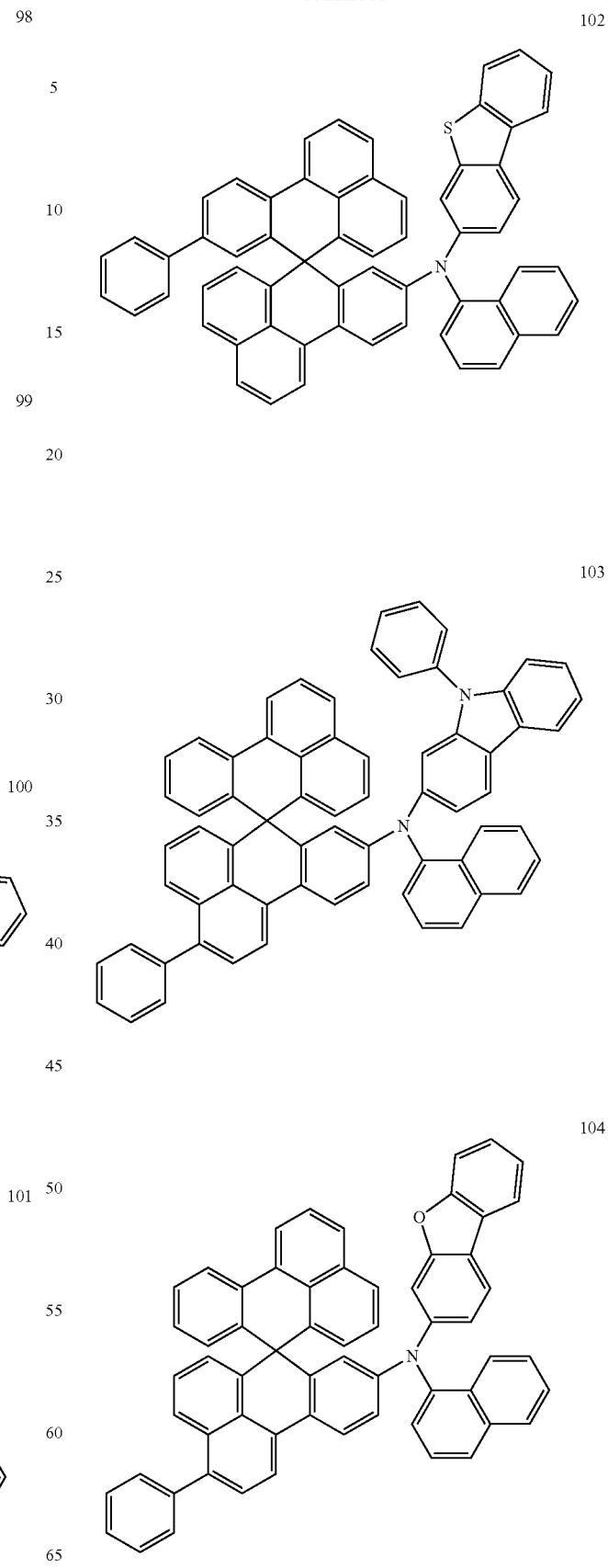

105
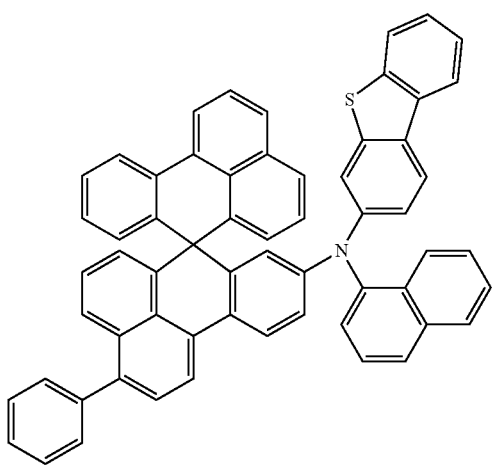
106
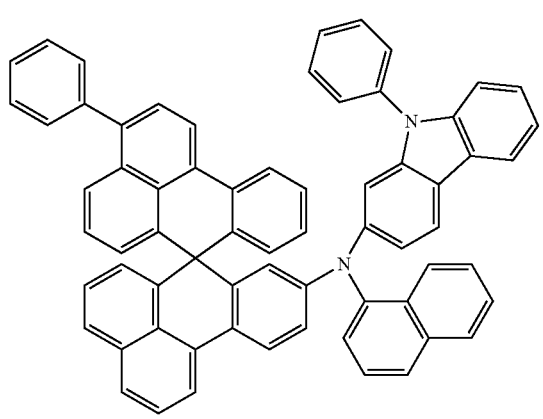
107
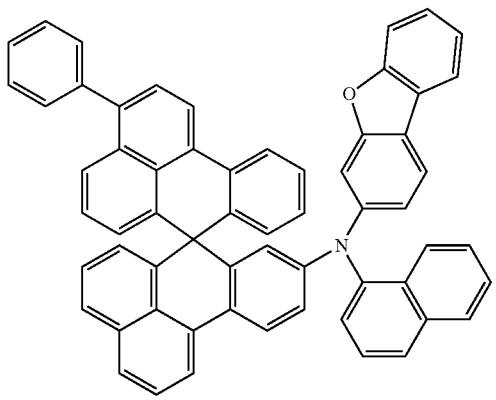
108
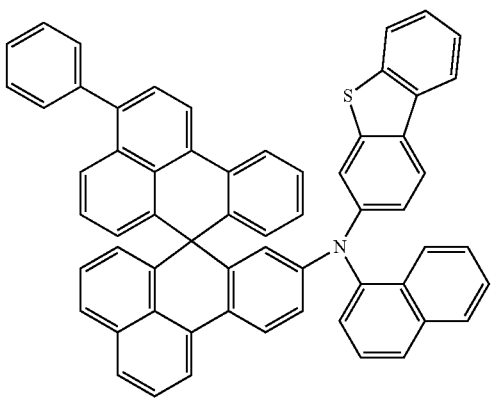
109
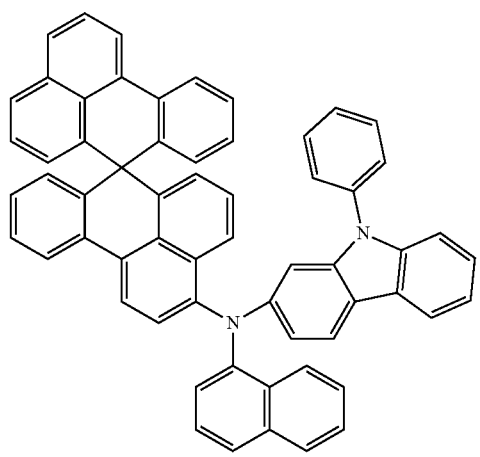
110
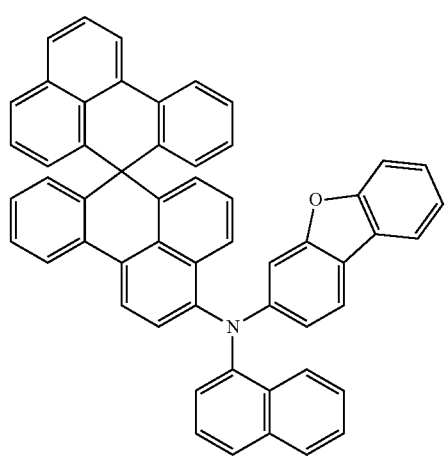

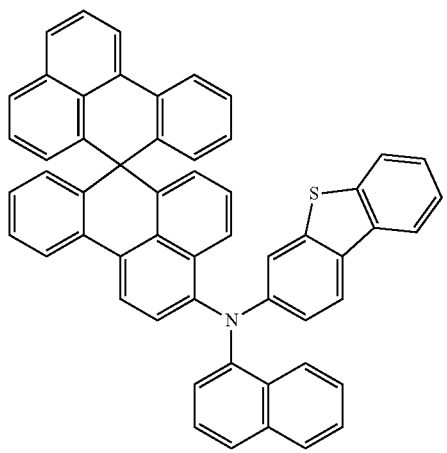
111
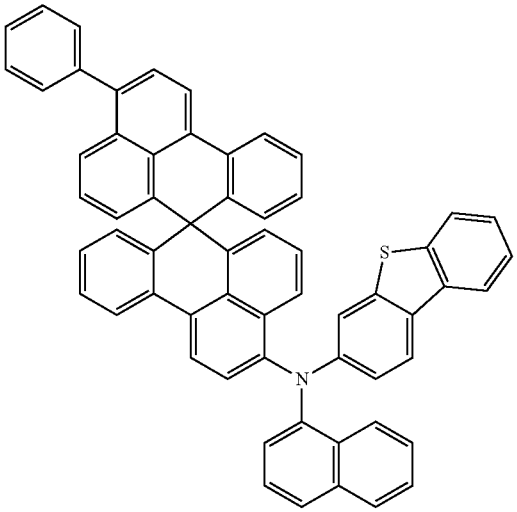
114
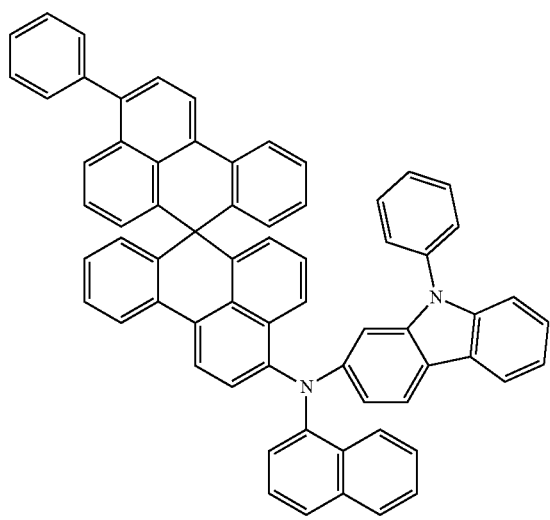
112
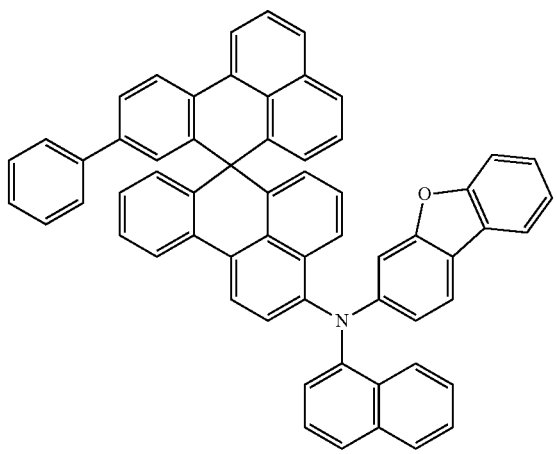
115
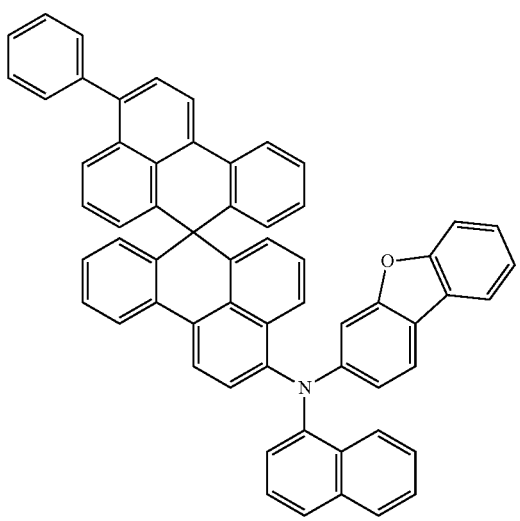
113
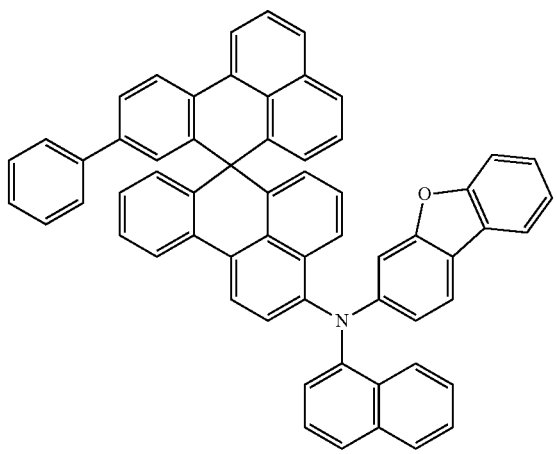
116

117
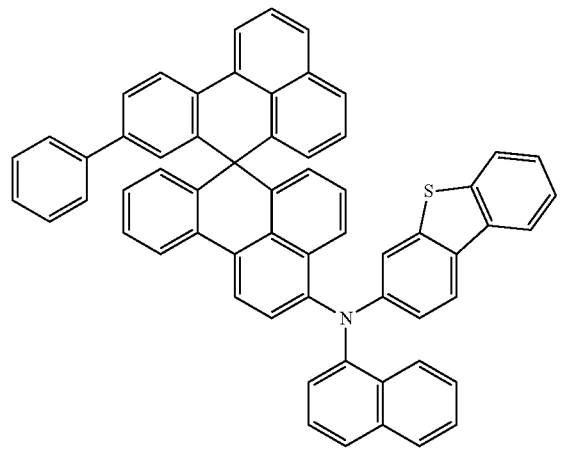
118
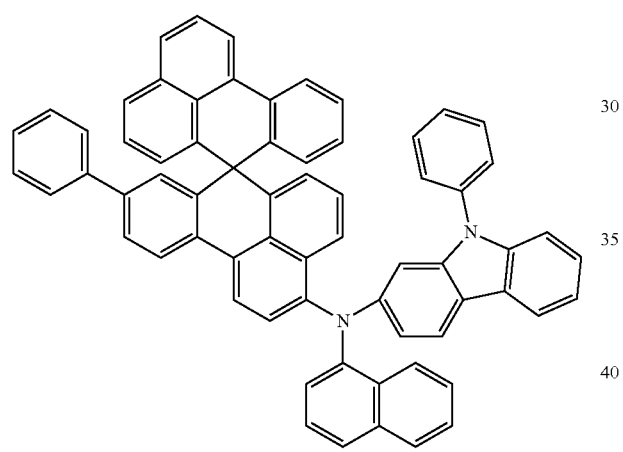
119
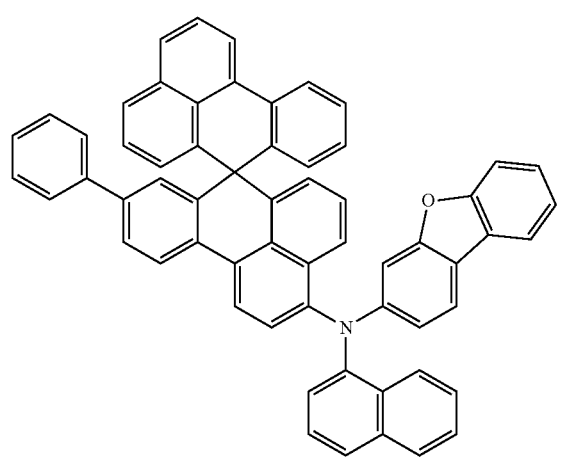
120
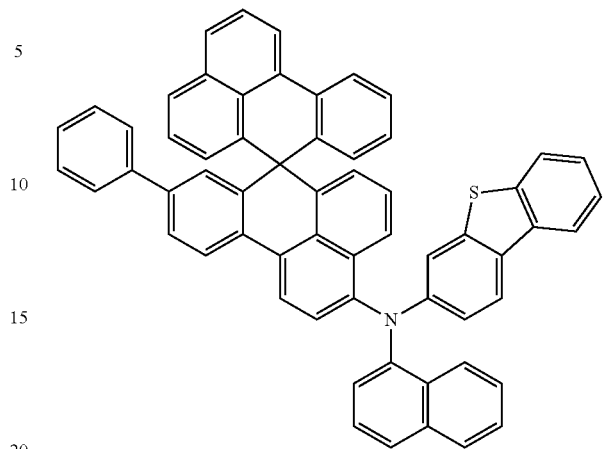
121
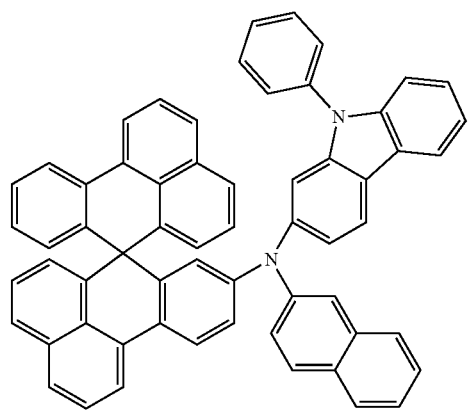
122
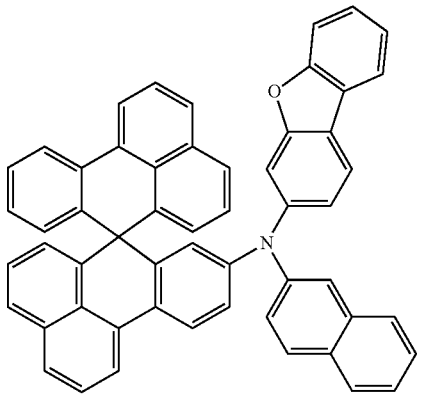

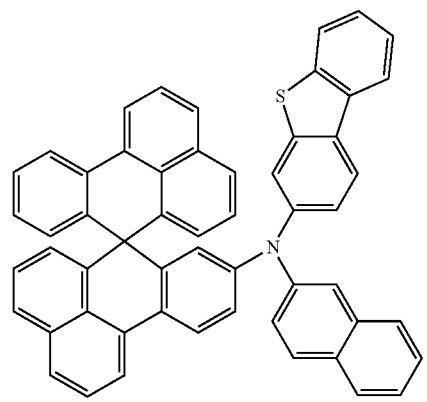
123
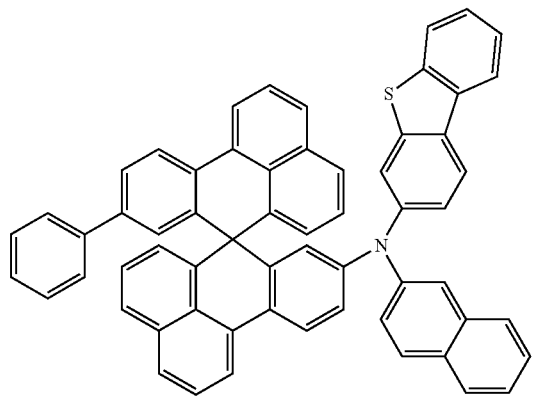
126
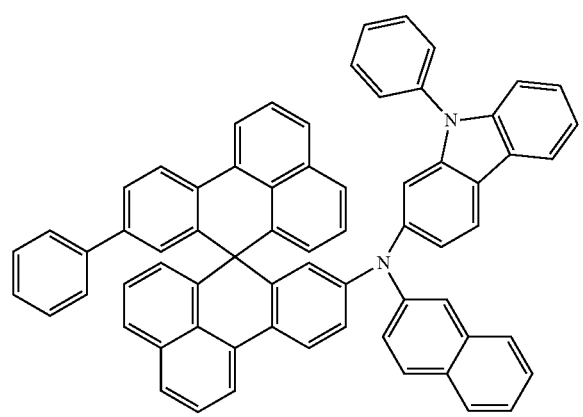
124
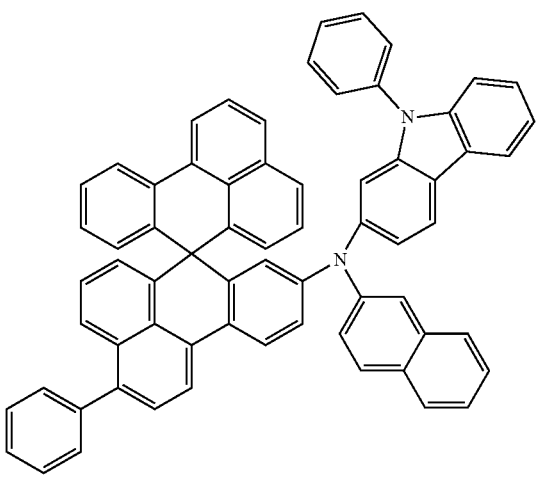
127
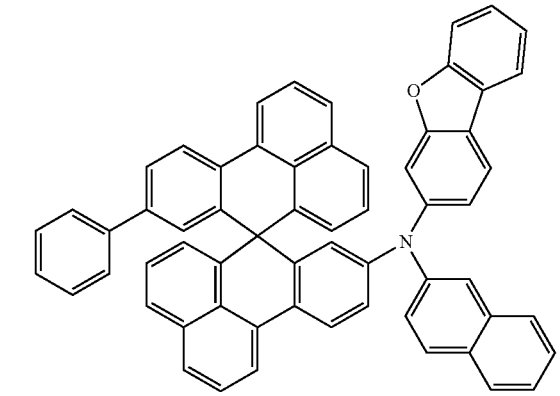
125
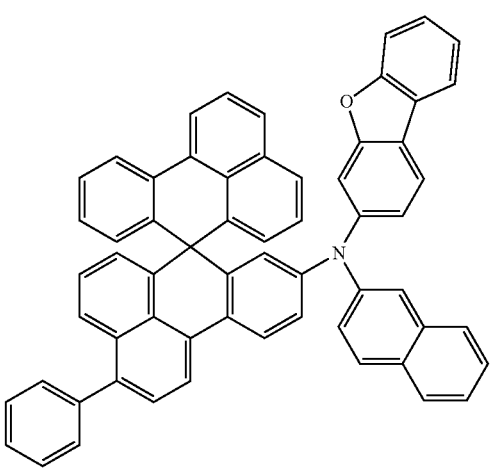
128

-continued
129
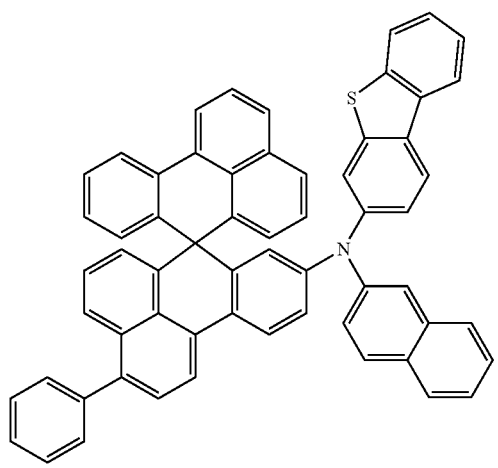
130
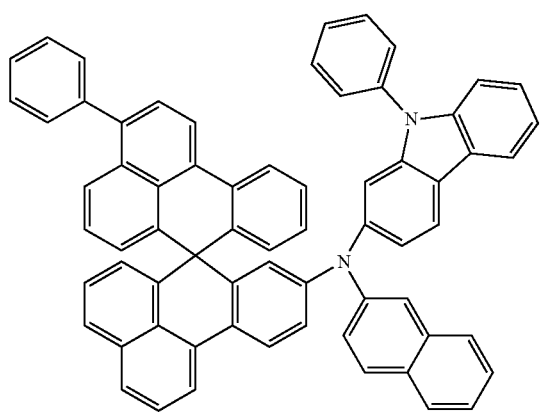
131
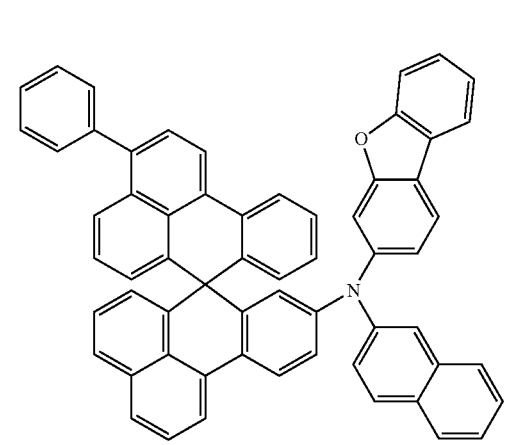
-continued
132
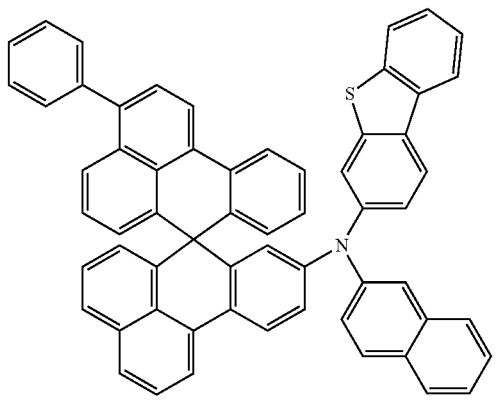
133
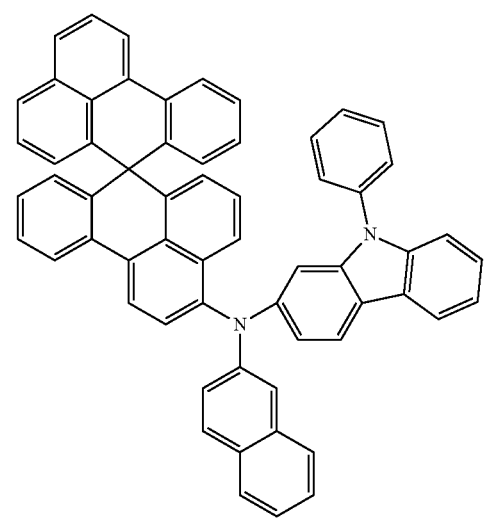
134
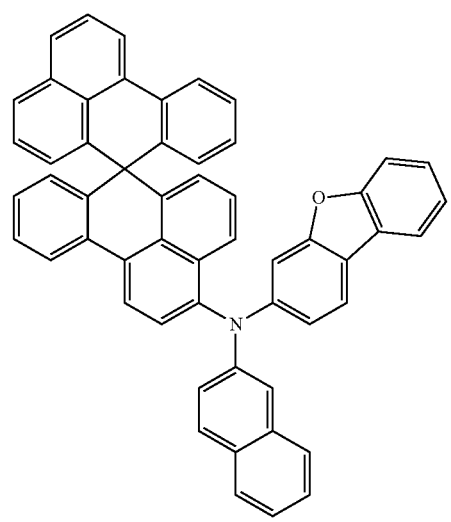

191
-continued
135
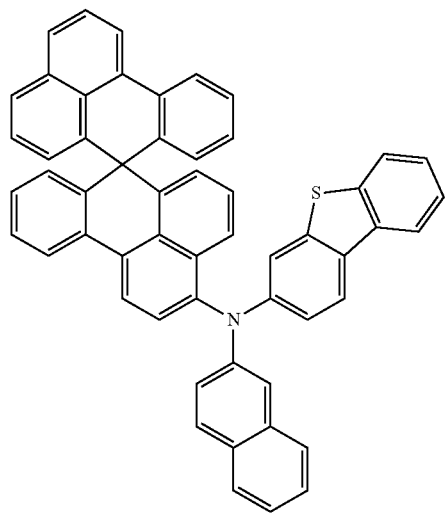
136
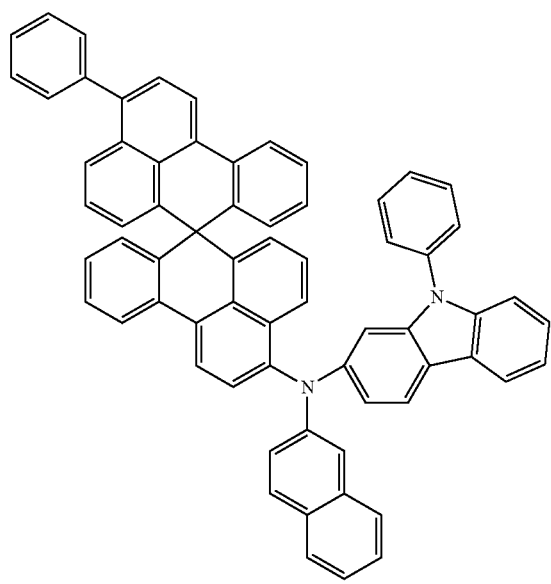
192
-continued
137
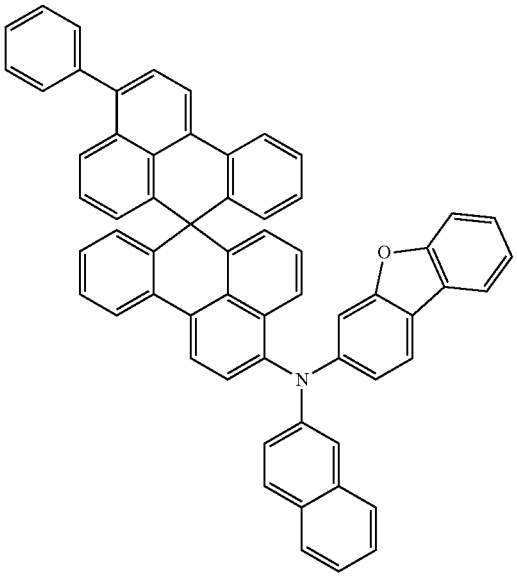
138

139
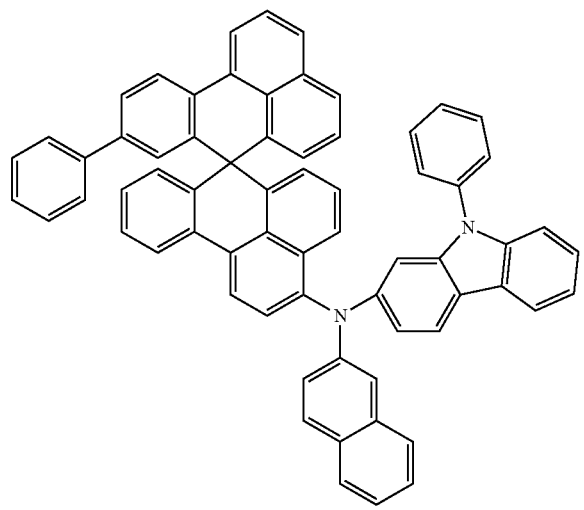
140
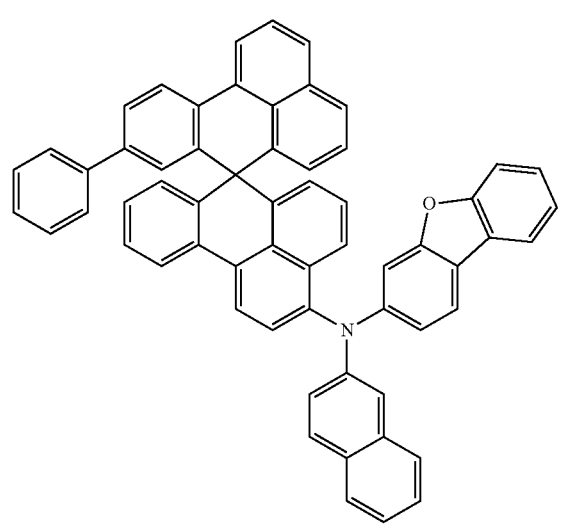
141
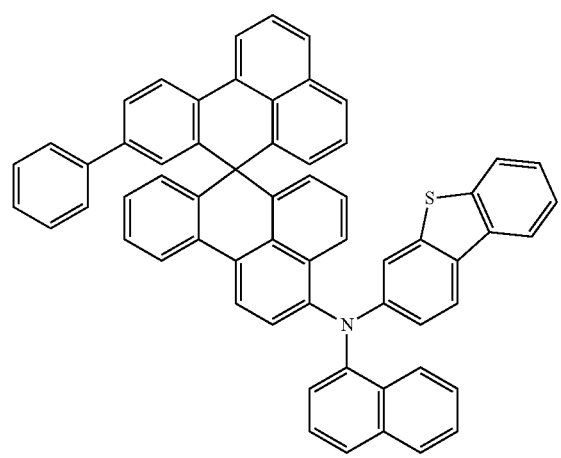
142
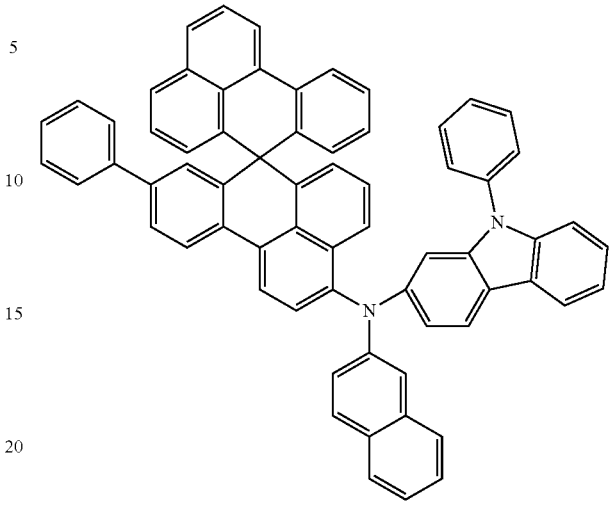
143
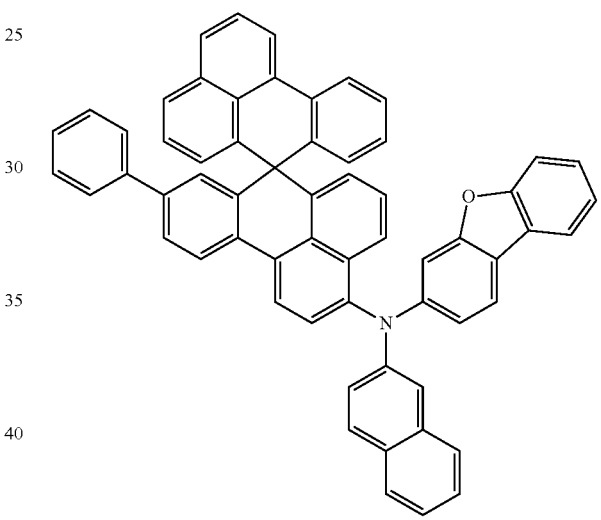
144
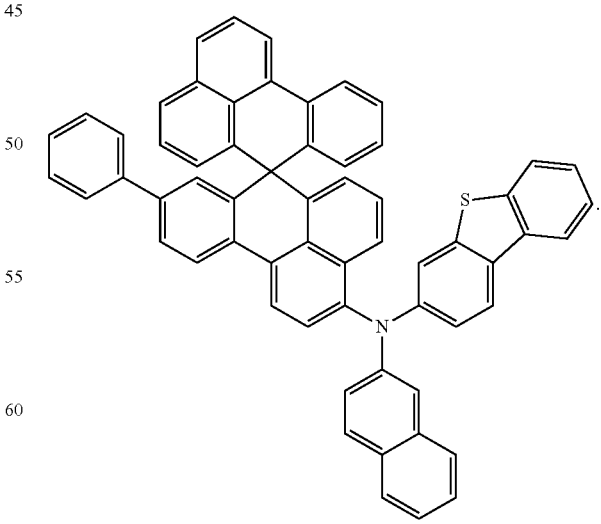

16. An amine compound represented by Formula 1:

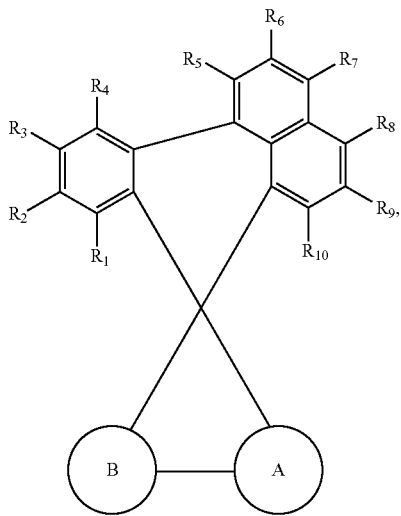

Formula 1 wherein, in Formula 1
$R_1$ to $R_{10}$ are each independently a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms,
at least one among $R_1$ to $R_{10}$ is represented by Formula 2, and
ring A and ring B are each independently represented by Formula 3 or Formula 4, and are represented by different formulae:

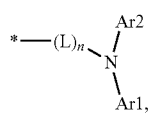

Formula 2 wherein, in Formula 2,
L is a direct linkage, a substituted or unsubstituted arylene group having 6 to 30 ring-forming carbon atoms, or a substituted or unsubstituted heteroarylene group having 2 to 30 ring-forming carbon atoms,
n is an integer of 0 to 3, and
Ar1 and Ar2 are each independently a substituted or unsubstituted aryl group having 6 to 30 ring-forming carbon atoms, or a substituted or unsubstituted heteroaryl group having 2 to 30 ring-forming carbon atoms:

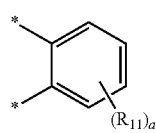

Formula 3

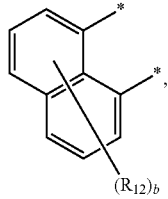

Formula 4 and
wherein, in Formula 3 and Formula 4,
$R_{11}$ and $R_{12}$ are each independently a hydrogen atom, a deuterium atom, a halogen atom, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms,
a is an integer of 0 to 4, and
b is an integer of 0 to 6.

17. The amine compound of claim 16, wherein Formula 1 is represented by Formula 5 or Formula 6:

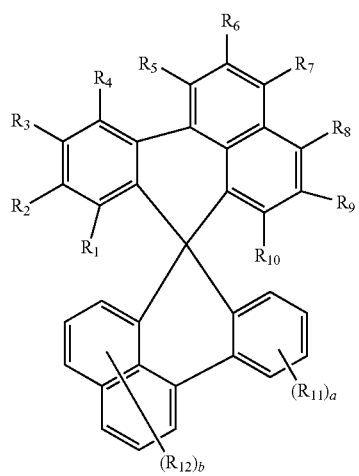

Formula 5

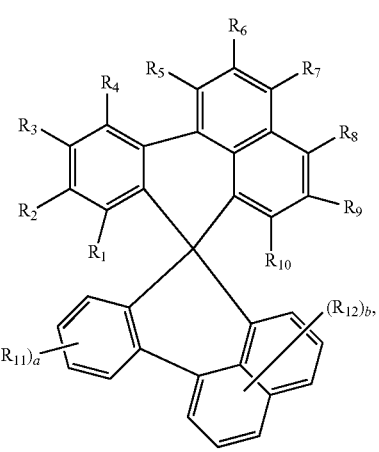

Formula 6 and
wherein, in Formula 5 and Formula 6,
$R_1$ to $R_{12}$, a, and b are the same as defined in Formula 1, Formula 3, and Formula 4.

18. The amine compound of claim 17, wherein Formula 5 is represented by Formula 7-1:

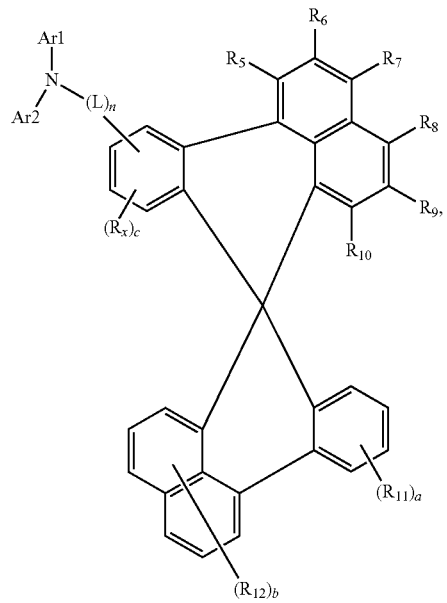

Formula 7-1

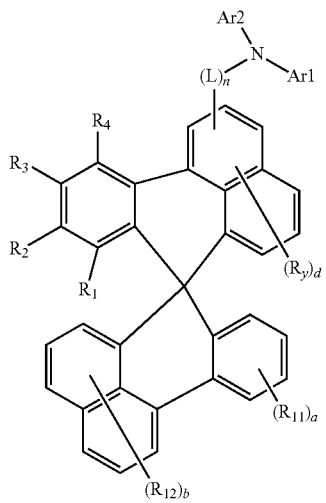

Formula 7-2

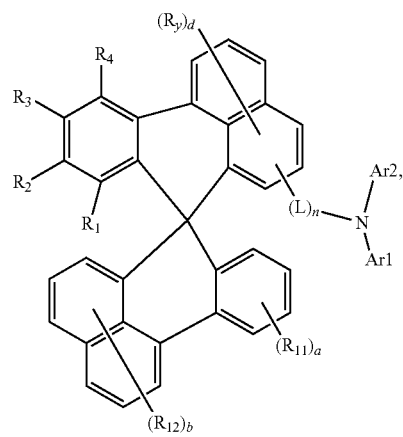

Formula 7-3 and wherein, in Formula 7-1, $R_x$, and $R_5$ to $R_{10}$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, c is an integer of 0 to 3, L is a direct linkage, a substituted or unsubstituted arylene group having 6 to 30 ring-forming carbon atoms, or a substituted or unsubstituted heteroarylene group having 2 to 30 ring-forming carbon atoms, n is an integer of 0 to 3, Ar1 and Ar2 are each independently a substituted or unsubstituted aryl group having 6 to 30 ring-forming carbon atoms, or a substituted or unsubstituted heteroaryl group having 2 to 30 ring-forming carbon atoms, and $R_{11}$, $R_{12}$, a, and b are the same as defined in Formula 5.

19. The amine compound of claim 17, wherein Formula 5 is represented by Formula 7-2 or Formula 7-3:

wherein, in Formula 7-2 and Formula 7-3, $R_y$, and $R_1$ to $R_4$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, d is an integer of 0 to 5, L is a direct linkage, a substituted or unsubstituted arylene group having 6 to 30 ring-forming carbon atoms, or a substituted or unsubstituted heteroarylene group having 2 to 30 ring-forming carbon atoms, n is an integer of 0 to 3, Ar1 and Ar2 are each independently a substituted or unsubstituted aryl group having 6 to 30 ring-forming carbon atoms, or a substituted or unsubstituted heteroaryl group having 2 to 30 ring-forming carbon atoms, and $R_{11}$, $R_{12}$, a, and b are the same as defined in Formula 5.

20. The amine compound of claim 17, wherein Formula 6 is represented by Formula 9-1:

Formula 9-1

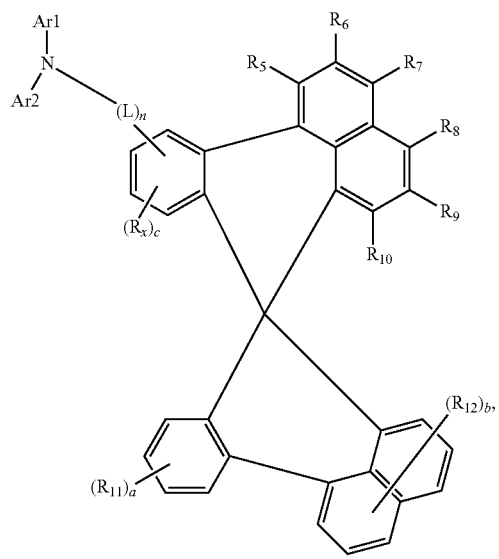

Formula 9-2

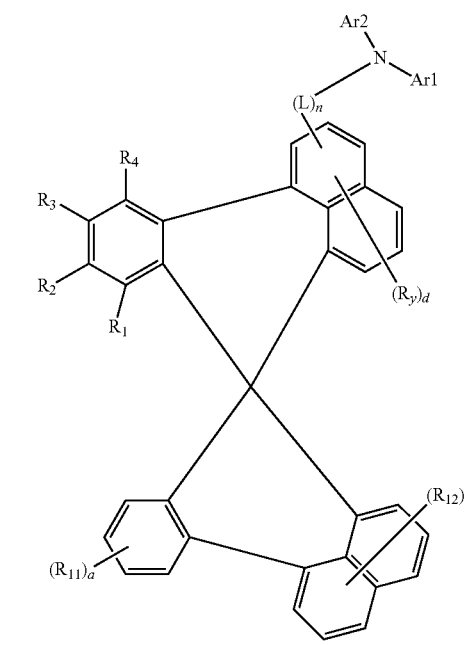

Formula 9-3

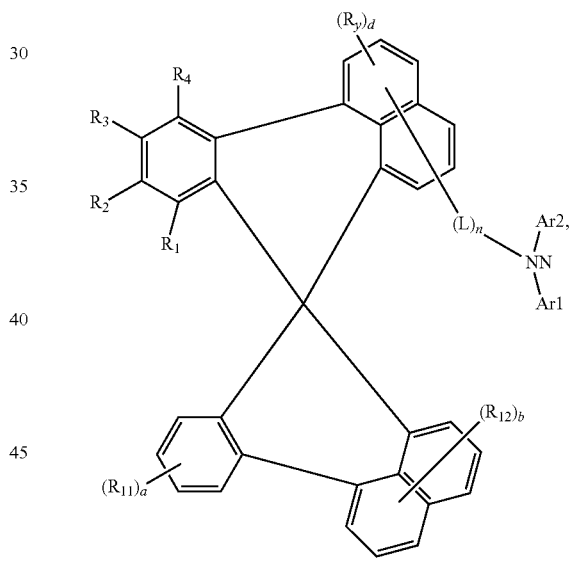

and wherein, in Formula 9-1, $R_x$, and $R_5$ to $R_{10}$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, c is an integer of 0 to 3, L is a direct linkage, a substituted or unsubstituted arylene group having 6 to 30 ring-forming carbon atoms, or a substituted or unsubstituted heteroarylene group having 2 to 30 ring-forming carbon atoms, n is an integer of 0 to 3, Ar1 and Ar2 are each independently a substituted or unsubstituted aryl group having 6 to 30 ring-forming carbon atoms, or a substituted or unsubstituted heteroaryl group having 2 to 30 ring-forming carbon atoms, and $R_{11}$, $R_{12}$, a, and b are the same as defined in Formula 6.

21. The amine compound of claim 17, wherein Formula 6 is represented by Formula 9-2 or Formula 9-3:

and wherein, in Formula 9-2 and Formula 9-3, $R_y$, and $R_1$ to $R_4$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, d is an integer of 0 to 5, L is a direct linkage, a substituted or unsubstituted arylene group having 6 to 30 ring-forming carbon atoms, or a substituted or unsubstituted heteroarylene group having 2 to 30 ring-forming carbon atoms, n is an integer of 0 to 3, Ar1 and Ar2 are each independently a substituted or unsubstituted aryl group having 6 to 30 ring-forming carbon atoms, or a substituted or unsubstituted heteroaryl group having 2 to 30 ring-forming carbon atoms, and
$R_{11}$, $R_{12}$, a, and b are the same as defined in Formula 6.
22. The amine compound of claim 16, wherein the amine compound represented by Formula 1 is at least one selected from among compounds represented by Compound Group 1:
Compound Group 1
1
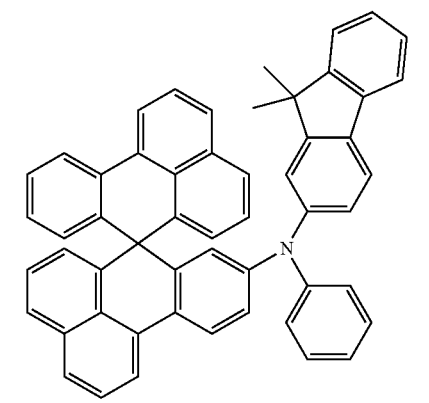
2
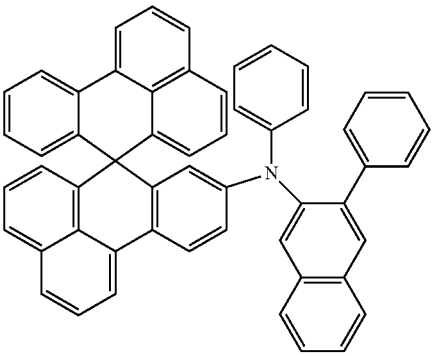
3
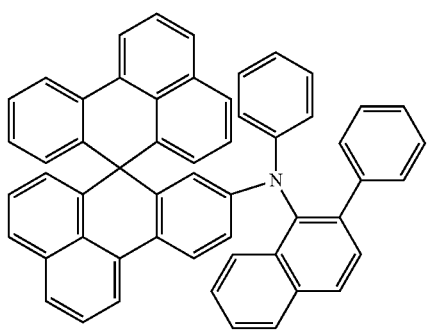
4
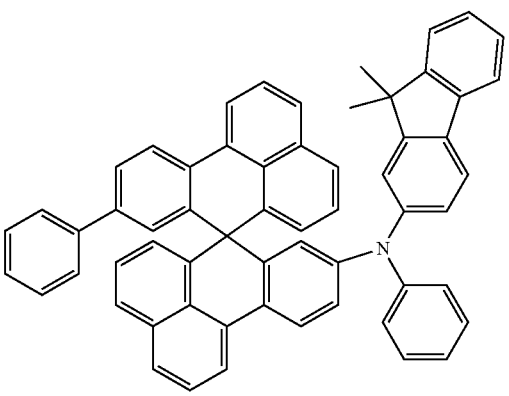
5
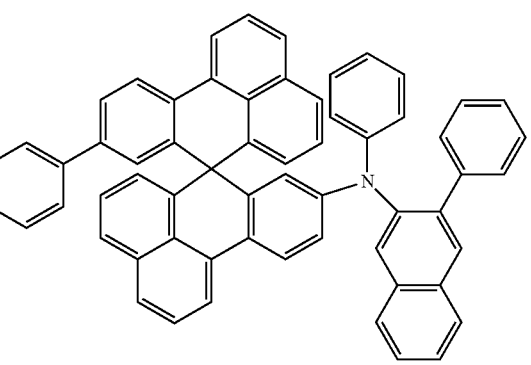
6
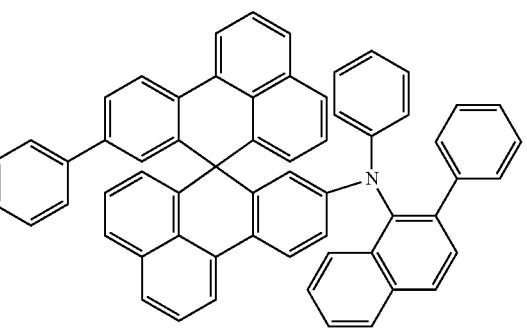
7
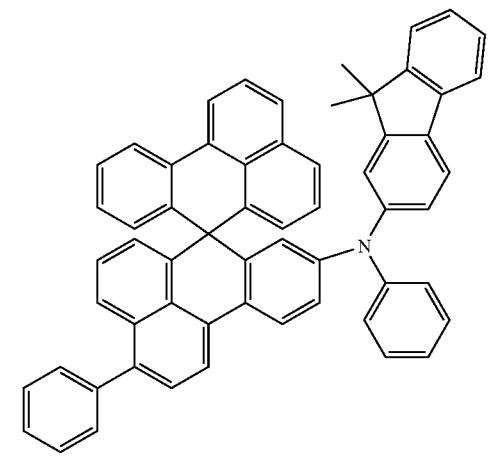

203
-continued
8
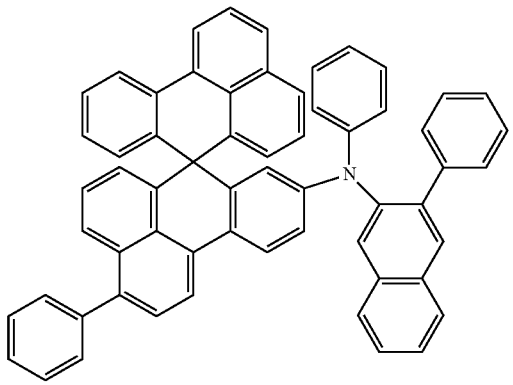
9
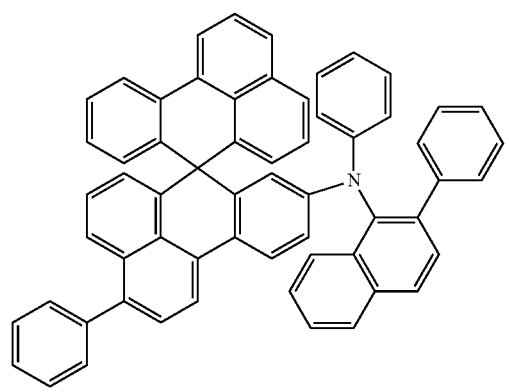
10
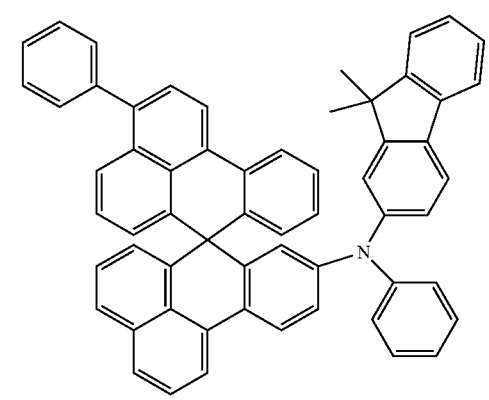
11
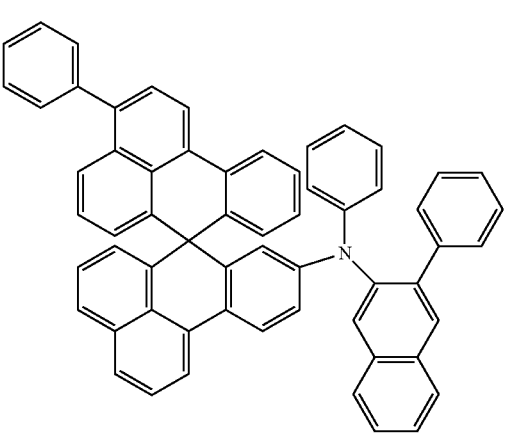
204
-continued
12
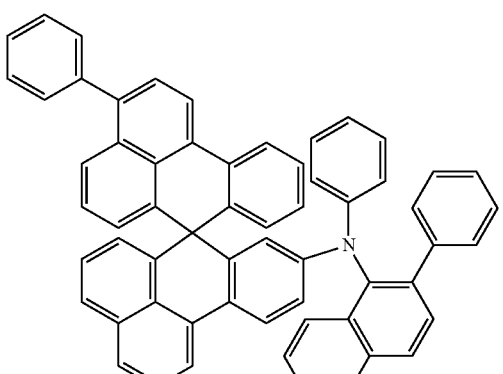
13
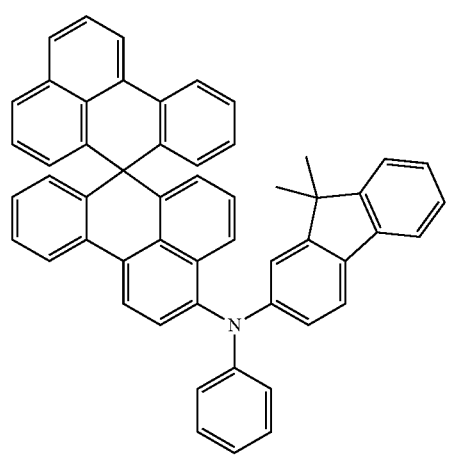
14
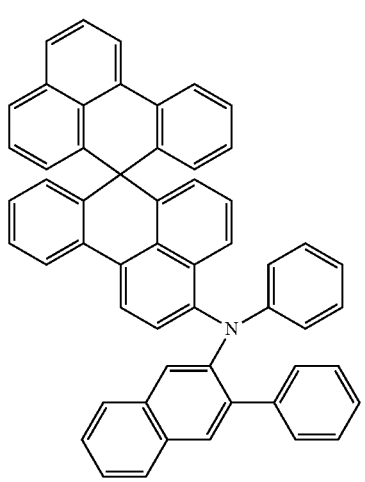

205
-continued
15
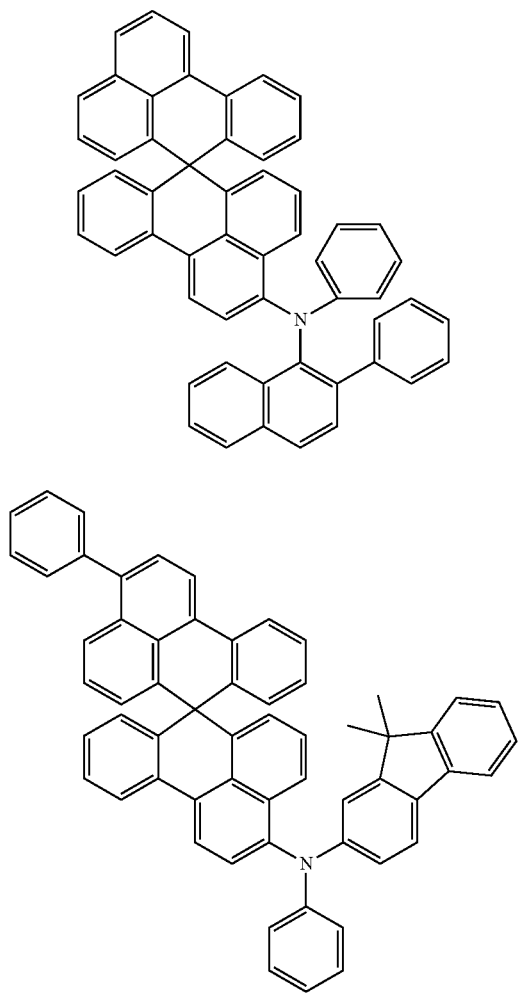
16
17
206
-continued
18
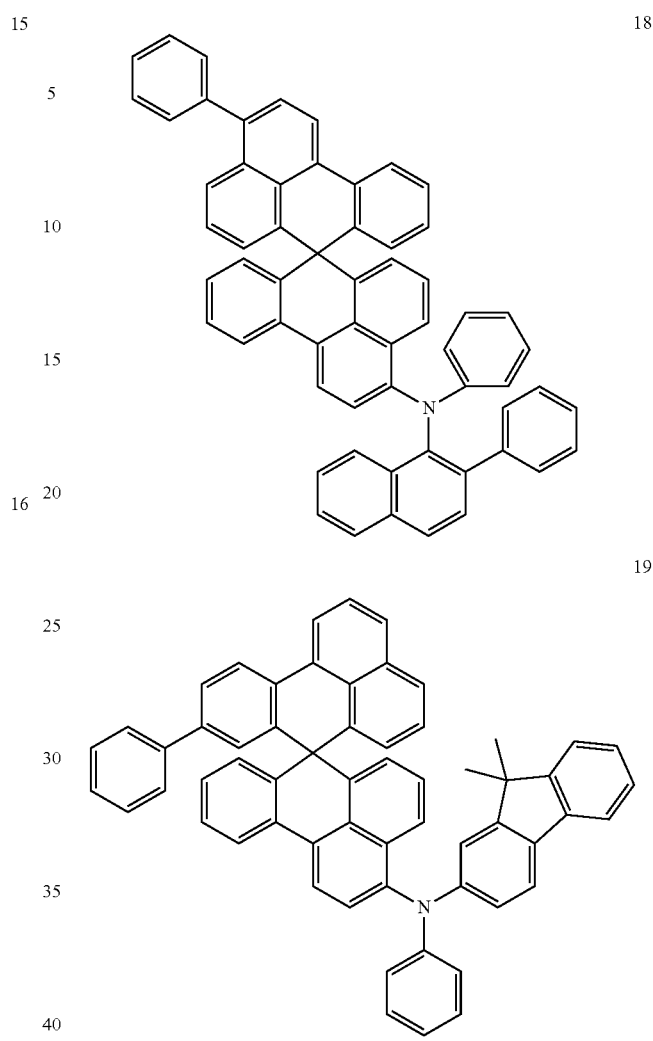
19
20
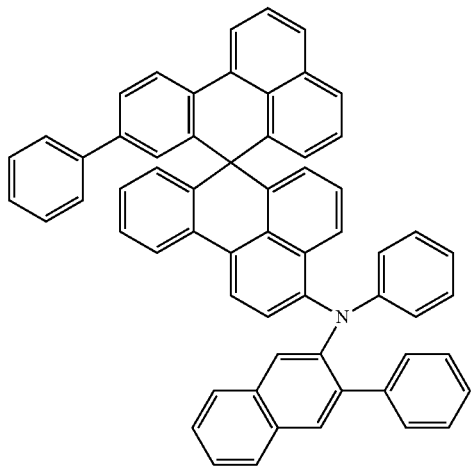

21
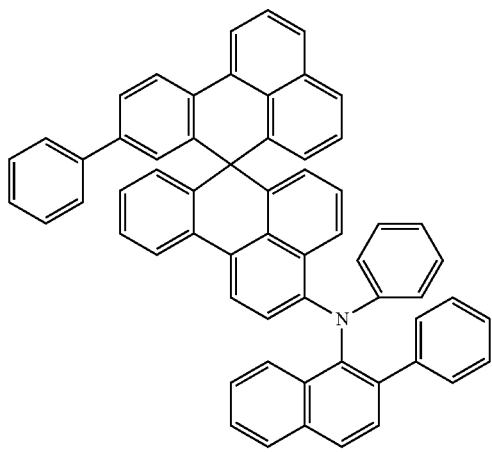
22
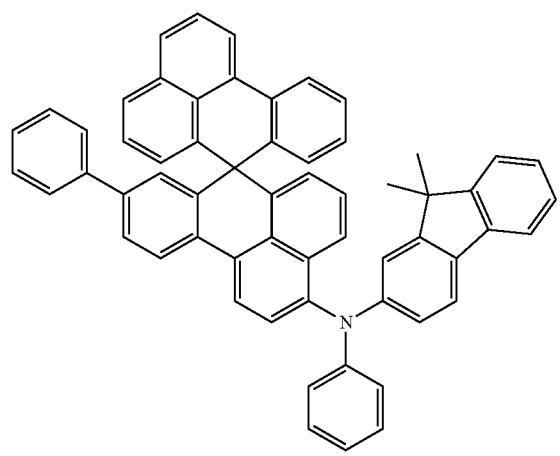
23
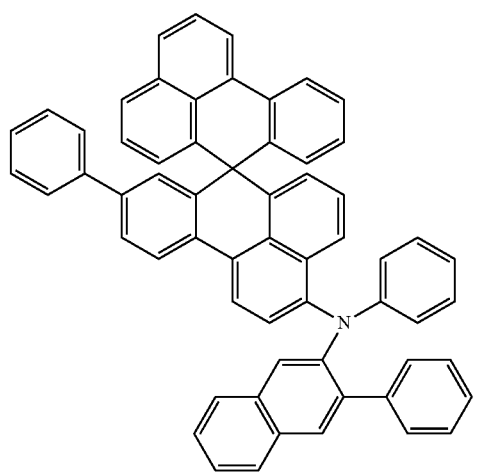
24
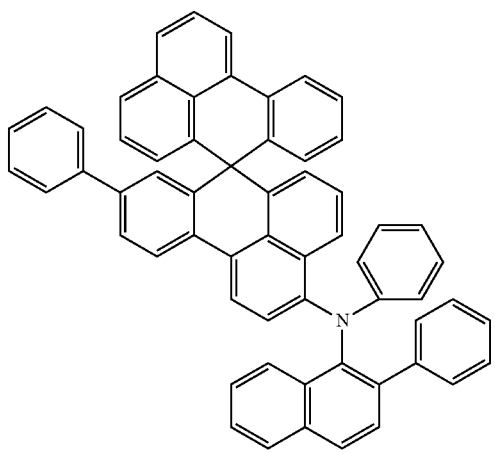
25
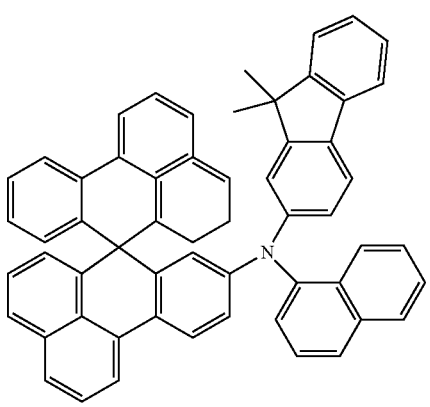
26
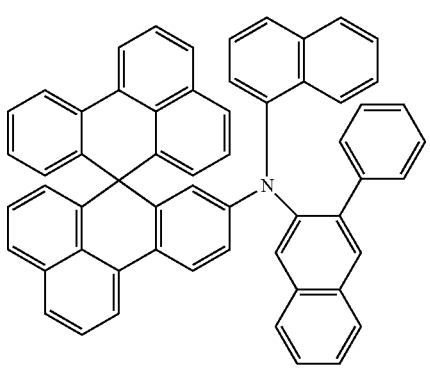
27
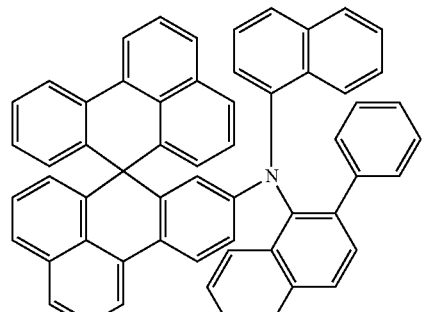

28
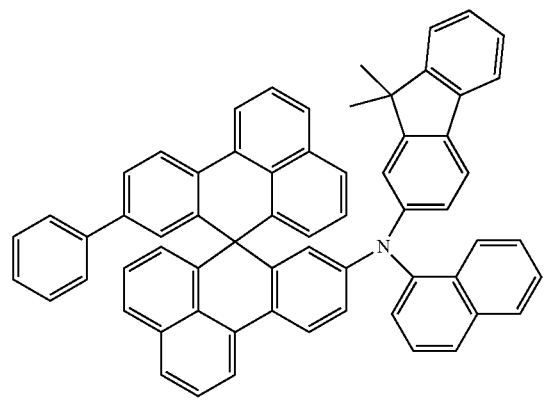
29
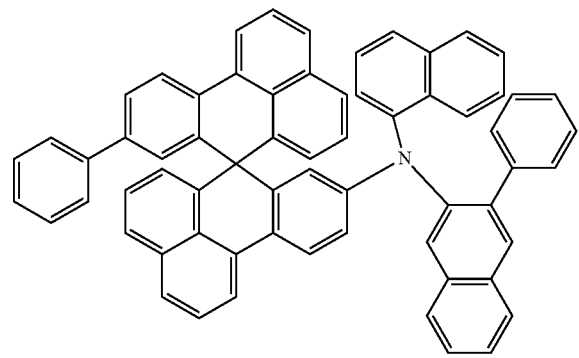
30
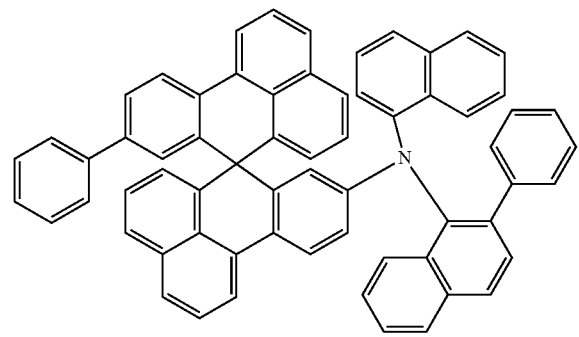
31
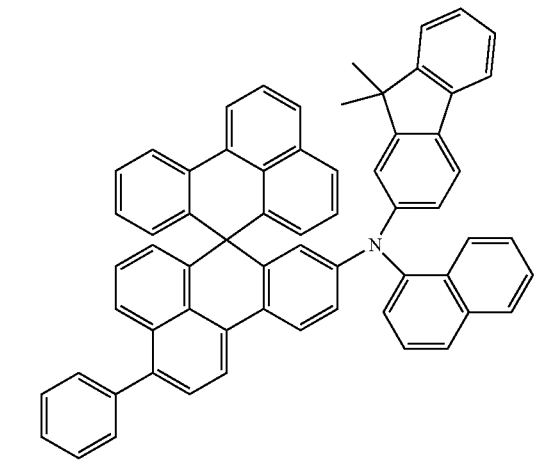
32
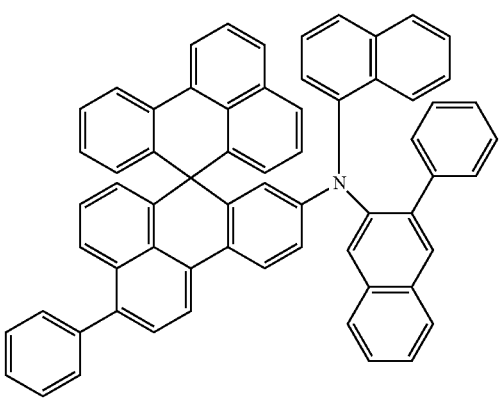
33
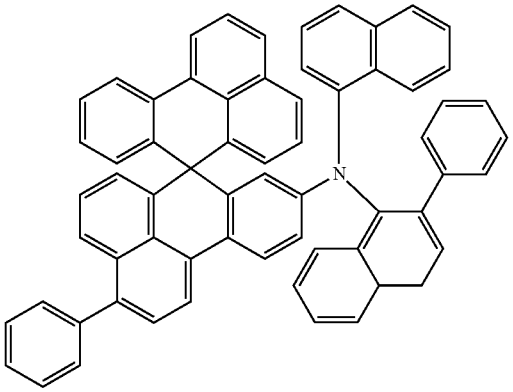
34
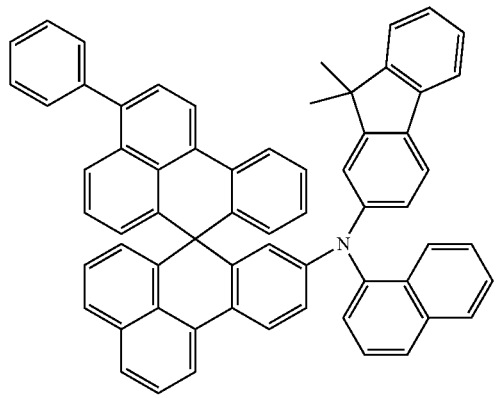
35
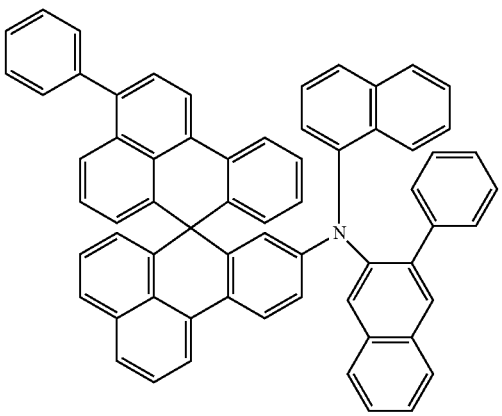

36
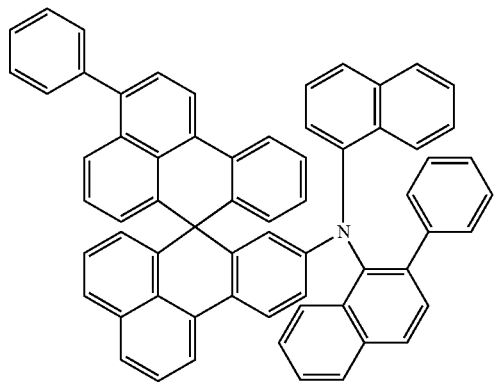
37
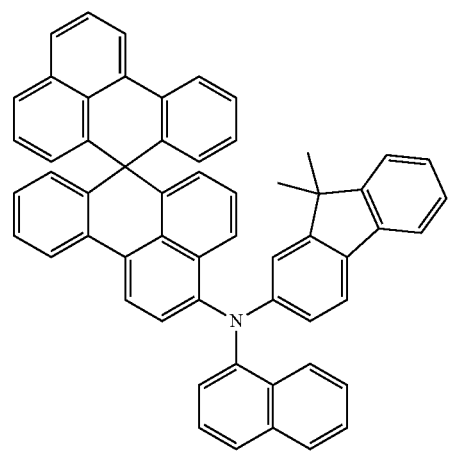
38
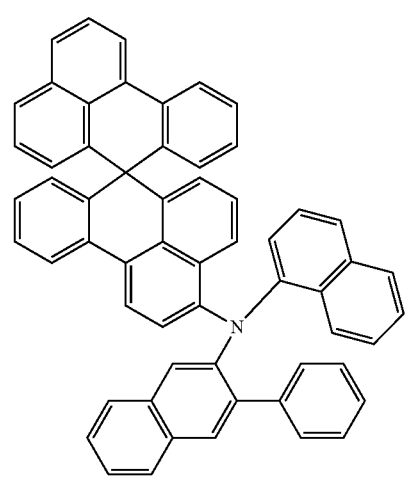
39
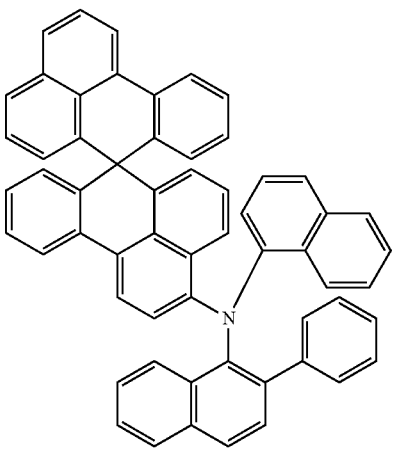
40
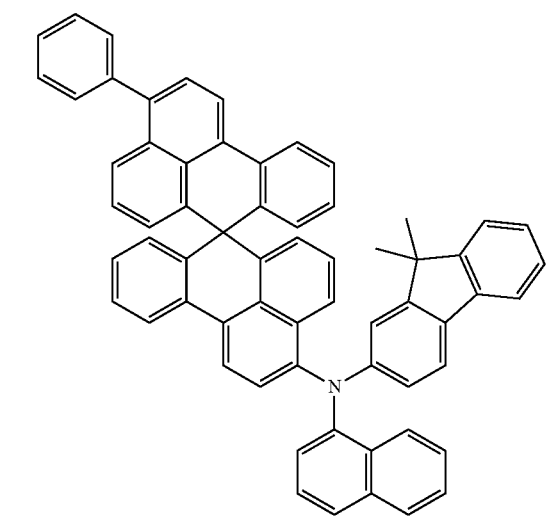
41
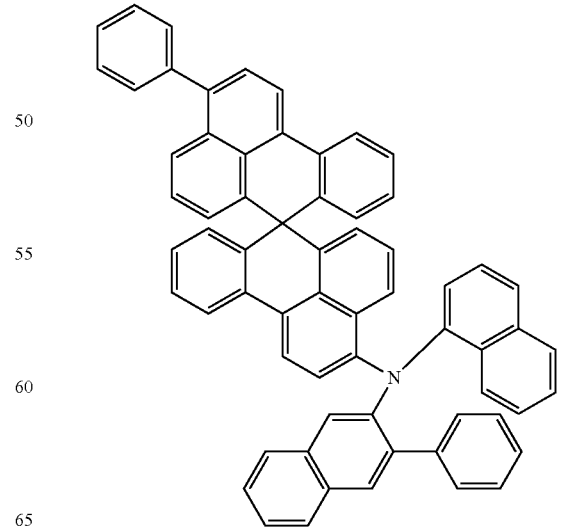

42
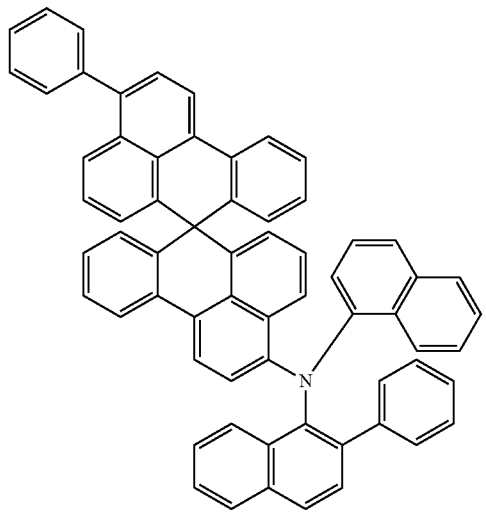
43
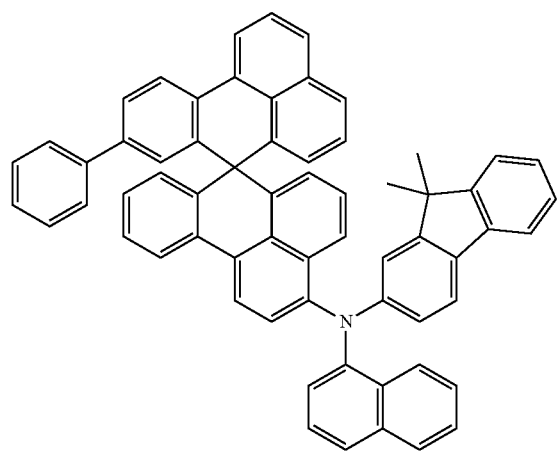
44
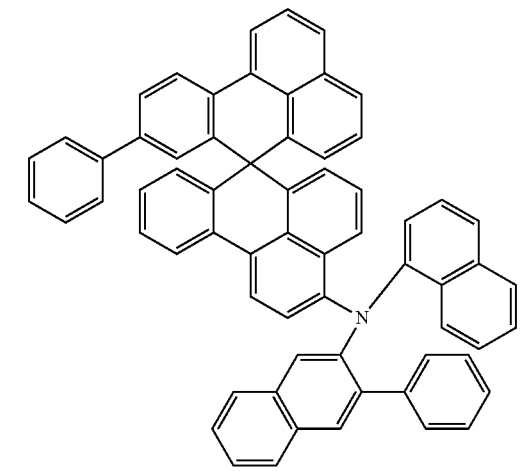
45
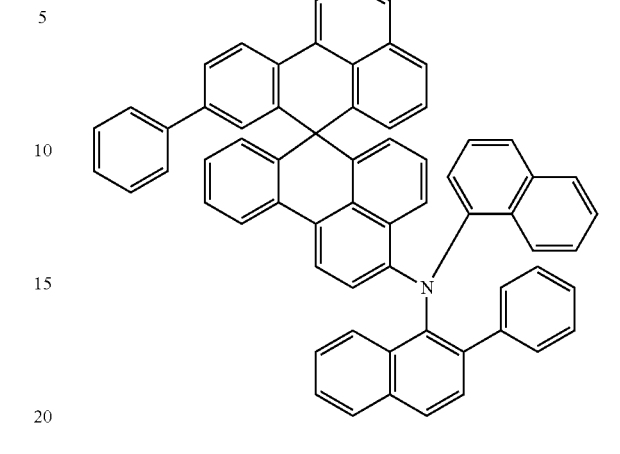
46
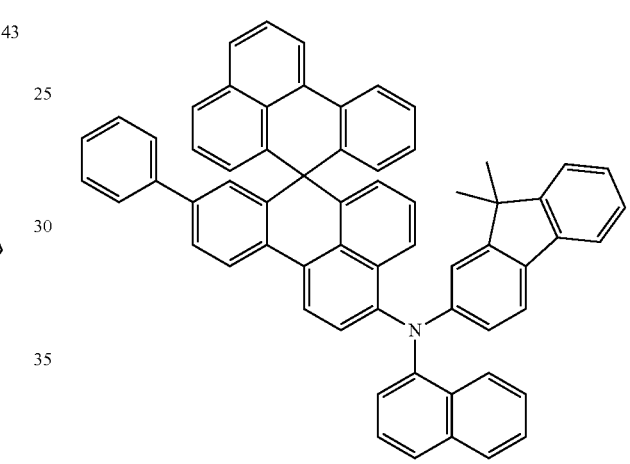
47
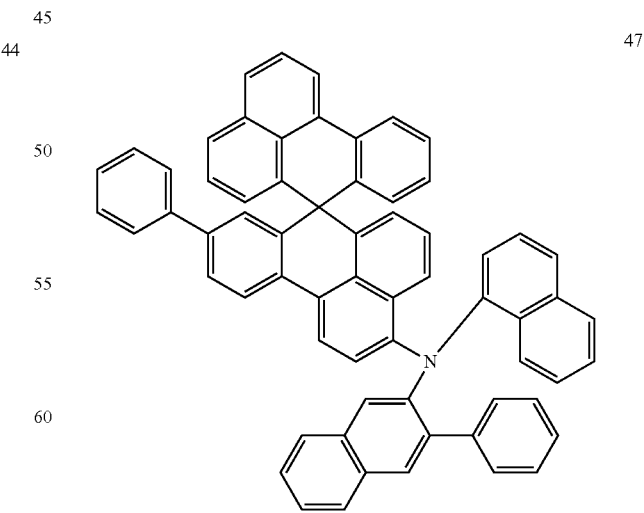

48
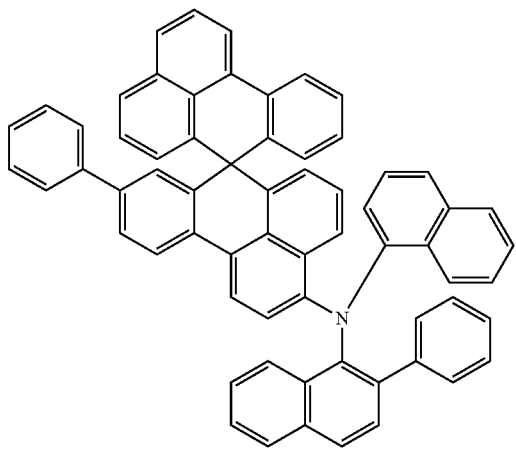
49
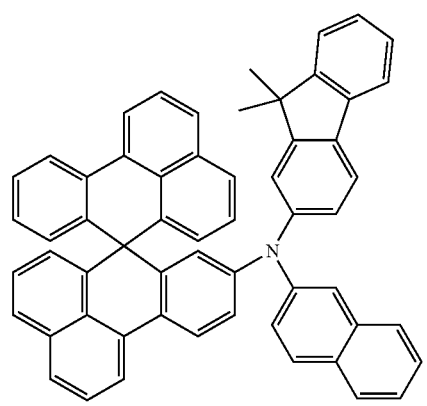
50
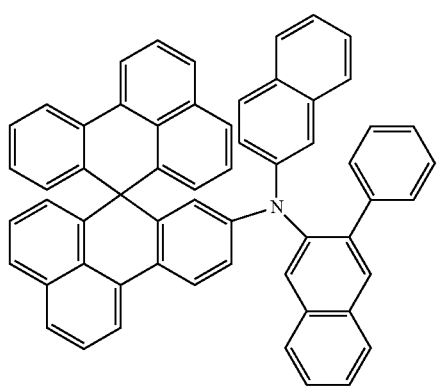
52
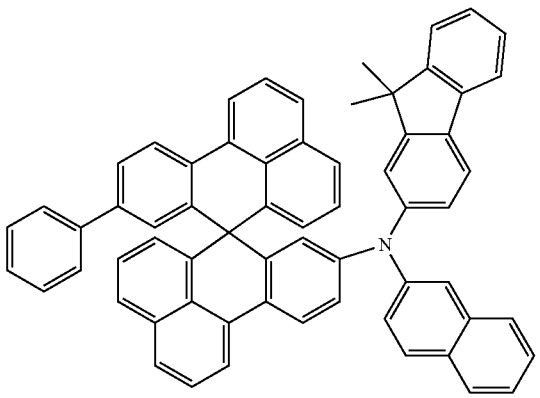
53
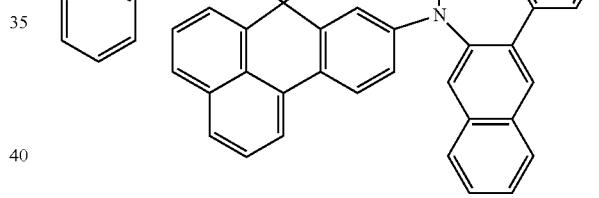
54
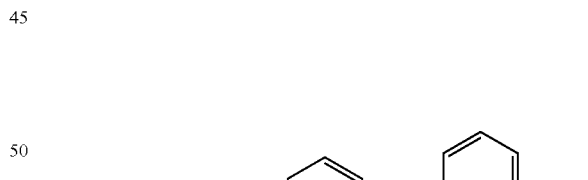
51
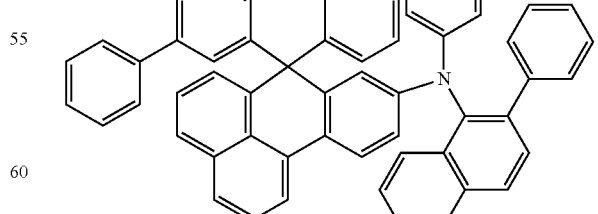

55
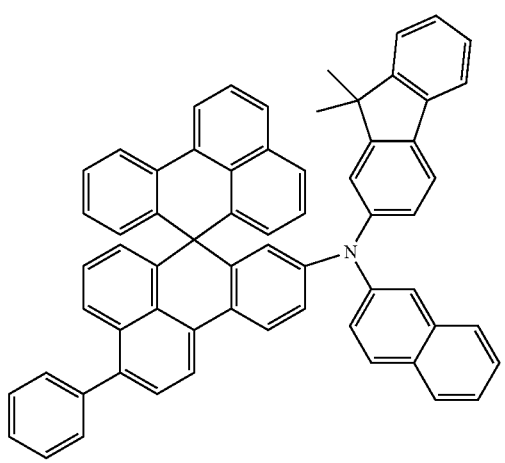
58
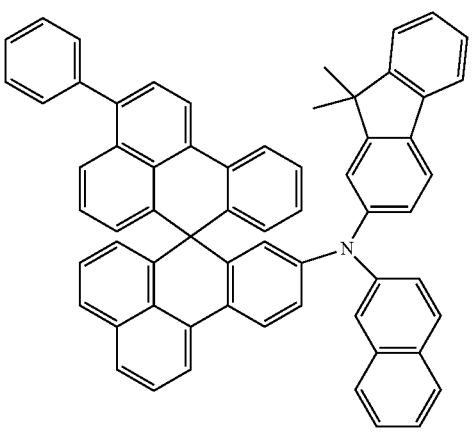
56
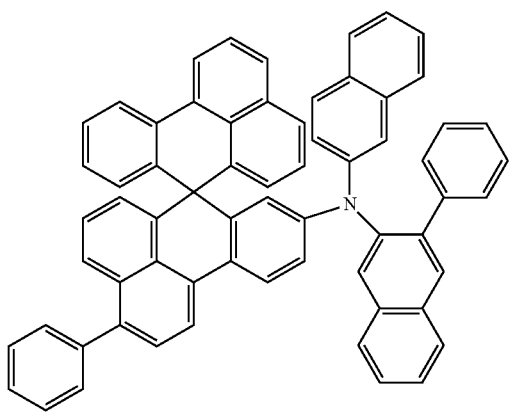
59
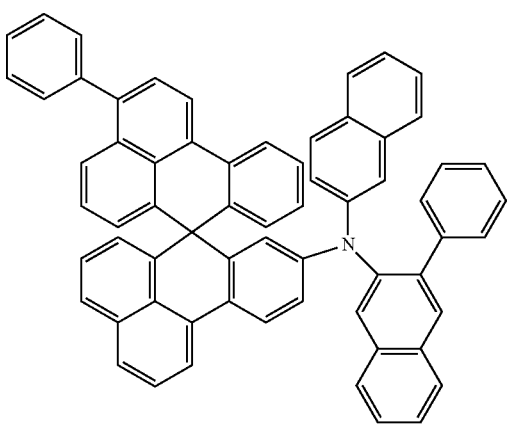
57
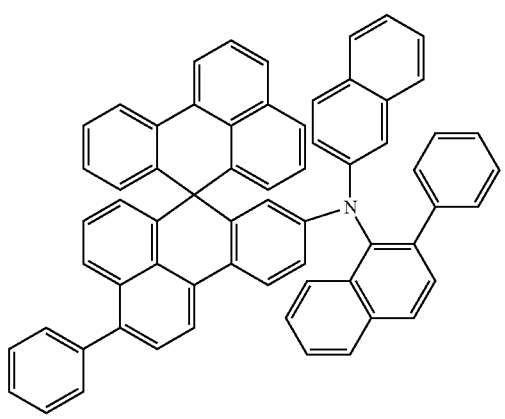
60
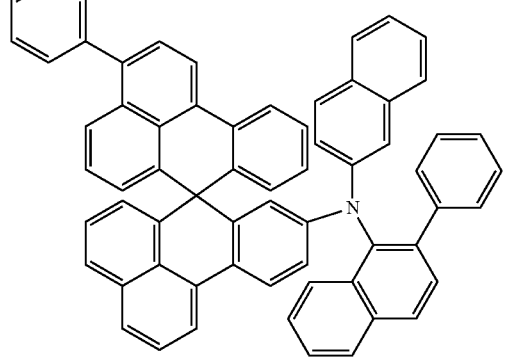

219
-continued
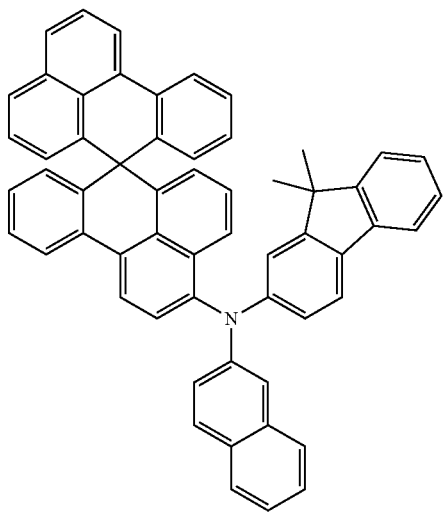
61
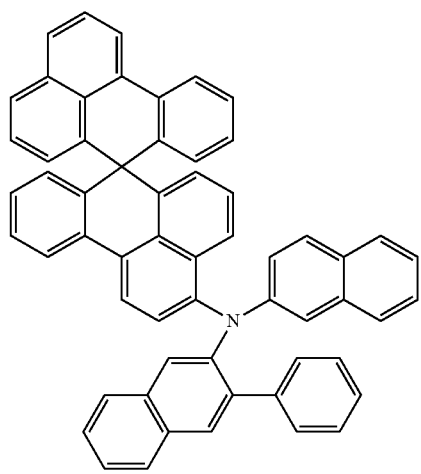
62
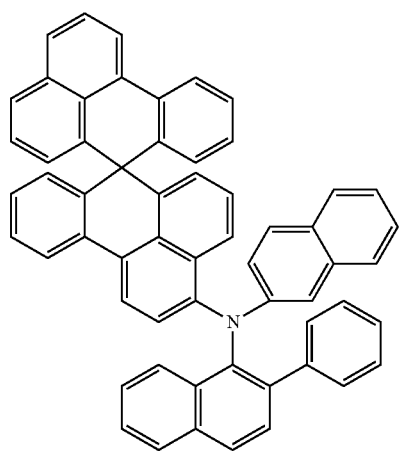
63
220
-continued
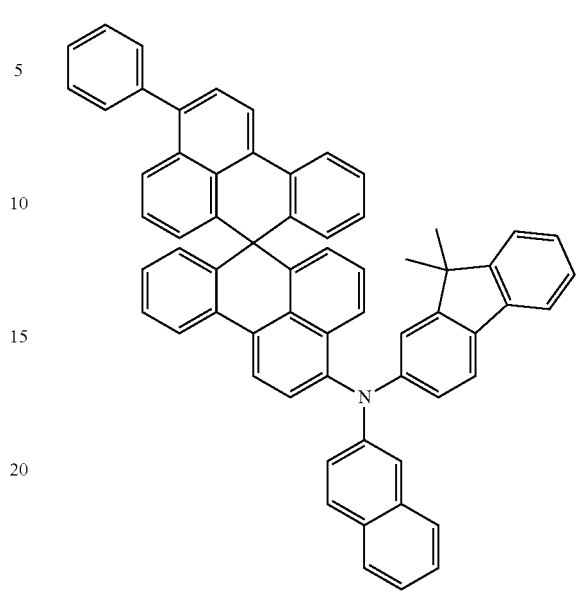
64
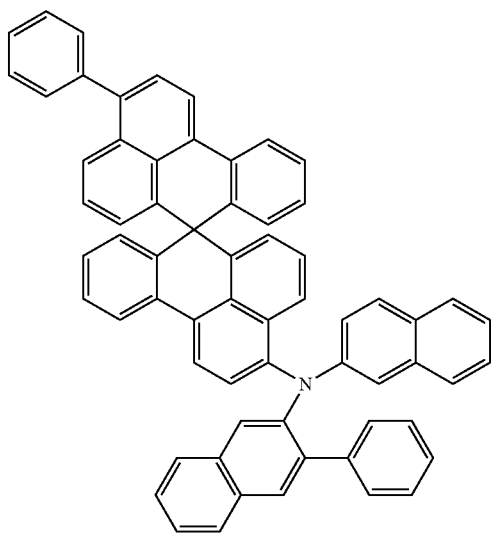
65
66

-continued
67
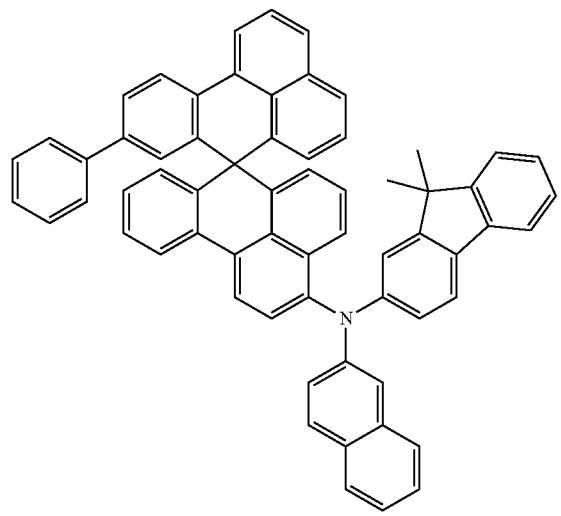
68
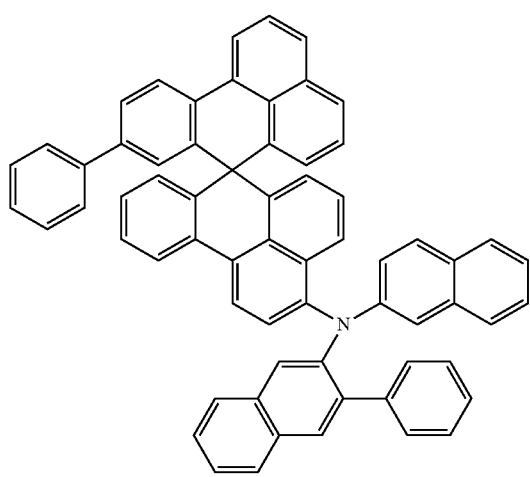
69
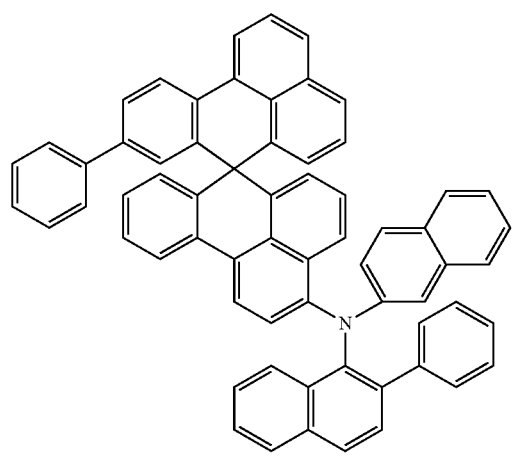
-continued
70
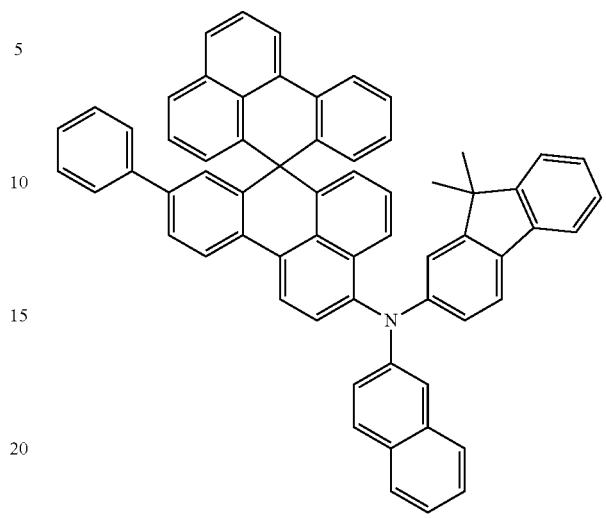
71
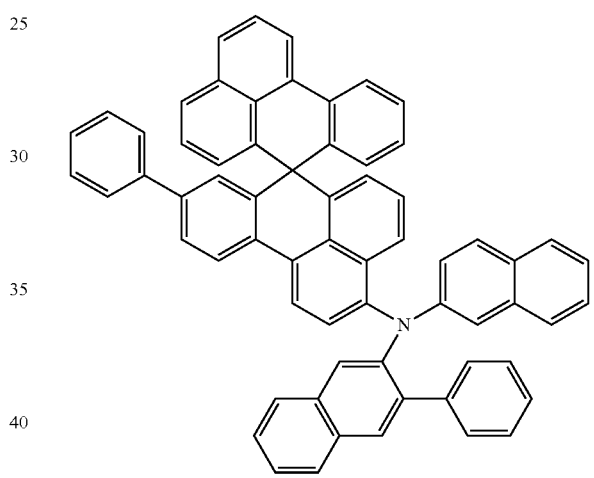
72
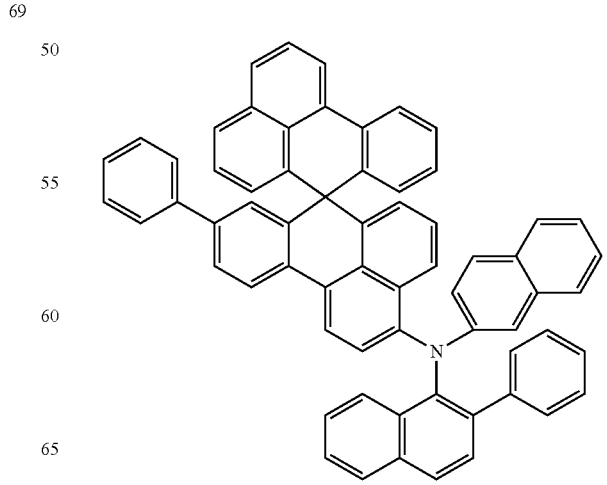

73
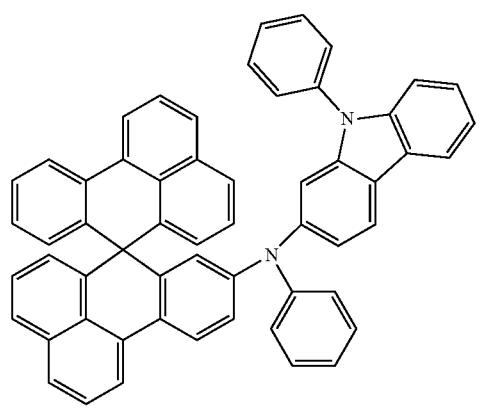
74
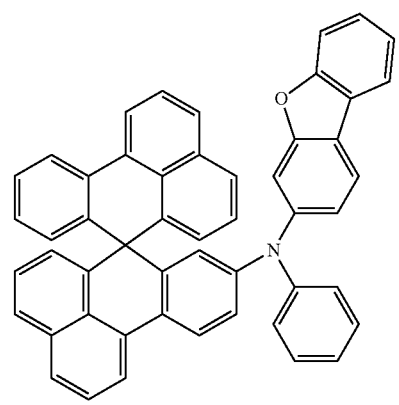
75
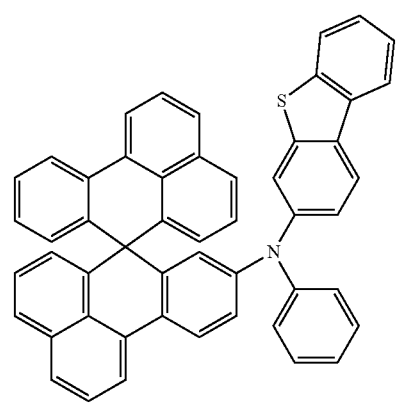
76
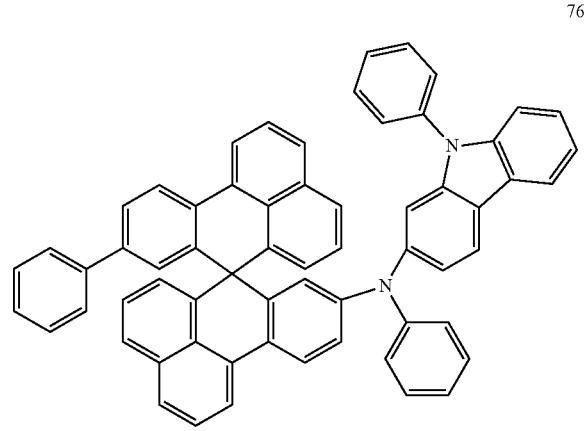
77
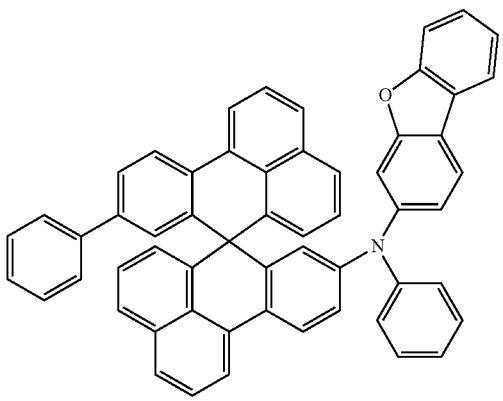
78
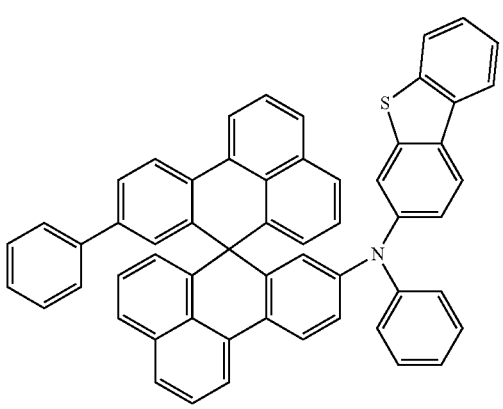
79
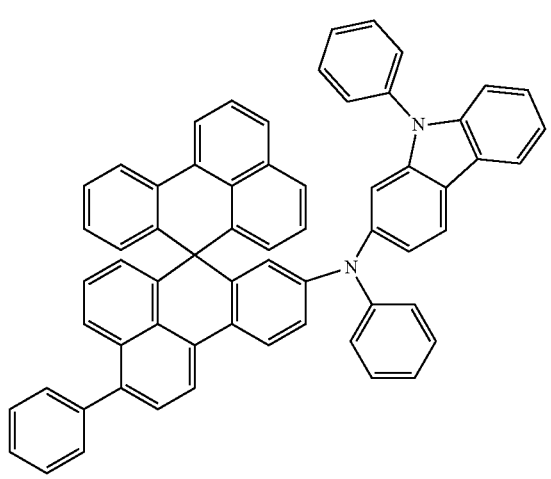

-continued
80
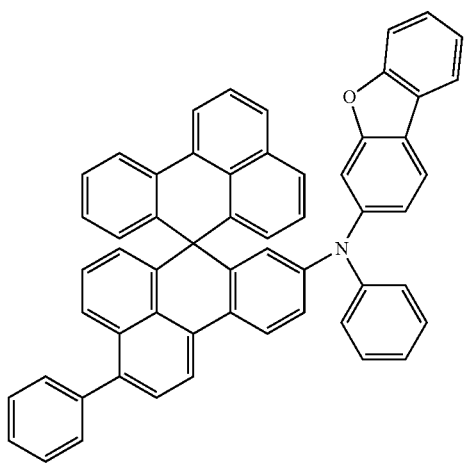
81
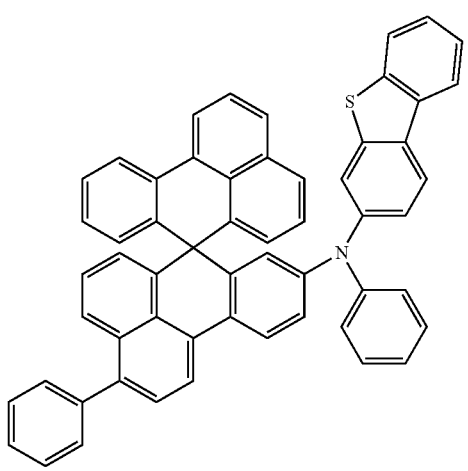
82
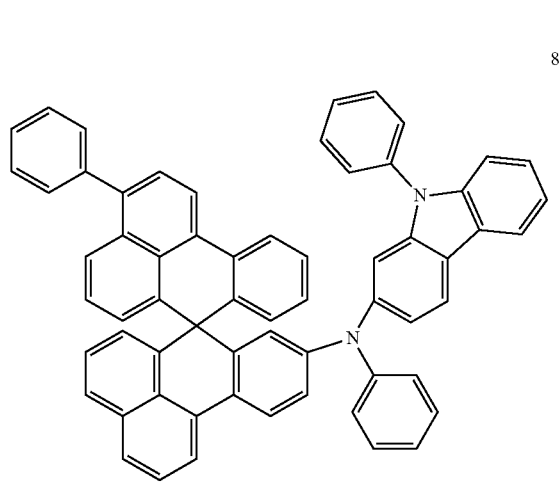
-continued
83
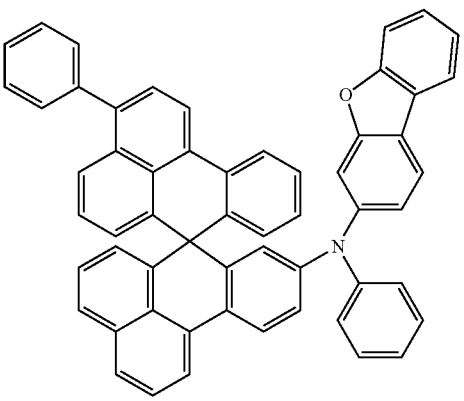
84
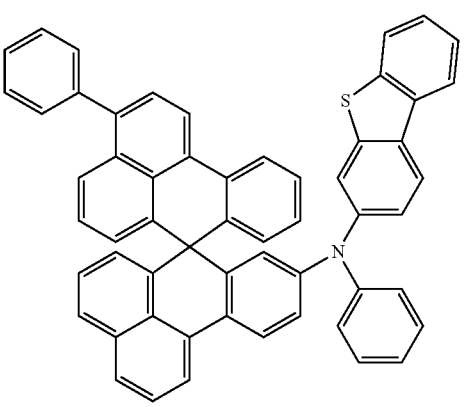
85
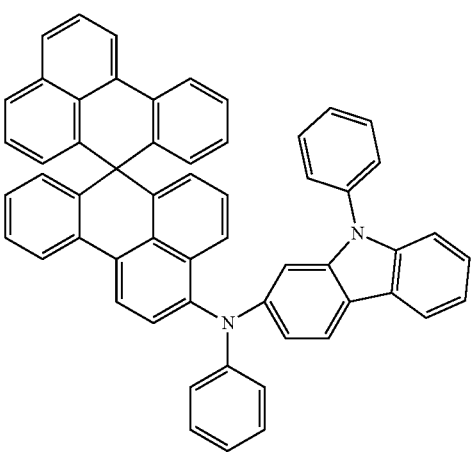

86
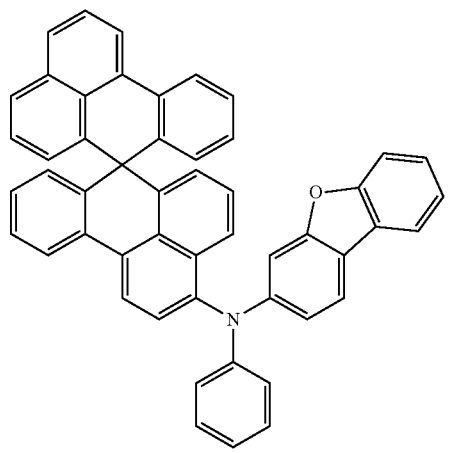
87
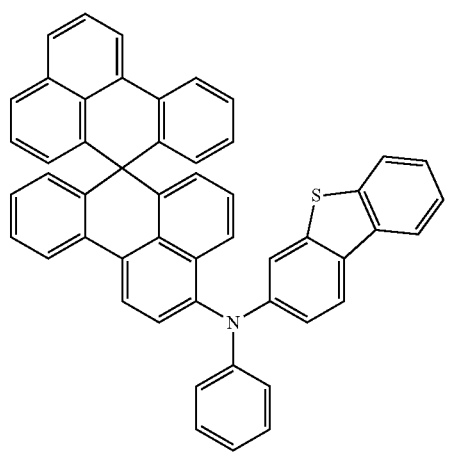
88
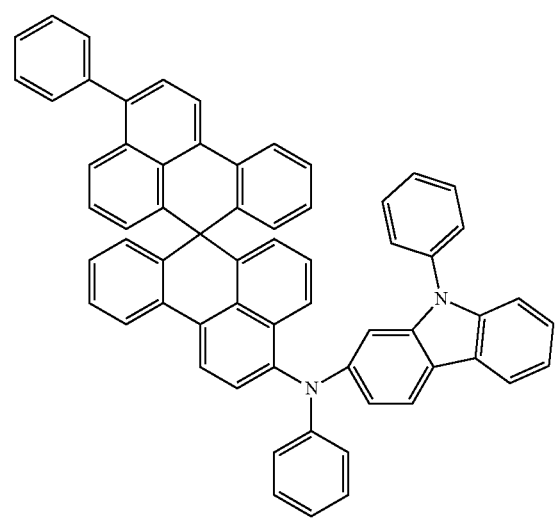
89
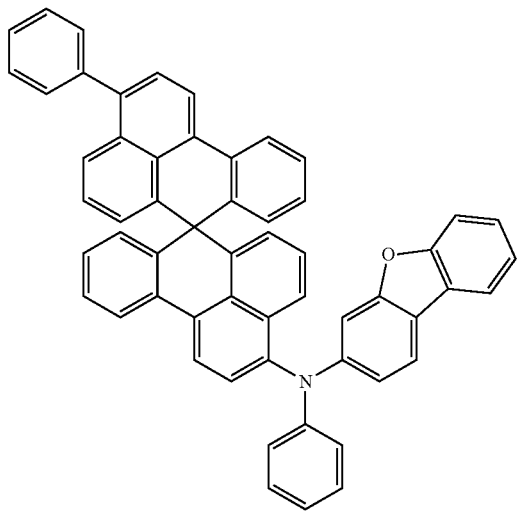
90
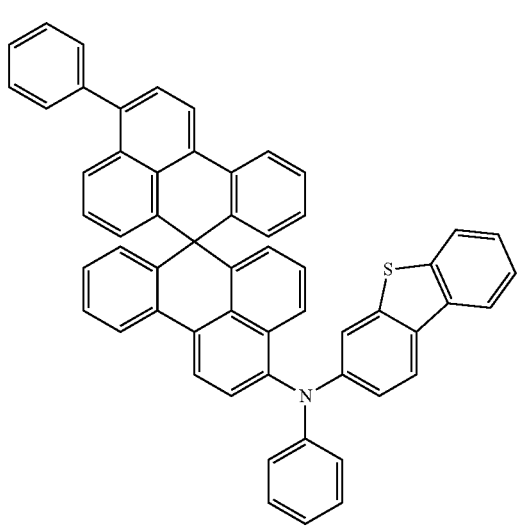
91
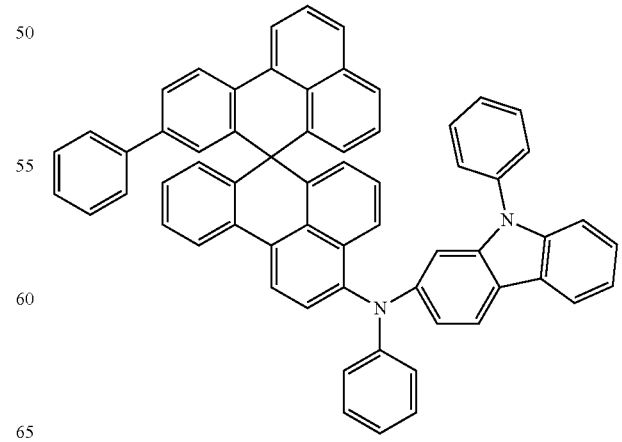

229
-continued
92
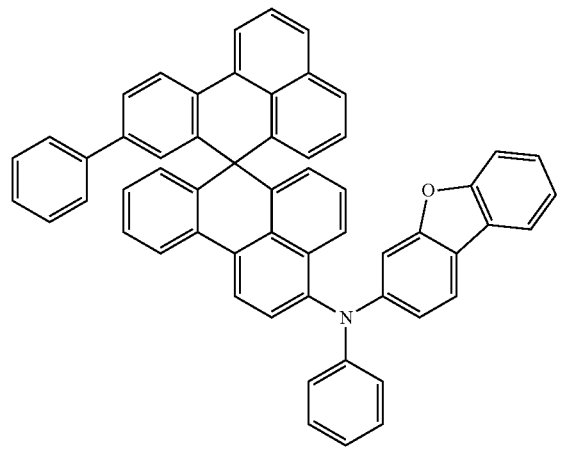
93
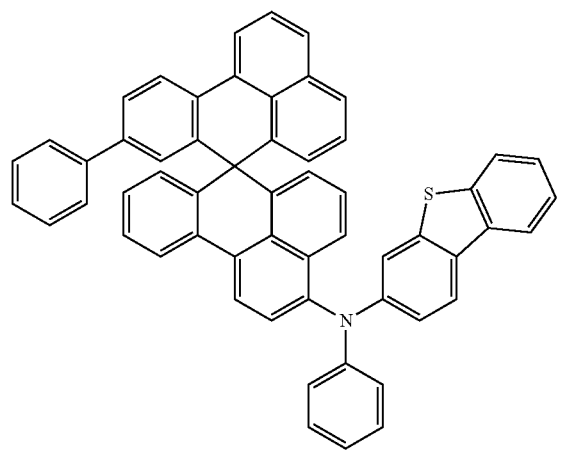
94
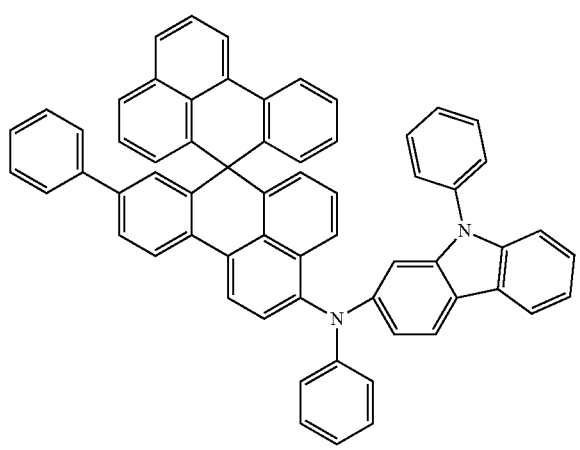
230
-continued
95
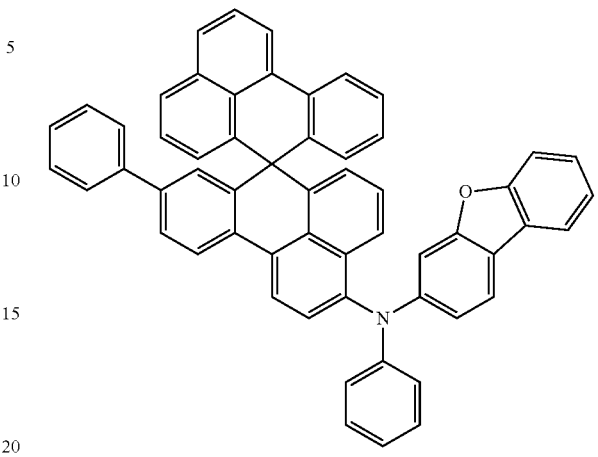
96
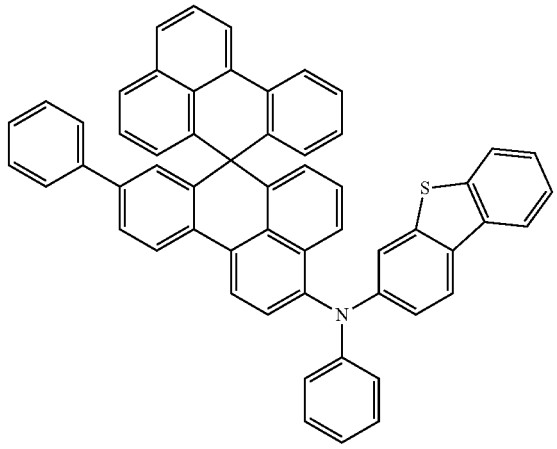
97
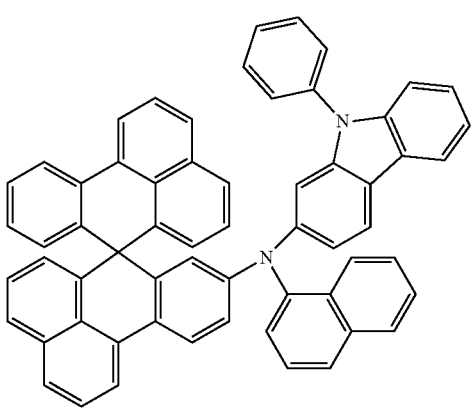

231
-continued
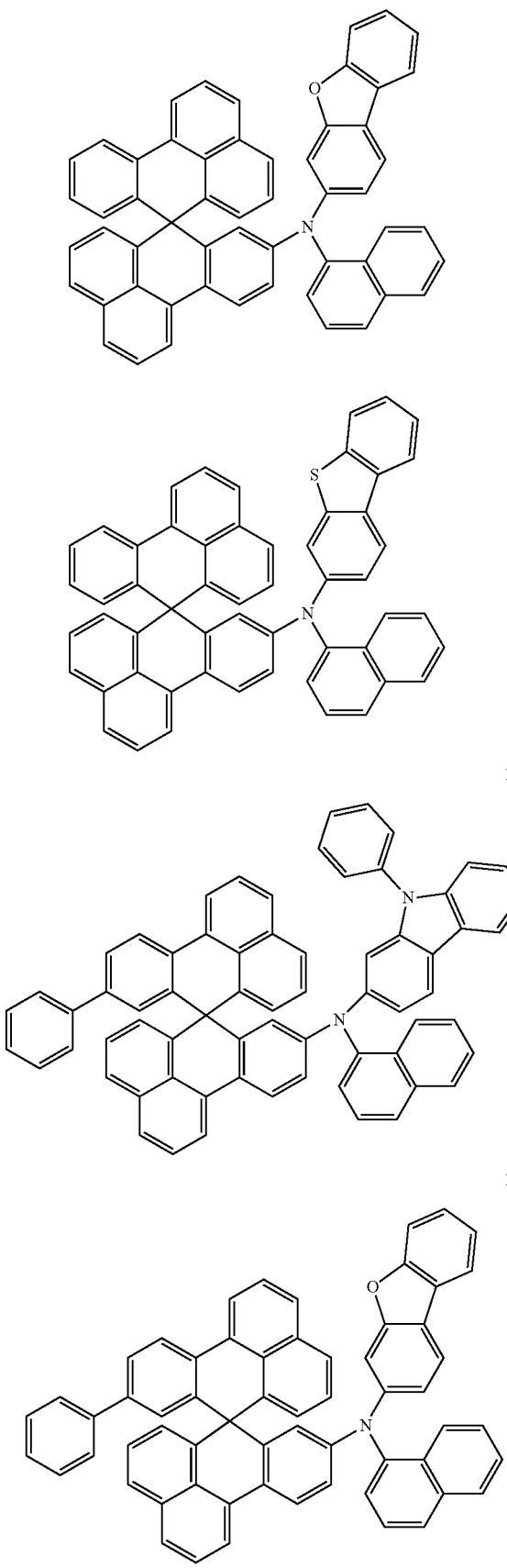
232
-continued
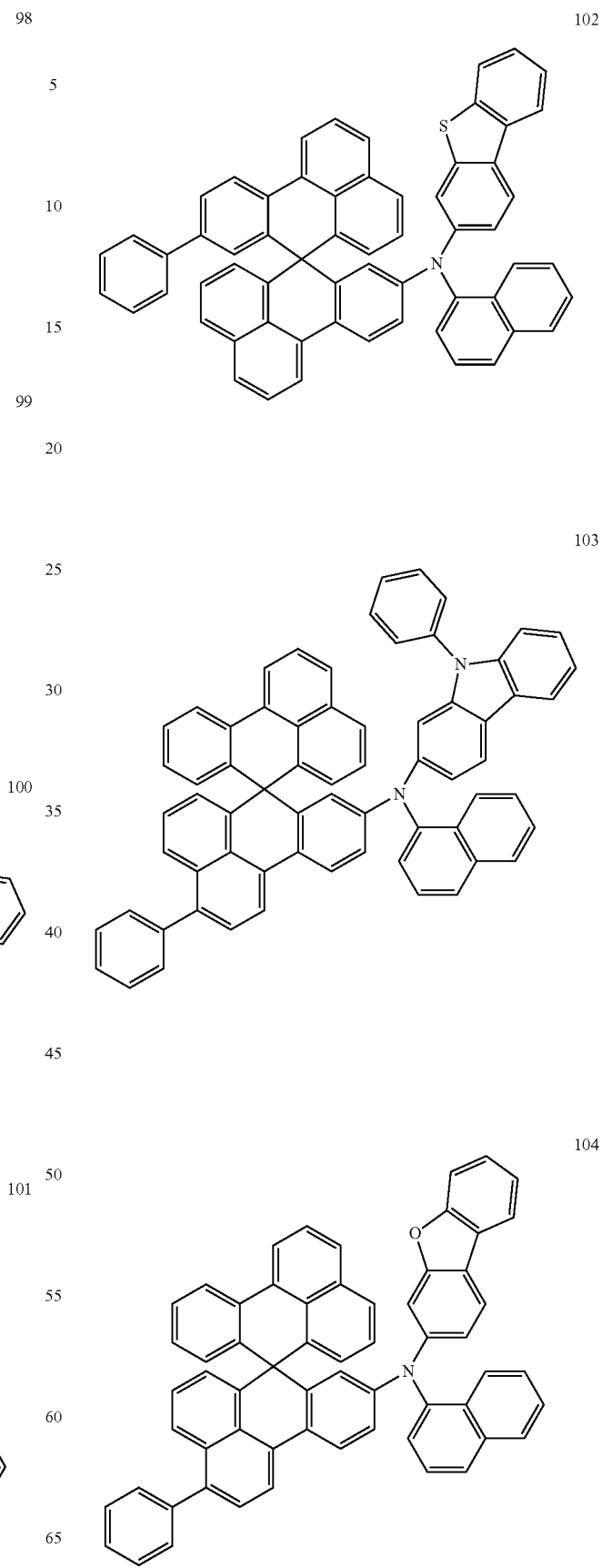

105
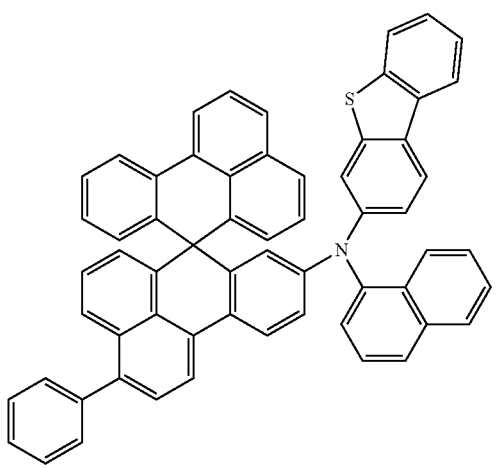
106
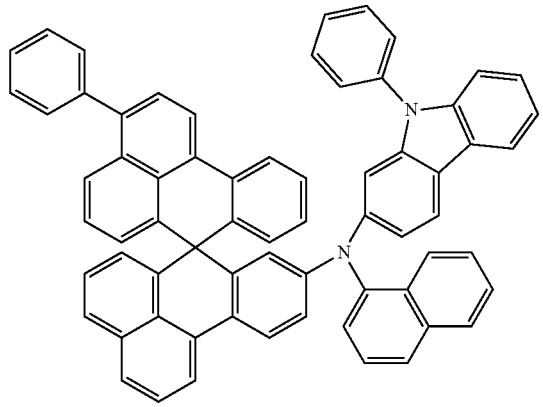
107
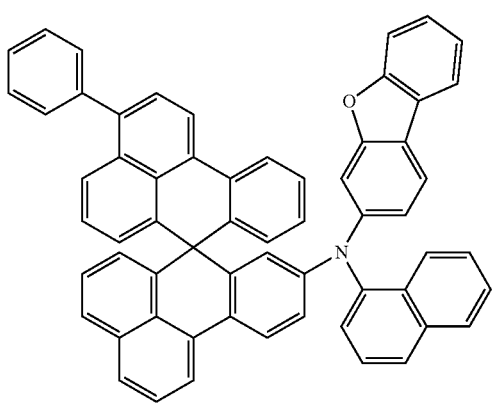
108
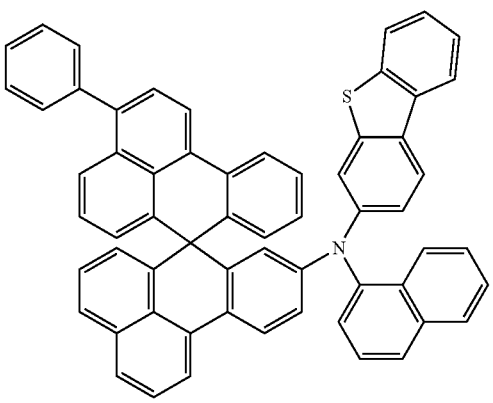
109
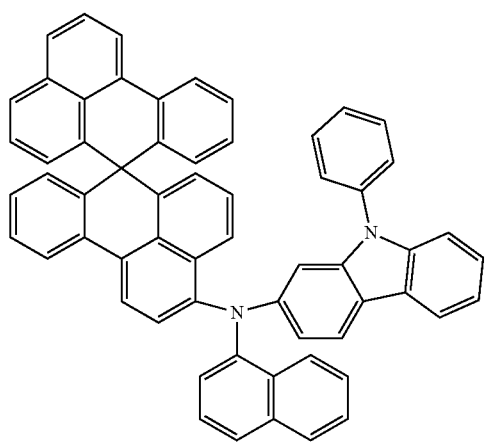
110
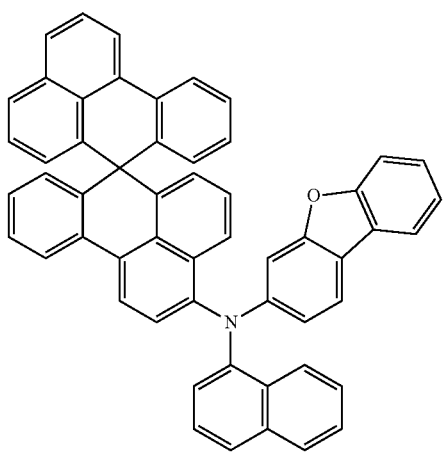

235
-continued
111
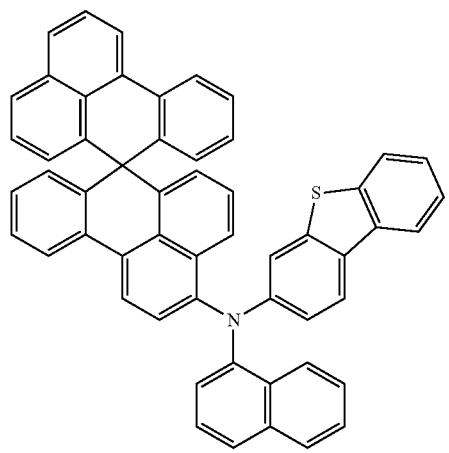
112
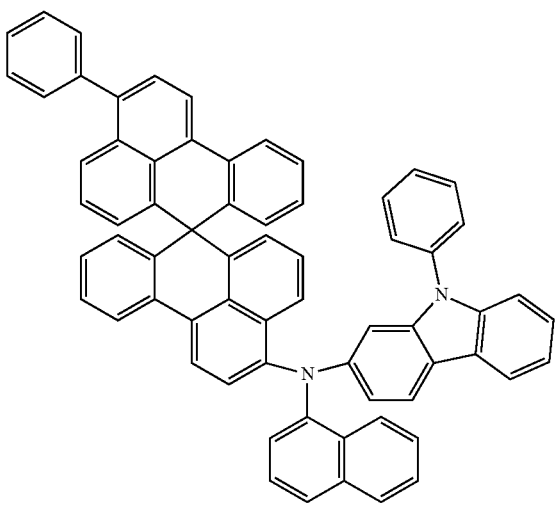
113
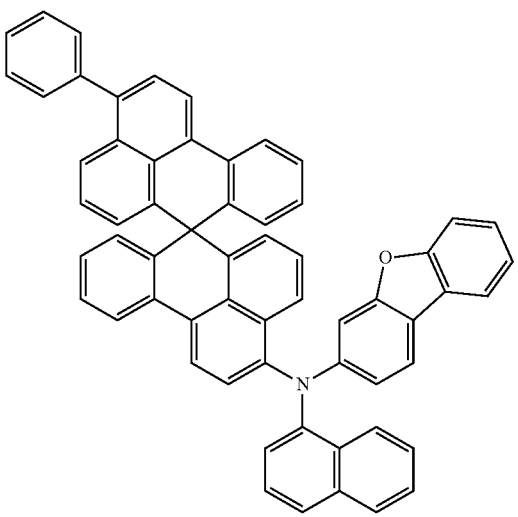
236
-continued
114
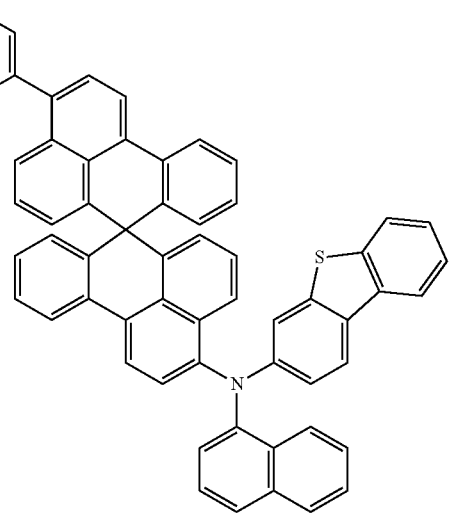
115
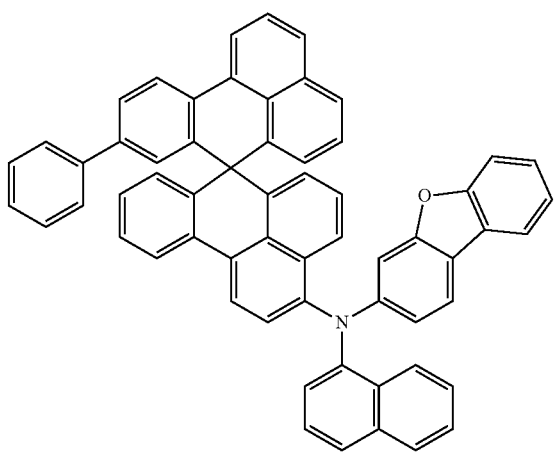
116

-continued
117
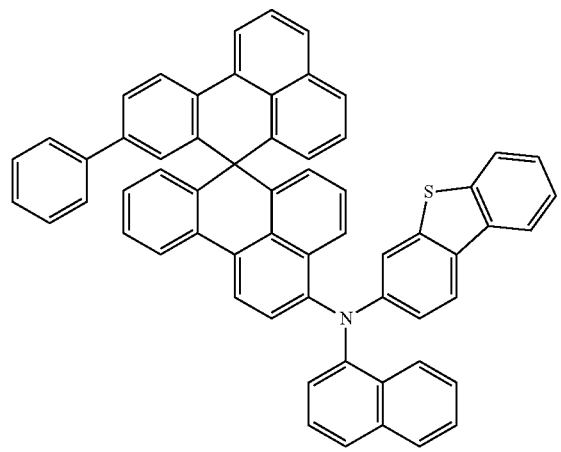
118
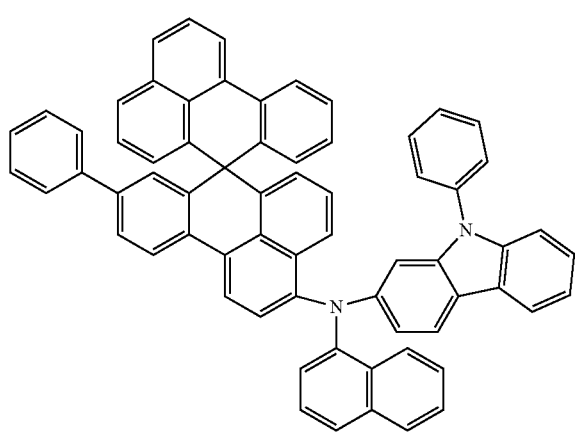
119
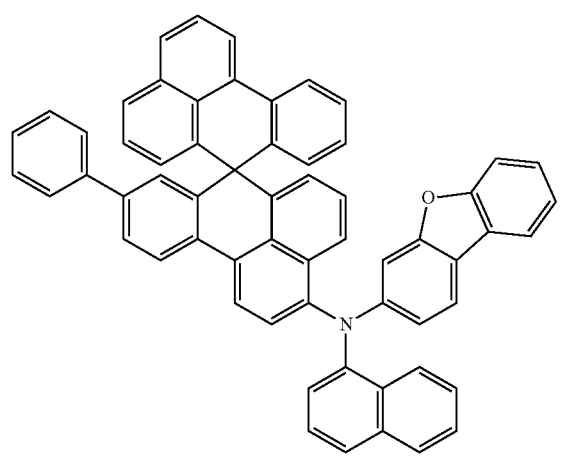
-continued
120
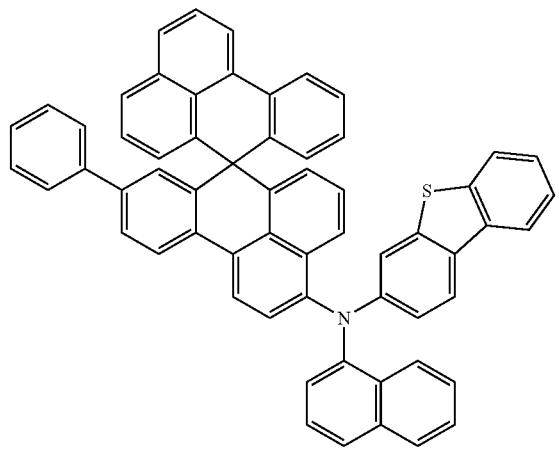
121
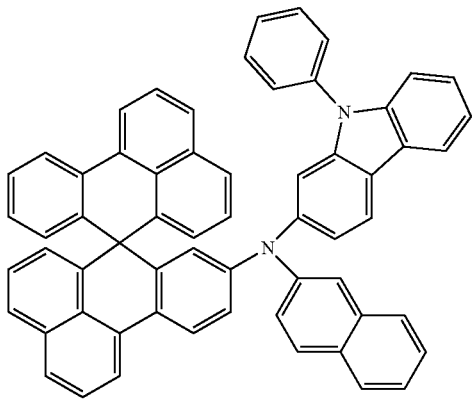
122
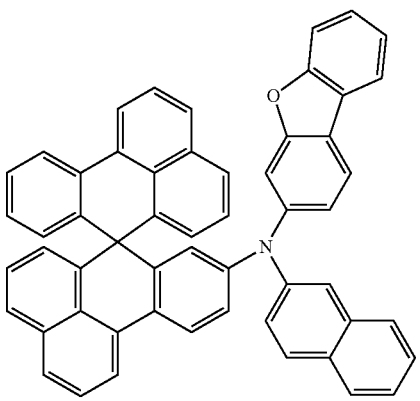

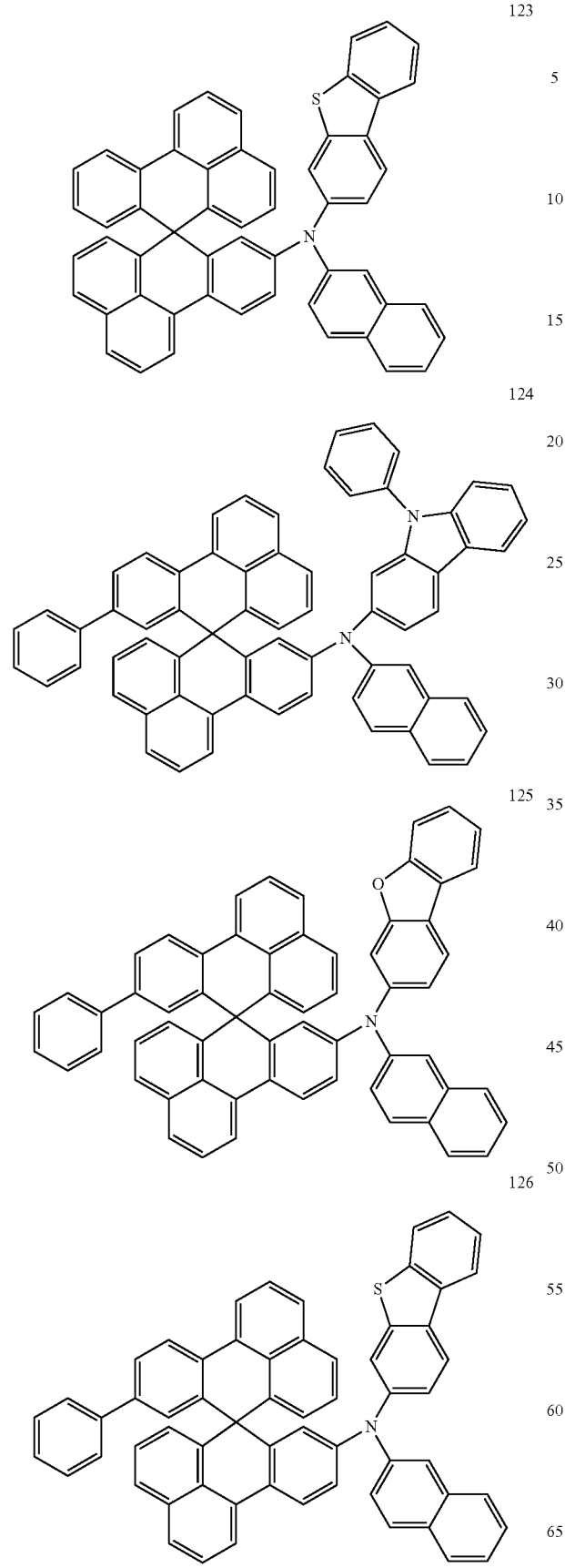
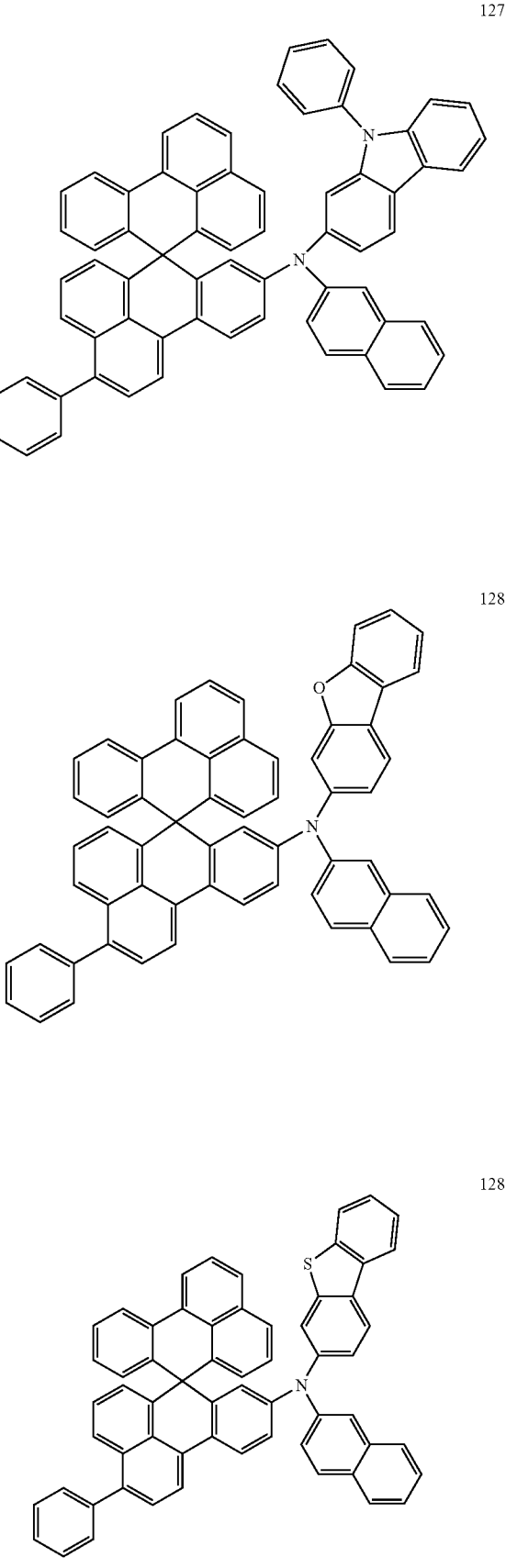

241
-continued
242
-continued
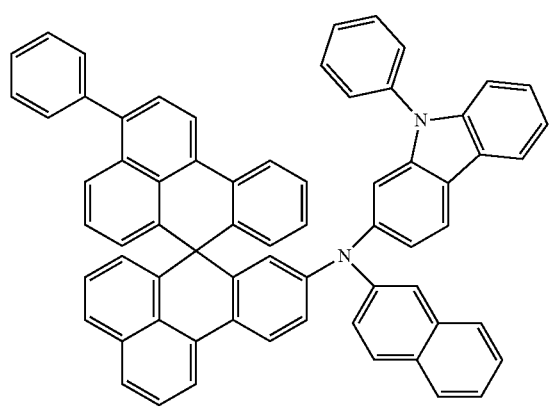
130
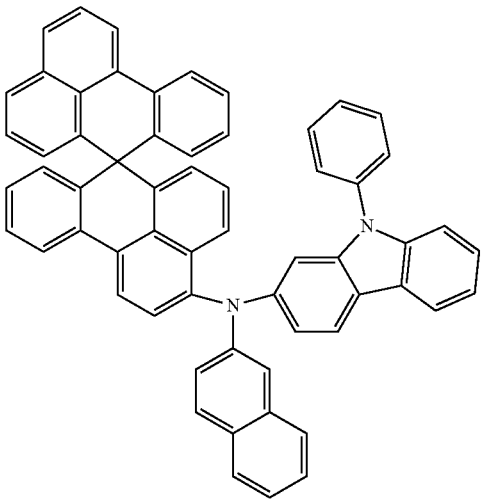
133
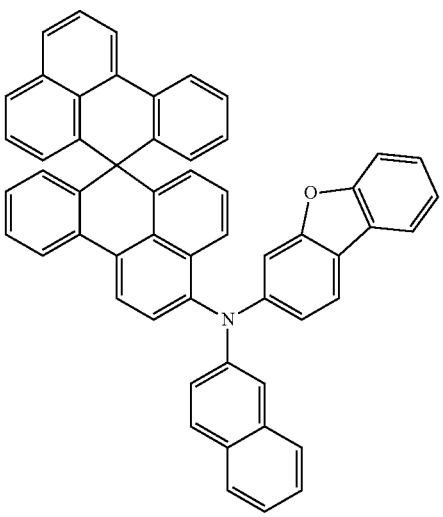
131
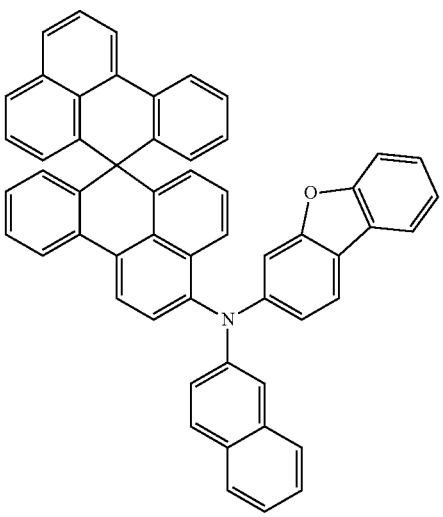
134
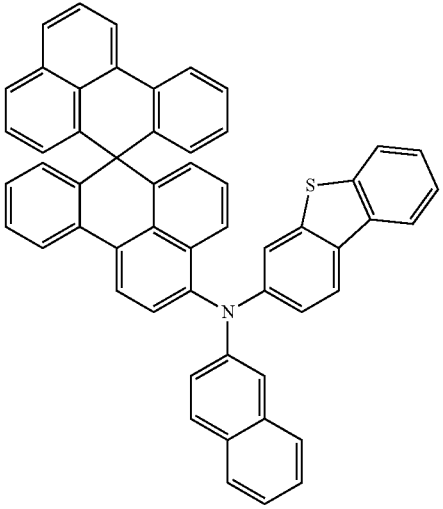
132
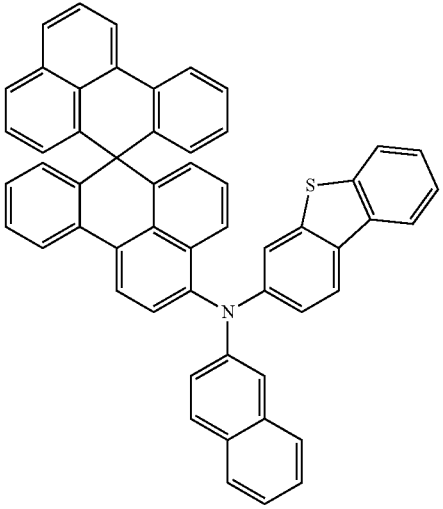
135

136
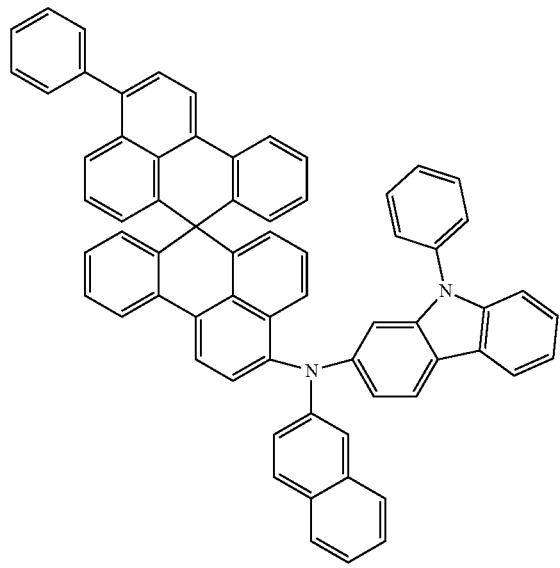
137
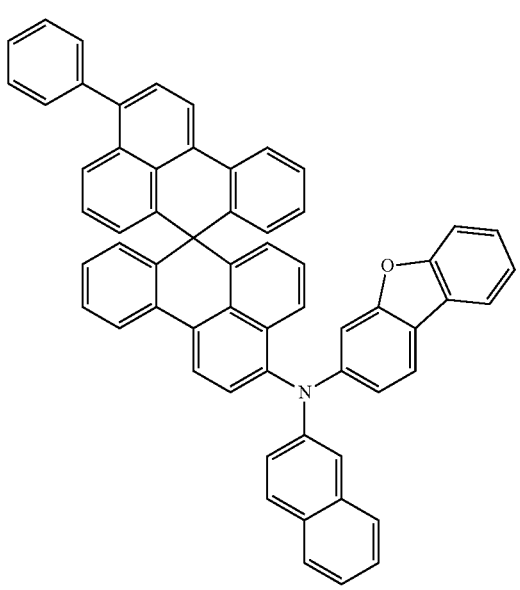
138
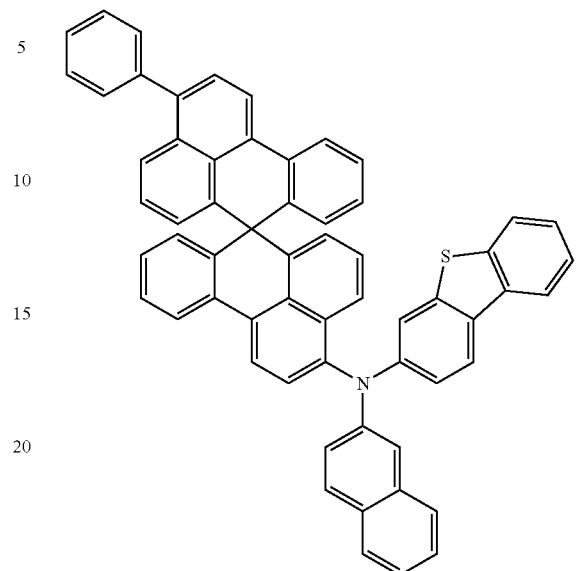
139
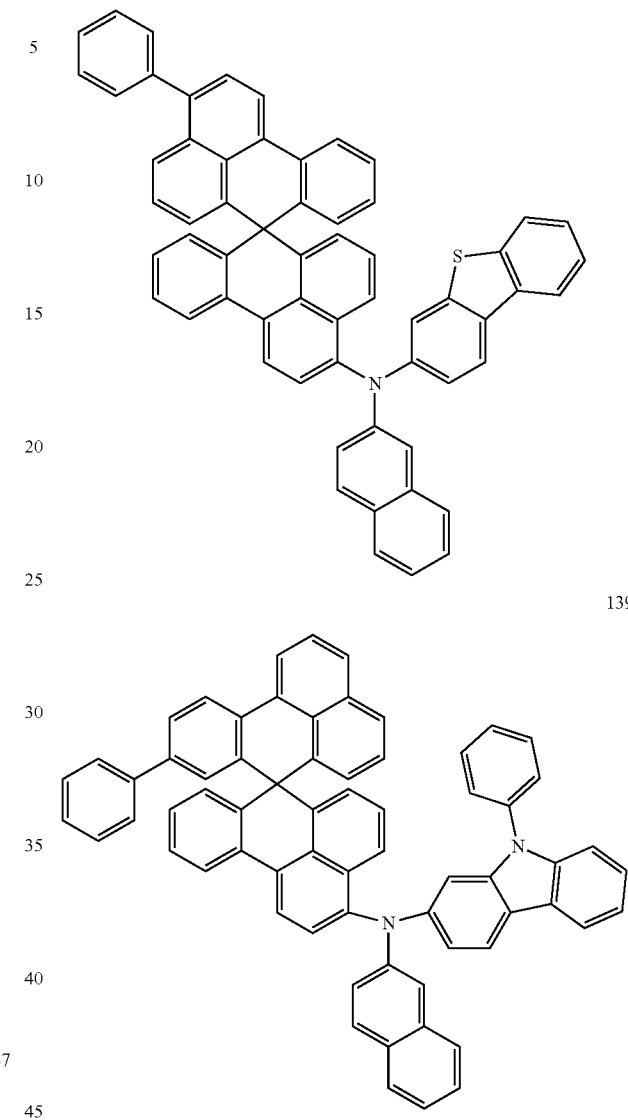
140
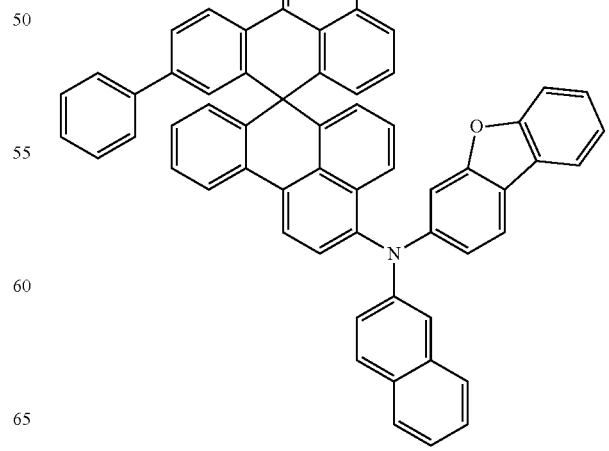

141
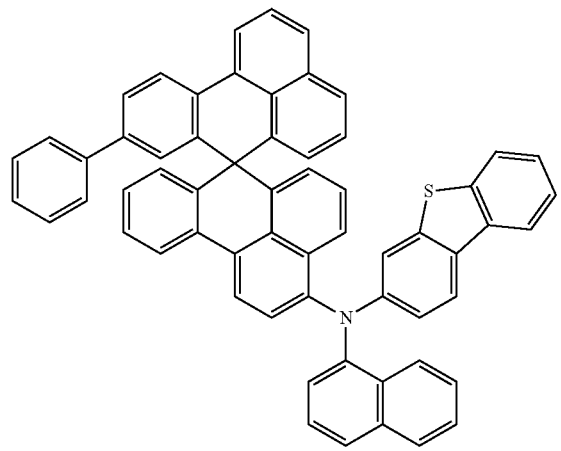
142
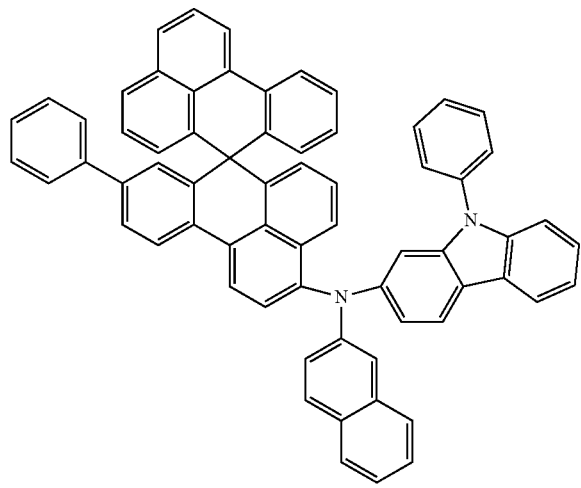
143
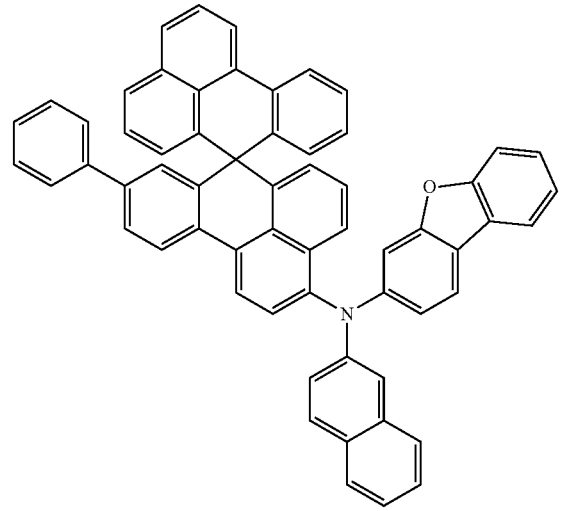
144
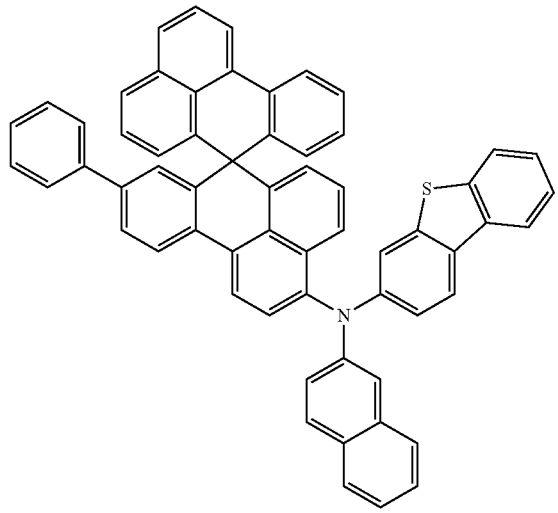
* * * * *

UNITED STATES PATENT AND TRADEMARK OFFICE
CERTIFICATE OF CORRECTION

PATENT NO. : 12,178,121 B2
APPLICATION NO. : 17/445815
DATED : December 24, 2024
INVENTOR(S) : Hankyu Pak et al.

Page 1 of 2

It is certified that error appears in the above-identified patent and that said Letters Patent is hereby corrected as shown below:

In the Claims

In Column 173, Lines 48-64, in Claim 15, Structure 82, delete

" 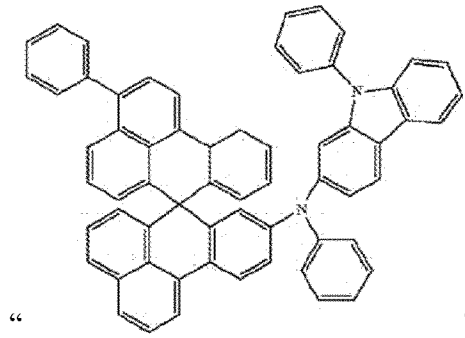   " and insert -- 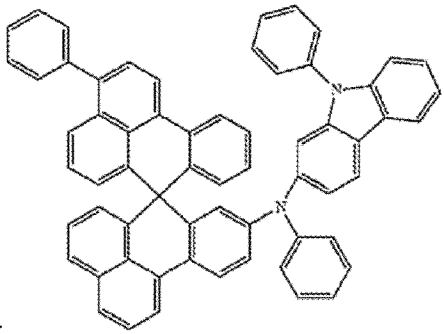   --.

In Column 195, Line 25, in Claim 16, after "1" insert -- , --.

In Column 208, Lines 22-37, in Claim 22, Structure 25, delete

" 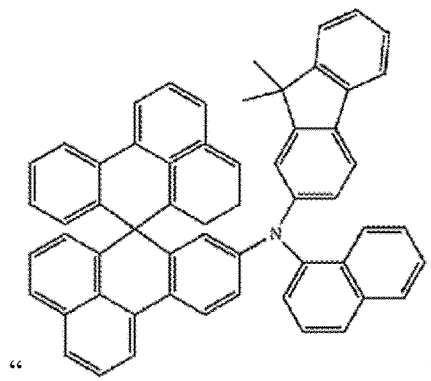   " and insert -- 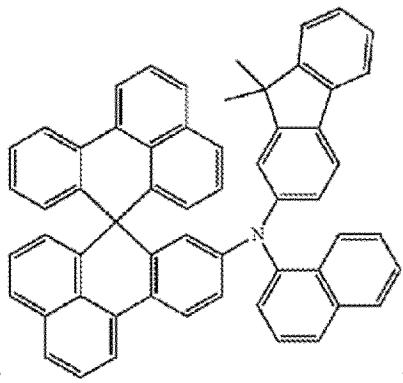   --.

Signed and Sealed this
Eighth Day of July, 2025

Coke Morgan Stewart
*Acting Director of the United States Patent and Trademark Office*

CERTIFICATE OF CORRECTION (continued)
U.S. Pat. No. 12,178,121 B2

In Column 210, Lines 20-34, in Claim 22, Structure 33, delete " 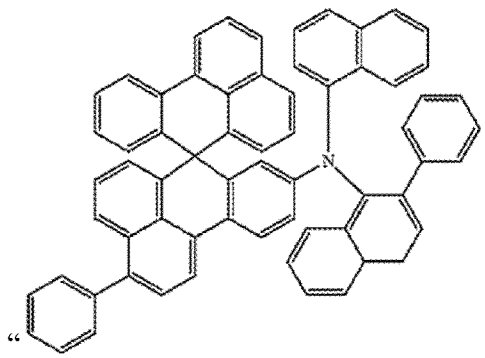 " and insert -- 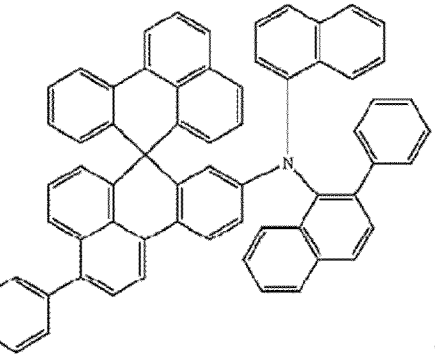 --.

In Column 240, Line 50, Claim 22, delete "128" and insert -- 129 --.